(12) United States Patent
Baird et al.

(10) Patent No.: US 6,503,886 B1
(45) Date of Patent: *Jan. 7, 2003

(54) COMPOSITIONS CONTAINING NUCLEIC ACIDS AND LIGANDS FOR THERAPEUTIC TREATMENT

(75) Inventors: J. Andrew Baird, San Diego; Lois Ann Chandler, Encinitas; Barbara A. Sosnowski, Coronado, all of CA (US)

(73) Assignee: Selective Genetics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/449,249

(22) Filed: Nov. 24, 1999

Related U.S. Application Data

(63) Continuation of application No. 08/718,904, filed on Sep. 24, 1996, now Pat. No. 6,037,329, which is a continuation-in-part of application No. 08/441,979, filed on May 16, 1995, now abandoned, which is a continuation-in-part of application No. 08/213,446, filed on Mar. 15, 1994, now abandoned, which is a continuation-in-part of application No. 08/213,447, filed on Mar. 15, 1994, now abandoned, which is a continuation-in-part of application No. 08/297,961, filed on Aug. 29, 1994, now abandoned, which is a continuation-in-part of application No. 08/305,771, filed on Sep. 13, 1994, now abandoned.

(51) Int. Cl.$^7$ ............................................... A61K 31/70
(52) U.S. Cl. ...................... 514/44; 435/320.1; 435/325; 435/455; 424/93.2
(58) Field of Search ............................ 435/320.1, 325, 435/455; 424/93.2; 514/49

(56) References Cited

U.S. PATENT DOCUMENTS

| | | | |
|---|---|---|---|
| 5,166,320 A | 11/1992 | Wu et al. | 530/395 |
| 5,169,933 A | 12/1992 | Anderson et al. | 530/391.3 |
| 5,308,622 A | 5/1994 | Casscells et al. | 424/422 |
| 5,354,844 A | 10/1994 | Beug et al. | 530/345 |
| 5,521,291 A | 5/1996 | Curiel et al. | 530/391.7 |
| 5,635,383 A | 6/1997 | Wu et al. | 435/455 |
| 5,679,637 A | 10/1997 | Lappi et al. | 514/2 |
| 5,707,969 A | 1/1998 | Nabel et al. | 514/44 |
| 5,830,686 A | 11/1998 | Henderson | 435/69.1 |
| 5,994,109 A | * 11/1999 | Woo et al. | 435/172.3 |
| 5,997,859 A | * 12/1999 | Barber et al. | 424/93.2 |

FOREIGN PATENT DOCUMENTS

| | | |
|---|---|---|
| WO | WO 90/12597 | 11/1990 |
| WO | WO 91/18012 | 11/1991 |
| WO | WO 92/04918 | 4/1992 |
| WO | WO 93/17669 | 9/1993 |
| WO | WO 93/25688 | 12/1993 |
| WO | WO 94/04696 | 3/1994 |
| WO | WO 94/25608 | 11/1994 |
| WO | WO 95/03831 | 2/1995 |
| WO | WO 95/22618 | 8/1995 |
| WO | WO 95/24928 | 9/1995 |
| WO | WO 95/28494 | 10/1995 |
| WO | WO 96/06641 | 3/1996 |
| WO | WO 96/08274 | 3/1996 |
| WO | WO 96/13599 | 5/1996 |

OTHER PUBLICATIONS

Sosnowski et al., "Targeting DNA through fibroblast growth factor receptors," *Proceedings of the American Association for Cancer Research* 37: 426, Abstract No. 2911, Mar. 1996.

Sosnowski et al., "Receptor Mediated Gene Delivery Through the FGF Receptor: Applications in the Eye," *Investigative Ophthalmology & Visual Science* 37(3):S187, Abstract No. 885, 1996.

Chen et al., "A novel gene delivery system using EGF receptor–mediated endocytosis," *FEBS Letters* 338: 167–169, 1994.

Chen et al., "Design of a genetic immunotoxin to eliminate toxin immunogenicity," *Gene Therapy* 2: 116–123, 1995.

Dauchel et al., "Modulation of Mitogenic Acitivity and Cellular Binding of Basic Fibroblast Growth Factor by Basic Proteins," *Journal of Cellular Biochemistry* 39: 411–420, 1989.

Fattom et al., "Comparative Immunogenicity of Conjugates Composed of the *Staphylococcus aureus* Type 8 Capsular Polysaccharide Bound to Carrier Proteins by Adipic Acid Dihydrazide or N–Succinimidyl–3–(2–Pyridyldithio) propionate," *Infection and Immunity* 60(2): 584–589, 1992.

Hoganson et al., "Comparison of the Effects of Three Different Toxin Genes and Their Levels of Expression on Cell Growth and Bystander Effect in Lung Adenocarcinoma," *Cancer Research* 56: 1315–1323, 1996.

Wagner et al., "Transferrin–polycation conjugates as carriers for DNA uptake into cells," *Proc. Natl. Acad. Sci. USA* 87: 3410–3414, 1990.

(List continued on next page.)

*Primary Examiner*—Dave T. Nguyen
(74) *Attorney, Agent, or Firm*—Seed Intellectual Property Law Group PLLC

(57) ABSTRACT

Preparations of conjugates of a receptor-binding internalized ligand and a cytocide-encoding agent and compositions containing such preparations are provided. The conjugates contain a polypeptide that is reactive with an FGF receptor, such as bFGF, or another heparin-binding growth factor, cytokine, or growth factor coupled to a nucleic acid binding domain. One or more linkers may be used in the conjugation. The linker is selected to increase the specificity, toxicity, solubility, serum stability, or intracellular availability, and promote nucleic acid condensation of the targeted moiety. The conjugates are complexed with a cytocide-encoding agent, such as DNA encoding saporin. Conjugates of a receptor-binding internalized ligand to a nucleic acid molecule are also provided.

29 Claims, 25 Drawing Sheets

OTHER PUBLICATIONS

Westby et al., "Separation and Characterization of Recombinant Proricin Containing an Alternative Protease–Sensitive Linker Sequence," *Bioconjugate Chem.* 3: 375–381, 1992.

Zenke et al., "Receptor–mediated endocytosis of transferrin–polycation conjugates: An efficient way to introduce DNA into hematopoietic cells," *Proc. Natl. Acad. Sci. USA* 87: 3655–3659, 1990.

Dauchel et al., *J. Cell. Biol.* 39(4): 411–420, 1989.

Vile et al., *Molecular Medicine Today* 4(2): 84–92, 1998.

Deonarain et al., *British J. Cancer* 70 (5): 786–94, 1994.

Thorpe et al., *Cancer Res.* 47: 592–5931, 1987.

Stein et al., *Mol. Cell Biol.* 14(5):3392–3402, 1994.

Kreitman et al., *P.N.A.S.* 91: 6889–6893, 1994.

Melton et al., *J. Natl. Cancer Inst.* 88(3/4):153–165, 1996.

Bicknell, *Analls of Oncology* 5(Suppl. 4): S45–S50.

Rieck et al., *Retinal Cell Biology/Cornea*, Abstract No. 16823.

Ngo et al., "The protein folding problem and tertiary structure function,"Birkhauser Boston Inc., 14, 491–495, 1994.

Crystal, *Science* 270: 404–410, 1995.

Ledley, *Hum. Gene Ther.* 6:1129–44, 1995.

Mastrangelo et al., *Seminars in Oncology* 23(1): 4–21, 1996.

Coglan, *New Scientist*, pp. 14–15, Nov. 1995.

Gunzberg et al., *Mol. Medicine Today* 4: 410–417, 1995.

\* cited by examiner

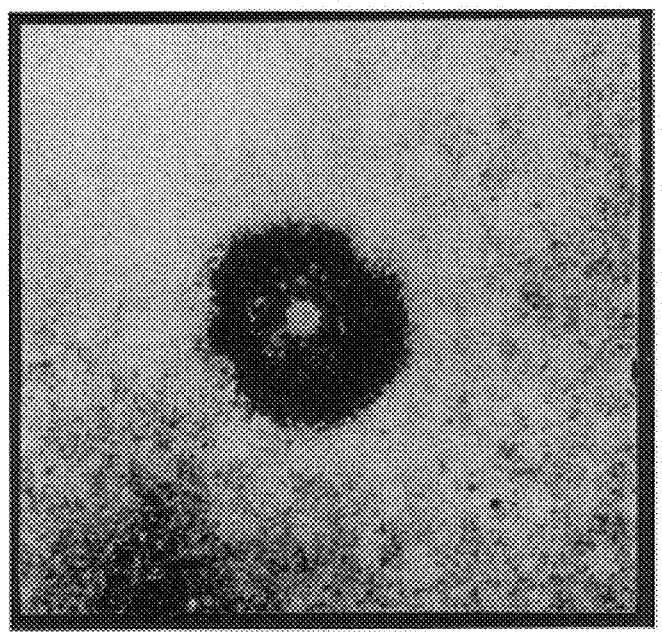
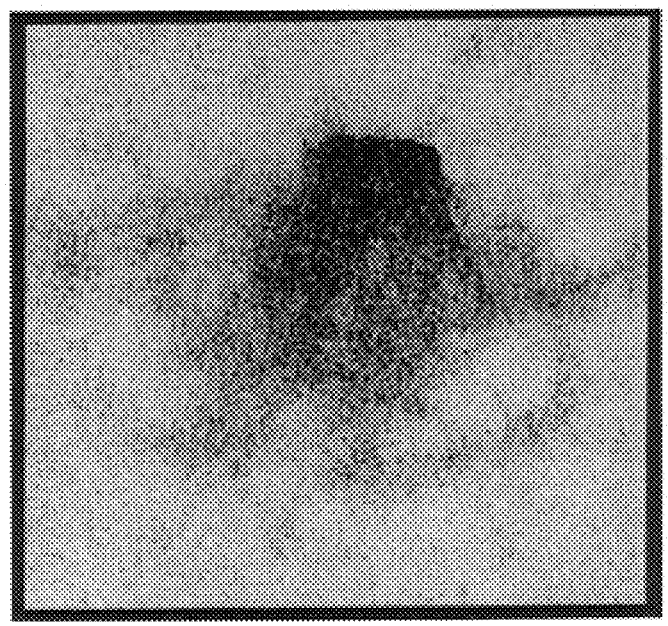
Fig. 5

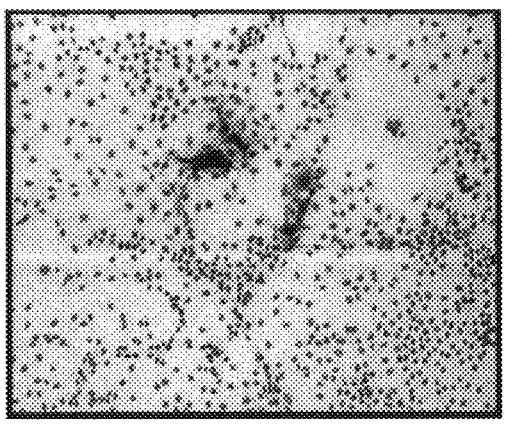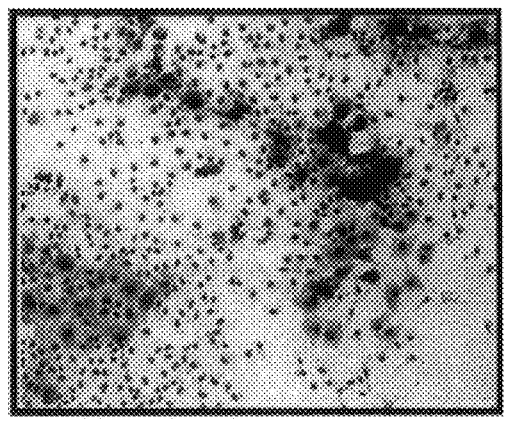
Fig. 9C

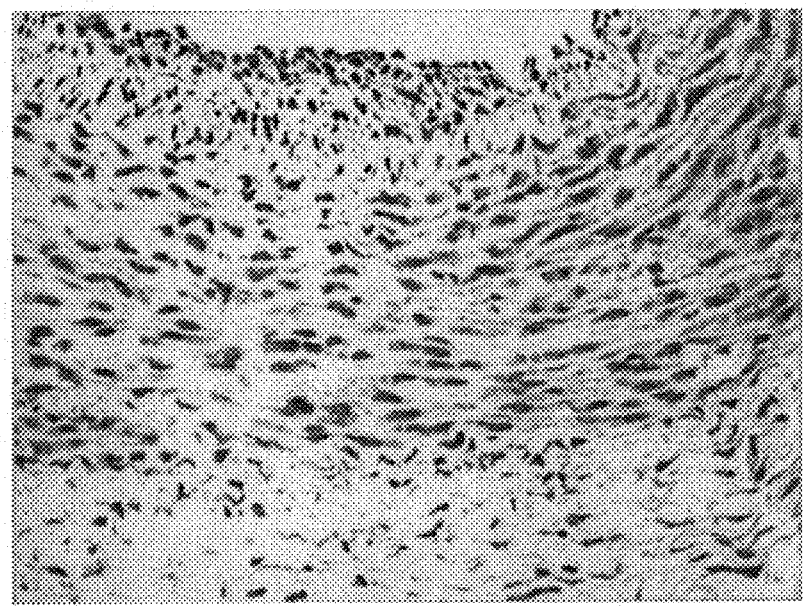
FGF2-K84-DNA Bgal (Promoterless)
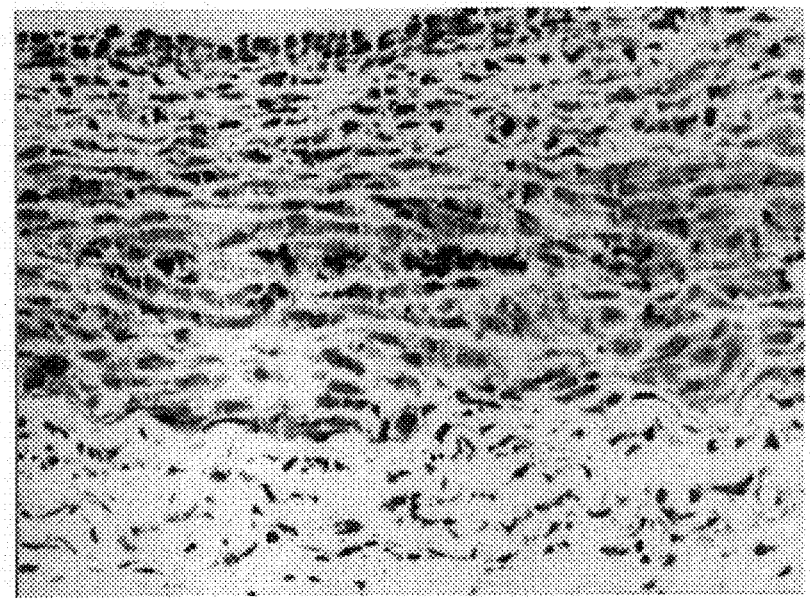
FGF2-K84-DNA Bgal (α-Actin)
*Fig. 17*

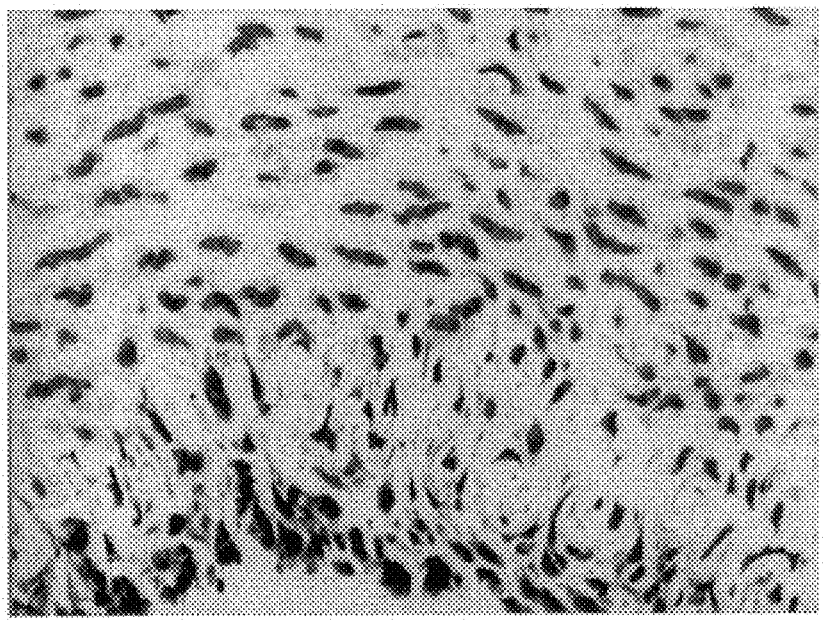
FGF2-K84-DNA Bgal (Promoterless)
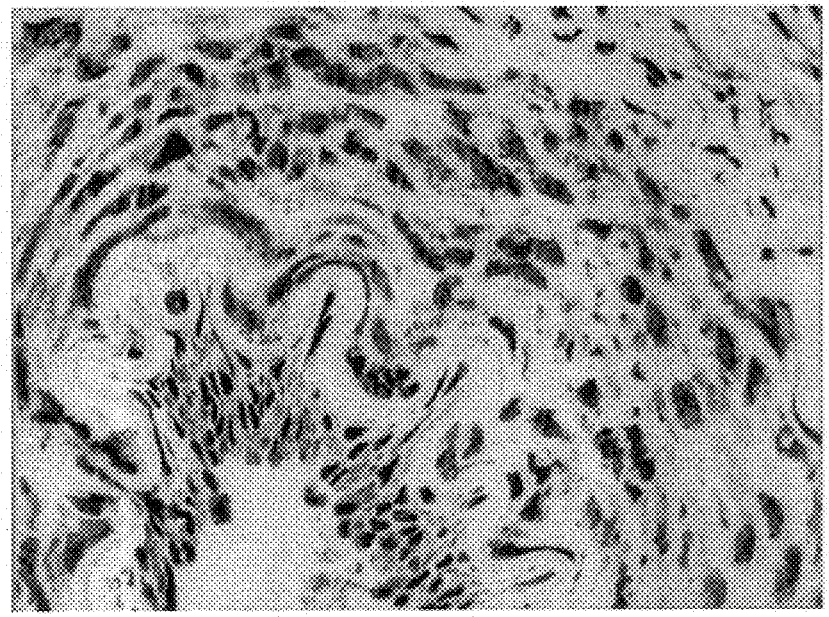
FGF2-K84-DNA Bgal (α-Actin)
*Fig. 18*

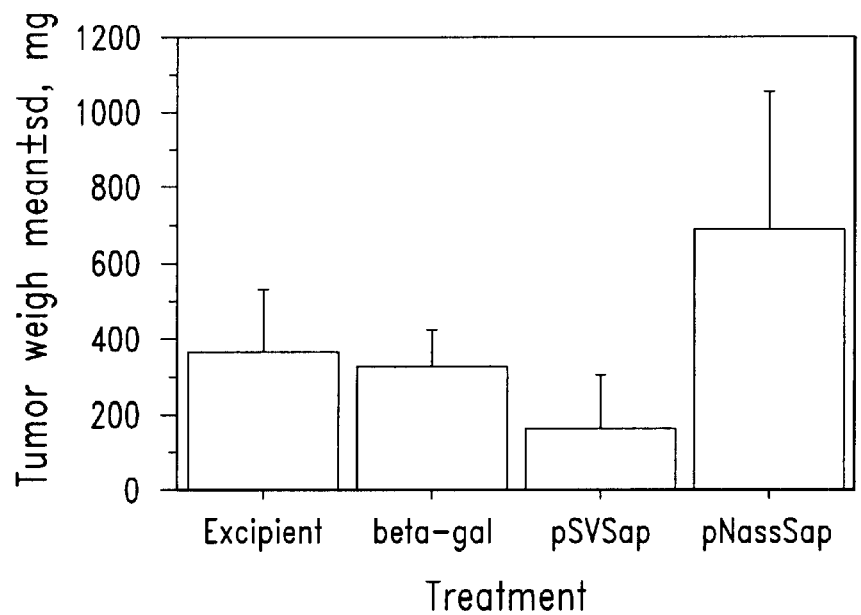
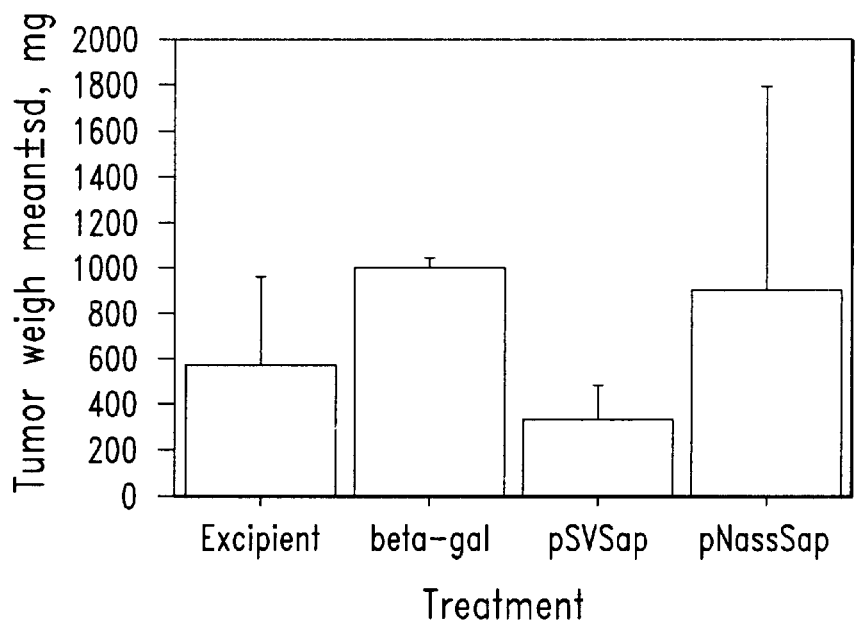
Fig. 21

SDS-PAGE

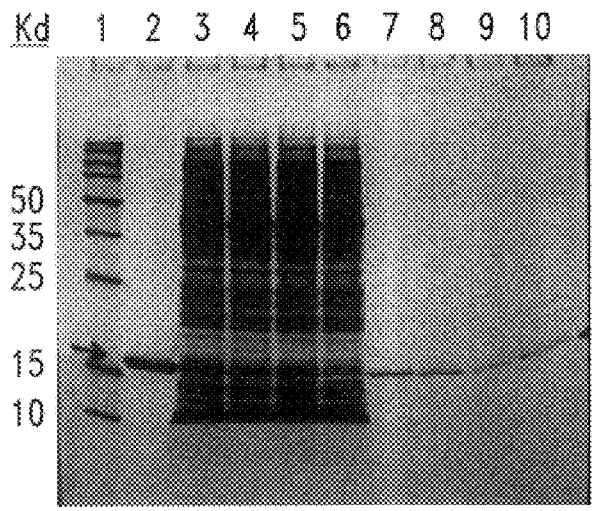

1. Novagen marker
2. FGF2 2μg purified PD
3. Crude lysis pZ150 20μl
4. Crude lysis R116I 20μl
5. Crude lysis R118K/K119E 20μl
6. Crude lysis Y120A 20μl
7. Purified pZ150 2μg
8. Purified R116I 2μg
9. Purified R118K/K119E 2μg
10. Purified Y120A 2μg

WESTERN

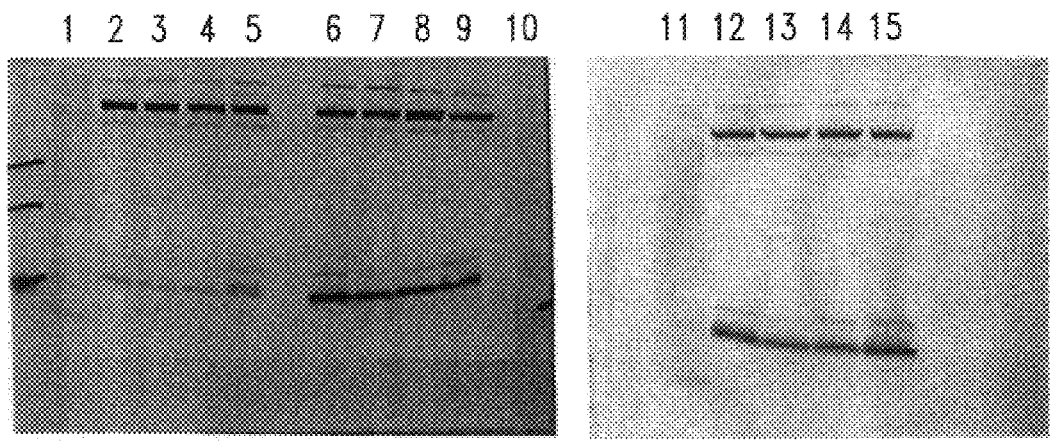

lane 1 rainbow markers
lane 2 t=0 R116I
lane 3 t=0 R118K/K119E
lane 4 t=0 Y120A
lane 5 pZ150 t=0
lane 6 blank
lane 7 t=1 R116I
lane 8 t=1 R118K/K119E lane 9 t=1 Y120A
lane 10 t=1 pZ150
lane 11 rainbow markers
lane 12 t=2 R116I
lane 13 t=2 R118K/K119E
lane 14 t=2 Y120A
lane 15 t=2 pZ150

*Fig. 23*

SEQUENCE LISTING (1) GENERAL INFORMATION:

(iii) NUMBER OF SEQUENCES: 128

(2) INFORMATION FOR SEQ ID NO: 1:

(i) SEQUENCE CHARACTERISTICS:
        (A) LENGTH: 473 base pairs
        (B) TYPE: nucleic acid
        (C) STRANDEDNESS: double
        (D) TOPOLOGY: both (ii) MOLECULE TYPE: cDNA (ix) FEATURE:
        (A) NAME/KEY: CDS
        (B) LOCATION: 13..456
        (D) OTHER INFORMATION: /product= "VEGF121-encoding DNA"

(ix) FEATURE:
        (A) NAME/KEY: CDS
        (B) LOCATION: 13..90
        (D) OTHER INFORMATION: /product= leader-encoding sequence (xi) SEQUENCE DESCRIPTION: SEQ ID NO: 1:

```
GGATCCGAAA CC ATG AAC TTT CTG CTG TCT TGG GTG CAT TGG AGC CTT            48
              Met Asn Phe Leu Leu Ser Trp Val His Trp Ser Leu
                1               5                  10

GCC TTG CTG CTC TAC CTC CAC CAT GCC AAG TGG TCC CAG GCT GCA CCC          96
Ala Leu Leu Leu Tyr Leu His His Ala Lys Trp Ser Gln Ala Ala Pro
         15                  20                  25

ATG GCA GAA GGA GGA GGG CAG AAT CAT CAC GAA GTG GTG AAG TTC ATG         144
Met Ala Glu Gly Gly Gly Gln Asn His His Glu Val Val Lys Phe Met
     30                  35                  40

GAT GTC TAT CAG CGC AGC TAC TGC CAT CCA ATC GAG ACC CTG GTG GAC         192
Asp Val Tyr Gln Arg Ser Tyr Cys His Pro Ile Glu Thr Leu Val Asp
 45                  50                  55                  60

ATC TTC CAG GAG TAC CCT GAT GAG ATC GAG TAC ATC TTC AAG CCA TCC         240
Ile Phe Gln Glu Tyr Pro Asp Glu Ile Glu Tyr Ile Phe Lys Pro Ser
```

```
TGT GTG CCC CTG ATG CGA TGC GGG GGC TGC TGC AAT GAC GAG GGC CTG      288
Cys Val Pro Leu Met Arg Cys Gly Gly Cys Cys Asn Asp Glu Gly Leu
            80                  85                  90

GAG TGT GTG CCC ACT GAG GAG TCC AAC ATC ACC ATG CAG ATT ATG CGG      336
Glu Cys Val Pro Thr Glu Glu Ser Asn Ile Thr Met Gln Ile Met Arg
        95                  100                 105

ATC AAA CCT CAC CAA GGC CAG CAC ATA GGA GAG ATG AGC TTC CTA CAG      384
Ile Lys Pro His Gln Gly Gln His Ile Gly Glu Met Ser Phe Leu Gln
    110                 115                 120

CAC AAC AAA TGT GAA TGC AGA CCA AAG AAA GAT AGA GCA AGA CAA GAA      432
His Asn Lys Cys Glu Cys Arg Pro Lys Lys Asp Arg Ala Arg Gln Glu
125                 130                 135                 140

AAA TGT GAC AAG CCG AGG CGG TGATGAATGA ATGAGGATCC                    473
Lys Cys Asp Lys Pro Arg Arg
                145
```

(2) INFORMATION FOR SEQ ID NO: 2:

(i) SEQUENCE CHARACTERISTICS:
        (A) LENGTH: 605 base pairs
        (B) TYPE: nucleic acid
        (C) STRANDEDNESS: double
        (D) TOPOLOGY: both (ii) MOLECULE TYPE: cDNA (ix) FEATURE:
        (A) NAME/KEY: CDS
        (B) LOCATION: 13..588
        (D) OTHER INFORMATION: /product= "VEGF165-encoding DNA"

(ix) FEATURE:
        (A) NAME/KEY: CDS
        (B) LOCATION: 13..90
        (D) OTHER INFORMATION: /product= "leader sequence-encoding DNA"

(xi) SEQUENCE DESCRIPTION: SEQ ID NO: 2:

```
GGATCCGAAA CC ATG AAC TTT CTG CTG TCT TGG GTG CAT TGG AGC CTT       48
              Met Asn Phe Leu Leu Ser Trp Val His Trp Ser Leu
              1               5                   10

GCC TTG CTG CTC TAC CTC CAC CAT GCC AAG TGG TCC CAG GCT GCA CCC      96
Ala Leu Leu Leu Tyr Leu His His Ala Lys Trp Ser Gln Ala Ala Pro
            15                  20                  25

ATG GCA GAA GGA GGA GGG CAG AAT CAT CAC GAA GTG GTG AAG TTC ATG     144
Met Ala Glu Gly Gly Gly Gln Asn His His Glu Val Val Lys Phe Met
        30                  35                  40

GAT GTC TAT CAG CGC AGC TAC TGC CAT CCA ATC GAG ACC CTG GTG GAC     192
Asp Val Tyr Gln Arg Ser Tyr Cys His Pro Ile Glu Thr Leu Val Asp
45                  50                  55                  60

ATC TTC CAG GAG TAC CCT GAT GAG ATC GAG TAC ATC TTC AAG CCA TCC     240
Ile Phe Gln Glu Tyr Pro Asp Glu Ile Glu Tyr Ile Phe Lys Pro Ser
            65                  70                  75

TGT GTG CCC CTG ATG CGA TGC GGG GGC TGC TGC AAT GAC GAG GGC CTG     288
Cys Val Pro Leu Met Arg Cys Gly Gly Cys Cys Asn Asp Glu Gly Leu
            80                  85                  90

GAG TGT GTG CCC ACT GAG GAG TCC AAC ATC ACC ATG CAG ATT ATG CGG     336
Glu Cys Val Pro Thr Glu Glu Ser Asn Ile Thr Met Gln Ile Met Arg
        95                  100                 105

ATC AAA CCT CAC CAA GGC CAG CAC ATA GGA GAG ATG AGC TTC CTA CAG     384
Ile Lys Pro His Gln Gly Gln His Ile Gly Glu Met Ser Phe Leu Gln
    110                 115                 120

CAC AAC AAA TGT GAA TGC AGA CCA AAG AAA GAT AGA GCA AGA CAA GAA     432
His Asn Lys Cys Glu Cys Arg Pro Lys Lys Asp Arg Ala Arg Gln Glu
```

```
His Asn Lys Cys Glu Cys Arg Pro Lys Lys Asp Arg Ala Arg Gln Glu
125                 130                 135                 140

AAT CCC TGT GGG CCT TGC TCA GAG CGG AGA AAG CAT TTG TTT GTA CAA         480
Asn Pro Cys Gly Pro Cys Ser Glu Arg Arg Lys His Leu Phe Val Gln
            145                 150                 155

GAT CCG CAG ACG TGT AAA TGT TCC TGC AAA AAC ACA GAC TCG CGT TGC         528
Asp Pro Gln Thr Cys Lys Cys Ser Cys Lys Asn Thr Asp Ser Arg Cys
        160                 165                 170

AAG GCG AGG CAG CTT GAG TTA AAC GAA CGT ACT TGC AGA TGT GAC AAG         576
Lys Ala Arg Gln Leu Glu Leu Asn Glu Arg Thr Cys Arg Cys Asp Lys
            175                 180                 185

CCG AGG CGG TGATGAATGA ATGAGGATCC                                       605
Pro Arg Arg
    190

(2) INFORMATION FOR SEQ ID NO: 3:

(i) SEQUENCE CHARACTERISTICS:
        (A) LENGTH: 677 base pairs
        (B) TYPE: nucleic acid
        (C) STRANDEDNESS: double
        (D) TOPOLOGY: both (ii) MOLECULE TYPE: cDNA (ix) FEATURE:
        (A) NAME/KEY: CDS
        (B) LOCATION: 13..657
        (D) OTHER INFORMATION: /product= "VEGF189-encoding DNA"

(ix) FEATURE:
        (A) NAME/KEY: CDS
        (B) LOCATION: 13..90
        (D) OTHER INFORMATION: /product= "leader sequence-encoding
            DNA"

(xi) SEQUENCE DESCRIPTION: SEQ ID NO: 3:

GGATCCGAAA CC ATG AAC TTT CTG CTG TCT TGG GTG CAT TGG AGC CTT           48
              Met Asn Phe Leu Leu Ser Trp Val His Trp Ser Leu
                1               5                   10

GCC TTG CTG CTC TAC CTC CAC CAT GCC AAG TGG TCC CAG GCT GCA CCC         96
Ala Leu Leu Leu Tyr Leu His His Ala Lys Trp Ser Gln Ala Ala Pro
            15                  20                  25

ATG GCA GAA GGA GGA GGG CAG AAT CAT CAC GAA GTG GTG AAG TTC ATG         144
Met Ala Glu Gly Gly Gly Gln Asn His His Glu Val Val Lys Phe Met
        30                  35                  40

GAT GTC TAT CAG CGC AGC TAC TGC CAT CCA ATC GAG ACC CTG GTG GAC         192
Asp Val Tyr Gln Arg Ser Tyr Cys His Pro Ile Glu Thr Leu Val Asp
45                  50                  55                  60

ATC TTC CAG GAG TAC CCT GAT GAG ATC GAG TAC ATC TTC AAG CCA TCC         240
Ile Phe Gln Glu Tyr Pro Asp Glu Ile Glu Tyr Ile Phe Lys Pro Ser
            65                  70                  75

TGT GTG CCC CTG ATG CGA TGC GGG GGC TGC TGC AAT GAC GAG GGC CTG         288
Cys Val Pro Leu Met Arg Cys Gly Gly Cys Cys Asn Asp Glu Gly Leu
        80                  85                  90

GAG TGT GTG CCC ACT GAG GAG TCC AAC ATC ACC ATG CAG ATT ATG CGG         336
Glu Cys Val Pro Thr Glu Glu Ser Asn Ile Thr Met Gln Ile Met Arg
    95                  100                 105

ATC AAA CCT CAC CAA GGC CAG CAC ATA GGA GAG ATG AGC TTC CTA CAG         384
Ile Lys Pro His Gln Gly Gln His Ile Gly Glu Met Ser Phe Leu Gln
        110                 115                 120

CAC AAC AAA TGT GAA TGC AGA CCA AAG AAG GAT AGA GCA AGA CAA GAA         432
His Asn Lys Cys Glu Cys Arg Pro Lys Lys Asp Arg Ala Arg Gln Glu
125                 130                 135                 140
```

```
AAA AAA TCA GTT CGA GGA AAG GGA AAG GGG CAA AAA CGA AAG CGC AAG        480
Lys Lys Ser Val Arg Gly Lys Gly Lys Gly Gln Lys Arg Lys Arg Lys
            145                 150                 155

AAA TCC CGG TAT AAG TCC TGG AGC GTT CCC TGT GGG CCT TGC TCA GAG        528
Lys Ser Arg Tyr Lys Ser Trp Ser Val Pro Cys Gly Pro Cys Ser Glu
        160                 165                 170

CGG AGA AAG CAT TTG TTT GTA CAA GAT CCG CAG ACG TGT AAA TGT TCC        576
Arg Arg Lys His Leu Phe Val Gln Asp Pro Gln Thr Cys Lys Cys Ser
            175                 180                 185

TGC AAA AAC ACA GAC TCG CGT TGC AAG GCG AGG CAG CTT GAG TTA AAC        624
Cys Lys Asn Thr Asp Ser Arg Cys Lys Ala Arg Gln Leu Glu Leu Asn
            190                 195                 200

GAA CGT ACT TGC AGA TGT GAC AAG CCG AGG CGG TGATGAATGA ATGAGGATCC      677
Glu Arg Thr Cys Arg Cys Asp Lys Pro Arg Arg
205                 210                 215

(2) INFORMATION FOR SEQ ID NO: 4:

(i) SEQUENCE CHARACTERISTICS:
        (A) LENGTH: 728 base pairs
        (B) TYPE: nucleic acid
        (C) STRANDEDNESS: double
        (D) TOPOLOGY: both (ii) MOLECULE TYPE: cDNA (ix) FEATURE:
        (A) NAME/KEY: CDS
        (B) LOCATION: 13..711
        (D) OTHER INFORMATION: /product= "VEGF206-encoding DNA"

(ix) FEATURE:
        (A) NAME/KEY: CDS
        (B) LOCATION: 13..90
        (D) OTHER INFORMATION: /product= leader sequence encoding DNA (xi) SEQUENCE DESCRIPTION: SEQ ID NO: 4:

GGATCCGAAA CC ATG AAC TTT CTG CTG TCT TGG GTG CAT TGG AGC CTT          48
              Met Asn Phe Leu Leu Ser Trp Val His Trp Ser Leu
                1               5                   10

GCC TTG CTG CTC TAC CTC CAC CAT GCC AAG TGG TCC CAG GCT GCA CCC        96
Ala Leu Leu Leu Tyr Leu His His Ala Lys Trp Ser Gln Ala Ala Pro
            15                  20                  25

ATG GCA GAA GGA GGA GGG CAG AAT CAT CAC GAA GTG GTG AAG TTC ATG        144
Met Ala Glu Gly Gly Gly Gln Asn His His Glu Val Val Lys Phe Met
        30                  35                  40

GAT GTC TAT CAG CGC AGC TAC TGC CAT CCA ATC GAG ACC CTG GTG GAC        192
Asp Val Tyr Gln Arg Ser Tyr Cys His Pro Ile Glu Thr Leu Val Asp
45                  50                  55                  60

ATC TTC CAG GAG TAC CCT GAT GAG ATC GAG TAC ATC TTC AAG CCA TCC        240
Ile Phe Gln Glu Tyr Pro Asp Glu Ile Glu Tyr Ile Phe Lys Pro Ser
                65                  70                  75

TGT GTG CCC CTG ATG CGA TGC GGG GGC TGC TGC AAT GAC GAG GGC CTG        288
Cys Val Pro Leu Met Arg Cys Gly Gly Cys Cys Asn Asp Glu Gly Leu
            80                  85                  90

GAG TGT GTG CCC ACT GAG GAG TCC AAC ATC ACC ATG CAG ATT ATG CGG        336
Glu Cys Val Pro Thr Glu Glu Ser Asn Ile Thr Met Gln Ile Met Arg
        95                  100                 105

ATC AAA CCT CAC CAA GGC CAG CAC ATA GGA GAG ATG AGC TTC CTA CAG        384
Ile Lys Pro His Gln Gly Gln His Ile Gly Glu Met Ser Phe Leu Gln
        110                 115                 120

CAC AAC AAA TGT GAA TGC AGA CCA AAG AAG GAT AGA GCA AGA CAA GAA        432
His Asn Lys Cys Glu Cys Arg Pro Lys Lys Asp Arg Ala Arg Gln Glu
125                 130                 135                 140
```

```
AAA AAA TCA GTT CGA GGA AAG GGA AAG GGG CAA AAA CGA AAG CGC AAG      480
Lys Lys Ser Val Arg Gly Lys Gly Lys Gly Gln Lys Arg Lys Arg Lys
            145                 150                 155

AAA TCC CGG TAT AAG TCC TGG AGC GTT TAC GTT GGT GCC CGC TGC TGT      528
Lys Ser Arg Tyr Lys Ser Trp Ser Val Tyr Val Gly Ala Arg Cys Cys
            160                 165                 170

CTA ATG CCC TGG AGC CTC CCT GGC CCC CAT CCC TGT GGG CCT TGC TCA      576
Leu Met Pro Trp Ser Leu Pro Gly Pro His Pro Cys Gly Pro Cys Ser
            175                 180                 185

GAG CGG AGA AAG CAT TTG TTT GTA CAA GAT CCG CAG ACG TGT AAA TGT      624
Glu Arg Arg Lys His Leu Phe Val Gln Asp Pro Gln Thr Cys Lys Cys
    190                 195                 200

TCC TGC AAA AAC ACA GAC TCG CGT TGC AAG GCG AGG CAG CTT GAG TTA      672
Ser Cys Lys Asn Thr Asp Ser Arg Cys Lys Ala Arg Gln Leu Glu Leu
205                 210                 215                 220

AAC GAA CGT ACT TGC AGA TGT GAC AAG CCG AGG CGG TGATGAATGA           718
Asn Glu Arg Thr Cys Arg Cys Asp Lys Pro Arg Arg
225                 230                 235

ATGAGGATCC                                                            728

(2) INFORMATION FOR SEQ ID NO: 5:

(i) SEQUENCE CHARACTERISTICS:
        (A) LENGTH: 208 amino acids
        (B) TYPE: amino acid
        (D) TOPOLOGY: linear (ii) MOLECULE TYPE: protein (ix) FEATURE:
        (A) NAME/KEY: CDS
        (B) LOCATION: 1..627
        (D) OTHER INFORMATION: /note "human HBEGF precursor"

(xi) SEQUENCE DESCRIPTION: SEQ ID NO: 5:

Met Lys Leu Leu Pro Ser Val Val Leu Lys Leu Phe Leu Ala Ala Val
 1               5                  10                  15

Leu Ser Ala Leu Val Thr Gly Glu Ser Leu Glu Arg Leu Arg Arg Gly
            20                  25                  30

Leu Ala Ala Gly Thr Ser Asn Pro Asp Pro Pro Thr Val Ser Thr Asp
        35                  40                  45

Gln Leu Leu Pro Leu Gly Gly Gly Arg Asp Arg Lys Val Arg Asp Leu
    50                  55                  60

Gln Glu Ala Asp Leu Asp Leu Leu Arg Val Thr Leu Ser Ser Lys Pro
65                  70                  75                  80

Gln Ala Leu Ala Thr Pro Asn Lys Glu Glu His Gly Lys Arg Lys Lys
                85                  90                  95

Lys Gly Lys Gly Leu Gly Lys Lys Arg Asp Pro Cys Leu Arg Lys Tyr
            100                 105                 110

Lys Asp Phe Cys Ile His Gly Glu Cys Lys Tyr Val Lys Glu Leu Arg
        115                 120                 125

Ala Pro Ser Cys Ile Cys His Pro Gly Tyr His Gly Glu Arg Cys His
    130                 135                 140

Gly Leu Ser Leu Pro Val Glu Asn Arg Leu Tyr Thr Tyr Asp His Thr
145                 150                 155                 160

Thr Ile Leu Ala Val Val Ala Val Val Leu Ser Ser Val Cys Leu Leu
                165                 170                 175

Val Ile Val Gly Leu Leu Met Phe Arg Tyr His Arg Arg Gly Gly Tyr
            180                 185                 190
```

Asp Val Glu Asn Glu Glu Lys Val Lys Leu Gly Met Thr Asn Ser His
    195                 200                 205

(2) INFORMATION FOR SEQ ID NO: 6:

(i) SEQUENCE CHARACTERISTICS:
        (A) LENGTH: 77 amino acids
        (B) TYPE: amino acid
        (C) STRANDEDNESS: unknown
        (D) TOPOLOGY: unknown (ii) MOLECULE TYPE: protein (ix) FEATURE:
        (D) OTHER INFORMATION: /note "human mature HBEGF"

(xi) SEQUENCE DESCRIPTION: SEQ ID NO: 6:

Arg Val Thr Leu Ser Ser Lys Pro Gln Ala Leu Ala Thr Pro Asn Lys
1                 5                   10                  15

Glu Glu His Gly Lys Arg Lys Lys Gly Lys Gly Leu Gly Lys Lys
                20                  25                  30

Arg Asp Pro Cys Leu Arg Lys Tyr Lys Asp Phe Cys Ile His Gly Glu
                35                  40                  45

Cys Lys Tyr Val Lys Glu Leu Arg Ala Pro Ser Cys Ile Cys His Pro
        50                  55                  60

Gly Tyr His Gly Glu Arg Cys His Gly Leu Ser Leu Pro
65                  70                  75

(2) INFORMATION FOR SEQ ID NO: 7:

(i) SEQUENCE CHARACTERISTICS:
        (A) LENGTH: 208 amino acids
        (B) TYPE: amino acid
        (C) STRANDEDNESS: unknown
        (D) TOPOLOGY: unknown (ii) MOLECULE TYPE: protein (ix) FEATURE:
        (D) OTHER INFORMATION: /note "monkey HBEGF precursor"

(xi) SEQUENCE DESCRIPTION: SEQ ID NO: 7:

Met Lys Leu Leu Pro Ser Val Val Leu Lys Leu Leu Leu Ala Ala Val
1                 5                   10                  15

Leu Ser Ala Leu Val Thr Gly Glu Ser Leu Glu Gln Leu Arg Arg Gly
                20                  25                  30

Leu Ala Ala Gly Thr Ser Asn Pro Asp Pro Ser Thr Gly Ser Thr Asp
                35                  40                  45

Gln Leu Leu Arg Leu Gly Gly Gly Arg Asp Arg Lys Val Arg Asp Leu
    50                  55                  60

Gln Glu Ala Asp Leu Asp Leu Leu Arg Val Thr Leu Ser Ser Lys Pro
65                  70                  75                  80

Gln Ala Leu Ala Thr Pro Ser Lys Glu Glu His Gly Lys Arg Lys Lys
                85                  90                  95

Lys Gly Lys Gly Leu Gly Lys Lys Arg Asp Pro Cys Leu Arg Lys Tyr
                100                 105                 110

Lys Asp Phe Cys Ile His Gly Glu Cys Lys Tyr Val Lys Glu Leu Arg
                115                 120                 125

Ala Pro Ser Cys Ile Cys His Pro Gly Tyr His Gly Glu Arg Cys His
                130                 135                 140

Gly Leu Ser Leu Pro Val Glu Asn Arg Leu Tyr Thr Tyr Asp His Thr
145                 150                 155                 160

```
Thr Ile Leu Ala Val Val Ala Val Val Leu Ser Ser Val Cys Leu Leu
                165                 170                 175

Val Ile Val Gly Leu Leu Met Phe Arg Tyr His Arg Arg Gly Gly Tyr
            180                 185                 190

Asp Val Glu Asn Glu Glu Lys Val Lys Leu Gly Met Thr Asn Ser His
        195                 200                 205
```

(2) INFORMATION FOR SEQ ID NO: 8:

(i) SEQUENCE CHARACTERISTICS:
        (A) LENGTH: 208 amino acids
        (B) TYPE: amino acid
        (C) STRANDEDNESS: unknown
        (D) TOPOLOGY: unknown (ii) MOLECULE TYPE: protein (ix) FEATURE:
        (D) OTHER INFORMATION: /note "rat HBEGF precursor"

(xi) SEQUENCE DESCRIPTION: SEQ ID NO: 8:

```
Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
            20                  25                  30

Leu Ala Ala Ala Thr Ser Asn Pro Asp Pro Pro Thr Gly Thr Thr Asn
            35                  40                  45

Gln Leu Leu Pro Thr Gly Ala Asp Arg Ala Gln Glu Val Gln Asp Leu
        50                  55                  60

Glu Gly Thr Asp Leu Asp Leu Phe Lys Val Ala Phe Ser Ser Lys Pro
65                  70                  75                  80

Gln Ala Leu Ala Thr Pro Gly Lys Glu Lys Asn Gly Lys Lys Lys Arg
                85                  90                  95

Lys Gly Lys Gly Leu Gly Lys Lys Arg Asp Pro Cys Leu Lys Lys Tyr
            100                 105                 110

Lys Asp Tyr Cys Ile His Gly Glu Cys Arg Tyr Leu Lys Glu Leu Arg
            115                 120                 125

Ile Pro Ser Cys His Cys Leu Pro Gly Tyr His Gly Gln Arg Cys His
        130                 135                 140

Gly Leu Thr Leu Pro Val Glu Asn Pro Leu Tyr Thr Tyr Asp His Thr
145                 150                 155                 160

Thr Val Leu Ala Val Val Ala Val Val Leu Ser Ser Val Cys Leu Leu
                165                 170                 175

Val Ile Val Gly Leu Leu Met Phe Arg Tyr His Arg Arg Gly Gly Tyr
            180                 185                 190

Asp Leu Glu Ser Glu Glu Lys Val Lys Leu Gly Met Ala Ser Ser His
        195                 200                 205
```

(2) INFORMATION FOR SEQ ID NO: 9:

(i) SEQUENCE CHARACTERISTICS:
        (A) LENGTH: 627 base pairs
        (B) TYPE: nucleic acid
        (C) STRANDEDNESS: double
        (D) TOPOLOGY: both (ii) MOLECULE TYPE: cDNA (ix) FEATURE:
        (A) NAME/KEY: CDS
        (B) LOCATION: 1..627

(D) OTHER INFORMATION: /note "human HBEGF precursor"

(xi) SEQUENCE DESCRIPTION: SEQ ID NO: 9:

| | | | | | | | | | | | | | | | | |
|---|---|---|---|---|---|---|---|---|---|---|---|---|---|---|---|---|
| ATG | AAG | CTG | CTG | CCG | TCG | GTG | GTG | CTG | AAG | CTC | TTT | CTG | GCT | GCA | GTT | 48 |
| Met | Lys | Leu | Leu | Pro | Ser | Val | Val | Leu | Lys | Leu | Phe | Leu | Ala | Ala | Val | |
| 1 | | | | 5 | | | | | 10 | | | | | 15 | | |
| CTC | TCG | GCA | CTG | GTG | ACT | GGC | GAG | AGC | CTG | GAG | CGG | CTT | CGG | AGA | GGG | 96 |
| Leu | Ser | Ala | Leu | Val | Thr | Gly | Glu | Ser | Leu | Glu | Arg | Leu | Arg | Arg | Gly | |
| | | | 20 | | | | | 25 | | | | | 30 | | | |
| CTA | GCT | GCT | GGA | ACC | AGC | AAC | CCG | GAC | CCT | CCC | ACT | GTA | TCC | ACG | GAC | 144 |
| Leu | Ala | Ala | Gly | Thr | Ser | Asn | Pro | Asp | Pro | Pro | Thr | Val | Ser | Thr | Asp | |
| | 35 | | | | | 40 | | | | | 45 | | | | | |
| CAG | CTG | CTA | CCC | CTA | GGA | GGC | GGC | CGG | GAC | CGG | AAA | GTC | CGT | GAC | TTG | 192 |
| Gln | Leu | Leu | Pro | Leu | Gly | Gly | Gly | Arg | Asp | Arg | Lys | Val | Arg | Asp | Leu | |
| | 50 | | | | | 55 | | | | | 60 | | | | | |
| CAA | GAG | GCA | GAT | CTG | GAC | CTT | TTG | AGA | GTC | ACT | TTA | TCC | TCC | AAG | CCA | 240 |
| Gln | Glu | Ala | Asp | Leu | Asp | Leu | Leu | Arg | Val | Thr | Leu | Ser | Ser | Lys | Pro | |
| 65 | | | | | 70 | | | | | 75 | | | | | 80 | |
| CAA | GCA | CTG | GCC | ACA | CCA | AAC | AAG | GAG | GAG | CAC | GGG | AAA | AGA | AAG | AAG | 288 |
| Gln | Ala | Leu | Ala | Thr | Pro | Asn | Lys | Glu | Glu | His | Gly | Lys | Arg | Lys | Lys | |
| | | | | 85 | | | | | 90 | | | | | 95 | | |
| AAA | GGC | AAG | GGG | CTA | GGG | AAG | AAG | AGG | GAC | CCA | TGT | CTT | CGG | AAA | TAC | 336 |
| Lys | Gly | Lys | Gly | Leu | Gly | Lys | Lys | Arg | Asp | Pro | Cys | Leu | Arg | Lys | Tyr | |
| | | | 100 | | | | | 105 | | | | | 110 | | | |
| AAG | GAC | TTC | TGC | ATC | CAT | GGA | GAA | TGC | AAA | TAT | GTG | AAG | GAG | CTC | CGG | 384 |
| Lys | Asp | Phe | Cys | Ile | His | Gly | Glu | Cys | Lys | Tyr | Val | Lys | Glu | Leu | Arg | |
| | | 115 | | | | | 120 | | | | | 125 | | | | |
| GCT | CCC | TCC | TGC | ATC | TGC | CAC | CCG | GGT | TAC | CAT | GGA | GAG | AGG | TGT | CAT | 432 |
| Ala | Pro | Ser | Cys | Ile | Cys | His | Pro | Gly | Tyr | His | Gly | Glu | Arg | Cys | His | |
| | 130 | | | | | 135 | | | | | 140 | | | | | |
| GGG | CTG | AGC | CTC | CCA | GTG | GAA | AAT | CGC | TTA | TAT | ACC | TAT | GAC | CAC | ACA | 480 |
| Gly | Leu | Ser | Leu | Pro | Val | Glu | Asn | Arg | Leu | Tyr | Thr | Tyr | Asp | His | Thr | |
| 145 | | | | | 150 | | | | | 155 | | | | | 160 | |
| ACC | ATC | CTG | GCC | GTG | GTG | GCT | GTG | GTG | CTG | TCA | TCT | GTC | TGT | CTG | CTG | 528 |
| Thr | Ile | Leu | Ala | Val | Val | Ala | Val | Val | Leu | Ser | Ser | Val | Cys | Leu | Leu | |
| | | | | 165 | | | | | 170 | | | | | 175 | | |
| GTC | ATC | GTG | GGG | CTT | CTC | ATG | TTT | AGG | TAC | CAT | AGG | AGA | GGA | GGT | TAT | 576 |
| Val | Ile | Val | Gly | Leu | Leu | Met | Phe | Arg | Tyr | His | Arg | Arg | Gly | Gly | Tyr | |
| | | | 180 | | | | | 185 | | | | | 190 | | | |
| GAT | GTG | GAA | AAT | GAA | GAG | AAA | GTG | AAG | TTG | GGC | ATG | ACT | AAT | TCC | CAC | 624 |
| Asp | Val | Glu | Asn | Glu | Glu | Lys | Val | Lys | Leu | Gly | Met | Thr | Asn | Ser | His | |
| | 195 | | | | | 200 | | | | | 205 | | | | | |
| TGA | | | | | | | | | | | | | | | | 627 |

(2) INFORMATION FOR SEQ ID NO: 10:

(i) SEQUENCE CHARACTERISTICS:
        (A) LENGTH: 155 amino acids
        (B) TYPE: amino acid
        (C) STRANDEDNESS: single
        (D) TOPOLOGY: unknown (ii) MOLECULE TYPE: peptide (ix) FEATURE:
        (D) OTHER INFORMATION: /note= "FGF-1"

(xi) SEQUENCE DESCRIPTION: SEQ ID NO: 10:

| | | | | | | | | | | | | | | |
|---|---|---|---|---|---|---|---|---|---|---|---|---|---|---|
| Met | Ala | Glu | Gly | Glu | Ile | Thr | Thr | Phe | Thr | Ala | Leu | Thr | Glu | Lys | Phe |
| 1 | | | | 5 | | | | | 10 | | | | | 15 | |
| Asn | Leu | Pro | Pro | Gly | Asn | Tyr | Lys | Lys | Pro | Lys | Leu | Leu | Tyr | Cys | Ser |
| | | | 20 | | | | | 25 | | | | | 30 | | |

```
Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
 50                  55                  60

Ser Val Gly Glu Val Tyr Ile Lys Ser Thr Glu Thr Gly Gln Tyr Leu
 65                  70                  75                  80

Ala Met Asp Thr Asp Gly Leu Leu Tyr Gly Ser Gln Thr Pro Asn Glu
            85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
 130                 135                 140

Ile Leu Phe Leu Pro Leu Pro Val Ser Ser Asp
 145                 150                 155
```

(2) INFORMATION FOR SEQ ID NO: 11:

(i) SEQUENCE CHARACTERISTICS:
       (A) LENGTH: 155 amino acids
       (B) TYPE: amino acid
       (C) STRANDEDNESS: single
       (D) TOPOLOGY: unknown (ii) MOLECULE TYPE: peptide (ix) FEATURE:
       (D) OTHER INFORMATION: /note= "FGF-2"

(xi) SEQUENCE DESCRIPTION: SEQ ID NO: 11:

```
Met Ala Ala Gly Ser Ile Thr Thr Leu Pro Ala Leu Pro Glu Asp Gly
 1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
            85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
 130                 135                 140

Ala Ile Leu Phe Leu Pro Met Ser Ala Lys Ser
 145                 150                 155
```

(2) INFORMATION FOR SEQ ID NO: 12:

(i) SEQUENCE CHARACTERISTICS:
       (A) LENGTH: 239 amino acids
       (B) TYPE: amino acid
       (C) STRANDEDNESS: single
       (D) TOPOLOGY: unknown (ii) MOLECULE TYPE: peptide (ix) FEATURE:
              (D) OTHER INFORMATION: /note= "FGF-3"

(xi) SEQUENCE DESCRIPTION: SEQ ID NO: 12:

Met Gly Leu Ile Trp Leu Leu Leu Ser Leu Leu Glu Pro Gly Trp
1               5                   10                  15

Pro Ala Ala Gly Pro Gly Ala Arg Leu Arg Arg Asp Ala Gly Gly Arg
            20                  25                  30

Gly Gly Val Tyr Glu His Leu Gly Ala Pro Arg Arg Lys Leu
            35                  40                  45

Tyr Cys Ala Thr Lys Tyr His Leu Gln Leu His Pro Ser Gly Arg Val
    50                  55                  60

Asn Gly Ser Leu Glu Asn Ser Ala Tyr Ser Ile Leu Glu Ile Thr Ala
65                  70                  75                  80

Val Glu Val Gly Ile Val Ala Ile Arg Gly Leu Phe Ser Gly Arg Tyr
                85                  90                  95

Leu Ala Met Asn Lys Arg Gly Arg Leu Tyr Ala Ser Glu His Tyr Ser
                100                 105                 110

Ala Glu Cys Glu Phe Val Glu Arg Ile His Glu Leu Gly Tyr Asn Thr
            115                 120                 125

Tyr Ala Ser Arg Leu Tyr Arg Thr Val Ser Ser Thr Pro Gly Ala Arg
    130                 135                 140

Arg Gln Pro Ser Ala Glu Arg Leu Trp Tyr Val Ser Val Asn Gly Lys
145                 150                 155                 160

Gly Arg Pro Arg Arg Gly Phe Lys Thr Arg Arg Thr Gln Lys Ser Ser
                165                 170                 175

Leu Phe Leu Pro Arg Val Leu Asp His Arg Asp His Glu Met Val Arg
                180                 185                 190

Gln Leu Gln Ser Gly Leu Pro Arg Pro Pro Gly Lys Gly Val Gln Pro
            195                 200                 205

Arg Arg Arg Arg Gln Lys Gln Ser Pro Asp Asn Leu Glu Pro Ser His
        210                 215                 220

Val Gln Ala Ser Arg Leu Gly Ser Gln Leu Glu Ala Ser Ala His
225                 230                 235

(2) INFORMATION FOR SEQ ID NO: 13:

(i) SEQUENCE CHARACTERISTICS:
              (A) LENGTH: 206 amino acids
              (B) TYPE: amino acid
              (C) STRANDEDNESS: single
              (D) TOPOLOGY: unknown (ii) MOLECULE TYPE: peptide (ix) FEATURE:
              (D) OTHER INFORMATION: /note= "FGF-4"

(xi) SEQUENCE DESCRIPTION: SEQ ID NO: 13:

Met Ser Gly Pro Gly Thr Ala Ala Val Ala Leu Leu Pro Ala Val Leu
1               5                   10                  15

Leu Ala Leu Leu Ala Pro Trp Ala Gly Arg Gly Gly Ala Ala Ala Pro
            20                  25                  30

Thr Ala Pro Asn Gly Thr Leu Glu Ala Glu Leu Glu Arg Arg Trp Glu
        35                  40                  45

Ser Leu Val Ala Leu Ser Leu Ala Arg Leu Pro Val Ala Ala Gln Pro

```
              50                  55                  60
Lys Glu Ala Ala Val Gln Ser Gly Ala Gly Asp Tyr Leu Gly Ile
 65                  70                  75                  80

Lys Arg Leu Arg Arg Leu Tyr Cys Asn Val Gly Ile Gly Phe His Leu
                 85                  90                  95

Gln Ala Leu Pro Asp Gly Arg Ile Gly Gly Ala His Ala Asp Thr Arg
                100                 105                 110

Asp Ser Leu Leu Glu Leu Ser Pro Val Glu Arg Gly Val Val Ser Ile
                115                 120                 125

Phe Gly Val Ala Ser Arg Phe Phe Val Ala Met Ser Ser Lys Gly Lys
            130                 135                 140

Leu Tyr Gly Ser Pro Phe Phe Thr Asp Glu Cys Thr Phe Lys Glu Ile
145                 150                 155                 160

Leu Leu Pro Asn Asn Tyr Asn Ala Tyr Glu Ser Tyr Lys Tyr Pro Gly
                165                 170                 175

Met Phe Ile Ala Leu Ser Lys Asn Gly Lys Thr Lys Lys Gly Asn Arg
                180                 185                 190

Val Ser Pro Thr Met Lys Val Thr His Phe Leu Pro Arg Leu
                195                 200                 205

(2) INFORMATION FOR SEQ ID NO: 14:

(i) SEQUENCE CHARACTERISTICS:
        (A) LENGTH: 268 amino acids
        (B) TYPE: amino acid
        (C) STRANDEDNESS: single
        (D) TOPOLOGY: unknown (ii) MOLECULE TYPE: peptide (ix) FEATURE:
        (D) OTHER INFORMATION: /note= "FGF-5"

(xi) SEQUENCE DESCRIPTION: SEQ ID NO: 14:

Met Ser Leu Ser Phe Leu Leu Leu Phe Phe Ser His Leu Ile Leu
 1               5                  10                  15

Ser Ala Trp Ala His Gly Glu Lys Arg Leu Ala Pro Lys Gly Gln Pro
                20                  25                  30

Gly Pro Ala Ala Thr Asp Arg Asn Pro Ile Gly Ser Ser Ser Arg Gln
                35                  40                  45

Ser Ser Ser Ser Ala Met Ser Ser Ser Ala Ser Ser Ser Pro Ala
 50                  55                  60

Ala Ser Leu Gly Ser Gln Gly Ser Gly Leu Glu Gln Ser Ser Phe Gln
 65                  70                  75                  80

Trp Ser Pro Ser Gly Arg Arg Thr Gly Ser Leu Tyr Cys Arg Val Gly
                85                  90                  95

Ile Gly Phe His Leu Gln Ile Tyr Pro Asp Gly Lys Val Asn Gly Ser
                100                 105                 110

His Glu Ala Asn Met Leu Ser Val Leu Glu Ile Phe Ala Val Ser Gln
                115                 120                 125

Gly Ile Val Gly Ile Arg Gly Val Phe Ser Asn Lys Phe Leu Ala Met
            130                 135                 140

Ser Lys Lys Gly Lys Leu His Ala Ser Ala Lys Phe Thr Asp Asp Cys
145                 150                 155                 160

Lys Phe Arg Glu Arg Phe Gln Glu Asn Ser Tyr Asn Thr Tyr Ala Ser
                165                 170                 175

Ala Ile His Arg Thr Glu Lys Thr Gly Arg Glu Trp Tyr Val Ala Leu
```

```
                    180              185              190
Asn Lys Arg Gly Lys Ala Lys Arg Gly Cys Ser Pro Arg Val Lys Pro
                195              200              205

Gln His Ile Ser Thr His Phe Leu Pro Arg Phe Lys Gln Ser Glu Gln
    210              215              220

Pro Glu Leu Ser Phe Thr Val Thr Val Pro Glu Lys Lys Asn Pro Pro
225              230              235              240

Ser Pro Ile Lys Ser Lys Ile Pro Leu Ser Ala Pro Arg Lys Asn Thr
                245              250              255

Asn Ser Val Lys Tyr Arg Leu Lys Phe Arg Phe Gly
                260              265
```

(2) INFORMATION FOR SEQ ID NO: 15:

(i) SEQUENCE CHARACTERISTICS:
        (A) LENGTH: 198 amino acids
        (B) TYPE: amino acid
        (C) STRANDEDNESS: single
        (D) TOPOLOGY: unknown (ii) MOLECULE TYPE: peptide (ix) FEATURE:
        (D) OTHER INFORMATION: /note= "FGF-6"

(xi) SEQUENCE DESCRIPTION: SEQ ID NO: 15:

```
Met Ser Arg Gly Ala Gly Arg Leu Gln Gly Thr Leu Trp Ala Leu Val
1               5                10               15

Phe Leu Gly Ile Leu Val Gly Met Val Val Pro Ser Pro Ala Gly Thr
                20               25               30

Arg Ala Asn Asn Thr Leu Leu Asp Ser Arg Gly Trp Gly Thr Leu Leu
                35               40               45

Ser Arg Ser Arg Ala Gly Leu Ala Gly Glu Ile Ala Gly Val Asn Trp
    50               55               60

Glu Ser Gly Tyr Leu Val Gly Ile Lys Arg Gln Arg Arg Leu Tyr Cys
65               70               75               80

Asn Val Gly Ile Gly Phe His Leu Gln Val Leu Pro Asp Gly Arg Ile
                85               90               95

Ser Gly Thr His Glu Glu Asn Pro Tyr Ser Leu Leu Glu Ile Ser Thr
                100              105              110

Val Glu Arg Gly Val Val Ser Leu Phe Gly Val Arg Ser Ala Leu Phe
                115              120              125

Val Ala Met Asn Ser Lys Gly Arg Leu Tyr Ala Thr Pro Ser Phe Gln
130              135              140

Glu Glu Cys Lys Phe Arg Glu Thr Leu Leu Pro Asn Asn Tyr Asn Ala
145              150              155              160

Tyr Glu Ser Asp Leu Tyr Gln Gly Thr Tyr Ile Ala Leu Ser Lys Tyr
                165              170              175

Gly Arg Val Lys Arg Gly Ser Lys Val Ser Pro Ile Met Thr Val Thr
                180              185              190

His Phe Leu Pro Arg Ile
                195
```

(2) INFORMATION FOR SEQ ID NO: 16:

(i) SEQUENCE CHARACTERISTICS:
        (A) LENGTH: 194 amino acids
        (B) TYPE: amino acid
        (C) STRANDEDNESS: single (D) TOPOLOGY: unknown (ii) MOLECULE TYPE: peptide (ix) FEATURE:
            (D) OTHER INFORMATION: /note= "FGF-7"

(xi) SEQUENCE DESCRIPTION: SEQ ID NO: 16:

Met His Lys Trp Ile Leu Thr Trp Ile Leu Pro Thr Leu Leu Tyr Arg
1               5                   10                  15

Ser Cys Phe His Ile Ile Cys Leu Val Gly Thr Ile Ser Leu Ala Cys
                20                  25                  30

Asn Asp Met Thr Pro Glu Gln Met Ala Thr Asn Val Asn Cys Ser Ser
            35                  40                  45

Pro Glu Arg His Thr Arg Ser Tyr Asp Tyr Met Glu Gly Gly Asp Ile
        50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
            100                 105                 110

Val Glu Ser Glu Phe Tyr Leu Ala Met Asn Lys Glu Gly Lys Leu Tyr
        115                 120                 125

Ala Lys Lys Glu Cys Asn Glu Asp Cys Asn Phe Lys Glu Leu Ile Leu
    130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
            180                 185                 190

Ile Thr (2) INFORMATION FOR SEQ ID NO: 17:

(i) SEQUENCE CHARACTERISTICS:
        (A) LENGTH: 215 amino acids
        (B) TYPE: amino acid
        (C) STRANDEDNESS: single
        (D) TOPOLOGY: unknown (ii) MOLECULE TYPE: peptide (ix) FEATURE:
            (D) OTHER INFORMATION: /note= "FGF-8"

(xi) SEQUENCE DESCRIPTION: SEQ ID NO: 17:

Met Gly Ser Pro Arg Ser Ala Leu Ser Cys Leu Leu Leu His Leu Leu
1               5                   10                  15

Val Leu Cys Leu Gln Ala Gln Val Thr Val Gln Ser Ser Pro Asn Phe
                20                  25                  30

Thr Gln His Val Arg Glu Gln Ser Leu Val Thr Asp Gln Leu Ser Arg
            35                  40                  45

Arg Leu Ile Arg Thr Tyr Gln Leu Tyr Ser Arg Thr Ser Gly Lys His
        50                  55                  60

Val Gln Val Leu Ala Asn Lys Arg Ile Asn Ala Met Ala Glu Asp Gly
65                  70                  75                  80

Asp Pro Phe Ala Lys Leu Ile Val Glu Thr Asp Thr Phe Gly Ser Arg

```
                    85                  90                  95
Val Arg Val Arg Gly Ala Glu Thr Gly Leu Tyr Ile Cys Met Asn Lys
            100                 105                 110

Lys Gly Lys Leu Ile Ala Lys Ser Asn Gly Lys Gly Lys Asp Cys Val
            115                 120                 125

Phe Thr Glu Ile Val Leu Glu Asn Asn Tyr Thr Ala Leu Gln Asn Ala
            130                 135                 140

Lys Tyr Glu Gly Trp Tyr Met Ala Phe Thr Arg Lys Gly Arg Pro Arg
145                 150                 155                 160

Lys Gly Ser Lys Thr Arg Gln His Gln Arg Glu Val His Phe Met Lys
            165                 170                 175

Arg Leu Pro Arg Gly His His Thr Thr Glu Gln Ser Leu Arg Phe Glu
            180                 185                 190

Phe Leu Asn Tyr Pro Pro Phe Thr Arg Ser Leu Arg Gly Ser Gln Arg
            195                 200                 205

Thr Trp Ala Pro Glu Pro Arg
210                 215

(2) INFORMATION FOR SEQ ID NO: 18:

(i) SEQUENCE CHARACTERISTICS:
        (A) LENGTH: 208 amino acids
        (B) TYPE: amino acid
        (C) STRANDEDNESS: single
        (D) TOPOLOGY: unknown (ii) MOLECULE TYPE: peptide (ix) FEATURE:
        (D) OTHER INFORMATION: /note= "FGF-9"

(xi) SEQUENCE DESCRIPTION: SEQ ID NO: 18:

Met Ala Pro Leu Gly Glu Val Gly Asn Tyr Phe Gly Val Gln Asp Ala
1               5                   10                  15

Val Pro Phe Gly Asn Val Pro Val Leu Pro Val Asp Ser Pro Val Leu
            20                  25                  30

Leu Ser Asp His Leu Gly Gln Ser Glu Ala Gly Gly Leu Pro Arg Gly
            35                  40                  45

Pro Ala Val Thr Asp Leu Asp His Leu Lys Gly Ile Leu Arg Arg Arg
50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
            85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
            115                 120                 125

Lys Leu Thr Gln Glu Cys Val Phe Arg Glu Gln Phe Glu Glu Asn Trp
            130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
            165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
```

(2) INFORMATION FOR SEQ ID NO: 19:

(i) SEQUENCE CHARACTERISTICS:
        (A) LENGTH: 804 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..804

(ix) FEATURE:
        (A) NAME/KEY: misc_feature
        (B) LOCATION: 1..804
        (D) OTHER INFORMATION: /note= "Nucleotide sequence
            corresponding to the clone M13 mp18-G4 in Example I.B.2."

(ix) FEATURE:
        (A) NAME/KEY: mat_peptide
        (B) LOCATION: 46..804
        (D) OTHER INFORMATION: /product= ""Saporin""

(xi) SEQUENCE DESCRIPTION: SEQ ID NO: 19:

```
GCA TGG ATC CTG CTT CAA TTT TCA GCT TGG ACA ACA ACT GAT GCG GTC        48
Ala Trp Ile Leu Leu Gln Phe Ser Ala Trp Thr Thr Thr Asp Ala Val
-15             -10                 -5                   1

ACA TCA ATC ACA TTA GAT CTA GTA AAT CCG ACC GCG GGT CAA TAC TCA        96
Thr Ser Ile Thr Leu Asp Leu Val Asn Pro Thr Ala Gly Gln Tyr Ser
             5                  10                  15

TCT TTT GTG GAT AAA ATC CGA AAC AAT GTA AAG GAT CCA AAC CTG AAA       144
Ser Phe Val Asp Lys Ile Arg Asn Asn Val Lys Asp Pro Asn Leu Lys
         20                  25                  30

TAC GGT GGT ACC GAC ATA GCC GTG ATA GGC CCA CCT TCT AAA GAA AAA       192
Tyr Gly Gly Thr Asp Ile Ala Val Ile Gly Pro Pro Ser Lys Glu Lys
     35                  40                  45

TTC CTT AGA ATT AAT TTC CAA AGT TCC CGA GGA ACG GTC TCA CTT GGC       240
Phe Leu Arg Ile Asn Phe Gln Ser Ser Arg Gly Thr Val Ser Leu Gly
 50                  55                  60                  65

CTA AAA CGC GAT AAC TTG TAT GTG GTC GCG TAT CTT GCA ATG GAT AAC       288
Leu Lys Arg Asp Asn Leu Tyr Val Val Ala Tyr Leu Ala Met Asp Asn
                 70                  75                  80

ACG AAT GTT AAT CGG GCA TAT TAC TTC AAA TCA GAA ATT ACT TCC GCC       336
Thr Asn Val Asn Arg Ala Tyr Tyr Phe Lys Ser Glu Ile Thr Ser Ala
             85                  90                  95

GAG TTA ACC GCC CTT TTC CCA GAG GCC ACA ACT GCA AAT CAG AAA GCT       384
Glu Leu Thr Ala Leu Phe Pro Glu Ala Thr Thr Ala Asn Gln Lys Ala
         100                 105                 110

TTA GAA TAC ACA GAA GAT TAT CAG TCG ATC GAA AAG AAT GCC CAG ATA       432
Leu Glu Tyr Thr Glu Asp Tyr Gln Ser Ile Glu Lys Asn Ala Gln Ile
     115                 120                 125

ACA CAG GGA GAT AAA AGT AGA AAA GAA CTC GGG TTG GGG ATC GAC TTA       480
Thr Gln Gly Asp Lys Ser Arg Lys Glu Leu Gly Leu Gly Ile Asp Leu
130                 135                 140                 145

CTT TTG ACG TTC ATG GAA GCA GTG AAC AAG AAG GCA CGT GTG GTT AAA       528
Leu Leu Thr Phe Met Glu Ala Val Asn Lys Lys Ala Arg Val Val Lys
                 150                 155                 160

AAC GAA GCT AGG TTT CTG CTT ATC GCT ATT CAA ATG ACA GCT GAG GTA       576
Asn Glu Ala Arg Phe Leu Leu Ile Ala Ile Gln Met Thr Ala Glu Val
             165                 170                 175

GCA CGA TTT AGG TAC ATT CAA AAC TTG GTA ACT AAG AAC TTC CCC AAC       624
```

```
Ala Arg Phe Arg Tyr Ile Gln Asn Leu Val Thr Lys Asn Phe Pro Asn
            180                 185                 190

AAG TTC GAC TCG GAT AAC AAG GTG ATT CAA TTT GAA GTC AGC TGG CGT        672
Lys Phe Asp Ser Asp Asn Lys Val Ile Gln Phe Glu Val Ser Trp Arg
    195                 200                 205

AAG ATT TCT ACG GCA ATA TAC GGG GAT GCC AAA AAC GGC GTG TTT AAT        720
Lys Ile Ser Thr Ala Ile Tyr Gly Asp Ala Lys Asn Gly Val Phe Asn
210                 215                 220                 225

AAA GAT TAT GAT TTC GGG TTT GGA AAA GTG AGG CAG GTG AAG GAC TTG        768
Lys Asp Tyr Asp Phe Gly Phe Gly Lys Val Arg Gln Val Lys Asp Leu
                    230                 235                 240

CAA ATG GGA CTC CTT ATG TAT TTG GGC AAA CCA AAG                        804
Gln Met Gly Leu Leu Met Tyr Leu Gly Lys Pro Lys
                245                 250

(2) INFORMATION FOR SEQ ID NO: 20:

(i) SEQUENCE CHARACTERISTICS:
          (A) LENGTH: 804 base pairs
          (B) TYPE: nucleic acid
          (C) STRANDEDNESS: double
          (D) TOPOLOGY: unknown (ii) MOLECULE TYPE: cDNA (ix) FEATURE:
          (A) NAME/KEY: CDS
          (B) LOCATION: 1..804

(ix) FEATURE:
          (A) NAME/KEY: misc_feature
          (B) LOCATION: 1..804
          (D) OTHER INFORMATION: /note= "Nucleotide sequence
               corresponding to the clone M13 mp18-G1 in Example I.B.2."

(ix) FEATURE:
          (A) NAME/KEY: mat_peptide
          (B) LOCATION: 46..804
          (D) OTHER INFORMATION: /product= "Saporin"

(xi) SEQUENCE DESCRIPTION: SEQ ID NO: 20:

GCA TGG ATC CTG CTT CAA TTT TCA GCT TGG ACA ACA ACT GAT GCG GTC         48
Ala Trp Ile Leu Leu Gln Phe Ser Ala Trp Thr Thr Thr Asp Ala Val
-15             -10                 -5                       1

ACA TCA ATC ACA TTA GAT CTA GTA AAT CCG ACC GCG GGT CAA TAC TCA         96
Thr Ser Ile Thr Leu Asp Leu Val Asn Pro Thr Ala Gly Gln Tyr Ser
                5                   10                  15

TCT TTT GTG GAT AAA ATC CGA AAC AAC GTA AAG GAT CCA AAC CTG AAA        144
Ser Phe Val Asp Lys Ile Arg Asn Asn Val Lys Asp Pro Asn Leu Lys
            20                  25                  30

TAC GGT GGT ACC GAC ATA GCC GTG ATA GGC CCA CCT TCT AAA GAA AAA        192
Tyr Gly Gly Thr Asp Ile Ala Val Ile Gly Pro Pro Ser Lys Glu Lys
        35                  40                  45

TTC CTT AGA ATT AAT TTC CAA AGT TCC CGA GGA ACG GTC TCA CTT GGC        240
Phe Leu Arg Ile Asn Phe Gln Ser Ser Arg Gly Thr Val Ser Leu Gly
50                  55                  60                  65

CTA AAA CGC GAT AAC TTG TAT GTG GTC GCG TAT CTT GCA ATG GAT AAC        288
Leu Lys Arg Asp Asn Leu Tyr Val Val Ala Tyr Leu Ala Met Asp Asn
                70                  75                  80

ACG AAT GTT AAT CGG GCA TAT TAC TTC AGA TCA GAA ATT ACT TCC GCC        336
Thr Asn Val Asn Arg Ala Tyr Tyr Phe Arg Ser Glu Ile Thr Ser Ala
            85                  90                  95

GAG TTA ACC GCC CTT TTC CCA GAG GCC ACA ACT GCA AAT CAG AAA GCT        384
Glu Leu Thr Ala Leu Phe Pro Glu Ala Thr Thr Ala Asn Gln Lys Ala
        100                 105                 110
```

```
TTA GAA TAC ACA GAA GAT TAT CAG TCG ATC GAA AAG AAT GCC CAG ATA      432
Leu Glu Tyr Thr Glu Asp Tyr Gln Ser Ile Glu Lys Asn Ala Gln Ile
115                 120                 125

ACA CAG GGA GAT AAA TCA AGA AAA GAA CTC GGG TTG GGG ATC GAC TTA      480
Thr Gln Gly Asp Lys Ser Arg Lys Glu Leu Gly Leu Gly Ile Asp Leu
130                 135                 140                 145

CTT TTG ACG TCC ATG GAA GCA GTG AAC AAG AAG GCA CGT GTG GTT AAA      528
Leu Leu Thr Ser Met Glu Ala Val Asn Lys Lys Ala Arg Val Val Lys
                150                 155                 160

AAC GAA GCT AGG TTT CTG CTT ATC GCT ATT CAA ATG ACA GCT GAG GTA      576
Asn Glu Ala Arg Phe Leu Leu Ile Ala Ile Gln Met Thr Ala Glu Val
            165                 170                 175

GCA CGA TTT CGG TAC ATT CAA AAC TTG GTA ACT AAG AAC TTC CCC AAC      624
Ala Arg Phe Arg Tyr Ile Gln Asn Leu Val Thr Lys Asn Phe Pro Asn
        180                 185                 190

AAG TTC GAC TCG GAT AAC AAG GTG ATT CAA TTT GAA GTC AGC TGG CGT      672
Lys Phe Asp Ser Asp Asn Lys Val Ile Gln Phe Glu Val Ser Trp Arg
    195                 200                 205

AAG ATT TCT ACG GCA ATA TAC GGA GAT GCC AAA AAC GGC GTG TTT AAT      720
Lys Ile Ser Thr Ala Ile Tyr Gly Asp Ala Lys Asn Gly Val Phe Asn
210                 215                 220                 225

AAA GAT TAT GAT TTC GGG TTT GGA AAA GTG AGG CAG GTG AAG GAC TTG      768
Lys Asp Tyr Asp Phe Gly Phe Gly Lys Val Arg Gln Val Lys Asp Leu
                230                 235                 240

CAA ATG GGA CTC CTT ATG TAT TTG GGC AAA CCA AAG                      804
Gln Met Gly Leu Leu Met Tyr Leu Gly Lys Pro Lys
            245                 250
```

(2) INFORMATION FOR SEQ ID NO: 21:

(i) SEQUENCE CHARACTERISTICS:
        (A) LENGTH: 804 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..804

(ix) FEATURE:
        (A) NAME/KEY: misc_feature
        (B) LOCATION: 1..804
        (D) OTHER INFORMATION: /note= "Nucleotide sequence
            corresponding to the clone M13 mp18-G2 in Example I.B.2."

(ix) FEATURE:
        (A) NAME/KEY: mat_peptide
        (B) LOCATION: 46..804
        (D) OTHER INFORMATION: /product= "Saporin"

(xi) SEQUENCE DESCRIPTION: SEQ ID NO: 21:

```
GCA TGG ATC CTG CTT CAA TTT TCA GCT TGG ACA ACA ACT GAT GCG GTC       48
Ala Trp Ile Leu Leu Gln Phe Ser Ala Trp Thr Thr Thr Asp Ala Val
-15             -10                 -5                      1

ACA TCA ATC ACA TTA GAT CTA GTA AAT CCG ACT GCG GGT CAA TAC TCA       96
Thr Ser Ile Thr Leu Asp Leu Val Asn Pro Thr Ala Gly Gln Tyr Ser
            5                   10                  15

TCT TTT GTG GAT AAA ATC CGA AAC AAC GTA AAG GAT CCA AAC CTG AAA      144
Ser Phe Val Asp Lys Ile Arg Asn Asn Val Lys Asp Pro Asn Leu Lys
        20                  25                  30

TAC GGT GGT ACC GAC ATA GCC GTG ATA GGC CCA CCT TCT AAA GAT AAA      192
Tyr Gly Gly Thr Asp Ile Ala Val Ile Gly Pro Pro Ser Lys Asp Lys
    35                  40                  45
```

-continued

```
TTC CTT AGA ATT AAT TTC CAA AGT TCC CGA GGA ACG GTC TCA CTT GGC      240
Phe Leu Arg Ile Asn Phe Gln Ser Ser Arg Gly Thr Val Ser Leu Gly
 50                  55                  60                  65

CTA AAA CGC GAT AAC TTG TAT GTG GTC GCG TAT CTT GCA ATG GAT AAC      288
Leu Lys Arg Asp Asn Leu Tyr Val Val Ala Tyr Leu Ala Met Asp Asn
                 70                  75                  80

ACG AAT GTT AAT CGG GCA TAT TAC TTC AAA TCA GAA ATT ACT TCC GCC      336
Thr Asn Val Asn Arg Ala Tyr Tyr Phe Lys Ser Glu Ile Thr Ser Ala
             85                  90                  95

GAG TTA ACC GCC CTT TTC CCA GAG GCC ACA ACT GCA AAT CAG AAA GCT      384
Glu Leu Thr Ala Leu Phe Pro Glu Ala Thr Thr Ala Asn Gln Lys Ala
            100                 105                 110

TTA GAA TAC ACA GAA GAT TAT CAG TCG ATC GAA AAG AAT GCC CAG ATA      432
Leu Glu Tyr Thr Glu Asp Tyr Gln Ser Ile Glu Lys Asn Ala Gln Ile
115                 120                 125

ACA CAG GGA GAT AAA AGT AGA AAA GAA CTC GGG TTG GGG ATC GAC TTA      480
Thr Gln Gly Asp Lys Ser Arg Lys Glu Leu Gly Leu Gly Ile Asp Leu
130                 135                 140                 145

CTT TTG ACG TTC ATG GAA GCA GTG AAC AAG AAG GCA CGT GTG GTT AAA      528
Leu Leu Thr Phe Met Glu Ala Val Asn Lys Lys Ala Arg Val Val Lys
                150                 155                 160

AAC GAA GCT AGG TTT CTG CTT ATC GCT ATT CAA ATG ACA GCT GAG GTA      576
Asn Glu Ala Arg Phe Leu Leu Ile Ala Ile Gln Met Thr Ala Glu Val
                165                 170                 175

GCA CGA TTT AGG TAC ATT CAA AAC TTG GTA ACT AAG AAC TTC CCC AAC      624
Ala Arg Phe Arg Tyr Ile Gln Asn Leu Val Thr Lys Asn Phe Pro Asn
            180                 185                 190

AAG TTC GAC TCG GAT AAC AAG GTG ATT CAA TTT GAA GTC AGC TGG CGT      672
Lys Phe Asp Ser Asp Asn Lys Val Ile Gln Phe Glu Val Ser Trp Arg
195                 200                 205

AAG ATT TCT ACG GCA ATA TAC GGG GAT GCC AAA AAC GGC GTG TTT AAT      720
Lys Ile Ser Thr Ala Ile Tyr Gly Asp Ala Lys Asn Gly Val Phe Asn
210                 215                 220                 225

AAA GAT TAT GAT TTC GGG TTT GGA AAA GTG AGG CAG GTG AAG GAC TTG      768
Lys Asp Tyr Asp Phe Gly Phe Gly Lys Val Arg Gln Val Lys Asp Leu
                230                 235                 240

CAA ATG GGA CTC CTT ATG TAT TTG GGC AAA CCA AAG                      804
Gln Met Gly Leu Leu Met Tyr Leu Gly Lys Pro Lys
                245                 250
```

(2) INFORMATION FOR SEQ ID NO: 22:

(i) SEQUENCE CHARACTERISTICS:
        (A) LENGTH: 804 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..804

(ix) FEATURE:
        (A) NAME/KEY: misc_feature
        (B) LOCATION: 1..804
        (D) OTHER INFORMATION: /note= "Nucleotide sequence
            corresponding to the clone M13 mp18-G7 in Example I.B.2."

(ix) FEATURE:
        (A) NAME/KEY: mat_peptide
        (B) LOCATION: 46..804
        (D) OTHER INFORMATION: /product= "Saporin"

-continued (xi) SEQUENCE DESCRIPTION: SEQ ID NO: 22:

```
GCA TGG ATC CTG CTT CAA TTT TCA GCT TGG ACA ACA ACT GAT GCG GTC      48
Ala Trp Ile Leu Leu Gln Phe Ser Ala Trp Thr Thr Thr Asp Ala Val
-15             -10                 -5                           1

ACA TCA ATC ACA TTA GAT CTA GTA AAT CCG ACC GCG GGT CAA TAC TCA      96
Thr Ser Ile Thr Leu Asp Leu Val Asn Pro Thr Ala Gly Gln Tyr Ser
             5                   10                  15

TCT TTT GTG GAT AAA ATC CGA AAC AAC GTA AAG GAT CCA AAC CTG AAA     144
Ser Phe Val Asp Lys Ile Arg Asn Asn Val Lys Asp Pro Asn Leu Lys
         20                  25                  30

TAC GGT GGT ACC GAC ATA GCC GTG ATA GGC CCA CCT TCT AAA GAA AAA     192
Tyr Gly Gly Thr Asp Ile Ala Val Ile Gly Pro Pro Ser Lys Glu Lys
     35                  40                  45

TTC CTT AGA ATT AAT TTC CAA AGT TCC CGA GGA ACG GTC TCA CTT GGC     240
Phe Leu Arg Ile Asn Phe Gln Ser Ser Arg Gly Thr Val Ser Leu Gly
 50                  55                  60                  65

CTA AAA CGC GAT AAC TTG TAT GTG GTC GCG TAT CTT GCA ATG GAT AAC     288
Leu Lys Arg Asp Asn Leu Tyr Val Val Ala Tyr Leu Ala Met Asp Asn
             70                  75                  80

ACG AAT GTT AAT CGG GCA TAT TAC TTC AGA TCA GAA ATT ACT TCC GCC     336
Thr Asn Val Asn Arg Ala Tyr Tyr Phe Arg Ser Glu Ile Thr Ser Ala
         85                  90                  95

GAG TTA ACC GCC CTT TTC CCA GAG GCC ACA ACT GCA AAT CAG AAA GCT     384
Glu Leu Thr Ala Leu Phe Pro Glu Ala Thr Thr Ala Asn Gln Lys Ala
     100                 105                 110

TTA GAA TAC ACA GAA GAT TAT CAG TCG ATC GAA AAG AAT GCC CAG ATA     432
Leu Glu Tyr Thr Glu Asp Tyr Gln Ser Ile Glu Lys Asn Ala Gln Ile
 115                 120                 125

ACA CAG GGA GAT AAA TCA AGA AAA GAA CTC GGG TTG GGG ATC GAC TTA     480
Thr Gln Gly Asp Lys Ser Arg Lys Glu Leu Gly Leu Gly Ile Asp Leu
130                 135                 140                 145

CTT TTG ACG TCC ATG GAA GCA GTG AAC AAG AAG GCA CGT GTG GTT AAA     528
Leu Leu Thr Ser Met Glu Ala Val Asn Lys Lys Ala Arg Val Val Lys
                 150                 155                 160

AAC GAA GCT AGA TTC CTT CTT ATC GCT ATT CAG ATG ACG GCT GAG GCA     576
Asn Glu Ala Arg Phe Leu Leu Ile Ala Ile Gln Met Thr Ala Glu Ala
             165                 170                 175

GCA CGA TTT AGG TAC ATA CAA AAC TTG GTA ATC AAG AAC TTT CCC AAC     624
Ala Arg Phe Arg Tyr Ile Gln Asn Leu Val Ile Lys Asn Phe Pro Asn
         180                 185                 190

AAG TTC AAC TCG GAA AAC AAA GTG ATT CAG TTT GAG GTT AAC TGG AAA     672
Lys Phe Asn Ser Glu Asn Lys Val Ile Gln Phe Glu Val Asn Trp Lys
     195                 200                 205

AAA ATT TCT ACG GCA ATA TAC GGG GAT GCC AAA AAC GGC GTG TTT AAT     720
Lys Ile Ser Thr Ala Ile Tyr Gly Asp Ala Lys Asn Gly Val Phe Asn
210                 215                 220                 225

AAA GAT TAT GAT TTC GGG TTT GGA AAA GTG AGG CAG GTG AAG GAC TTG     768
Lys Asp Tyr Asp Phe Gly Phe Gly Lys Val Arg Gln Val Lys Asp Leu
                 230                 235                 240

CAA ATG GGA CTC CTT ATG TAT TTG GGC AAA CCA AAG                     804
Gln Met Gly Leu Leu Met Tyr Leu Gly Lys Pro Lys
             245                 250
```

(2) INFORMATION FOR SEQ ID NO: 23:

(i) SEQUENCE CHARACTERISTICS:
        (A) LENGTH: 804 base pairs
        (B) TYPE: nucleic acid
        (C) STRANDEDNESS: double
        (D) TOPOLOGY: unknown -continued

```
    (ii) MOLECULE TYPE: cDNA (ix) FEATURE:
         (A) NAME/KEY: CDS
         (B) LOCATION: 1..804

(ix) FEATURE:
         (A) NAME/KEY: misc_feature
         (B) LOCATION: 1..804
         (D) OTHER INFORMATION: /note= "Nucleotide sequence
             corresponding to the clone M13 mp18-G9 in Example I.B.2."

(ix) FEATURE:
         (A) NAME/KEY: mat_peptide
         (B) LOCATION: 46..804
         (D) OTHER INFORMATION: /product= "Saporin"

(xi) SEQUENCE DESCRIPTION: SEQ ID NO: 23:

GCA TGG ATC CTG CTT CAA TTT TCA GCT TGG ACA ACA ACT GAT GCG GTC        48
Ala Trp Ile Leu Leu Gln Phe Ser Ala Trp Thr Thr Thr Asp Ala Val
-15          -10                  -5                    1

ACA TCA ATC ACA TTA GAT CTA GTA AAT CCG ACC GCG GGT CAA TAC TCA        96
Thr Ser Ile Thr Leu Asp Leu Val Asn Pro Thr Ala Gly Gln Tyr Ser
            5                  10                  15

TCT TTT GTG GAT AAA ATC CGA AAC AAC GTA AAG GAT CCA AAC CTG AAA       144
Ser Phe Val Asp Lys Ile Arg Asn Asn Val Lys Asp Pro Asn Leu Lys
        20                  25                  30

TAC GGT GGT ACC GAC ATA GCC GTG ATA GGC CCA CCT TCT AAA GAA AAA       192
Tyr Gly Gly Thr Asp Ile Ala Val Ile Gly Pro Pro Ser Lys Glu Lys
    35                  40                  45

TTC CTT AGA ATT AAT TTC CAA AGT TCC CGA GGA ACG TCA CTT GGC            240
Phe Leu Arg Ile Asn Phe Gln Ser Ser Arg Gly Thr Val Ser Leu Gly
50                  55                  60                  65

CTA AAA CGC GAT AAC TTG TAT GTG GTC GCG TAT CTT GCA ATG GAT AAC       288
Leu Lys Arg Asp Asn Leu Tyr Val Val Ala Tyr Leu Ala Met Asp Asn
                70                  75                  80

ACG AAT GTT AAT CGG GCA TAT TAC TTC AGA TCA GAA ATT ACT TCC GCC       336
Thr Asn Val Asn Arg Ala Tyr Tyr Phe Arg Ser Glu Ile Thr Ser Ala
            85                  90                  95

GAG TTA ACC GCC CTT TTC CCA GAG GCC ACA ACT GCA AAT CAG AAA GCT       384
Glu Leu Thr Ala Leu Phe Pro Glu Ala Thr Thr Ala Asn Gln Lys Ala
        100                 105                 110

TTA GAA TAC ACA GAA GAT TAT CAG TCG ATT GAA AAG AAT GCC CAG ATA       432
Leu Glu Tyr Thr Glu Asp Tyr Gln Ser Ile Glu Lys Asn Ala Gln Ile
    115                 120                 125

ACA CAA GGA GAT CAA AGT AGA AAA GAA CTC GGG TTG GGG ATT GAC TTA       480
Thr Gln Gly Asp Gln Ser Arg Lys Glu Leu Gly Leu Gly Ile Asp Leu
130                 135                 140                 145

CTT TCA ACG TCC ATG GAA GCA GTG AAC AAG AAG GCA CGT GTG GTT AAA       528
Leu Ser Thr Ser Met Glu Ala Val Asn Lys Lys Ala Arg Val Val Lys
                150                 155                 160

GAC GAA GCT AGA TTC CTT CTT ATC GCT ATT CAG ATG ACG GCT GAG GCA       576
Asp Glu Ala Arg Phe Leu Leu Ile Ala Ile Gln Met Thr Ala Glu Ala
            165                 170                 175

GCG CGA TTT AGG TAC ATA CAA AAC TTG GTA ATC AAG AAC TTT CCC AAC       624
Ala Arg Phe Arg Tyr Ile Gln Asn Leu Val Ile Lys Asn Phe Pro Asn
        180                 185                 190

AAG TTC AAC TCG GAA AAC AAA GTG ATT CAG TTT GAG GTT AAC TGG AAA       672
Lys Phe Asn Ser Glu Asn Lys Val Ile Gln Phe Glu Val Asn Trp Lys
    195                 200                 205

AAA ATT TCT ACG GCA ATA TAC GGG GAT GCC AAA AAC GGC GTG TTT AAT       720
Lys Ile Ser Thr Ala Ile Tyr Gly Asp Ala Lys Asn Gly Val Phe Asn
210                 215                 220                 225
```

```
AAA GAT TAT GAT TTC GGG TTT GGA AAA GTG AGG CAG GTG AAG GAC TTG        768
Lys Asp Tyr Asp Phe Gly Phe Gly Lys Val Arg Gln Val Lys Asp Leu
            230                 235                 240

CAA ATG GGA CTC CTT ATG TAT TTG GGC AAA CCA AAG                        804
Gln Met Gly Leu Leu Met Tyr Leu Gly Lys Pro Lys
            245                 250
```

(2) INFORMATION FOR SEQ ID NO: 24:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: CDS
        (B) LOCATION: 1..7
        (D) OTHER INFORMATION: /product= nuclear translocation
            sequence (xi) SEQUENCE DESCRIPTION: SEQ ID NO: 24:

```
Pro Lys Lys Arg Lys Val Glu
 1               5
```

(2) INFORMATION FOR SEQ ID NO: 25:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: CDS
        (B) LOCATION: 1..8
        (D) OTHER INFORMATION: /product= nuclear translocation
            sequence (xi) SEQUENCE DESCRIPTION: SEQ ID NO: 25:

```
Pro Pro Lys Lys Ala Arg Glu Val
 1               5
```

(2) INFORMATION FOR SEQ ID NO: 26:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: CDS
        (B) LOCATION: 1..9
        (D) OTHER INFORMATION: /product= nuclear translocation
            sequence (xi) SEQUENCE DESCRIPTION: SEQ ID NO: 26:

```
Pro Ala Ala Lys Arg Val Lys Leu Asp
 1               5
```

(2) INFORMATION FOR SEQ ID NO: 27:

(i) SEQUENCE CHARACTERISTICS:
        (A) LENGTH: 5 amino acids (B) TYPE: amino acid
        (C) STRANDEDNESS: single
        (D) TOPOLOGY: unknown (ii) MOLECULE TYPE: peptide (ix) FEATURE:
        (A) NAME/KEY: CDS
        (B) LOCATION: 1..5
        (D) OTHER INFORMATION: /product= nuclear translocation
            sequence (xi) SEQUENCE DESCRIPTION: SEQ ID NO: 27:

Lys Arg Pro Arg Pro
 1               5

(2) INFORMATION FOR SEQ ID NO: 28:

(i) SEQUENCE CHARACTERISTICS:
        (A) LENGTH: 5 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: CDS
        (B) LOCATION: 1..5
        (D) OTHER INFORMATION: /product= nuclear translocation
            sequence (xi) SEQUENCE DESCRIPTION: SEQ ID NO: 28:

Lys Ile Pro Ile Lys
 1               5

(2) INFORMATION FOR SEQ ID NO: 29:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: CDS
        (B) LOCATION: 1..9
        (D) OTHER INFORMATION: /product= nuclear translocation
            sequence (xi) SEQUENCE DESCRIPTION: SEQ ID NO: 29:

Gly Lys Arg Lys Arg Lys Ser
 1               5

(2) INFORMATION FOR SEQ ID NO: 30:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: CDS
        (B) LOCATION: 1..9
        (D) OTHER INFORMATION: /product= nuclear translocation
            sequence (xi) SEQUENCE DESCRIPTION: SEQ ID NO: 30:

```
Ser Lys Arg Val Ala Lys Arg Lys Leu
 1               5
```

(2) INFORMATION FOR SEQ ID NO: 31:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: CDS
        (B) LOCATION: 1..9
        (D) OTHER INFORMATION: /product= nuclear translocation
            sequence (xi) SEQUENCE DESCRIPTION: SEQ ID NO: 31:

```
Ser His Trp Lys Gln Lys Arg Lys Phe
 1               5
```

(2) INFORMATION FOR SEQ ID NO: 32:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: CDS
        (B) LOCATION: 1..8
        (D) OTHER INFORMATION: /product= nuclear translocation
            sequence (xi) SEQUENCE DESCRIPTION: SEQ ID NO: 32:

```
Pro Leu Leu Lys Lys Ile Lys Gln
 1               5
```

(2) INFORMATION FOR SEQ ID NO: 33:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: CDS
        (B) LOCATION: 1..7
        (D) OTHER INFORMATION: /product= nuclear translocation
            sequence (xi) SEQUENCE DESCRIPTION: SEQ ID NO: 33:

```
Pro Gln Pro Lys Lys Lys Pro
 1               5
```

(2) INFORMATION FOR SEQ ID NO: 34:

(i) SEQUENCE CHARACTERISTICS:
        (A) LENGTH: 15 amino acids
        (B) TYPE: amino acid
        (C) STRANDEDNESS: single
        (D) TOPOLOGY: unknown

```
    (ii) MOLECULE TYPE: peptide (ix) FEATURE:
         (A) NAME/KEY: CDS
         (B) LOCATION: 1..15
         (D) OTHER INFORMATION: /product= nuclear translocation
             sequence (xi) SEQUENCE DESCRIPTION: SEQ ID NO: 34:

Pro Gly Lys Arg Lys Lys Glu Met Thr Lys Gln Lys Glu Val Pro
 1               5                  10                  15

(2) INFORMATION FOR SEQ ID NO: 35:

(i) SEQUENCE CHARACTERISTICS:
         (A) LENGTH: 12 amino acids
         (B) TYPE: amino acid
         (C) STRANDEDNESS: single
         (D) TOPOLOGY: unknown (ii) MOLECULE TYPE: peptide (ix) FEATURE:
         (A) NAME/KEY: CDS
         (B) LOCATION: 1..12
         (D) OTHER INFORMATION: /product= nuclear translocation
             sequence (xi) SEQUENCE DESCRIPTION: SEQ ID NO: 35:

Gly Arg Lys Lys Arg Arg Gln Arg Arg Arg Ala Pro
 1               5                  10

(2) INFORMATION FOR SEQ ID NO: 36:

(i) SEQUENCE CHARACTERISTICS:
         (A) LENGTH: 7 amino acids
         (B) TYPE: amino acid
         (C) STRANDEDNESS: single
         (D) TOPOLOGY: unknown (ii) MOLECULE TYPE: peptide (ix) FEATURE:
         (A) NAME/KEY: CDS
         (B) LOCATION: 1..7
         (D) OTHER INFORMATION: /product= nuclear translocation
             sequence (xi) SEQUENCE DESCRIPTION: SEQ ID NO: 36:

Asn Tyr Lys Lys Pro Lys Leu
 1               5

(2) INFORMATION FOR SEQ ID NO: 37:

(i) SEQUENCE CHARACTERISTICS:
         (A) LENGTH: 7 amino acids
         (B) TYPE: amino acid
         (C) STRANDEDNESS: single
         (D) TOPOLOGY: unknown (ii) MOLECULE TYPE: peptide (ix) FEATURE:
         (A) NAME/KEY: CDS
         (B) LOCATION: 1..7
         (D) OTHER INFORMATION: /product= nuclear translocation
             sequence (xi) SEQUENCE DESCRIPTION: SEQ ID NO: 37:

His Phe Lys Asp Pro Lys Arg
 1               5
```

(2) INFORMATION FOR SEQ ID NO: 38:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: CDS
        (B) LOCATION: 1..7
        (D) OTHER INFORMATION: /product= nuclear translocation
            sequence (xi) SEQUENCE DESCRIPTION: SEQ ID NO: 38:

Ala Pro Arg Arg Arg Lys Leu
 1              5

(2) INFORMATION FOR SEQ ID NO: 39:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: CDS
        (B) LOCATION: 1..6
        (D) OTHER INFORMATION: /product= nuclear translocation
            sequence (xi) SEQUENCE DESCRIPTION: SEQ ID NO: 39:

Ile Lys Arg Leu Arg Arg
 1              5

(2) INFORMATION FOR SEQ ID NO: 40:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: CDS
        (B) LOCATION: 1..6
        (D) OTHER INFORMATION: /product= nuclear translocation
            sequence (xi) SEQUENCE DESCRIPTION: SEQ ID NO: 40:

Ile Lys Arg Gln Arg Arg
 1              5

(2) INFORMATION FOR SEQ ID NO: 41:

(i) SEQUENCE CHARACTERISTICS:
        (A) LENGTH: 5 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: CDS

```
            (B) LOCATION: 1..5
            (D) OTHER INFORMATION: /product= nuclear translocation
                sequence (xi) SEQUENCE DESCRIPTION: SEQ ID NO: 41:

Ile Arg Val Arg Arg
 1               5

(2) INFORMATION FOR SEQ ID NO: 42:

(i) SEQUENCE CHARACTERISTICS:
        (A) LENGTH: 4 amino acids
        (B) TYPE: amino acid
        (C) STRANDEDNESS: single
        (D) TOPOLOGY: /note= "Cytoplasmic Translocation
            Signal"

(ix) FEATURE:

(xi) SEQUENCE DESCRIPTION: SEQ ID NO: 42:

Lys Asp Glu Leu
 1

(2) INFORMATION FOR SEQ ID NO: 43:

(i) SEQUENCE CHARACTERISTICS:
        (A) LENGTH: 4 amino acids
        (B) TYPE: amino acid
        (C) STRANDEDNESS: single
        (D) TOPOLOGY: /note= "Cytoplasmic Translocation
            Signal"

(ix) FEATURE:

(xi) SEQUENCE DESCRIPTION: SEQ ID NO: 43:

Arg Asp Glu Leu
 1

(2) INFORMATION FOR SEQ ID NO: 44:

(i) SEQUENCE CHARACTERISTICS:
        (A) LENGTH: 4 amino acids
        (B) TYPE: amino acid
        (C) STRANDEDNESS: single
        (D) TOPOLOGY: /note= "Cytoplasmic Translocation
            Signal"

(ix) FEATURE:

(xi) SEQUENCE DESCRIPTION: SEQ ID NO: 44:

Lys Glu Glu Leu
 1

(2) INFORMATION FOR SEQ ID NO: 45:

(i) SEQUENCE CHARACTERISTICS:
        (A) LENGTH: 23 amino acids
        (B) TYPE: amino acid
        (C) STRANDEDNESS: single
        (D) TOPOLOGY: linear (ix) FEATURE:
        (D) OTHER INFORMATION: /note= "Endosome-disruptive peptide
            INF"

(xi) SEQUENCE DESCRIPTION: SEQ ID NO: 45:

Gly Leu Phe Glu Ala Ile Glu Gly Phe Ile Glu Asn Gly Trp Glu Gly
 1               5                  10                  15

Met Ile Asp Gly Gly Gly Cys
```

20

(2) INFORMATION FOR SEQ ID NO: 46:

(i) SEQUENCE CHARACTERISTICS:
        (A) LENGTH: 24 amino acids
        (B) TYPE: amino acid
        (C) STRANDEDNESS: single
        (D) TOPOLOGY: linear (ix) FEATURE:
        (D) OTHER INFORMATION: /note= "Endosome-disruptive peptide INF"

(xi) SEQUENCE DESCRIPTION: SEQ ID NO: 46:

Gly Leu Phe Glu Ala Ile Glu Gly Phe Ile Glu Asn Gly Trp Glu Gly
1               5                   10                  15

Met Ile Asp Gly Trp Tyr Gly Cys
                20

(2) INFORMATION FOR SEQ ID NO: 47:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: Gly4Ser with NcoI ends
        (B) LOCATION: 3..26

(xi) SEQUENCE DESCRIPTION: SEQ ID NO: 47:

CCATGGGCGG CGGCGGCTCT GCCATGG                                        27

(2) INFORMATION FOR SEQ ID NO: 48:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: (Gly4Ser)2 with NcoI ends
        (B) LOCATION: 3..41

(xi) SEQUENCE DESCRIPTION: SEQ ID NO: 48:

CCATGGGCGG CGGCGGCTCT GGCGGCGGCG GCTCTGCCAT GG                       42

(2) INFORMATION FOR SEQ ID NO: 49:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: (Ser4Gly)4 with NcoI ends
        (B) LOCATION: 3..74

(xi) SEQUENCE DESCRIPTION: SEQ ID NO: 49:

CCATGGCCTC GTCGTCGTCG GGCTCGTCGT CGTCGGGCTC GTCGTCGTCG GGCTCGTCGT    60

```
CGTCGGGCGC CATGG                                                          75
```

(2) INFORMATION FOR SEQ ID NO: 50:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: (Ser4Gly)2
        (B) LOCATION: 3..45

(xi) SEQUENCE DESCRIPTION: SEQ ID NO: 50:

```
CCATGGCCTC GTCGTCGTCG GGCTCGTCGT CGTCGGGCGC CATGG                         45
```

(2) INFORMATION FOR SEQ ID NO: 51:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: CDS
        (B) LOCATION: 1..8
        (D) OTHER INFORMATION: /product= Flexible linker (xi) SEQUENCE DESCRIPTION: SEQ ID NO: 51:

```
Ala Ala Pro Ala Ala Ala Pro Ala
  1               5
```

(2) INFORMATION FOR SEQ ID NO: 52:

(i) SEQUENCE CHARACTERISTICS:
        (A) LENGTH: 465 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..465

(ix) FEATURE:
        (A) NAME/KEY: mat_peptide
        (B) LOCATION: 1..465
        (D) OTHER INFORMATION: /product= "bFGF"

(xi) SEQUENCE DESCRIPTION: SEQ ID NO: 52:

```
ATG GCA GCA GGA TCA ATA ACA ACA TTA CCC GCC TTG CCC GAG GAT GGC          48
Met Ala Ala Gly Ser Ile Thr Thr Leu Pro Ala Leu Pro Glu Asp Gly
  1               5                  10                  15

GGC AGC GGC GCC TTC CCG CCC GGC CAC TTC AAG GAC CCC AAG CGG CTG          96
Gly Ser Gly Ala Phe Pro Pro Gly His Phe Lys Asp Pro Lys Arg Leu
                 20                  25                  30

TAC TGC AAA AAC GGG GGC TTC TTC CTG CGC ATC CAC CCC GAC GGC CGA         144
Tyr Cys Lys Asn Gly Gly Phe Phe Leu Arg Ile His Pro Asp Gly Arg
             35                  40                  45

GTT GAC GGG GTC CGG GAG AAG AGC GAC CCT CAC ATC AAG CTT CAA CTT         192
Val Asp Gly Val Arg Glu Lys Ser Asp Pro His Ile Lys Leu Gln Leu
         50                  55                  60
```

```
CAA GCA GAA GAG AGA GGA GTT GTG TCT ATC AAA GGA GTG TGT GCT AAC         240
Gln Ala Glu Glu Arg Gly Val Val Ser Ile Lys Gly Val Cys Ala Asn
 65              70                  75                  80

CGT TAC CTG GCT ATG AAG GAA GAT GGA AGA TTA CTG GCT TCT AAA TGT         288
Arg Tyr Leu Ala Met Lys Glu Asp Gly Arg Leu Leu Ala Ser Lys Cys
                 85                  90                  95

GTT ACG GAT GAG TGT TTC TTT TTT GAA CGA TTG GAA TCT AAT AAC TAC         336
Val Thr Asp Glu Cys Phe Phe Phe Glu Arg Leu Glu Ser Asn Asn Tyr
                100                 105                 110

AAT ACT TAC CGG TCA AGG AAA TAC ACC AGT TGG TAT GTG GCA TTG AAA         384
Asn Thr Tyr Arg Ser Arg Lys Tyr Thr Ser Trp Tyr Val Ala Leu Lys
            115                 120                 125

CGA ACT GGG CAG TAT AAA CTT GGA TCC AAA ACA GGA CCT GGG CAG AAA         432
Arg Thr Gly Gln Tyr Lys Leu Gly Ser Lys Thr Gly Pro Gly Gln Lys
       130                 135                 140

GCT ATA CTT TTT CTT CCA ATG TCT GCT AAG AGC                             465
Ala Ile Leu Phe Leu Pro Met Ser Ala Lys Ser
145                 150                 155

(2) INFORMATION FOR SEQ ID NO: 53:

(i) SEQUENCE CHARACTERISTICS:
        (A) LENGTH: 1230 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..1230

(ix) FEATURE:
        (A) NAME/KEY: mat_peptide
        (B) LOCATION: 1..465
        (D) OTHER INFORMATION: /product= "bFGF"

(ix) FEATURE:
        (A) NAME/KEY: mat_peptide
        (B) LOCATION: 472..1230
        (D) OTHER INFORMATION: /product= "Saporin"

(xi) SEQUENCE DESCRIPTION: SEQ ID NO: 53:

ATG GCT GCT GGT TCT ATC ACT ACT CTG CCG GCT CTG CCG GAA GAC GGT          48
Met Ala Ala Gly Ser Ile Thr Thr Leu Pro Ala Leu Pro Glu Asp Gly
 1               5                  10                  15

GGT TCT GGT GCT TTC CCG CCC GGC CAC TTC AAG GAC CCC AAG CGG CTG          96
Gly Ser Gly Ala Phe Pro Pro Gly His Phe Lys Asp Pro Lys Arg Leu
                20                  25                  30

TAC TGC AAA AAC GGG GGC TTC TTC CTG CGC ATC CAC CCC GAC GGC CGA         144
Tyr Cys Lys Asn Gly Gly Phe Phe Leu Arg Ile His Pro Asp Gly Arg
            35                  40                  45

GTT GAC GGG GTC CGG GAG AAG AGC GAC CCT CAC ATC AAG CTT CAA CTT         192
Val Asp Gly Val Arg Glu Lys Ser Asp Pro His Ile Lys Leu Gln Leu
        50                  55                  60

CAA GCA GAA GAG AGA GGA GTT GTG TCT ATC AAA GGA GTG TGT GCT AAC         240
Gln Ala Glu Glu Arg Gly Val Val Ser Ile Lys Gly Val Cys Ala Asn
 65              70                  75                  80

CGT TAC CTG GCT ATG AAG GAA GAT GGA AGA TTA CTG GCT TCT AAA TGT         288
Arg Tyr Leu Ala Met Lys Glu Asp Gly Arg Leu Leu Ala Ser Lys Cys
                 85                  90                  95

GTT ACG GAT GAG TGT TTC TTT TTT GAA CGA TTG GAA TCT AAT AAC TAC         336
Val Thr Asp Glu Cys Phe Phe Phe Glu Arg Leu Glu Ser Asn Asn Tyr
                100                 105                 110
```

```
AAT ACT TAC CGG TCA AGG AAA TAC ACC AGT TGG TAT GTG GCA TTG AAA         384
Asn Thr Tyr Arg Ser Arg Lys Tyr Thr Ser Trp Tyr Val Ala Leu Lys
            115                 120                 125

CGA ACT GGG CAG TAT AAA CTT GGA TCC AAA ACA GGA CCT GGG CAG AAA         432
Arg Thr Gly Gln Tyr Lys Leu Gly Ser Lys Thr Gly Pro Gly Gln Lys
        130                 135                 140

GCT ATA CTT TTT CTT CCA ATG TCT GCT AAG AGC GCC ATG GTC ACA TCA         480
Ala Ile Leu Phe Leu Pro Met Ser Ala Lys Ser Ala Met Val Thr Ser
145                 150                 155                 160

ATC ACA TTA GAT CTA GTA AAT CCG ACC GCG GGT CAA TAC TCA TCT TTT         528
Ile Thr Leu Asp Leu Val Asn Pro Thr Ala Gly Gln Tyr Ser Ser Phe
            165                 170                 175

GTG GAT AAA ATC CGA AAC AAC GTA AAG GAT CCA AAC CTG AAA TAC GGT         576
Val Asp Lys Ile Arg Asn Asn Val Lys Asp Pro Asn Leu Lys Tyr Gly
        180                 185                 190

GGT ACC GAC ATA GCC GTG ATA GGC CCA CCT TCT AAA GAA AAA TTC CTT         624
Gly Thr Asp Ile Ala Val Ile Gly Pro Pro Ser Lys Glu Lys Phe Leu
            195                 200                 205

AGA ATT AAT TTC CAA AGT TCC CGA GGA ACG GTC TCA CTT GGC CTA AAA         672
Arg Ile Asn Phe Gln Ser Ser Arg Gly Thr Val Ser Leu Gly Leu Lys
        210                 215                 220

CGC GAT AAC TTG TAT GTG GTC GCG TAT CTT GCA ATG GAT AAC ACG AAT         720
Arg Asp Asn Leu Tyr Val Val Ala Tyr Leu Ala Met Asp Asn Thr Asn
225                 230                 235                 240

GTT AAT CGG GCA TAT TAC TTC AAA TCA GAA ATT ACT TCC GCC GAG TTA         768
Val Asn Arg Ala Tyr Tyr Phe Lys Ser Glu Ile Thr Ser Ala Glu Leu
            245                 250                 255

ACC GCC CTT TTC CCA GAG GCC ACA ACT GCA AAT CAG AAA GCT TTA GAA         816
Thr Ala Leu Phe Pro Glu Ala Thr Thr Ala Asn Gln Lys Ala Leu Glu
            260                 265                 270

TAC ACA GAA GAT TAT CAG TCG ATC GAA AAG AAT GCC CAG ATA ACA CAG         864
Tyr Thr Glu Asp Tyr Gln Ser Ile Glu Lys Asn Ala Gln Ile Thr Gln
            275                 280                 285

GGA GAT AAA AGT AGA AAA GAA CTC GGG TTG GGG ATC GAC TTA CTT TTG         912
Gly Asp Lys Ser Arg Lys Glu Leu Gly Leu Gly Ile Asp Leu Leu Leu
        290                 295                 300

ACG TTC ATG GAA GCA GTG AAC AAG AAG GCA CGT GTG GTT AAA AAC GAA         960
Thr Phe Met Glu Ala Val Asn Lys Lys Ala Arg Val Val Lys Asn Glu
305                 310                 315                 320

GCT AGG TTT CTG CTT ATC GCT ATT CAA ATG ACA GCT GAG GTA GCA CGA        1008
Ala Arg Phe Leu Leu Ile Ala Ile Gln Met Thr Ala Glu Val Ala Arg
            325                 330                 335

TTT AGG TAC ATT CAA AAC TTG GTA ACT AAG AAC TTC CCC AAC AAG TTC        1056
Phe Arg Tyr Ile Gln Asn Leu Val Thr Lys Asn Phe Pro Asn Lys Phe
            340                 345                 350

GAC TCG GAT AAC AAG GTG ATT CAA TTT GAA GTC AGC TGG CGT AAG ATT        1104
Asp Ser Asp Asn Lys Val Ile Gln Phe Glu Val Ser Trp Arg Lys Ile
            355                 360                 365

TCT ACG GCA ATA TAC GGG GAT GCC AAA AAC GGC GTG TTT AAT AAA GAT        1152
Ser Thr Ala Ile Tyr Gly Asp Ala Lys Asn Gly Val Phe Asn Lys Asp
        370                 375                 380

TAT GAT TTC GGG TTT GGA AAA GTG AGG CAG GTG AAG GAC TTG CAA ATG        1200
Tyr Asp Phe Gly Phe Gly Lys Val Arg Gln Val Lys Asp Leu Gln Met
385                 390                 395                 400

GGA CTC CTT ATG TAT TTG GGC AAA CCA AAG                                1230
Gly Leu Leu Met Tyr Leu Gly Lys Pro Lys
            405                 410
```

(2) INFORMATION FOR SEQ ID NO: 54:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_recomb
        (B) LOCATION: 6..11
        (D) OTHER INFORMATION: /standard_name= "EcoRI Restriction
            Site"

(ix) FEATURE:
        (A) NAME/KEY: sig_peptide
        (B) LOCATION: 12..30
        (D) OTHER INFORMATION: /function= "N-terminal extension" /
            product= "Native sapor (xi) SEQUENCE DESCRIPTION: SEQ ID NO: 54:

CTGCAGAATT CGCATGGATC CTGCTTCAAT                                              30

(2) INFORMATION FOR SEQ ID NO: 55:

(i) SEQUENCE CHARACTERISTICS:
        (A) LENGTH: 30 base pairs
        (B) TYPE: nucleic acid
        (C) STRANDEDNESS: single
        (D) TOPOLOGY: /note= "Anti-sense stop codon"

(ii) MOLECULE TYPE: DNA (genomic)

(iv) ANTI-SENSE: YES (ix) FEATURE:
        (A) NAME/KEY: misc_recomb
        (B) LOCATION: 6..11
        (D) OTHER INFORMATION: /standard_name= "EcoRI Restriction
            Site"

(ix) FEATURE:
        (A) NAME/KEY: terminator
        (B) LOCATION: 23..25

(xi) SEQUENCE DESCRIPTION: SEQ ID NO: 55:

CTGCAGAATT CGCCTCGTTT GACTACTTTG                                              30

(2) INFORMATION FOR SEQ ID NO: 56:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 56:

AGGAGTGTCT GCTAACC                                                            17

(2) INFORMATION FOR SEQ ID NO: 57:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 57:

```
TTCTAAATCG GTTACCGATG ACTG                                              24

(2) INFORMATION FOR SEQ ID NO: 58:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 58:

CATATGTGTG AGCTACTGTC GCCACCGCTC                                        30

(2) INFORMATION FOR SEQ ID NO: 59:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 59:

GGATCCGAGC ACCTGGTATA TCGGTGGGGG                                        30

(2) INFORMATION FOR SEQ ID NO: 60:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 60:

GGATCCGCCT CGTTTGACTA CTT                                               23

(2) INFORMATION FOR SEQ ID NO: 61:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (D) OTHER INFORMATION:/product= bacteriophage lambda CII
            ribosome binding site (xi) SEQUENCE DESCRIPTION: SEQ ID NO: 61:

GTCGACCAAG CTTGGGCATA CATTCAATCA ATTGTTATCT AAGGAAATAC TTACATATG        59

(2) INFORMATION FOR SEQ ID NO: 62:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (D) OTHER INFORMATION: /product= trp promoter (xi) SEQUENCE DESCRIPTION: SEQ ID NO: 62:
```

```
GAATTCCCCT GTTGACAATT AATCATCGAA CTAGTTAACT AGTACGCAGC TTGGCTGCAG      60
```

(2) INFORMATION FOR SEQ ID NO: 63:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_recomb
        (B) LOCATION: 11..16
        (D) OTHER INFORMATION: /standard_name= "Nco I restriction
            enzyme recognition sit (ix) FEATURE:
        (A) NAME/KEY: mat_peptide
        (B) LOCATION: 1..10
        (D) OTHER INFORMATION: /product= "Carboxy terminus of
            mature FGF protein"

(xi) SEQUENCE DESCRIPTION: SEQ ID NO: 63:

```
GCTAAGAGCG CCATGGAGA                                                  19
```

(2) INFORMATION FOR SEQ ID NO: 64:

(i) SEQUENCE CHARACTERISTICS:
        (A) LENGTH: 21 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..12
        (D) OTHER INFORMATION: /product= "Carboxy terminus of
            wild type FGF"

(ix) FEATURE:
        (A) NAME/KEY: misc_recomb
        (B) LOCATION: 13..18
        (D) OTHER INFORMATION: /standard_name= "Nco I restriction
            enzyme recognition sit (xi) SEQUENCE DESCRIPTION: SEQ ID NO: 64:

```
GCT AAG AGC TGACCATGGA GA                                             21
Ala Lys Ser
  1
```

(2) INFORMATION FOR SEQ ID NO: 65:

(i) SEQUENCE CHARACTERISTICS:
        (A) LENGTH: 102 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..96
        (D) OTHER INFORMATION: /product= "pFGFNcoI"
            /note= "Equals the plasmid pFC80 wih native FGF
            stop codon removed."

(ix) FEATURE:
        (A) NAME/KEY: misc_recomb
        (B) LOCATION: 29..34

(D) OTHER INFORMATION: /standard_name= "Nco I restriction
enzyme recognition sit (xi) SEQUENCE DESCRIPTION: SEQ ID NO: 65:

```
CTT TTT CTT CCA ATG TCT GCT AAG AGC GCC ATG GAG ATC CGG CTG AAT        48
Leu Phe Leu Pro Met Ser Ala Lys Ser Ala Met Glu Ile Arg Leu Asn
 1               5                  10                  15

GGT GCA GTT CTG TAC CGG TTT TCC TGT GCC GTC TTT CAG GAC TCC TGAAATCTT 102
Gly Ala Val Leu Tyr Arg Phe Ser Cys Ala Val Phe Gln Asp Ser
            20                  25                  30
```

(2) INFORMATION FOR SEQ ID NO: 66:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: Cathepsin B linker
        (B) LOCATION: 3..35

(xi) SEQUENCE DESCRIPTION: SEQ ID NO: 66:

CCATGGCCCT GGCCCTGGCC CTGGCCCTGG CCATGG    36

(2) INFORMATION FOR SEQ ID NO: 67:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: Cathepsin D linker
        (B) LOCATION: 3..50

(xi) SEQUENCE DESCRIPTION: SEQ ID NO: 67:

CCATGGGCCG ATCGGGCTTC CTGGGCTTCG GCTTCCTGGG CTTCGCCATGG    51

(2) INFORMATION FOR SEQ ID NO: 68:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: "Trypsin linker"
        (B) LOCATION: 3..95

(xi) SEQUENCE DESCRIPTION: SEQ ID NO: 68:

CCATGGGCCG ATCGGGCGGT GGGTGCGCTG GTAATAGAGT CAGAAGATCA GTCGGAAGCA    60

GCCTGTCTTG CGGTGGTCTC GACCTGCAGG CCATGG    96

(2) INFORMATION FOR SEQ ID NO: 69:

(i) SEQUENCE CHARACTERISTICS:
        (A) LENGTH: 18 base pairs
        (B) TYPE: nucleic acid
        (C) STRANDEDNESS: double (D) TOPOLOGY: unknown (ii) MOLECULE TYPE: cDNA (ix) FEATURE:
        (A) NAME/KEY: CDS
        (B) LOCATION: 1..18
        (D) OTHER INFORMATION: /product= Thrombin substrate linker (xi) SEQUENCE DESCRIPTION: SEQ ID NO: 69:

CTG GTG CCG CGC GGC AGC                                              18
Leu Val Pro Arg Gly Ser
 1               5

(2) INFORMATION FOR SEQ ID NO: 70:

(i) SEQUENCE CHARACTERISTICS:
        (A) LENGTH: 15 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..15
        (D) OTHER INFORMATION: /product= Enterokinase substrate linker (xi) SEQUENCE DESCRIPTION: SEQ ID NO: 70:

GAC GAC GAC GAC CCA                                                  15
Asp Asp Asp Asp Lys
 1               5

(2) INFORMATION FOR SEQ ID NO: 71:

(i) SEQUENCE CHARACTERISTICS:
        (A) LENGTH: 12 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..12
        (D) OTHER INFORMATION: /product= Factor Xa substrate (xi) SEQUENCE DESCRIPTION: SEQ ID NO: 71:

ATC GAA GGT CGT                                                      12
Ile Glu Gly Arg
 1

(2) INFORMATION FOR SEQ ID NO: 72:

(i) SEQUENCE CHARACTERISTICS:
        (A) LENGTH: 1260 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..1260

(ix) FEATURE:
        (A) NAME/KEY: mat_peptide
        (B) LOCATION: 1..465
        (D) OTHER INFORMATION: /product= "bFGF"

-continued (ix) FEATURE:
        (A) NAME/KEY: mat_peptide
        (B) LOCATION: 466...501
        (D) OTHER INFORMATION: /product= "Cathepsin B linker"

(ix) FEATURE:
        (A) NAME/KEY: mat_peptide
        (B) LOCATION: 502..1260
        (D) OTHER INFORMATION: /product= "Saporin"

(xi) SEQUENCE DESCRIPTION: SEQ ID NO: 72:

```
ATG GCA GCA GGA TCA ATA ACA ACA TTA CCC GCC TTG CCC GAG GAT GGC        48
Met Ala Ala Gly Ser Ile Thr Thr Leu Pro Ala Leu Pro Glu Asp Gly
 1               5                  10                  15

GGC AGC GGC GCC TTC CCG CCC GGC CAC TTC AAG GAC CCC AAG CGG CTG        96
Gly Ser Gly Ala Phe Pro Pro Gly His Phe Lys Asp Pro Lys Arg Leu
            20                  25                  30

TAC TGC AAA AAC GGG GGC TTC TTC CTG CGC ATC CAC CCC GAC GGC CGA       144
Tyr Cys Lys Asn Gly Gly Phe Phe Leu Arg Ile His Pro Asp Gly Arg
        35                  40                  45

GTT GAC GGG GTC CGG GAG AAG AGC GAC CCT CAC ATC AAG CTT CAA CTT       192
Val Asp Gly Val Arg Glu Lys Ser Asp Pro His Ile Lys Leu Gln Leu
    50                  55                  60

CAA GCA GAA GAG AGA GGA GTT GTG TCT ATC AAA GGA GTG TGT GCT AAC       240
Gln Ala Glu Glu Arg Gly Val Val Ser Ile Lys Gly Val Cys Ala Asn
65                  70                  75                  80

CGT TAC CTG GCT ATG AAG GAA GAT GGA AGA TTA CTG GCT TCT AAA TGT       288
Arg Tyr Leu Ala Met Lys Glu Asp Gly Arg Leu Leu Ala Ser Lys Cys
                85                  90                  95

GTT ACG GAT GAG TGT TTC TTT TTT GAA CGA TTG GAA TCT AAT AAC TAC       336
Val Thr Asp Glu Cys Phe Phe Phe Glu Arg Leu Glu Ser Asn Asn Tyr
            100                 105                 110

AAT ACT TAC CGG TCA AGG AAA TAC ACC AGT TGG TAT GTG GCA TTG AAA       384
Asn Thr Tyr Arg Ser Arg Lys Tyr Thr Ser Trp Tyr Val Ala Leu Lys
        115                 120                 125

CGA ACT GGG CAG TAT AAA CTT GGA TCC AAA ACA GGA CCT GGG CAG AAA       432
Arg Thr Gly Gln Tyr Lys Leu Gly Ser Lys Thr Gly Pro Gly Gln Lys
    130                 135                 140

GCT ATA CTT TTT CTT CCA ATG TCT GCT AAG AGC GCC ATG GCC CTG GCC       480
Ala Ile Leu Phe Leu Pro Met Ser Ala Lys Ser Ala Met Ala Leu Ala
145                 150                 155                 160

CTG GCC CTG GCC CTG GCC ATG GTC ACA TCA ATC ACA TTA GAT CTA GTA       528
Leu Ala Leu Ala Leu Ala Met Val Thr Ser Ile Thr Leu Asp Leu Val
                165                 170                 175

AAT CCG ACC GCG GGT CAA TAC TCA TCT TTT GTG GAT AAA ATC CGA AAC       576
Asn Pro Thr Ala Gly Gln Tyr Ser Ser Phe Val Asp Lys Ile Arg Asn
            180                 185                 190

AAC GTA AAG GAT CCA AAC CTG AAA TAC GGT GGT ACC GAC ATA GCC GTG       624
Asn Val Lys Asp Pro Asn Leu Lys Tyr Gly Gly Thr Asp Ile Ala Val
        195                 200                 205

ATA GGC CCA CCT TCT AAA GAA AAA TTC CTT AGA ATT AAT TTC CAA AGT       672
Ile Gly Pro Pro Ser Lys Glu Lys Phe Leu Arg Ile Asn Phe Gln Ser
    210                 215                 220

TCC CGA GGA ACG GTC TCA CTT GGC CTA AAA CGC GAT AAC TTG TAT GTG       720
Ser Arg Gly Thr Val Ser Leu Gly Leu Lys Arg Asp Asn Leu Tyr Val
225                 230                 235                 240

GTC GCG TAT CTT GCA ATG GAT AAC ACG AAT GTT AAT CGG GCA TAT TAC       768
Val Ala Tyr Leu Ala Met Asp Asn Thr Asn Val Asn Arg Ala Tyr Tyr
                245                 250                 255

TTC AAA TCA GAA ATT ACT TCC GCC GAG TTA ACC GCC CTT TTC CCA GAG       816
Phe Lys Ser Glu Ile Thr Ser Ala Glu Leu Thr Ala Leu Phe Pro Glu
            260                 265                 270
```

-continued

```
GCC ACA ACT GCA AAT CAG AAA GCT TTA GAA TAC ACA GAA GAT TAT CAG        864
Ala Thr Thr Ala Asn Gln Lys Ala Leu Glu Tyr Thr Glu Asp Tyr Gln
            275                 280                 285

TCG ATC GAA AAG AAT GCC CAG ATA ACA CAG GGA GAT AAA AGT AGA AAA        912
Ser Ile Glu Lys Asn Ala Gln Ile Thr Gln Gly Asp Lys Ser Arg Lys
            290                 295                 300

GAA CTC GGG TTG GGG ATC GAC TTA CTT TTG ACG TTC ATG GAA GCA GTG        960
Glu Leu Gly Leu Gly Ile Asp Leu Leu Leu Thr Phe Met Glu Ala Val
305                 310                 315                 320

AAC AAG AAG GCA CGT GTG GTT AAA AAC GAA GCT AGG TTT CTG CTT ATC       1008
Asn Lys Lys Ala Arg Val Val Lys Asn Glu Ala Arg Phe Leu Leu Ile
            325                 330                 335

GCT ATT CAA ATG ACA GCT GAG GTA GCA CGA TTT AGG TAC ATT CAA AAC       1056
Ala Ile Gln Met Thr Ala Glu Val Ala Arg Phe Arg Tyr Ile Gln Asn
            340                 345                 350

TTG GTA ACT AAG AAC TTC CCC AAC AAG TTC GAC TCG GAT AAC AAG GTG       1104
Leu Val Thr Lys Asn Phe Pro Asn Lys Phe Asp Ser Asp Asn Lys Val
            355                 360                 365

ATT CAA TTT GAA GTC AGC TGG CGT AAG ATT TCT ACG GCA ATA TAC GGG       1152
Ile Gln Phe Glu Val Ser Trp Arg Lys Ile Ser Thr Ala Ile Tyr Gly
            370                 375                 380

GAT GCC AAA AAC GGC GTG TTT AAT AAA GAT TAT GAT TTC GGG TTT GGA       1200
Asp Ala Lys Asn Gly Val Phe Asn Lys Asp Tyr Asp Phe Gly Phe Gly
385                 390                 395                 400

AAA GTG AGG CAG GTG AAG GAC TTG CAA ATG GGA CTC CTT ATG TAT TTG       1248
Lys Val Arg Gln Val Lys Asp Leu Gln Met Gly Leu Leu Met Tyr Leu
            405                 410                 415

GGC AAA CCA AAG                                                        1260
Gly Lys Pro Lys
            420
```

(2) INFORMATION FOR SEQ ID NO: 73:

(i) SEQUENCE CHARACTERISTICS:
  (A) LENGTH: 1275 base pairs
  (B) TYPE: nucleic acid
  (C) STRANDEDNESS: double
  (D) TOPOLOGY: unknown (ii) MOLECULE TYPE: cDNA (ix) FEATURE:
  (A) NAME/KEY: CDS
  (B) LOCATION: 1..1275

(ix) FEATURE:
  (A) NAME/KEY: mat_peptide
  (B) LOCATION: 1..465
  (D) OTHER INFORMATION: /product= "bFGF"

(ix) FEATURE:
  (A) NAME/KEY: mat_peptide
  (B) LOCATION: 466...516
  (D) OTHER INFORMATION: /product= "Cathepsin D linker"

(ix) FEATURE:
  (A) NAME/KEY: mat_peptide
  (B) LOCATION: 517..1275
  (D) OTHER INFORMATION: /product= "Saporin"

(xi) SEQUENCE DESCRIPTION: SEQ ID NO: 73:

```
ATG GCA GCA GGA TCA ATA ACA ACA TTA CCC GCC TTG CCC GAG GAT GGC         48
Met Ala Ala Gly Ser Ile Thr Thr Leu Pro Ala Leu Pro Glu Asp Gly
1                   5                   10                  15

GGC AGC GGC GCC TTC CCG CCC GGC CAC TTC AAG GAC CCC AAG CGG CTG         96
Gly Ser Gly Ala Phe Pro Pro Gly His Phe Lys Asp Pro Lys Arg Leu
```

-continued

```
                     20                      25                      30
TAC TGC AAA AAC GGG GGC TTC TTC CTG CGC ATC CAC CCC GAC GGC CGA        144
Tyr Cys Lys Asn Gly Gly Phe Phe Leu Arg Ile His Pro Asp Gly Arg
             35                      40                      45

GTT GAC GGG GTC CGG GAG AAG AGC GAC CCT CAC ATC AAG CTT CAA CTT        192
Val Asp Gly Val Arg Glu Lys Ser Asp Pro His Ile Lys Leu Gln Leu
         50                      55                      60

CAA GCA GAA GAG AGA GGA GTT GTG TCT ATC AAA GGA GTG TGT GCT AAC        240
Gln Ala Glu Glu Arg Gly Val Val Ser Ile Lys Gly Val Cys Ala Asn
 65                      70                      75                  80

CGT TAC CTG GCT ATG AAG GAA GAT GGA AGA TTA CTG GCT TCT AAA TGT        288
Arg Tyr Leu Ala Met Lys Glu Asp Gly Arg Leu Leu Ala Ser Lys Cys
                     85                      90                      95

GTT ACG GAT GAG TGT TTC TTT TTT GAA CGA TTG GAA TCT AAT AAC TAC        336
Val Thr Asp Glu Cys Phe Phe Phe Glu Arg Leu Glu Ser Asn Asn Tyr
                100                     105                     110

AAT ACT TAC CGG TCA AGG AAA TAC ACC AGT TGG TAT GTG GCA TTG AAA        384
Asn Thr Tyr Arg Ser Arg Lys Tyr Thr Ser Trp Tyr Val Ala Leu Lys
             115                     120                     125

CGA ACT GGG CAG TAT AAA CTT GGA TCC AAA ACA GGA CCT GGG CAG AAA        432
Arg Thr Gly Gln Tyr Lys Leu Gly Ser Lys Thr Gly Pro Gly Gln Lys
         130                     135                     140

GCT ATA CTT TTT CTT CCA ATG TCT GCT AAG AGC GCC ATG GGC CGA TCG        480
Ala Ile Leu Phe Leu Pro Met Ser Ala Lys Ser Ala Met Gly Arg Ser
145                     150                     155                 160

GGC TTC CTG GGC TTC GGC TTC CTG GGC TTC GCC ATG GTC ACA TCA ATC        528
Gly Phe Leu Gly Phe Gly Phe Leu GLy Phe Ala Met Val Thr Ser Ile
                     165                     170                     175

ACA TTA GAT CTA GTA AAT CCG ACC GCG GGT CAA TAC TCA TCT TTT GTG        576
Thr Leu Asp Leu Val Asn Pro Thr Ala Gly Gln Tyr Ser Ser Phe Val
                180                     185                     190

GAT AAA ATC CGA AAC AAC GTA AAG GAT CCA AAC CTG AAA TAC GGT GGT        624
Asp Lys Ile Arg Asn Asn Val Lys Asp Pro Asn Leu Lys Tyr Gly Gly
             195                     200                     205

ACC GAC ATA GCC GTG ATA GGC CCA CCT TCT AAA GAA AAA TTC CTT AGA        672
Thr Asp Ile Ala Val Ile Gly Pro Pro Ser Lys Glu Lys Phe Leu Arg
         210                     215                     220

ATT AAT TTC CAA AGT TCC CGA GGA ACG GTC TCA CTT GGC CTA AAA CGC        720
Ile Asn Phe Gln Ser Ser Arg Gly Thr Val Ser Leu Gly Leu Lys Arg
225                     230                     235                 240

GAT AAC TTG TAT GTG GTC GCG TAT CTT GCA ATG GAT AAC ACG AAT GTT        768
Asp Asn Leu Tyr Val Val Ala Tyr Leu Ala Met Asp Asn Thr Asn Val
                     245                     250                     255

AAT CGG GCA TAT TAC TTC AAA TCA GAA ATT ACT TCC GCC GAG TTA ACC        816
Asn Arg Ala Tyr Tyr Phe Lys Ser Glu Ile Thr Ser Ala Glu Leu Thr
                260                     265                     270

GCC CTT TTC CCA GAG GCC ACA ACT GCA AAT CAG AAA GCT TTA GAA TAC        864
Ala Leu Phe Pro Glu Ala Thr Thr Ala Asn Gln Lys Ala Leu Glu Tyr
             275                     280                     285

ACA GAA GAT TAT CAG TCG ATC GAA AAG AAT GCC CAG ATA ACA CAG GGA        912
Thr Glu Asp Tyr Gln Ser Ile Glu Lys Asn Ala Gln Ile Thr Gln Gly
         290                     295                     300

GAT AAA AGT AGA AAA GAA CTC GGG TTG GGG ATC GAC TTA CTT TTG ACG        960
Asp Lys Ser Arg Lys Glu Leu Gly Leu Gly Ile Asp Leu Leu Leu Thr
305                     310                     315                 320

TTC ATG GAA GCA GTG AAC AAG AAG GCA CGT GTG GTT AAA AAC GAA GCT       1008
Phe Met Glu Ala Val Asn Lys Lys Ala Arg Val Val Lys Asn Glu Ala
                     325                     330                     335

AGG TTT CTG CTT ATC GCT ATT CAA ATG ACA GCT GAG GTA GCA CGA TTT       1056
```

```
Arg Phe Leu Leu Ile Ala Ile Gln Met Thr Ala Glu Val Ala Arg Phe
            340                 345                 350

AGG TAC ATT CAA AAC TTG GTA ACT AAG AAC TTC CCC AAC AAG TTC GAC      1104
Arg Tyr Ile Gln Asn Leu Val Thr Lys Asn Phe Pro Asn Lys Phe Asp
            355                 360                 365

TCG GAT AAC AAG GTG ATT CAA TTT GAA GTC AGC TGG CGT AAG ATT TCT      1152
Ser Asp Asn Lys Val Ile Gln Phe Glu Val Ser Trp Arg Lys Ile Ser
370                 375                 380

ACG GCA ATA TAC GGG GAT GCC AAA AAC GGC GTG TTT AAT AAA GAT TAT      1200
Thr Ala Ile Tyr Gly Asp Ala Lys Asn Gly Val Phe Asn Lys Asp Tyr
385                 390                 395                 400

GAT TTC GGG TTT GGA AAA GTG AGG CAG GTG AAG GAC TTG CAA ATG GGA      1248
Asp Phe Gly Phe Gly Lys Val Arg Gln Val Lys Asp Leu Gln Met Gly
            405                 410                 415

CTC CTT ATG TAT TTG GGC AAA CCA AAG                                  1275
Leu Leu Met Tyr Leu Gly Lys Pro Lys
            420                 425

(2) INFORMATION FOR SEQ ID NO: 74:

(i) SEQUENCE CHARACTERISTICS:
        (A) LENGTH: 1251 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..1251

(ix) FEATURE:
        (A) NAME/KEY: mat_peptide
        (B) LOCATION: 1..465
        (D) OTHER INFORMATION: /product= "bFGF"

(ix) FEATURE:
        (A) NAME/KEY: mat_peptide
        (B) LOCATION: 466..492
        (D) OTHER INFORMATION: /product= " Gly4Ser linker"

(ix) FEATURE:
        (A) NAME/KEY: mat_peptide
        (B) LOCATION: 493..1251
        (D) OTHER INFORMATION: /product= "Saporin"

(xi) SEQUENCE DESCRIPTION: SEQ ID NO: 74:

ATG GCA GCA GGA TCA ATA ACA ACA TTA CCC GCC TTG CCC GAG GAT GGC       48
Met Ala Ala Gly Ser Ile Thr Thr Leu Pro Ala Leu Pro Glu Asp Gly
1               5                   10                  15

GGC AGC GGC GCC TTC CCG CCC GGC CAC TTC AAG GAC CCC AAG CGG CTG       96
Gly Ser Gly Ala Phe Pro Pro Gly His Phe Lys Asp Pro Lys Arg Leu
                20                  25                  30

TAC TGC AAA AAC GGG GGC TTC TTC CTG CGC ATC CAC CCC GAC GGC CGA      144
Tyr Cys Lys Asn Gly Gly Phe Phe Leu Arg Ile His Pro Asp Gly Arg
            35                  40                  45

GTT GAC GGG GTC CGG GAG AAG AGC GAC CCT CAC ATC AAG CTT CAA CTT      192
Val Asp Gly Val Arg Glu Lys Ser Asp Pro His Ile Lys Leu Gln Leu
        50                  55                  60

CAA GCA GAA GAG AGA GGA GTT GTG TCT ATC AAA GGA GTG TGT GCT AAC      240
Gln Ala Glu Glu Arg Gly Val Val Ser Ile Lys Gly Val Cys Ala Asn
65                  70                  75                  80

CGT TAC CTG GCT ATG AAG GAA GAT GGA AGA TTA CTG GCT TCT AAA TGT      288
Arg Tyr Leu Ala Met Lys Glu Asp Gly Arg Leu Leu Ala Ser Lys Cys
                85                  90                  95
```

```
                                                                -continued

GTT ACG GAT GAG TGT TTC TTT TTT GAA CGA TTG GAA TCT AAT AAC TAC        336
Val Thr Asp Glu Cys Phe Phe Phe Glu Arg Leu Glu Ser Asn Asn Tyr
            100                 105                 110

AAT ACT TAC CGG TCA AGG AAA TAC ACC AGT TGG TAT GTG GCA TTG AAA        384
Asn Thr Tyr Arg Ser Arg Lys Tyr Thr Ser Trp Tyr Val Ala Leu Lys
            115                 120                 125

CGA ACT GGG CAG TAT AAA CTT GGA TCC AAA ACA GGA CCT GGG CAG AAA        432
Arg Thr Gly Gln Tyr Lys Leu Gly Ser Lys Thr Gly Pro Gly Gln Lys
130                 135                 140

GCT ATA CTT TTT CTT CCA ATG TCT GCT AAG AGC GCC ATG GGC GGC GGC        480
Ala Ile Leu Phe Leu Pro Met Ser Ala Lys Ser Ala Met Gly Gly Gly
145                 150                 155                 160

GGC TCT GCC ATG GTC ACA TCA ATC ACA TTA GAT CTA GTA AAT CCG ACC        528
Gly Ser Ala Met Val Thr Ser Ile Thr Leu Asp Leu Val Asn Pro Thr
                165                 170                 175

GCG GGT CAA TAC TCA TCT TTT GTG GAT AAA ATC CGA AAC AAC GTA AAG        576
Ala Gly Gln Tyr Ser Ser Phe Val Asp Lys Ile Arg Asn Asn Val Lys
            180                 185                 190

GAT CCA AAC CTG AAA TAC GGT GGT ACC GAC ATA GCC GTG ATA GGC CCA        624
Asp Pro Asn Leu Lys Tyr Gly Gly Thr Asp Ile Ala Val Ile Gly Pro
            195                 200                 205

CCT TCT AAA GAA AAA TTC CTT AGA ATT AAT TTC CAA AGT TCC CGA GGA        672
Pro Ser Lys Glu Lys Phe Leu Arg Ile Asn Phe Gln Ser Ser Arg Gly
210                 215                 220

ACG GTC TCA CTT GGC CTA AAA CGC GAT AAC TTG TAT GTG GTC GCG TAT        720
Thr Val Ser Leu Gly Leu Lys Arg Asp Asn Leu Tyr Val Val Ala Tyr
225                 230                 235                 240

CTT GCA ATG GAT AAC ACG AAT GTT AAT CGG GCA TAT TAC TTC AAA TCA        768
Leu Ala Met Asp Asn Thr Asn Val Asn Arg Ala Tyr Tyr Phe Lys Ser
                245                 250                 255

GAA ATT ACT TCC GCC GAG TTA ACC GCC CTT TTC CCA GAG GCC ACA ACT        816
Glu Ile Thr Ser Ala Glu Leu Thr Ala Leu Phe Pro Glu Ala Thr Thr
            260                 265                 270

GCA AAT CAG AAA GCT TTA GAA TAC ACA GAA GAT TAT CAG TCG ATC GAA        864
Ala Asn Gln Lys Ala Leu Glu Tyr Thr Glu Asp Tyr Gln Ser Ile Glu
            275                 280                 285

AAG AAT GCC CAG ATA ACA CAG GGA GAT AAA AGT AGA AAA GAA CTC GGG        912
Lys Asn Ala Gln Ile Thr Gln Gly Asp Lys Ser Arg Lys Glu Leu Gly
290                 295                 300

TTG GGG ATC GAC TTA CTT TTG ACG TTC ATG GAA GCA GTG AAC AAG AAG        960
Leu Gly Ile Asp Leu Leu Leu Thr Phe Met Glu Ala Val Asn Lys Lys
305                 310                 315                 320

GCA CGT GTG GTT AAA AAC GAA GCT AGG TTT CTG CTT ATC GCT ATT CAA       1008
Ala Arg Val Val Lys Asn Glu Ala Arg Phe Leu Leu Ile Ala Ile Gln
                325                 330                 335

ATG ACA GCT GAG GTA GCA CGA TTT AGG TAC ATT CAA AAC TTG GTA ACT       1056
Met Thr Ala Glu Val Ala Arg Phe Arg Tyr Ile Gln Asn Leu Val Thr
            340                 345                 350

AAG AAC TTC CCC AAC AAG TTC GAC TCG GAT AAC AAG GTG ATT CAA TTT       1104
Lys Asn Phe Pro Asn Lys Phe Asp Ser Asp Asn Lys Val Ile Gln Phe
            355                 360                 365

GAA GTC AGC TGG CGT AAG ATT TCT ACG GCA ATA TAC GGG GAT GCC AAA       1152
Glu Val Ser Trp Arg Lys Ile Ser Thr Ala Ile Tyr Gly Asp Ala Lys
370                 375                 380

AAC GGC GTG TTT AAT AAA GAT TAT GAT TTC GGG TTT GGA AAA GTG AGG       1200
Asn Gly Val Phe Asn Lys Asp Tyr Asp Phe Gly Phe Gly Lys Val Arg
385                 390                 395                 400

CAG GTG AAG GAC TTG CAA ATG GGA CTC CTT ATG TAT TTG GGC AAA CCA       1248
Gln Val Lys Asp Leu Gln Met Gly Leu Leu Met Tyr Leu Gly Lys Pro
                405                 410                 415
```

```
AAG                                                                  1251
Lys (2) INFORMATION FOR SEQ ID NO: 75:

(i) SEQUENCE CHARACTERISTICS:
        (A) LENGTH: 1266 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..1266

(ix) FEATURE:
        (A) NAME/KEY: mat_peptide
        (B) LOCATION: 1..465
        (D) OTHER INFORMATION: /product= "bFGF"

(ix) FEATURE:
        (A) NAME/KEY: mat_peptide
        (B) LOCATION: 466..507
        (D) OTHER INFORMATION: /product= " (Gly4Ser)2 linker"

(ix) FEATURE:
        (A) NAME/KEY: mat_peptide
        (B) LOCATION: 508..1266
        (D) OTHER INFORMATION: /product= "Saporin"

(xi) SEQUENCE DESCRIPTION: SEQ ID NO: 75:

ATG GCA GCA GGA TCA ATA ACA ACA TTA CCC GCC TTG CCC GAG GAT GGC         48
Met Ala Ala Gly Ser Ile Thr Thr Leu Pro Ala Leu Pro Glu Asp Gly
 1               5                  10                  15

GGC AGC GGC GCC TTC CCG CCC GGC CAC TTC AAG GAC CCC AAG CGG CTG         96
Gly Ser Gly Ala Phe Pro Pro Gly His Phe Lys Asp Pro Lys Arg Leu
             20                  25                  30

TAC TGC AAA AAC GGG GGC TTC TTC CTG CGC ATC CAC CCC GAC GGC CGA        144
Tyr Cys Lys Asn Gly Gly Phe Phe Leu Arg Ile His Pro Asp Gly Arg
         35                  40                  45

GTT GAC GGG GTC CGG GAG AAG AGC GAC CCT CAC ATC AAG CTT CAA CTT        192
Val Asp Gly Val Arg Glu Lys Ser Asp Pro His Ile Lys Leu Gln Leu
     50                  55                  60

CAA GCA GAA GAG AGA GGA GTT GTG TCT ATC AAA GGA GTG TGT GCT AAC        240
Gln Ala Glu Glu Arg Gly Val Val Ser Ile Lys Gly Val Cys Ala Asn
 65                  70                  75                  80

CGT TAC CTG GCT ATG AAG GAA GAT GGA AGA TTA CTG GCT TCT AAA TGT        288
Arg Tyr Leu Ala Met Lys Glu Asp Gly Arg Leu Leu Ala Ser Lys Cys
                 85                  90                  95

GTT ACG GAT GAG TGT TTC TTT TTT GAA CGA TTG GAA TCT AAT AAC TAC        336
Val Thr Asp Glu Cys Phe Phe Phe Glu Arg Leu Glu Ser Asn Asn Tyr
            100                 105                 110

AAT ACT TAC CGG TCA AGG AAA TAC ACC AGT TGG TAT GTG GCA TTG AAA        384
Asn Thr Tyr Arg Ser Arg Lys Tyr Thr Ser Trp Tyr Val Ala Leu Lys
        115                 120                 125

CGA ACT GGG CAG TAT AAA CTT GGA TCC AAA ACA GGA CCT GGG CAG AAA        432
Arg Thr Gly Gln Tyr Lys Leu Gly Ser Lys Thr Gly Pro Gly Gln Lys
    130                 135                 140

GCT ATA CTT TTT CTT CCA ATG TCT GCT AAG AGC GCC ATG GGC GGC GGC        480
Ala Ile Leu Phe Leu Pro Met Ser Ala Lys Ser Ala Met Gly Gly Gly
145                 150                 155                 160

GGC TCT GGC GGC GGC GGC TCT GCC ATG GTC ACA TCA ATC ACA TTA GAT        528
Gly Ser Gly Gly Gly Gly Ser Ala Met Val Thr Ser Ile Thr Leu Asp
                165                 170                 175
```

```
CTA GTA AAT CCG ACC GCG GGT CAA TAC TCA TCT TTT GTG GAT AAA ATC        576
Leu Val Asn Pro Thr Ala Gly Gln Tyr Ser Ser Phe Val Asp Lys Ile
            180                 185                 190

CGA AAC AAC GTA AAG GAT CCA AAC CTG AAA TAC GGT GGT ACC GAC ATA        624
Arg Asn Asn Val Lys Asp Pro Asn Leu Lys Tyr Gly Gly Thr Asp Ile
                195                 200                 205

GCC GTG ATA GGC CCA CCT TCT AAA GAA AAA TTC CTT AGA ATT AAT TTC        672
Ala Val Ile Gly Pro Pro Ser Lys Glu Lys Phe Leu Arg Ile Asn Phe
        210                 215                 220

CAA AGT TCC CGA GGA ACG GTC TCA CTT GGC CTA AAA CGC GAT AAC TTG        720
Gln Ser Ser Arg Gly Thr Val Ser Leu Gly Leu Lys Arg Asp Asn Leu
225                 230                 235                 240

TAT GTG GTC GCG TAT CTT GCA ATG GAT AAC ACG AAT GTT AAT CGG GCA        768
Tyr Val Val Ala Tyr Leu Ala Met Asp Asn Thr Asn Val Asn Arg Ala
                245                 250                 255

TAT TAC TTC AAA TCA GAA ATT ACT TCC GCC GAG TTA ACC GCC CTT TTC        816
Tyr Tyr Phe Lys Ser Glu Ile Thr Ser Ala Glu Leu Thr Ala Leu Phe
                260                 265                 270

CCA GAG GCC ACA ACT GCA AAT CAG AAA GCT TTA GAA TAC ACA GAA GAT        864
Pro Glu Ala Thr Thr Ala Asn Gln Lys Ala Leu Glu Tyr Thr Glu Asp
            275                 280                 285

TAT CAG TCG ATC GAA AAG AAT GCC CAG ATA ACA CAG GGA GAT AAA AGT        912
Tyr Gln Ser Ile Glu Lys Asn Ala Gln Ile Thr Gln Gly Asp Lys Ser
        290                 295                 300

AGA AAA GAA CTC GGG TTG GGG ATC GAC TTA CTT TTG ACG TTC ATG GAA        960
Arg Lys Glu Leu Gly Leu Gly Ile Asp Leu Leu Leu Thr Phe Met Glu
305                 310                 315                 320

GCA GTG AAC AAG AAG GCA CGT GTG GTT AAA AAC GAA GCT AGG TTT CTG       1008
Ala Val Asn Lys Lys Ala Arg Val Val Lys Asn Glu Ala Arg Phe Leu
                325                 330                 335

CTT ATC GCT ATT CAA ATG ACA GCT GAG GTA GCA CGA TTT AGG TAC ATT       1056
Leu Ile Ala Ile Gln Met Thr Ala Glu Val Ala Arg Phe Arg Tyr Ile
                340                 345                 350

CAA AAC TTG GTA ACT AAG AAC TTC CCC AAC AAG TTC GAC TCG GAT AAC       1104
Gln Asn Leu Val Thr Lys Asn Phe Pro Asn Lys Phe Asp Ser Asp Asn
            355                 360                 365

AAG GTG ATT CAA TTT GAA GTC AGC TGG CGT AAG ATT TCT ACG GCA ATA       1152
Lys Val Ile Gln Phe Glu Val Ser Trp Arg Lys Ile Ser Thr Ala Ile
        370                 375                 380

TAC GGG GAT GCC AAA AAC GGC GTG TTT AAT AAA GAT TAT GAT TTC GGG       1200
Tyr Gly Asp Ala Lys Asn Gly Val Phe Asn Lys Asp Tyr Asp Phe Gly
385                 390                 395                 400

TTT GGA AAA GTG AGG CAG GTG AAG GAC TTG CAA ATG GGA CTC CTT ATG       1248
Phe Gly Lys Val Arg Gln Val Lys Asp Leu Gln Met Gly Leu Leu Met
                405                 410                 415

TAT TTG GGC AAA CCA AAG                                                1266
Tyr Leu Gly Lys Pro Lys
            420

(2) INFORMATION FOR SEQ ID NO: 76:

(i) SEQUENCE CHARACTERISTICS:
        (A) LENGTH: 1320 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..1320
```

```
    (ix) FEATURE:
         (A) NAME/KEY: mat_peptide
         (B) LOCATION: 1..465
         (D) OTHER INFORMATION: /product= "bFGF"

(ix) FEATURE:
         (A) NAME/KEY: mat_peptide
         (B) LOCATION: 466..561
         (D) OTHER INFORMATION: /product= "Trypsin linker"

(ix) FEATURE:
         (A) NAME/KEY: mat_peptide
         (B) LOCATION: 562..1320
         (D) OTHER INFORMATION: /product= "Saporin"

(xi) SEQUENCE DESCRIPTION: SEQ ID NO: 76:
```

| | | | | | | | | | | | | | | | | |
|---|---|---|---|---|---|---|---|---|---|---|---|---|---|---|---|---|
| ATG | GCA | GCA | GGA | TCA | ATA | ACA | ACA | TTA | CCC | GCC | TTG | CCC | GAG | GAT | GGC | 48 |
| Met | Ala | Ala | Gly | Ser | Ile | Thr | Thr | Leu | Pro | Ala | Leu | Pro | Glu | Asp | Gly | |
| 1 | | | | 5 | | | | | 10 | | | | | 15 | | |
| GGC | AGC | GGC | GCC | TTC | CCG | CCC | GGC | CAC | TTC | AAG | GAC | CCC | AAG | CGG | CTG | 96 |
| Gly | Ser | Gly | Ala | Phe | Pro | Pro | Gly | His | Phe | Lys | Asp | Pro | Lys | Arg | Leu | |
| | | | 20 | | | | | 25 | | | | | 30 | | | |
| TAC | TGC | AAA | AAC | GGG | GGC | TTC | TTC | CTG | CGC | ATC | CAC | CCC | GAC | GGC | CGA | 144 |
| Tyr | Cys | Lys | Asn | Gly | Gly | Phe | Phe | Leu | Arg | Ile | His | Pro | Asp | Gly | Arg | |
| | | 35 | | | | | 40 | | | | | 45 | | | | |
| GTT | GAC | GGG | GTC | CGG | GAG | AAG | AGC | GAC | CCT | CAC | ATC | AAG | CTT | CAA | CTT | 192 |
| Val | Asp | Gly | Val | Arg | Glu | Lys | Ser | Asp | Pro | His | Ile | Lys | Leu | Gln | Leu | |
| | 50 | | | | | 55 | | | | | 60 | | | | | |
| CAA | GCA | GAA | GAG | AGA | GGA | GTT | GTG | TCT | ATC | AAA | GGA | GTG | TGT | GCT | AAC | 240 |
| Gln | Ala | Glu | Glu | Arg | Gly | Val | Val | Ser | Ile | Lys | Gly | Val | Cys | Ala | Asn | |
| 65 | | | | | 70 | | | | | 75 | | | | | 80 | |
| CGT | TAC | CTG | GCT | ATG | AAG | GAA | GAT | GGA | AGA | TTA | CTG | GCT | TCT | AAA | TGT | 288 |
| Arg | Tyr | Leu | Ala | Met | Lys | Glu | Asp | Gly | Arg | Leu | Leu | Ala | Ser | Lys | Cys | |
| | | | | 85 | | | | | 90 | | | | | 95 | | |
| GTT | ACG | GAT | GAG | TGT | TTC | TTT | TTT | GAA | CGA | TTG | GAA | TCT | AAT | AAC | TAC | 336 |
| Val | Thr | Asp | Glu | Cys | Phe | Phe | Phe | Glu | Arg | Leu | Glu | Ser | Asn | Asn | Tyr | |
| | | | 100 | | | | | 105 | | | | | 110 | | | |
| AAT | ACT | TAC | CGG | TCA | AGG | AAA | TAC | ACC | AGT | TGG | TAT | GTG | GCA | TTG | AAA | 384 |
| Asn | Thr | Tyr | Arg | Ser | Arg | Lys | Tyr | Thr | Ser | Trp | Tyr | Val | Ala | Leu | Lys | |
| | | 115 | | | | | 120 | | | | | 125 | | | | |
| CGA | ACT | GGG | CAG | TAT | AAA | CTT | GGA | TCC | AAA | ACA | GGA | CCT | GGG | CAG | AAA | 432 |
| Arg | Thr | Gly | Gln | Tyr | Lys | Leu | Gly | Ser | Lys | Thr | Gly | Pro | Gly | Gln | Lys | |
| | 130 | | | | | 135 | | | | | 140 | | | | | |
| GCT | ATA | CTT | TTT | CTT | CCA | ATG | TCT | GCT | AAG | AGC | GCC | ATG | GGC | CGA | TCG | 480 |
| Ala | Ile | Leu | Phe | Leu | Pro | Met | Ser | Ala | Lys | Ser | Ala | Met | Gly | Arg | Ser | |
| 145 | | | | | 150 | | | | | 155 | | | | | 160 | |
| GGC | GGT | GGG | TGC | GCT | GGT | AAT | AGA | GTC | AGA | AGA | TCA | GTC | GGA | AGC | AGC | 528 |
| Gly | Gly | Gly | Cys | Ala | Gly | Asn | Arg | Val | Arg | Arg | Ser | Val | Gly | Ser | Ser | |
| | | | | 165 | | | | | 170 | | | | | 175 | | |
| CTG | TCT | TGC | GGT | GGT | CTC | GAC | CTG | CAG | GCC | ATG | GTC | ACA | TCA | ATC | ACA | 576 |
| Leu | Ser | Cys | Gly | Gly | Leu | Asp | Leu | Gln | Ala | Met | Val | Thr | Ser | Ile | Thr | |
| | | | 180 | | | | | 185 | | | | | 190 | | | |
| TTA | GAT | CTA | GTA | AAT | CCG | ACC | GCG | GGT | CAA | TAC | TCA | TCT | TTT | GTG | GAT | 624 |
| Leu | Asp | Leu | Val | Asn | Pro | Thr | Ala | Gly | Gln | Tyr | Ser | Ser | Phe | Val | Asp | |
| | | 195 | | | | | 200 | | | | | 205 | | | | |
| AAA | ATC | CGA | AAC | AAC | GTA | AAG | GAT | CCA | AAC | CTG | AAA | TAC | GGT | GGT | ACC | 672 |
| Lys | Ile | Arg | Asn | Asn | Val | Lys | Asp | Pro | Asn | Leu | Lys | Tyr | Gly | Gly | Thr | |
| | 210 | | | | | 215 | | | | | 220 | | | | | |
| GAC | ATA | GCC | GTG | ATA | GGC | CCA | CCT | TCT | AAA | GAA | AAA | TTC | CTT | AGA | ATT | 720 |
| Asp | Ile | Ala | Val | Ile | Gly | Pro | Pro | Ser | Lys | Glu | Lys | Phe | Leu | Arg | Ile | |
| 225 | | | | | 230 | | | | | 235 | | | | | 240 | |
| AAT | TTC | CAA | AGT | TCC | CGA | GGA | ACG | GTC | TCA | CTT | GGC | CTA | AAA | CGC | GAT | 768 |

-continued

```
                Asn Phe Gln Ser Ser Arg Gly Thr Val Ser Leu Gly Leu Lys Arg Asp
                                245                 250                 255

AAC TTG TAT GTG GTC GCG TAT CTT GCA ATG GAT AAC ACG AAT GTT AAT        816
Asn Leu Tyr Val Val Ala Tyr Leu Ala Met Asp Asn Thr Asn Val Asn
            260                 265                 270

CGG GCA TAT TAC TTC AAA TCA GAA ATT ACT TCC GCC GAG TTA ACC GCC        864
Arg Ala Tyr Tyr Phe Lys Ser Glu Ile Thr Ser Ala Glu Leu Thr Ala
            275                 280                 285

CTT TTC CCA GAG GCC ACA ACT GCA AAT CAG AAA GCT TTA GAA TAC ACA        912
Leu Phe Pro Glu Ala Thr Thr Ala Asn Gln Lys Ala Leu Glu Tyr Thr
    290                 295                 300

GAA GAT TAT CAG TCG ATC GAA AAG AAT GCC CAG ATA ACA CAG GGA GAT        960
Glu Asp Tyr Gln Ser Ile Glu Lys Asn Ala Gln Ile Thr Gln Gly Asp
305                 310                 315                 320

AAA AGT AGA AAA GAA CTC GGG TTG GGG ATC GAC TTA CTT TTG ACG TTC       1008
Lys Ser Arg Lys Glu Leu Gly Leu Gly Ile Asp Leu Leu Leu Thr Phe
                325                 330                 335

ATG GAA GCA GTG AAC AAG AAG GCA CGT GTG GTT AAA AAC GAA GCT AGG       1056
Met Glu Ala Val Asn Lys Lys Ala Arg Val Val Lys Asn Glu Ala Arg
                340                 345                 350

TTT CTG CTT ATC GCT ATT CAA ATG ACA GCT GAG GTA GCA CGA TTT AGG       1104
Phe Leu Leu Ile Ala Ile Gln Met Thr Ala Glu Val Ala Arg Phe Arg
                355                 360                 365

TAC ATT CAA AAC TTG GTA ACT AAG AAC TTC CCC AAC AAG TTC GAC TCG       1152
Tyr Ile Gln Asn Leu Val Thr Lys Asn Phe Pro Asn Lys Phe Asp Ser
370                 375                 380

GAT AAC AAG GTG ATT CAA TTT GAA GTC AGC TGG CGT AAG ATT TCT ACG       1200
Asp Asn Lys Val Ile Gln Phe Glu Val Ser Trp Arg Lys Ile Ser Thr
385                 390                 395                 400

GCA ATA TAC GGG GAT GCC AAA AAC GGC GTG TTT AAT AAA GAT TAT GAT       1248
Ala Ile Tyr Gly Asp Ala Lys Asn Gly Val Phe Asn Lys Asp Tyr Asp
                405                 410                 415

TTC GGG TTT GGA AAA GTG AGG CAG GTG AAG GAC TTG CAA ATG GGA CTC       1296
Phe Gly Phe Gly Lys Val Arg Gln Val Lys Asp Leu Gln Met Gly Leu
                420                 425                 430

CTT ATG TAT TTG GGC AAA CCA AAG                                       1320
Leu Met Tyr Leu Gly Lys Pro Lys
            435                 440
```

(2) INFORMATION FOR SEQ ID NO: 77:

(i) SEQUENCE CHARACTERISTICS:
        (A) LENGTH: 1299 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..1299

(ix) FEATURE:
        (A) NAME/KEY: mat_peptide
        (B) LOCATION: 1..465
        (D) OTHER INFORMATION: /product= "bFGF"

(ix) FEATURE:
        (A) NAME/KEY: mat_peptide
        (B) LOCATION: 466..540
        (D) OTHER INFORMATION: /product= "(Ser4Gly)4linker"

(ix) FEATURE:
        (A) NAME/KEY: mat_peptide
        (B) LOCATION: 541..1299

(D) OTHER INFORMATION: /product= "Saporin"

(xi) SEQUENCE DESCRIPTION: SEQ ID NO: 77:

```
ATG GCA GCA GGA TCA ATA ACA ACA TTA CCC GCC TTG CCC GAG GAT GGC      48
Met Ala Ala Gly Ser Ile Thr Thr Leu Pro Ala Leu Pro Glu Asp Gly
 1               5                  10                  15

GGC AGC GGC GCC TTC CCG CCC GGC CAC TTC AAG GAC CCC AAG CGG CTG      96
Gly Ser Gly Ala Phe Pro Pro Gly His Phe Lys Asp Pro Lys Arg Leu
                20                  25                  30

TAC TGC AAA AAC GGG GGC TTC TTC CTG CGC ATC CAC CCC GAC GGC CGA     144
Tyr Cys Lys Asn Gly Gly Phe Phe Leu Arg Ile His Pro Asp Gly Arg
            35                  40                  45

GTT GAC GGG GTC CGG GAG AAG AGC GAC CCT CAC ATC AAG CTT CAA CTT     192
Val Asp Gly Val Arg Glu Lys Ser Asp Pro His Ile Lys Leu Gln Leu
 50                  55                  60

CAA GCA GAA GAG AGA GGA GTT GTG TCT ATC AAA GGA GTG TGT GCT AAC     240
Gln Ala Glu Glu Arg Gly Val Val Ser Ile Lys Gly Val Cys Ala Asn
 65                  70                  75                  80

CGT TAC CTG GCT ATG AAG GAA GAT GGA AGA TTA CTG GCT TCT AAA TGT     288
Arg Tyr Leu Ala Met Lys Glu Asp Gly Arg Leu Leu Ala Ser Lys Cys
                85                  90                  95

GTT ACG GAT GAG TGT TTC TTT TTT GAA CGA TTG GAA TCT AAT AAC TAC     336
Val Thr Asp Glu Cys Phe Phe Phe Glu Arg Leu Glu Ser Asn Asn Tyr
                100                 105                 110

AAT ACT TAC CGG TCA AGG AAA TAC ACC AGT TGG TAT GTG GCA TTG AAA     384
Asn Thr Tyr Arg Ser Arg Lys Tyr Thr Ser Trp Tyr Val Ala Leu Lys
            115                 120                 125

CGA ACT GGG CAG TAT AAA CTT GGA TCC AAA ACA GGA CCT GGG CAG AAA     432
Arg Thr Gly Gln Tyr Lys Leu Gly Ser Lys Thr Gly Pro Gly Gln Lys
        130                 135                 140

GCT ATA CTT TTT CTT CCA ATG TCT GCT AAG AGC GCC ATG GCC TCG TCG     480
Ala Ile Leu Phe Leu Pro Met Ser Ala Lys Ser Ala Met Ala Ser Ser
145                 150                 155                 160

TCG TCG GGC TCG TCG TCG TCG GGC TCG TCG TCG TCG GGC TCG TCG TCG     528
Ser Ser Gly Ser Ser Ser Ser Gly Ser Ser Ser Ser Gly Ser Ser Ser
                165                 170                 175

TCG GGC GCC ATG GTC ACA TCA ATC ACA TTA GAT CTA GTA AAT CCG ACC     576
Ser Gly Ala Met Val Thr Ser Ile Thr Leu Asp Leu Val Asn Pro Thr
                180                 185                 190

GCG GGT CAA TAC TCA TCT TTT GTG GAT AAA ATC CGA AAC AAC GTA AAG     624
Ala Gly Gln Tyr Ser Ser Phe Val Asp Lys Ile Arg Asn Asn Val Lys
            195                 200                 205

GAT CCA AAC CTG AAA TAC GGT GGT ACC GAC ATA GCC GTG ATA GGC CCA     672
Asp Pro Asn Leu Lys Tyr Gly Gly Thr Asp Ile Ala Val Ile Gly Pro
        210                 215                 220

CCT TCT AAA GAA AAA TTC CTT AGA ATT AAT TTC CAA AGT CCC GA GGA      720
Pro Ser Lys Glu Lys Phe Leu Arg Ile Asn Phe Gln Ser Ser Arg Gly
225                 230                 235                 240

ACG GTC TCA CTT GGC CTA AAA CGC GAT AAC TTG TAT GTG GTC GCG TAT     768
Thr Val Ser Leu Gly Leu Lys Arg Asp Asn Leu Tyr Val Val Ala Tyr
                245                 250                 255

CTT GCA ATG GAT AAC ACG AAT GTT AAT CGG GCA TAT TAC TTC AAA TCA     816
Leu Ala Met Asp Asn Thr Asn Val Asn Arg Ala Tyr Tyr Phe Lys Ser
                260                 265                 270

GAA ATT ACT TCC GCC GAG TTA ACC GCC CTT TTC CCA GAG GCC ACA ACT     864
Glu Ile Thr Ser Ala Glu Leu Thr Ala Leu Phe Pro Glu Ala Thr Thr
            275                 280                 285

GCA AAT CAG AAA GCT TTA GAA TAC ACA GAA GAT TAT CAG TCG ATC GAA     912
Ala Asn Gln Lys Ala Leu Glu Tyr Thr Glu Asp Tyr Gln Ser Ile Glu
        290                 295                 300
```

```
AAG AAT GCC CAG ATA ACA CAG GGA GAT AAA AGT AGA AAA GAA CTC GGG         960
Lys Asn Ala Gln Ile Thr Gln Gly Asp Lys Ser Arg Lys Glu Leu Gly
305                 310                 315                 320

TTG GGG ATC GAC TTA CTT TTG ACG TTC ATG GAA GCA GTG AAC AAG AAG        1008
Leu Gly Ile Asp Leu Leu Leu Thr Phe Met Glu Ala Val Asn Lys Lys
                325                 330                 335

GCA CGT GTG GTT AAA AAC GAA GCT AGG TTT CTG CTT ATC GCT ATT CAA        1056
Ala Arg Val Val Lys Asn Glu Ala Arg Phe Leu Leu Ile Ala Ile Gln
            340                 345                 350

ATG ACA GCT GAG GTA GCA CGA TTT AGG TAC ATT CAA AAC TTG GTA ACT        1104
Met Thr Ala Glu Val Ala Arg Phe Arg Tyr Ile Gln Asn Leu Val Thr
        355                 360                 365

AAG AAC TTC CCC AAC AAG TTC GAC TCG GAT AAC AAG GTG ATT CAA TTT        1152
Lys Asn Phe Pro Asn Lys Phe Asp Ser Asp Asn Lys Val Ile Gln Phe
    370                 375                 380

GAA GTC AGC TGG CGT AAG ATT TCT ACG GCA ATA TAC GGG GAT GCC AAA        1200
Glu Val Ser Trp Arg Lys Ile Ser Thr Ala Ile Tyr Gly Asp Ala Lys
385                 390                 395                 400

AAC GGC GTG TTT AAT AAA GAT TAT GAT TTC GGG TTT GGA AAA GTG AGG        1248
Asn Gly Val Phe Asn Lys Asp Tyr Asp Phe Gly Phe Gly Lys Val Arg
                405                 410                 415

CAG GTG AAG GAC TTG CAA ATG GGA CTC CTT ATG TAT TTG GGC AAA CCA        1296
Gln Val Lys Asp Leu Gln Met Gly Leu Leu Met Tyr Leu Gly Lys Pro
            420                 425                 430

AAG                                                                    1299
Lys
```

(2) INFORMATION FOR SEQ ID NO: 78:

(i) SEQUENCE CHARACTERISTICS:
        (A) LENGTH: 1269 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..1269

(ix) FEATURE:
        (A) NAME/KEY: mat_peptide
        (B) LOCATION: 1..465
        (D) OTHER INFORMATION: /product= "bFGF"

(ix) FEATURE:
        (A) NAME/KEY: mat_peptide
        (B) LOCATION: 466..510
        (D) OTHER INFORMATION: /product= "(Ser4Gly)2 linker"

(ix) FEATURE:
        (A) NAME/KEY: mat_peptide
        (B) LOCATION: 511..1269
        (D) OTHER INFORMATION: /product= "Saporin"

(xi) SEQUENCE DESCRIPTION: SEQ ID NO: 78:

```
ATG GCA GCA GGA TCA ATA ACA ACA TTA CCC GCC TTG CCC GAG GAT GGC          48
Met Ala Ala Gly Ser Ile Thr Thr Leu Pro Ala Leu Pro Glu Asp Gly
1               5                   10                  15

GGC AGC GGC GCC TTC CCG CCC GGC CAC TTC AAG GAC CCC AAG CGG CTG          96
Gly Ser Gly Ala Phe Pro Pro Gly His Phe Lys Asp Pro Lys Arg Leu
                20                  25                  30

TAC TGC AAA AAC GGG GGC TTC TTC CTG CGC ATC CAC CCC GAC GGC CGA         144
Tyr Cys Lys Asn Gly Gly Phe Phe Leu Arg Ile His Pro Asp Gly Arg
            35                  40                  45
```

```
GTT GAC GGG GTC CGG GAG AAG AGC GAC CCT CAC ATC AAG CTT CAA CTT      192
Val Asp Gly Val Arg Glu Lys Ser Asp Pro His Ile Lys Leu Gln Leu
 50                  55                  60

CAA GCA GAA GAG AGA GGA GTT GTG TCT ATC AAA GGA GTG TGT GCT AAC      240
Gln Ala Glu Glu Arg Gly Val Val Ser Ile Lys Gly Val Cys Ala Asn
 65                  70                  75                  80

CGT TAC CTG GCT ATG AAG GAA GAT GGA AGA TTA CTG GCT TCT AAA TGT      288
Arg Tyr Leu Ala Met Lys Glu Asp Gly Arg Leu Leu Ala Ser Lys Cys
                 85                  90                  95

GTT ACG GAT GAG TGT TTC TTT TTT GAA CGA TTG GAA TCT AAT AAC TAC      336
Val Thr Asp Glu Cys Phe Phe Phe Glu Arg Leu Glu Ser Asn Asn Tyr
                100                 105                 110

AAT ACT TAC CGG TCA AGG AAA TAC ACC AGT TGG TAT GTG GCA TTG AAA      384
Asn Thr Tyr Arg Ser Arg Lys Tyr Thr Ser Trp Tyr Val Ala Leu Lys
            115                 120                 125

CGA ACT GGG CAG TAT AAA CTT GGA TCC AAA ACA GGA CCT GGG CAG AAA      432
Arg Thr Gly Gln Tyr Lys Leu Gly Ser Lys Thr Gly Pro Gly Gln Lys
        130                 135                 140

GCT ATA CTT TTT CTT CCA ATG TCT GCT AAG AGC GCC ATG GCC TCG TCG      480
Ala Ile Leu Phe Leu Pro Met Ser Ala Lys Ser Ala Met Ala Ser Ser
145                 150                 155                 160

TCG TCG GGC TCG TCG TCG TCG GGC GCC ATG GTC ACA TCA ATC ACA TTA      528
Ser Ser Gly Ser Ser Ser Ser Gly Ala Met Val Thr Ser Ile Thr Leu
                165                 170                 175

GAT CTA GTA AAT CCG ACC GCG GGT CAA TAC TCA TCT TTT GTG GAT AAA      576
Asp Leu Val Asn Pro Thr Ala Gly Gln Tyr Ser Ser Phe Val Asp Lys
            180                 185                 190

ATC CGA AAC AAC GTA AAG GAT CCA AAC CTG AAA TAC GGT GGT ACC GAC      624
Ile Arg Asn Asn Val Lys Asp Pro Asn Leu Lys Tyr Gly Gly Thr Asp
        195                 200                 205

ATA GCC GTG ATA GGC CCA CCT TCT AAA GAA AAA TTC CTT AGA ATT AAT      672
Ile Ala Val Ile Gly Pro Pro Ser Lys Glu Lys Phe Leu Arg Ile Asn
210                 215                 220

TTC CAA AGT TCC CGA GGA ACG GTC TCA CTT GGC CTA AAA CGC GAT AAC      720
Phe Gln Ser Ser Arg Gly Thr Val Ser Leu Gly Leu Lys Arg Asp Asn
225                 230                 235                 240

TTG TAT GTG GTC GCG TAT CTT GCA ATG GAT AAC ACG AAT GTT AAT CGG      768
Leu Tyr Val Val Ala Tyr Leu Ala Met Asp Asn Thr Asn Val Asn Arg
                245                 250                 255

GCA TAT TAC TTC AAA TCA GAA ATT ACT TCC GCC GAG TTA ACC GCC CTT      816
Ala Tyr Tyr Phe Lys Ser Glu Ile Thr Ser Ala Glu Leu Thr Ala Leu
            260                 265                 270

TTC CCA GAG GCC ACA ACT GCA AAT CAG AAA GCT TTA GAA TAC ACA GAA      864
Phe Pro Glu Ala Thr Thr Ala Asn Gln Lys Ala Leu Glu Tyr Thr Glu
        275                 280                 285

GAT TAT CAG TCG ATC GAA AAG AAT GCC CAG ATA ACA CAG GGA GAT AAA      912
Asp Tyr Gln Ser Ile Glu Lys Asn Ala Gln Ile Thr Gln Gly Asp Lys
290                 295                 300

AGT AGA AAA GAA CTC GGG TTG GGG ATC GAC TTA CTT TTG ACG TTC ATG      960
Ser Arg Lys Glu Leu Gly Leu Gly Ile Asp Leu Leu Leu Thr Phe Met
305                 310                 315                 320

GAA GCA GTG AAC AAG AAG GCA CGT GTG GTT AAA AAC GAA GCT AGG TTT     1008
Glu Ala Val Asn Lys Lys Ala Arg Val Val Lys Asn Glu Ala Arg Phe
                325                 330                 335

CTG CTT ATC GCT ATT CAA ATG ACA GCT GAG GTA GCA CGA TTT AGG TAC     1056
Leu Leu Ile Ala Ile Gln Met Thr Ala Glu Val Ala Arg Phe Arg Tyr
            340                 345                 350

ATT CAA AAC TTG GTA ACT AAG AAC TTC CCC AAC AAG TTC GAC TCG GAT     1104
Ile Gln Asn Leu Val Thr Lys Asn Phe Pro Asn Lys Phe Asp Ser Asp
```

```
             355                 360                 365
AAC AAG GTG ATT CAA TTT GAA GTC AGC TGG CGT AAG ATT TCT ACG GCA     1152
Asn Lys Val Ile Gln Phe Glu Val Ser Trp Arg Lys Ile Ser Thr Ala
        370                 375                 380

ATA TAC GGG GAT GCC AAA AAC GGC GTG TTT AAT AAA GAT TAT GAT TTC     1200
Ile Tyr Gly Asp Ala Lys Asn Gly Val Phe Asn Lys Asp Tyr Asp Phe
385                 390                 395                 400

GGG TTT GGA AAA GTG AGG CAG GTG AAG GAC TTG CAA ATG GGA CTC CTT     1248
Gly Phe Gly Lys Val Arg Gln Val Lys Asp Leu Gln Met Gly Leu Leu
                405                 410                 415

ATG TAT TTG GGC AAA CCA AAG                                          1269
Met Tyr Leu Gly Lys Pro Lys
            420
```

(2) INFORMATION FOR SEQ ID NO: 79:

(i) SEQUENCE CHARACTERISTICS:
        (A) LENGTH: 765 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..762
        (D) OTHER INFORMATION: /product= "Mammalian codon
            optimized saporin"

(xi) SEQUENCE DESCRIPTION: SEQ ID NO: 79:

```
ATG GTG ACC TCC ATC ACC CTG GAC CTG GTG AAC CCC ACC GCC GGC CAG       48
Met Val Thr Ser Ile Thr Leu Asp Leu Val Asn Pro Thr Ala Gly Gln
1               5                   10                  15

TAC TCC TCC TTC GTG GAC AAG ATC CGC AAC AAC GTG AAG GAC CCC AAC       96
Tyr Ser Ser Phe Val Asp Lys Ile Arg Asn Asn Val Lys Asp Pro Asn
                20                  25                  30

CTG AAG TAC GGC GGC ACC GAC ATC GCC GTG ATC GGC CCC CCC TCC AAG      144
Leu Lys Tyr Gly Gly Thr Asp Ile Ala Val Ile Gly Pro Pro Ser Lys
            35                  40                  45

GAG AAG TTC CTG CGC ATC AAC TTC CAG TCC TCC CGC GGC ACC GTG TCC      192
Glu Lys Phe Leu Arg Ile Asn Phe Gln Ser Ser Arg Gly Thr Val Ser
        50                  55                  60

CTG GGC CTG AAG CGC GAC AAC CTG TAC GTG GTG GCC TAC CTG GCC ATG      240
Leu Gly Leu Lys Arg Asp Asn Leu Tyr Val Val Ala Tyr Leu Ala Met
65                  70                  75                  80

GAC AAC ACC AAC GTG AAC CGC GCC TAC TAC TTC AAG TCC GAG ATC ACC      288
Asp Asn Thr Asn Val Asn Arg Ala Tyr Tyr Phe Lys Ser Glu Ile Thr
                85                  90                  95

TCC GCC GAG CTG ACC GCC CTG TTC CCT GAG GCC ACC ACC GCC AAC CAG      336
Ser Ala Glu Leu Thr Ala Leu Phe Pro Glu Ala Thr Thr Ala Asn Gln
            100                 105                 110

AAG GCC CTG GAG TAC ACC GAG GAC TAC CAG TCC ATC GAG AAG AAC GCC      384
Lys Ala Leu Glu Tyr Thr Glu Asp Tyr Gln Ser Ile Glu Lys Asn Ala
        115                 120                 125

CAG ATC ACC CAG GGC GAC AAG TCC CGC AAG GAG CTC GGG CTG GGC ATC      432
Gln Ile Thr Gln Gly Asp Lys Ser Arg Lys Glu Leu Gly Leu Gly Ile
            130                 135                 140

GAC CTG CTG CTG ACC TTC ATG GAG GCC GTG AAC AAG AAG GCC CGC GTG      480
Asp Leu Leu Leu Thr Phe Met Glu Ala Val Asn Lys Lys Ala Arg Val
145                 150                 155                 160

GTG AAG AAC GAG GCC CGC TTC CTG CTG ATC GCC ATC CAG ATG ACC GCC      528
Val Lys Asn Glu Ala Arg Phe Leu Leu Ile Ala Ile Gln Met Thr Ala
                165                 170                 175
```

-continued

| | |
|---|---|
| GAG GTG GCC CGC TTC CGC TAC ATC CAG AAC CTG GTG ACC AAG AAC TTC<br>Glu Val Ala Arg Phe Arg Tyr Ile Gln Asn Leu Val Thr Lys Asn Phe<br>        180                          185                      190 | 576 |
| CCC AAC AAG TTC GAC TCC GAC AAC AAG GTG ATC CAG TTC GAG GTC AGC<br>Pro Asn Lys Phe Asp Ser Asp Asn Lys Val Ile Gln Phe Glu Val Ser<br>        195                          200                      205 | 624 |
| TGG CGC AAG ATC TCC ACC GCC ATC TAC GGC GAC GCC AAG AAC GGC GTG<br>Trp Arg Lys Ile Ser Thr Ala Ile Tyr Gly Asp Ala Lys Asn Gly Val<br>210                          215                      220 | 672 |
| TTC AAC AAG GAC TAC GAC TTC GGC TTC GGC AAG GTG CGC CAG GTG AAG<br>Phe Asn Lys Asp Tyr Asp Phe Gly Phe Gly Lys Val Arg Gln Val Lys<br>225                          230                      235                      240 | 720 |
| GAC CTG CAG ATG GGC CTG CTG ATG TAC CTG GGC AAG CCC AAG<br>Asp Leu Gln Met Gly Leu Leu Met Tyr Leu Gly Lys Pro Lys<br>                  245                          250 | 762 |
| TAG | 765 |

(2) INFORMATION FOR SEQ ID NO: 80:

(i) SEQUENCE CHARACTERISTICS:
        (A) LENGTH: 1233 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1230
        (D) OTHER INFORMATION: /product= "E. coli codon optimized
            FGF-SAP"

(xi) SEQUENCE DESCRIPTION: SEQ ID NO: 80:

| | |
|---|---|
| ATG GCA GCG GGT TCT ATT ACT ACC CTG CCG GCG CTG CCG GAG GAC GGC<br>Met Ala Ala Gly Ser Ile Thr Thr Leu Pro Ala Leu Pro Glu Asp Gly<br>255                          260                      265                      270 | 48 |
| GGT TCT GGC GCT TTC CCA CCG GGC CAC TTT AAG GAC CCG AAA CGC CTG<br>Gly Ser Gly Ala Phe Pro Pro Gly His Phe Lys Asp Pro Lys Arg Leu<br>        275                          280                      285 | 96 |
| TAT TGC AAA AAC GGT GGT TTT TTC CTG CGT ATC CAC CCG GAT GGC CGC<br>Tyr Cys Lys Asn Gly Gly Phe Phe Leu Arg Ile His Pro Asp Gly Arg<br>            290                      295                      300 | 144 |
| GTC GAT GGC GTC CGC GAA AAG TCT GAT CCG CAC ATC AAA CTG CAA TTG<br>Val Asp Gly Val Arg Glu Lys Ser Asp Pro His Ile Lys Leu Gln Leu<br>305                          310                      315 | 192 |
| CAA GCA GAG GAA CGC GGT GTT GTA AGC ATC AAG GGC GTT TGC GCG AAT<br>Gln Ala Glu Glu Arg Gly Val Val Ser Ile Lys Gly Val Cys Ala Asn<br>        320                          325                      330 | 240 |
| CGT TAC CTG GCG ATG AAA GAG GAT GGC CGC CTG CTG GCC TCC AAG TGT<br>Arg Tyr Leu Ala Met Lys Glu Asp Gly Arg Leu Leu Ala Ser Lys Cys<br>335                          340                      345                      350 | 288 |
| GTA ACC GAT GAA TGC TTC TTC TTT GAA CGT CTG GAG TCG AAC AAT TAT<br>Val Thr Asp Glu Cys Phe Phe Phe Glu Arg Leu Glu Ser Asn Asn Tyr<br>            355                        360                      365 | 336 |
| AAC ACC TAT CGT AGC CGT AAG TAC ACC TCG TGG TAC GTA GCA TTG AAA<br>Asn Thr Tyr Arg Ser Arg Lys Tyr Thr Ser Trp Tyr Val Ala Leu Lys<br>        370                          375                      380 | 384 |
| CGC ACC GGT CAG TAC AAA CTG GGT TCG AAG ACG GGT CCA GGT CAG AAA<br>Arg Thr Gly Gln Tyr Lys Leu Gly Ser Lys Thr Gly Pro Gly Gln Lys<br>385                          390                      395 | 432 |
| GCA ATT CTG TTC CTG CCA ATG TCG GCC AAA TCG GCC ATG GTC ACT TCT<br>Ala Ile Leu Phe Leu Pro Met Ser Ala Lys Ser Ala Met Val Thr Ser<br>        400                          405                      410 | 480 |

```
ATC ACG CTG GAT CTG GTC AAC CCG ACC GCT GGT CAG TAC AGC TCG TTT      528
Ile Thr Leu Asp Leu Val Asn Pro Thr Ala Gly Gln Tyr Ser Ser Phe
415                 420                 425                 430

GTC GAT AAG ATT CGT AAT AAT GTG AAA GAT CCG AAT TTA AAA TAC GGT      576
Val Asp Lys Ile Arg Asn Asn Val Lys Asp Pro Asn Leu Lys Tyr Gly
                435                 440                 445

GGC ACG GAT ATT GCA GTG ATT GGC CCG CCG TCT AAG GAA AAG TTC TTG      624
Gly Thr Asp Ile Ala Val Ile Gly Pro Pro Ser Lys Glu Lys Phe Leu
            450                 455                 460

CGT ATT AAC TTT CAA AGC TCT CGC GGC ACT GTG TCT CTG GGC TTA AAA      672
Arg Ile Asn Phe Gln Ser Ser Arg Gly Thr Val Ser Leu Gly Leu Lys
                465                 470                 475

CGC GAT AAT TTG TAC GTT GTA GCG TAC CTG GCG ATG GAT AAT ACC AAT      720
Arg Asp Asn Leu Tyr Val Val Ala Tyr Leu Ala Met Asp Asn Thr Asn
480                 485                 490

GTA AAC CGT GCT TAC TAT TTC AAA AGC GAA ATT ACC TCT GCT GAA CTG      768
Val Asn Arg Ala Tyr Tyr Phe Lys Ser Glu Ile Thr Ser Ala Glu Leu
495                 500                 505                 510

ACT GCA TTA TTC CCG GAA GCG ACT ACT GCC AAT CAG AAA GCC CTG GAA      816
Thr Ala Leu Phe Pro Glu Ala Thr Thr Ala Asn Gln Lys Ala Leu Glu
                515                 520                 525

TAT ACC GAA GAT TAT CAG TCG ATT GAA AAA AAC GCG CAA ATT ACC CAG      864
Tyr Thr Glu Asp Tyr Gln Ser Ile Glu Lys Asn Ala Gln Ile Thr Gln
            530                 535                 540

GGC GAC AAA TCG CGC AAA GAG TTG GGT CTG GGT ATT GAC CTG CTG CTG      912
Gly Asp Lys Ser Arg Lys Glu Leu Gly Leu Gly Ile Asp Leu Leu Leu
                545                 550                 555

ACG TTT ATG GAG GCG GTC AAC AAA AAA GCT CGT GTA GTG AAA AAC GAA      960
Thr Phe Met Glu Ala Val Asn Lys Lys Ala Arg Val Val Lys Asn Glu
560                 565                 570

GCT CGC TTT CTG CTG ATC GCT ATT CAA ATG ACT GCT GAA GTT GCT CGT     1008
Ala Arg Phe Leu Leu Ile Ala Ile Gln Met Thr Ala Glu Val Ala Arg
575                 580                 585                 590

TTC CGT TAC ATT CAG AAC TTG GTT ACT AAG AAC TTT CCG AAC AAA TTC     1056
Phe Arg Tyr Ile Gln Asn Leu Val Thr Lys Asn Phe Pro Asn Lys Phe
                595                 600                 605

GAC TCC GAT AAT AAG GTT ATT CAG TTC GAA GTG AGC TGG CGC AAG ATT     1104
Asp Ser Asp Asn Lys Val Ile Gln Phe Glu Val Ser Trp Arg Lys Ile
            610                 615                 620

TCG ACG GCT ATT TAT GGC GAT GCC AAA AAC GGC GTA TTT AAC AAA GAT     1152
Ser Thr Ala Ile Tyr Gly Asp Ala Lys Asn Gly Val Phe Asn Lys Asp
                625                 630                 635

TAT GAC TTC GGT TTT GGC AAG GTT CGT CAG GTG AAA GAT TTG CAG ATG     1200
Tyr Asp Phe Gly Phe Gly Lys Val Arg Gln Val Lys Asp Leu Gln Met
640                 645                 650

GGT CTG CTG ATG TAC TTG GGC AAG CCG AAA TAA                         1233
Gly Leu Leu Met Tyr Leu Gly Lys Pro Lys
655                 660
```

(2) INFORMATION FOR SEQ ID NO: 81:

(i) SEQUENCE CHARACTERISTICS:
        (A) LENGTH: 465 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..462
        (D) OTHER INFORMATION: /product= "FGF 2 - Ile Mutation at
           Residue 116"

(xi) SEQUENCE DESCRIPTION: SEQ ID NO: 81:

```
ATG GCA GCA GGA TCA ATA ACA ACA TTA CCC GCC TTG CCC GAG GAT GGC      48
Met Ala Ala Gly Ser Ile Thr Thr Leu Pro Ala Leu Pro Glu Asp Gly
                415                 420                 425

GGC AGC GGC GCC TTC CCG CCC GGC CAC TTC AAG GAC CCC AAG CGG CTG      96
Gly Ser Gly Ala Phe Pro Pro Gly His Phe Lys Asp Pro Lys Arg Leu
                430                 435                 440

TAC TGC AAA AAC GGG GGC TTC TTC CTG CGC CAC CCC GAC GGC CGA GTT     144
Tyr Cys Lys Asn Gly Gly Phe Phe Leu Arg His Pro Asp Gly Arg Val
                445                 450                 455

GAC GGG GTC CGG GAG AAG AGC GAC CCT CAC ATC AAG CTT CAA CTT CAA     192
Asp Gly Val Arg Glu Lys Ser Asp Pro His Ile Lys Leu Gln Leu Gln
                460                 465                 470

GCA GAA GAG AGA GGA GTT GTG TCT ATC AAA GGA GTG TGT GCT AAC CGT     240
Ala Glu Glu Arg Gly Val Val Ser Ile Lys Gly Val Cys Ala Asn Arg
475                 480                 485                 490

TAC CTG GCT ATG AAG GAA GAT GGA AGA TTA CTG GCT TCT AAA TGT GTT     288
Tyr Leu Ala Met Lys Glu Asp Gly Arg Leu Leu Ala Ser Lys Cys Val
                495                 500                 505

ACG GAT GAG TGT TTC TTT TTT GAA CGA TTG GAA TCT AAT AAC TAC AAT     336
Thr Asp Glu Cys Phe Phe Phe Glu Arg Leu Glu Ser Asn Asn Tyr Asn
                510                 515                 520

ACT TAC ATA TCA AGG AAA TAC ACC AGT TGG TAT GTG GCA TTG AAA CGA     384
Thr Tyr Ile Ser Arg Lys Tyr Thr Ser Trp Tyr Val Ala Leu Lys Arg
                525                 530                 535

ACT GGG CAG TAT AAA CTT GGA TCC AAA ACA GGA CCT GGG CAG AAA GCT     432
Thr Gly Gln Tyr Lys Leu Gly Ser Lys Thr Gly Pro Gly Gln Lys Ala
                540                 545                 550

ATA CTT TTT CTT CCA ATG TCT GCT AAG AGC TAA                         465
Ile Leu Phe Leu Pro Met Ser Ala Lys Ser
555                 560
```

(2) INFORMATION FOR SEQ ID NO: 82:

(i) SEQUENCE CHARACTERISTICS:
        (A) LENGTH: 465 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..462
        (D) OTHER INFORMATION: /product= "FGF 2 - Glu Mutation at
            Residue 119"

(xi) SEQUENCE DESCRIPTION: SEQ ID NO: 82:

```
ATG GCA GCA GGA TCA ATA ACA ACA TTA CCC GCC TTG CCC GAG GAT GGC      48
Met Ala Ala Gly Ser Ile Thr Thr Leu Pro Ala Leu Pro Glu Asp Gly
155                 160                 165                 170

GGC AGC GGC GCC TTC CCG CCC GGC CAC TTC AAG GAC CCC AAG CGG CTG      96
Gly Ser Gly Ala Phe Pro Pro Gly His Phe Lys Asp Pro Lys Arg Leu
                175                 180                 185

TAC TGC AAA AAC GGG GGC TTC TTC CTG CGC CAC CCC GAC GGC CGA GTT     144
Tyr Cys Lys Asn Gly Gly Phe Phe Leu Arg His Pro Asp Gly Arg Val
                190                 195                 200

GAC GGG GTC CGG GAG AAG AGC GAC CCT CAC ATC AAG CTT CAA CTT CAA     192
Asp Gly Val Arg Glu Lys Ser Asp Pro His Ile Lys Leu Gln Leu Gln
                205                 210                 215

GCA GAA GAG AGA GGA GTT GTG TCT ATC AAA GGA GTG TGT GCT AAC CGT     240
Ala Glu Glu Arg Gly Val Val Ser Ile Lys Gly Val Cys Ala Asn Arg
                220                 225                 230
```

```
TAC CTG GCT ATG AAG GAA GAT GGA AGA TTA CTG GCT TCT AAA TGT GTT        288
Tyr Leu Ala Met Lys Glu Asp Gly Arg Leu Leu Ala Ser Lys Cys Val
235                 240                 245                 250

ACG GAT GAG TGT TTC TTT TTT GAA CGA TTG GAA TCT AAT AAC TAC AAT        336
Thr Asp Glu Cys Phe Phe Phe Glu Arg Leu Glu Ser Asn Asn Tyr Asn
                255                 260                 265

ACT TAC CGG TCA AGG GAA TAC ACC AGT TGG TAT GTG GCA TTG AAA CGA        384
Thr Tyr Arg Ser Arg Glu Tyr Thr Ser Trp Tyr Val Ala Leu Lys Arg
                270                 275                 280

ACT GGG CAG TAT AAA CTT GGA TCC AAA ACA GGA CCT GGG CAG AAA GCT        432
Thr Gly Gln Tyr Lys Leu Gly Ser Lys Thr Gly Pro Gly Gln Lys Ala
                285                 290                 295

ATA CTT TTT CTT CCA ATG TCT GCT AAG AGC TAA                            465
Ile Leu Phe Leu Pro Met Ser Ala Lys Ser
300                 305
```

(2) INFORMATION FOR SEQ ID NO: 83:

(i) SEQUENCE CHARACTERISTICS:
        (A) LENGTH: 465 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..462
        (D) OTHER INFORMATION: /product= "FGF 2 - Ala Mutation at
            Residue 120"

(xi) SEQUENCE DESCRIPTION: SEQ ID NO: 83:

```
ATG GCA GCA GGA TCA ATA ACA ACA TTA CCC GCC TTG CCC GAG GAT GGC         48
Met Ala Ala Gly Ser Ile Thr Thr Leu Pro Ala Leu Pro Glu Asp Gly
155                 160                 165                 170

GGC AGC GGC GCC TTC CCG CCC GGC CAC TTC AAG GAC CCC AAG CGG CTG         96
Gly Ser Gly Ala Phe Pro Pro Gly His Phe Lys Asp Pro Lys Arg Leu
                175                 180                 185

TAC TGC AAA AAC GGG GGC TTC TTC CTG CGC CAC CCC GAC GGC CGA GTT        144
Tyr Cys Lys Asn Gly Gly Phe Phe Leu Arg His Pro Asp Gly Arg Val
                190                 195                 200

GAC GGG GTC CGG GAG AAG AGC GAC CCT CAC ATC AAG CTT CAA CTT CAA        192
Asp Gly Val Arg Glu Lys Ser Asp Pro His Ile Lys Leu Gln Leu Gln
                205                 210                 215

GCA GAA GAG AGA GGA GTT GTG TCT ATC AAA GGA GTG TGT GCT AAC CGT        240
Ala Glu Glu Arg Gly Val Val Ser Ile Lys Gly Val Cys Ala Asn Arg
220                 225                 230

TAC CTG GCT ATG AAG GAA GAT GGA AGA TTA CTG GCT TCT AAA TGT GTT        288
Tyr Leu Ala Met Lys Glu Asp Gly Arg Leu Leu Ala Ser Lys Cys Val
235                 240                 245                 250

ACG GAT GAG TGT TTC TTT TTT GAA CGA TTG GAA TCT AAT AAC TAC AAT        336
Thr Asp Glu Cys Phe Phe Phe Glu Arg Leu Glu Ser Asn Asn Tyr Asn
                255                 260                 265

ACT TAC CGG TCA AGG AAA GCA ACC AGT TGG TAT GTG GCA TTG AAA CGA        384
Thr Tyr Arg Ser Arg Lys Ala Thr Ser Trp Tyr Val Ala Leu Lys Arg
                270                 275                 280

ACT GGG CAG TAT AAA CTT GGA TCC AAA ACA GGA CCT GGG CAG AAA GCT        432
Thr Gly Gln Tyr Lys Leu Gly Ser Lys Thr Gly Pro Gly Gln Lys Ala
                285                 290                 295

ATA CTT TTT CTT CCA ATG TCT GCT AAG AGC TAA                            465
Ile Leu Phe Leu Pro Met Ser Ala Lys Ser
300                 305
```

(2) INFORMATION FOR SEQ ID NO: 84:

(i) SEQUENCE CHARACTERISTICS:
    (A) LENGTH: 465 base pairs
    (B) TYPE: nucleic acid
    (C) STRANDEDNESS: single
    (D) TOPOLOGY: linear (ix) FEATURE:
    (A) NAME/KEY: CDS
    (B) LOCATION: 1..462
    (D) OTHER INFORMATION: /product= "FGF 2 - Trp Mutation at
        Residue 123"

(xi) SEQUENCE DESCRIPTION: SEQ ID NO: 84:

```
ATG GCA GCA GGA TCA ATA ACA ACA TTA CCC GCC TTG CCC GAG GAT GGC      48
Met Ala Ala Gly Ser Ile Thr Thr Leu Pro Ala Leu Pro Glu Asp Gly
155             160             165             170

GGC AGC GGC GCC TTC CCG CCC GGC CAC TTC AAG GAC CCC AAG CGG CTG      96
Gly Ser Gly Ala Phe Pro Pro Gly His Phe Lys Asp Pro Lys Arg Leu
            175             180             185

TAC TGC AAA AAC GGG GGC TTC TTC CTG CGC CAC CCC GAC GGC CGA GTT     144
Tyr Cys Lys Asn Gly Gly Phe Phe Leu Arg His Pro Asp Gly Arg Val
        190             195             200

GAC GGG GTC CGG GAG AAG AGC GAC CCT CAC ATC AAG CTT CAA CTT CAA     192
Asp Gly Val Arg Glu Lys Ser Asp Pro His Ile Lys Leu Gln Leu Gln
    205             210             215

GCA GAA GAG AGA GGA GTT GTG TCT ATC AAA GGA GTG TGT GCT AAC CGT     240
Ala Glu Glu Arg Gly Val Val Ser Ile Lys Gly Val Cys Ala Asn Arg
220             225             230

TAC CTG GCT ATG AAG GAA GAT GGA AGA TTA CTG GCT TCT AAA TGT GTT     288
Tyr Leu Ala Met Lys Glu Asp Gly Arg Leu Leu Ala Ser Lys Cys Val
235             240             245             250

ACG GAT GAG TGT TTC TTT TTT GAA CGA TTG GAA TCT AAT AAC TAC AAT     336
Thr Asp Glu Cys Phe Phe Phe Glu Arg Leu Glu Ser Asn Asn Tyr Asn
            255             260             265

ACT TAC CGG TCA AGG AAA TAC ACC AGT GCA TAT GTG GCA TTG AAA CGA     384
Thr Tyr Arg Ser Arg Lys Tyr Thr Ser Ala Tyr Val Ala Leu Lys Arg
        270             275             280

ACT GGG CAG TAT AAA CTT GGA TCC AAA ACA GGA CCT GGG CAG AAA GCT     432
Thr Gly Gln Tyr Lys Leu Gly Ser Lys Thr Gly Pro Gly Gln Lys Ala
    285             290             295

ATA CTT TTT CTT CCA ATG TCT GCT AAG AGC TAA                         465
Ile Leu Phe Leu Pro Met Ser Ala Lys Ser
300             305
```

(2) INFORMATION FOR SEQ ID NO: 85:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ix) FEATURE:
        (D) OTHER INFORMATION: /note= "Primer for Protamine"

(xi) SEQUENCE DESCRIPTION: SEQ ID NO: 85:

TACATGCCAT GGCCAGGTAC AGATGCTGTC GCAGCCAGAG CCGGAGCAGA TATTACCGCC      60

(2) INFORMATION FOR SEQ ID NO: 86:

(i) SEQUENCE CHARACTERISTICS:
        (A) LENGTH: 60 base pairs
        (B) TYPE: nucleic acid
        (C) STRANDEDNESS: single
        (D) TOPOLOGY: linear

```
    (ix) FEATURE:
         (D) OTHER INFORMATION: /note= "Primer for Protamine"

(xi) SEQUENCE DESCRIPTION: SEQ ID NO: 86:

GCAGCTCCGC CTCCTTCGTC TGCGACTTCT TTGTCTCTGG CGGTAATATC TGCTCCGGCT      60

(2) INFORMATION FOR SEQ ID NO: 87:

(i) SEQUENCE CHARACTERISTICS:
         (A) LENGTH: 60 base pairs
         (B) TYPE: nucleic acid
         (C) STRANDEDNESS: single
         (D) TOPOLOGY: linear (ix) FEATURE:
         (D) OTHER INFORMATION: /note= "Primer for Protamine"

(xi) SEQUENCE DESCRIPTION: SEQ ID NO: 87:

GACGAAGGAG GCGGAGCTGC CAGACACGGA GGAGAGCCAT GAGGTGCTGC CGCCCCAGGT      60

(2) INFORMATION FOR SEQ ID NO: 88:

(i) SEQUENCE CHARACTERISTICS:
         (A) LENGTH: 59 base pairs
         (B) TYPE: nucleic acid
         (C) STRANDEDNESS: single
         (D) TOPOLOGY: linear (ix) FEATURE:
         (D) OTHER INFORMATION: /note= "Primer for Protamine"

(xi) SEQUENCE DESCRIPTION: SEQ ID NO: 88:

ATATATCCTA GGTTAGTGTC TTCTACATCT CGGTCTGTAC CTGGGGCGGC AGCACCTCA       59

(2) INFORMATION FOR SEQ ID NO: 89:

(i) SEQUENCE CHARACTERISTICS:
         (A) LENGTH: 66 base pairs
         (B) TYPE: nucleic acid
         (C) STRANDEDNESS: single
         (D) TOPOLOGY: linear (ix) FEATURE:
         (D) OTHER INFORMATION: /note= "Primer for Mammalian Codon
               Preferred Saporin"

(xi) SEQUENCE DESCRIPTION: SEQ ID NO: 89:

CGTATCAGGC GGCCGCCGCC ATGGTGACCT CCATCACCCT GGACCTGGTG AACCCCACCG      60

CCGGCC                                                                66

(2) INFORMATION FOR SEQ ID NO: 90:

(i) SEQUENCE CHARACTERISTICS:
         (A) LENGTH: 69 base pairs
         (B) TYPE: nucleic acid
         (C) STRANDEDNESS: single
         (D) TOPOLOGY: linear (ix) FEATURE:
         (D) OTHER INFORMATION: /note= "Primer for Mammalian Codon
               Preferred Saporin"

(xi) SEQUENCE DESCRIPTION: SEQ ID NO: 90:

TTGGGGTCCT TCACGTTGTT GCGGATCTTG TCCACGAAGG AGGAGTACTG GCCGGCGGTG      60

GGGTTCACC                                                             69
```

(2) INFORMATION FOR SEQ ID NO: 91:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ix) FEATURE:
        (D) OTHER INFORMATION: /note= "Primer for Mammalian Codon
            Preferred Saporin"

(xi) SEQUENCE DESCRIPTION: SEQ ID NO: 91:

AACAACGTGA AGGACCCCAA CCTGAAGTAC GGCGGCACCG ACATCGCCGT GATCGGCCCC    60

CCCTC    65

(2) INFORMATION FOR SEQ ID NO: 92:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ix) FEATURE:
        (D) OTHER INFORMATION: /note= "Primer for Mammalian Codon
            Preferred Saporin"

(xi) SEQUENCE DESCRIPTION: SEQ ID NO: 92:

GTGCCGCGGG AGGACTGGAA GTTGATGCGC AGGAACTTCT CCTTGGAGGG GGGGCCGATC    60

ACGGC    65

(2) INFORMATION FOR SEQ ID NO: 93:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ix) FEATURE:
        (D) OTHER INFORMATION: /note= "Primer for Mammalian Codon
            Preferred Saporin"

(xi) SEQUENCE DESCRIPTION: SEQ ID NO: 93:

CTCCCGCGGC ACCGTGTCCC TGGGCCTGAA GCGCGACAAC CTGTACGTGG TGGCCTACCT    60

GGCCATGGAC AACAC    75

(2) INFORMATION FOR SEQ ID NO: 94:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ix) FEATURE:
        (D) OTHER INFORMATION: /note= "Primer for Mammalian Codon
            Preferred Saporin"

(xi) SEQUENCE DESCRIPTION: SEQ ID NO: 94:

GCGGTCAGCT CGGCGGAGGT GATCTCGGAC TTGAAGTAGT AGGCGCGGTT CACGTTGGTG    60

TTGTCCATGG CCAGGTA    77

(2) INFORMATION FOR SEQ ID NO: 95:

(i) SEQUENCE CHARACTERISTICS:

(A) LENGTH: 78 base pairs
        (B) TYPE: nucleic acid
        (C) STRANDEDNESS: single
        (D) TOPOLOGY: linear (ix) FEATURE:
        (D) OTHER INFORMATION: /note= "Primer for Mammalian Codon
            Preferred Saporin"

(xi) SEQUENCE DESCRIPTION: SEQ ID NO: 95:

GCCGAGCTGA CCGCCCTGTT CCCTGAGGCC ACCACCGCCA ACCAGAAGGC CCTGGAGTAC      60

ACCGAGGACT ACCAGTCC                                                    78

(2) INFORMATION FOR SEQ ID NO: 96:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: /note= "Primer for Mammalian Codon
            Preferred Saporin"

(xi) SEQUENCE DESCRIPTION: SEQ ID NO: 96:

AGCCCGAGCT CCTTGCGGGA CTTGTCGCCC TGGGTGATCT GGGCGTTCTT CTCGATGGAC      60

TGGTAGTCCT CGGTGT                                                      76

(2) INFORMATION FOR SEQ ID NO: 97:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ix) FEATURE:
        (D) OTHER INFORMATION: /note= "Primer for Mammalian Codon
            Preferred Saporin"

(xi) SEQUENCE DESCRIPTION: SEQ ID NO: 97:

TATAGAATTC CTCGGGCTGG GCATCGACCT GCTGCTGACC TTCATGGAGG CCGTGAACAA      60

GAAGGCCCGC GTGG                                                        74

(2) INFORMATION FOR SEQ ID NO: 98:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ix) FEATURE:
        (D) OTHER INFORMATION: /note= "Primer for Mammalian Codon
            Preferred Saporin"

(xi) SEQUENCE DESCRIPTION: SEQ ID NO: 98:

CGGCGGTCAT CTGGATGGCG ATCAGCAGGA AGCGGGCCTC GTTCTTCACC ACGCGGGCCT      60

TCTTGTTC                                                               68

(2) INFORMATION FOR SEQ ID NO: 99:

(i) SEQUENCE CHARACTERISTICS:
        (A) LENGTH: 70 base pairs
        (B) TYPE: nucleic acid
        (C) STRANDEDNESS: single (D) TOPOLOGY: linear (ix) FEATURE:
            (D) OTHER INFORMATION: /note= "Primer for Mammalian Codon
                Preferred Saporin"

(xi) SEQUENCE DESCRIPTION: SEQ ID NO: 99:

CGCCATCCAG ATGACCGCCG AGGTGGCCCG CTTCCGCTAC ATCCAGAACC TGGTGACCAA    60

GAACTTCCCC                                                          70

(2) INFORMATION FOR SEQ ID NO: 100:

(i) SEQUENCE CHARACTERISTICS:
            (A) LENGTH: 76 base pairs
            (B) TYPE: nucleic acid
            (C) STRANDEDNESS: single
            (D) TOPOLOGY: linear (ix) FEATURE:
            (D) OTHER INFORMATION: /note= "Primer for Mammalian Codon
                Preferred Saporin"

(xi) SEQUENCE DESCRIPTION: SEQ ID NO: 100:

GGCGGATCCC AGCTGACCTC GAACTGGATC ACCTTGTTGT CGGAGTCGAA CTTGTTGGGG    60

AAGTTCTTGG TCACCA                                                   76

(2) INFORMATION FOR SEQ ID NO: 101:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ix) FEATURE:
            (D) OTHER INFORMATION: /note= "Primer for Mammalian Codon
                Preferred Saporin"

(xi) SEQUENCE DESCRIPTION: SEQ ID NO: 101:

CCGGGATCCG TCAGCTGGCG CAAGATCTCC ACCGCCATCT ACGGCGACGC CAAGAACGGC    60

G                                                                   61

(2) INFORMATION FOR SEQ ID NO: 102:

(i) SEQUENCE CHARACTERISTICS:
            (A) LENGTH: 64 base pairs
            (B) TYPE: nucleic acid
            (C) STRANDEDNESS: single
            (D) TOPOLOGY: linear (ix) FEATURE:
            (D) OTHER INFORMATION: /note= "Primer for Mammalian Codon
                Preferred Saporin"

(xi) SEQUENCE DESCRIPTION: SEQ ID NO: 102:

GCACCTTGCC GAAGCCGAAG TCGTAGTCCT TGTTGAACAC GCCGTTCTTG GCGTCGCCGT    60

AGAT                                                                64

(2) INFORMATION FOR SEQ ID NO: 103:

(i) SEQUENCE CHARACTERISTICS:
            (A) LENGTH: 58 base pairs
            (B) TYPE: nucleic acid
            (C) STRANDEDNESS: single
            (D) TOPOLOGY: linear (ix) FEATURE:

(D) OTHER INFORMATION: /note= "Primer for Mammalian Codon
            Preferred Saporin"

(xi) SEQUENCE DESCRIPTION: SEQ ID NO: 103:

TTCGGCTTCG GCAAGGTGCG CCAGGTGAAG GACCTGCAGA TGGGCCTGCT GATGTACC         58

(2) INFORMATION FOR SEQ ID NO: 104:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ix) FEATURE:
        (D) OTHER INFORMATION: /note= "Primer for Mammalian Codon
            Preferred Saporin"

(xi) SEQUENCE DESCRIPTION: SEQ ID NO: 104:

TGAACGTGGC GGCCGCCTAC TTGGGCTTGC CCAGGTACAT CAGCAGGCCC AT               52

(2) INFORMATION FOR SEQ ID NO: 105:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: /note= "Primer for SAP-6"

(xi) SEQUENCE DESCRIPTION: SEQ ID NO: 105:

CATATGTGTG TCACATCAAT CACATTAGAT                                       30

(2) INFORMATION FOR SEQ ID NO: 106:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ix) FEATURE:
        (D) OTHER INFORMATION: /note= "Primer for SAP-6"

(xi) SEQUENCE DESCRIPTION: SEQ ID NO: 106:

CAGGTTTGGA TCCTTTACGT T                                                21

(2) INFORMATION FOR SEQ ID NO: 107:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 107:

TATATAGAAT TCGTAGACAA AGCTAATGCA CCAAAA                                 36

(2) INFORMATION FOR SEQ ID NO: 108:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 108:

TATATACTCG AGCACTGGGT GGTGTTCAGG GAAGCT                                  36

(2) INFORMATION FOR SEQ ID NO: 109:

(i) SEQUENCE CHARACTERISTICS:
        (A) LENGTH: 700 base pairs
        (B) TYPE: nucleic acid
        (C) STRANDEDNESS: single
        (D) TOPOLOGY: linear (xi) SEQUENCE DESCRIPTION: SEQ ID NO: 109:

GAATTCGTAG ACAAAGCTAA TGCACCAAAA AAATGAATGT AGTTATAGTA ATGCTAACAT         60

CCAAATTCCT CTTTGTAAGA CATAGGCCTG TCAACCTTGT CTCCATACTT CAATTCCTAT        120

TTCCACTCAC CTCCCTCAAG AACTTGATTT ATAAACAGTG TGCCTACCAT AAAATCATCA        180

CTCCCTCTAT GTATTTATAG ACGACTGAAG GAATATCTTT CTTCTTTGCA TGCTACCGTG        240

GTAGAAGGGT TTTAAAAGTC CGTGCTAGGC AGAGGCAGCC CTTTCTGCCC CTTTCTGTTC        300

TCAGTTTATT AGGAAATGGC CTGAAATTCC AGCATGATAG CAAGCTGGCA TCCTCTGTGG        360

AATGTGCAAA CCATGCCTGC ATCTGCCCAT TACCCTAGCT CAGTGTCTCT GGGCATTTCT        420

GCAGTTGTTC TGAAGGCTTG GCGTGTTTAT CTCCCACAGG CGGCTGAACC GCCTCCCGTT        480

TCATGAGCAG ACCAGTGGAA TGCAGTGGAA GAGACCCAGG CCTCCGGCCA CCCAGATTAG        540

AGAGTTTTGT GCTGAGGTCC CTATATGGTT GTGTTAGACT GAACGACAGG CTCAAGTCTG        600

TCTTTGCTCC TTGTTTGGGA AGCAAGTGGG AGGAGAGCAG GCCAAGGGGC TATATAACCC        660

TTCAGCTTTC AGCTTCCCTG AACACCACCC AGTGCTCGAG                             700

(2) INFORMATION FOR SEQ ID NO: 110:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (xi) SEQUENCE DESCRIPTION: SEQ ID NO: 110:

TATAGAATTC CTGTGTCTAA CGGGGGTGTG TGCTCTCCCT CCTCTGGCGA CCATGAGGAA         60

ACCCCCGGCA GGACAAGGTG                                                    80

(2) INFORMATION FOR SEQ ID NO: 111:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (xi) SEQUENCE DESCRIPTION: SEQ ID NO: 111:

CCTGCCCAGT GACTGGCAGA TGAGAAGCTC CATTGTCGCC CCAGGGAGTA TGGGGCACAG         60

GCGCCTCCTT GGGTTG                                                        76

(2) INFORMATION FOR SEQ ID NO: 112:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (xi) SEQUENCE DESCRIPTION: SEQ ID NO: 112:

ATCTGCCAGT CACTGGGCAG GGGCTACGTG CCAGGGACCA TGCTAGTTCT CTGCACACCT    60

TGTCCTGCCG GGGGTT    76

(2) INFORMATION FOR SEQ ID NO: 113:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO: 113:

TATAGGATCC TGGACTCAGC TGAGGCCCGC CTGGGCACCC TGGGGCTCCC GGGAGGCAGA    60

CAACCCAAGG AGGCGCCTGT G    81

(2) INFORMATION FOR SEQ ID NO: 114:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO: 114:

TATAGGATCC GGGCCTCAGC TGAGTCCAGG CCTCGGGGAC AGTCCGTGCA CGCTCCTGGG    60

GCTGGGGGCG GGC    73

(2) INFORMATION FOR SEQ ID NO: 115:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO: 115:

TTCATGAGCT CACGCCTTTC CAGAGAAATC CCTTAATGCC GCCATTCTGC TGGTGGCATA    60

TATAGGGAGG GCTCGGCCTT G    81

(2) INFORMATION FOR SEQ ID NO: 116:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO: 116:

GGAAAGGCGT GAGCTCATGA AGAAGGCTGC TCAGTCAGCA GAAACGTGGC TGGGACAAGT    60

GCCCGCCCCC AGCCCAGGA G    81

(2) INFORMATION FOR SEQ ID NO: 117:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (xi) SEQUENCE DESCRIPTION: SEQ ID NO: 117:

TATATACTCG AGCGGGGACC TGGAGGCTGG CAGGAGTCAG CGGGGCCTCT GGCAGCCAGT    60

GTGGAGCCAA GGCCGAGCCC TCCCTATA    88

(2) INFORMATION FOR SEQ ID NO: 118:

(i) SEQUENCE CHARACTERISTICS:
        (A) LENGTH: 462 base pairs
        (B) TYPE: nucleic acid
        (C) STRANDEDNESS: single
        (D) TOPOLOGY: linear (xi) SEQUENCE DESCRIPTION: SEQ ID NO: 118:

```
GAATTCCTGT GTCTAACGGG GGTGTGTGCT CTCCCTCCTC TGGCGACCAT GAGGAAACCC      60
CCGGCAGGAC AAGGTGTGCA GAGAACTAGC ATGGTCCCTG GCACGTAGCC CCTGCCCAGT     120
GACTGGCAGA TGAGAAGCTC CATTGTCGCC CCAGGGAGTA TGGGGCACAG GCGCCTCCTT     180
GGGTTGTCTG CCTCCCGGGA GCCCCAGGGT GCCCAGGCGG GCCTCAGCTG AGTCCAGGCC     240
TCGGGGACAG TCCGTGCACG CTCCTGGGGC TGGGGGCGGG CACTTGTCCC AGCCACGTTT     300
CTGCTGACTG AGCAGCCTTC TTCATGAGCT CACGCCTTTC CAGAGAAATC CCTTAATGCC     360
GCCATTCTGC TGGTGGCATA TATAGGGAGG GCTCGGCCTT GGCTCCACAC TGGCTGCCAG     420
AGGCCCCGCT GACTCCTGCC AGCCTCCAGG TCCCCGCTCG AG                        462
```

(2) INFORMATION FOR SEQ ID NO: 119:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 119:

```
ATTAATTATA GATCTCAGCT CTTAGCAGAC ATTGG                                 35
```

(2) INFORMATION FOR SEQ ID NO: 120:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 120:

```
GCTTGGGCAT ACATTCAATC AATTGTTATC                                       30
```

(2) INFORMATION FOR SEQ ID NO: 121:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO: 121:

```
CGTAATATGG TCTCAATATG TAAGTATTGT AGTTATTAGA                            40
```

(2) INFORMATION FOR SEQ ID NO: 122:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO: 122:

```
CGTAATATGG TCTCAATATC AAGGAAATAC ACCAGTTGG                             39
```

(2) INFORMATION FOR SEQ ID NO: 123:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 123:

CGGATATGGT CTCAGAATAC ACCAGTTGGT ATGTG         35

(2) INFORMATION FOR SEQ ID NO: 124:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 124:

CGTAATATGG TCTCAATTCC CTTGACCGGT AAGTATTG      38

(2) INFORMATION FOR SEQ ID NO: 125:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 125:

CGAATATGGT CTCAGCAACC AGTTGGTATG TGGCA         35

(2) INFORMATION FOR SEQ ID NO: 126:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 126:

CGTAACATGG TCTCATTGCT TTCCTTGACC GGTAAGT       37

(2) INFORMATION FOR SEQ ID NO: 127:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 127:

GCTATTAGGT CTCAGCATAT GTGGCATTGA AACGAAC       37

(2) INFORMATION FOR SEQ ID NO: 128:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 128:

CGAATTAGGT CTCAATGCAC TGGTGTATTT CCTTGACC      38

COMPOSITIONS CONTAINING NUCLEIC ACIDS AND LIGANDS FOR THERAPEUTIC TREATMENT

CROSS-REFERENCE TO RELATED APPLICATION

This application is a continuation of U.S. application Ser. No. 08/718,904, filed Sep. 24, 1996, which issued as U.S. Pat. No. 6,037,329 on Mar. 14, 2000; which is a continuation-in-part of U.S. application Ser. No. 08/441,979, filed May 16, 1995, now abandoned; which application is a continuation-in-part of U.S. application Ser. Nos. 08/213,446, filed Mar. 15, 1994, now abandoned; Ser. No. 08/213,447, filed Mar. 15, 1994, now abandoned; Ser. No. 08/297,961, filed Aug. 29, 1994, now abandoned; and Ser. No. 08/305,771, filed Sep. 13, 1994, now abandoned.

TECHNICAL FIELD

The present invention relates generally to the treatment of diseases, and more specifically, to the preparation and use of complexes containing receptor-binding internalized ligands NABD and cytocide-encoding agents to alter the function, gene expression, or viability of a cell in a therapeutic manner.

BACKGROUND OF THE INVENTION

A major goal of treatment of neoplastic diseases and hyperproliferative disorders is to ablate the abnormally growing cells while leaving normal cells untouched. Various methods are under development for providing treatment, but none provide the requisite degree of specificity.

One method of treatment is to provide toxins. Immunotoxins and cytotoxins are protein conjugates of toxin molecules with either antibodies or factors which bind to receptors on target cells. Three major problems may limit the usefulness of immunotoxins. First. the antibodies may react with more than one cell surface molecule, thereby effecting delivery to multiple cell types, possibly including normal cells. Second, even if the antibody is specific, the antibody reactive molecule may be present on normal cells. Third, the toxin molecule may be toxic to cells prior to delivery and internalization. Cytotoxins suffer from similar disadvantages of specificity and toxicity. Another limitation in the therapeutic use of immunotoxins and cytotoxins is the relatively low ratio of therapeutic to toxic dosage. Additionally, it may be difficult to direct sufficient concentrations of the toxin into the cytoplasm and intracellular compartments in which the agent can exert its desired activity.

Given these limitations, cytotoxic therapy has been attempted using viral vectors to deliver DNA encoding the toxins into cells. If eukaryotic viruses are used, such as the retroviruses currently in use, they may recombine with host DNA to produce infectious virus. Moreover, because retroviral vectors are often inactivated by the complement system, use in vivo is limited. Retroviral vectors also lack specificity in delivery; receptors for most viral vectors are present on a large fraction, if not all, cells. Thus, infection with such a viral vector will infect normal as well as abnormal cells. Because of this general infection mechanism, it is not desirable for the viral vector to directly encode a cytotoxic molecule.

While delivery of nucleic acids offers advantages over delivery of cytotoxic proteins such as reduced toxicity prior to internalization, there is a need for high specificity of delivery, which is currently unavailable with the present systems.

In view of the problems associated with gene therapy, there is a compelling need for improved treatments which are more effective and are not associated with such disadvantages. The present invention exploits the use of conjugates which have increased specificity and deliver higher amounts of nucleic acids to targeted cells, while providing other related advantages.

SUMMARY OF THE INVENTION

The present invention generally provides therapeutic compositions. In one aspect, the composition has the formula: receptor-binding internalized ligand—nucleic acid binding domain—cytocide-encoding agent. The receptor-binding internalized ligand is a polypeptide reactive with a cell surface receptor, the nucleic acid binding domain binds to a nucleic acid. the cytocide-encoding agent is a nucleic acid molecule encoding a cytocide and which binds to the nucleic acid binding domain, and the composition binds to the cell surface receptor and internalizes the cytocide-encoding agent in cells bearing the receptor. In another aspect, the composition has the formula: receptor-binding internalized ligand-nucleic acid binding domain-prodrug-encoding agent.

In certain embodiments, the receptor-binding internalized ligand is a polypeptide reactive with an FGF receptor, VEGF receptor, HBEGF receptor, or a cytokine. In other embodiments, the cytocide-encoding agent encodes a protein that inhibits protein synthesis and is preferably a ribosome inactivating protein, most preferably saporin. The protein is gelonin or diphtheria toxin in other embodiments. In other embodiments, the prodrug-encoding agent encodes HSV-thymidine kinase.

The nucleic acid binding domain is poly-L-lysine in one embodiment. In other embodiments, the nucleic acid binding domain is a transcription factor selected from the group consisting of helix-turn-helix motif proteins, homeodomain proteins, zinc finger motif proteins, steroid receptor proteins, leucine zipper motif proteins, helix-loop-helix motif proteins, and β-sheet motif proteins. In other embodiments, the nucleic acid binding domain binds nonspecifically to nucleic acids and is selected from the group consisting of poly-L-lysine, protamine, histone and spermine. In a preferred embodiment, the nucleic acid binding domain binds the coding region of a ribosome inactivating protein such as saporin. In another preferred embodiment, FGF is conjugated to poly-L-lysine.

In yet other embodiments, the cytocide-encoding agent contains a tissue-specific promoter, such as alpha-crystalline, gamma-crystalline, α-fetoprotein, CEA, prostate-specific antigen, erbB-2, tyrosinase, α-actin, c-myc, VEGF receptor, FGF receptor or cyclin D.

In another aspect, the composition also contains a linker. In various embodiments, the linker increases the flexibility of the conjugate and is $(Gly_m Ser_p)_n$, $(Ala\ Ala\ Pro\ Ala)_n$, wherein n is 1 to 6, m is 1 to 6 and p is 1 to 4, or the linker is a disulfide bond.

In yet another aspect, the composition has the formula: receptor-binding internalized ligand-cytocide encoding agent-nucleic acid binding domain, wherein the receptor-binding internalized ligand is conjugated to the cytocide-encoding agent, which is bound to the nucleic acid binding domain to form a complex.

In other aspects, the invention provides methods for preventing excessive cell proliferation in the anterior eye following surgery, treating corneal clouding following excimer laser surgery, preventing closure of a trabeculectomy, preventing pterygii recurrence, treating hyperproliferative diseases in the back of the eye, such as macular degeneration, diabetic retinopathy and proliferative virtreal retinopathy, treating smooth muscle cell hyperplasia after a wound healing response to a procedure, e.g., vein grafting, endarterectomies and arteriovenous shunts and treating cancer. In these aspects, an effective amount of the compositions described above are administered.

BRIEF DESCRIPTION OF THE DRAWINGS

FIG. 5 are photographs of toroid formation observed by electron microscopy. The upper panel shows an example of a toroid; the lower panel shows an incomplete toroid.

FIG. 9C are photographs of cells stained for β-gal activity following transfection of COS cells with (right panel) or without (left panel) endosome disruptive peptide and FGF2–K84–pSVβ-gal.

FIG. 17 is an X-gal stain of arterial tissue after delivery of β-gal under control of α-actin promoter or no promoter.

FIG. 18 is an antibody stain of arterial tissue after delivery of β-gal under control of α-actin promoter or no promoter.

FIG. 21 shows rumor weight at 48 and 72 hours after delivery of a complex containing DNA encoding β-gal or saporin under control of SV40 promoter or saporin without a promoter or excipient.

FIG. 23 shows SDS-PAGE and Western analysis of FGF mutants.

DETAILED DESCRIPTION OF THE INVENTION

Definitions

Figure 1:
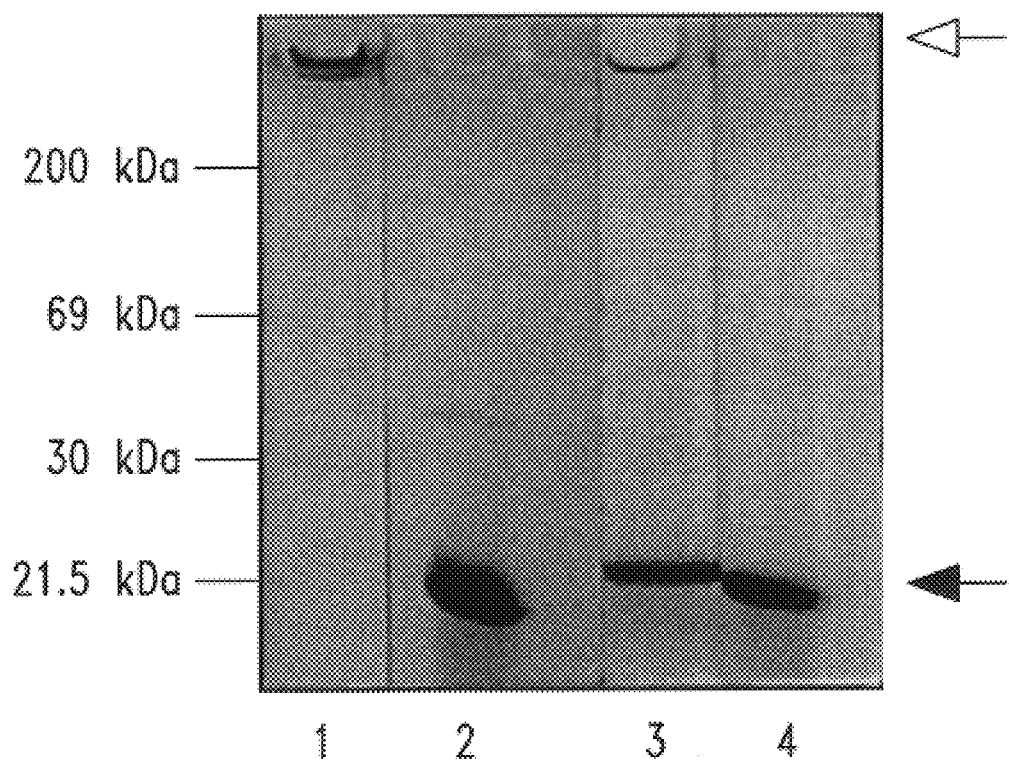
FIG. 1 is a photograph of an SDS-PAGE of FGF2–K152 under non-reducing (left) and reducing (right) conditions. Lane 1, FGF2–K152; lane 2, FGF2; lane 3, FGF2–K152: lane 4, FGF2. The open arrow identifies material unable to enter the gel. The closed arrow identifies a protein band corresponding to FGF2.

All U.S. patents and all publications mentioned herein are incorporated in their entirety by reference thereto.

The "amino acids," which occur in the various amino acid sequences appearing herein, are identified according to their well known, three letter or one letter abbreviations. The nucleotides, which occur in the various DNA fragments, are designated with the standard single letter designations used routinely in the art.

As used herein, to "bind to a receptor" refers to the ability of a ligand to specifically recognize and detectably bind to such receptors, as assayed by standard in vitro assays. For example, as used herein, binding measures the capacity of a VEGF conjugate, VEGF monomer, or VEGF dimer to recognize a VEGF receptor on a vascular endothelial cell, such as an aortic vascular endothelial cell line, using a procedure substantially as described in Moscatelli, *J. Cell Physiol.* 131:123–130, 1987.

As used herein, "biological activity" refers to the activities of a compound or physiological responses that result upon in vivo administration of a compound, composition or other mixture. Biological activity thus encompasses therapeutic effects and pharmaceutical activity of such compounds, compositions and mixtures. Such biological activity may be defined with reference to particular in vitro activities as measured in a defined assay. For example, within the context of this invention the biological activity of FGF, or fragments of FGF, refers to the ability of FGF to bind to cells bearing FGF receptors and internalize a linked agent. Such activity is typically assessed in vitro by linking the FGF to a cytotoxic agent, such as saporin, contacting cells bearing FGF receptors (e.g., fibroblasts), with the conjugate and assessing cell proliferation or growth. In vivo activity may be determined using recognized animal models, such as the mouse xenograft model for anti-tumor activity (see, e.g., Beitz et al., *Cancer Research* 52:227–230, 1992; Houghton et al., *Cancer Res.* 42:535–539, 1982; Bogden et al., *Cancer* (Philadelphia) 48:10–20, 1981; Hoogenhout et al., *Int. J. Radiat. Oncol., Biol. Phys.* 9:871–879, 1983; Stastny et al., *Cancer Res.* 53:5740–5744, 1993).

As used herein, the "biological activity of a cytocide-encoding agent," such as DNA encoding saporin, refers to the ability of the product to interfere with the metabolism of the cell by inhibiting protein synthesis. Such biological or cytotoxic activity may be assayed by any method known to those of skill in the art including, but not limited to, in vitro assays that measure protein synthesis and in vivo assays that assess cytotoxicity by measuring the effect on cell proliferation or on protein synthesis. Assays that assess cytotoxicity in targeted cells are particularly preferred.

As used herein, a "conjugate" refers to a molecule that contains at least one receptor-internalized binding ligand and at least one nucleic acid binding domain that are linked directly or via a linker and that are produced by chemical coupling methods or by recombinant expression of chimeric DNA molecules to produce fusion proteins.

A "cytocide-encoding agent" is a nucleic acid molecule that encodes a product that results in cell death and generally acts by inhibiting protein synthesis. Such a product may act by cleaving rRNA or ribonucloprotein, inhibiting an elongation factor, cleaving mRNA, or other mechanism that reduces protein synthesis to a level such that the cell cannot survive. The product may be a protein, ribozyme, antisense, and the like. The nucleic acid molecule may contain additional elements besides the cytocide gene. Such elements include a promoter, enhancer, splice site, transcription terminator, poly(A) signal sequence, bacterial or mammalian origin of replication, selection marker, and the like.

As used herein, the term "cytotoxic agent" refers to a molecule capable of inhibiting cell function. The agent may inhibit proliferation or may be toxic to cells. A variety of cytotoxic agents can be used and include those that inhibit protein synthesis and those that inhibit expression of certain genes essential for cellular growth or survival. Cytotoxic agents include those that result in cell death and those that inhibit cell growth, proliferation and/or differentiation.

As used herein, protein cytotoxic agents include, but are not limited to, saporin, the ricins, abrin and other ribosome inactivating proteins (RIPs), aquatic-derived cytotoxins, *Pseudomonas exotoxin*, inhibitors of DNA, RNA or protein synthesis, antisense nucleic acids, other metabolic inhibitors (e.g., DNA cleaving molecules), prodrugs (e.g., thymidine kinase from HSV and bacterial cytosine deaminase), and light-activated porphyrin. While saporin is the preferred RIP, other suitable RIPs include ricin, ricin A chain, maize RIP, gelonin, diphtheria toxin, diphtheria toxin A chain, trichosanthin, tritin, pokeweed antiviral protein (PAP), mirabilis antiviral protein (MAP), Dianthins 32 and 30, abrin, monordin, bryodin, shiga, a catalytic inhibitor of protein biosynthesis from cucumber seeds (see, e.g., WO 93/24620), *Pseudomonas exotoxin*, biologically active fragments of cytotoxins and others known to those of skill in this art. Suitable cytotoxic agents also include cytotoxic molecules that inhibit cellular metabolic processes, including transcription, translation, biosynthetic or degradative pathways, DNA synthesis, and other such processes that kill cells or inhibit cell proliferation.

"Heparin-binding growth factor" refers to any member of a family of heparin-binding growth factor proteins, in which at least one member of the family binds heparin. Preferred growth factors in this regard include FGF, VEGF, and HBEGF. Such growth factors encompass isoforms, peptide fragments derived from a family member, splice variants, and single or multiple exons, some forms of which may not bind heparin.

As used herein, to "hybridize" under conditions of a specified stringency is used to describe the stability of hybrids formed between two single-stranded nucleic acid molecules. Stringency of hybridization is typically expressed in conditions of ionic strength and temperature at which such hybrids are annealed and washed. Typically high, medium and low stringency encompass the following conditions or equivalent conditions thereto:

1) high stringency: 0.1×SSPE or SSC, 0.1% SDS, 65° C.
2) medium stringency: 0.2×SSPE or SSC, 0.1% SDS, 50° C.
3) low stringency: 1.0×SSPE or SSC, 0.1% SDS, 50° C.

"Nucleic acid binding domain" (NABD) refers to a molecule, usually a protein, polypeptide, or peptide (but may also be a polycation) that binds nucleic acids, such as DNA or RNA. The NABD may bind to single or double strands of RNA or DNA or mixed RNA/DNA hybrids. The nucleic acid binding domain may bind to a specific sequence or bind irrespective of the sequence.

As used herein, "nucleic acids" refer to RNA or DNA that are intended for internalization into a cell and includes, but are not limited to, DNA encoding a therapeutic protein, DNA encoding a cytotoxic protein, DNA encoding a prodrug, cytocide, ribozyme, or antisense the complement of these DNAs, an antisense nucleic acid, and other such molecules. Reference to nucleic acids includes duplex DNA, single-stranded DNA, RNA in any form, including triplex, duplex or single-stranded RNA, anti-sense RNA, polynucleotides, oligonucleotides, single nucleotides, chimeras, and derivatives thereof.

Nucleic acids may be composed of the well-known deoxyribonucleotides and ribonucleotides composed of the bases adenosine, cytosine, guanine, thymidine, and uridine. As well, various other nucleotide derivatives and non-phosphate backbones or phosphate-derivative backbones may be used. For example, because normal phosphodiester oligonucleotides (referred to as PO oligonucleotides) are sensitive to DNA- and RNA-specific nucleases, oligonucleotides resistant to cleavage, such as those in which the phosphate group has been altered to a phosphotriester, methylphosphonate, or phosphorothioate may be used (see U.S. Pat. No. 5,218,088).

As used herein, "operative linkage" or operative association of DNA encoding a product to regulatory and effector sequences of nucleotides, such as promoters, enhancers, transcriptional and translational stop sites, refers to the functional relationship between such DNA and such sequences of nucleotides. For example, operative linkage of DNA encoding a cytocide to a promoter refers to the physical and functional relationship between the DNA and the promoter such that transcription of the DNA is initiated from the promoter by an RNA polymerase that specifically recognizes, binds to and transcribes the DNA.

As used herein, the term "polypeptide reactive with an FGF receptor" refers to any polypeptide that specifically interacts with an FGF receptor, preferably the high-affinity FGF receptor, and that is transported into the cell by virtue of its interaction with the FGF receptor. Polypeptides reactive with an FGF receptor are also called FGF proteins. Such polypeptides include, but are not limited to, FGF-1 to FGF-9. For example, bFGF (FGF-2) should be generally understood to refer to polypeptides having substantially the same amino acid sequences and receptor-targeting activity as that of bovine bFGF or human bFGF. It is understood that differences in amino acid sequences can occur among FGFs of different species as well as among FGFs from individual organisms or species. In addition, chimeras or hybrids of any of FGF-1 through FGF-9, or FGFs that have deletions (see, e.g., PCT Application No. WO 90/02800), insertions or substitutions of amino acids are within the scope of FGF proteins, as long as the resulting peptide or protein specifically interacts with an FGF receptor and is internalized by virtue of this interaction.

As used herein, a "prodrug" is a compound that metabolizes or otherwise converts an inactive, nontoxic compound to a biologically, pharmaceutically, therapeutically, of toxic active form of the compound. A prodrug may also be a pharmaceutically inactive compound that is modified upon administration to yield an active compound through metabolic or other processes. The prodrug may alter the metabolic stability or the transport characteristics of a drug, mask side effects or toxicity, improve or alter other characteristics or properties of a drug. By virtue of knowledge of pharmacodynamic processes and drug metabolism in vivo, those of skill in this art, once a pharmaceutically active compound is known, can design inactive forms of the compound (see, e.g., Nogrady, *Medicinal Chemistry A Biochemical Approach*, Oxford University Press, New York, pages 388–392, 1985).

As used herein, "receptor-binding internalized ligand" or "ligand" refers to any peptide, polypeptide, protein or non-protein, such as a peptidomimetic, that is capable of binding to a cell-surface molecule and is internalized. Within the context of this invention, the receptor-binding internalized ligand is conjugated to a nucleic acid binding domain, either as a fusion protein or through chemical conjugation, and is used to deliver a cytocide-encoding or pro-drug encoding agent to a cell. In one aspect, the ligand is directly conjugated to a nucleic acid molecule, which may be further complexed with a nucleic acid binding domain. Such ligands include growth factors, cytokines, antibodies, hormones, and the like.

As used herein, "saporin" (abbreviated herein as SAP) refers to a polypeptide isolated from the leaves or seeds of *Saponaria officinalis*, as well as modified forms that have amino acid substitutions, deletions, insertions or additions, which express substantial ribosome inactivating activity. Purified preparations of saporin are frequently observed to include several molecular isoforms of the protein. It is understood that differences in amino acid sequences can occur in saporin from different species as well as between saporin molecules from individual organisms of the same species. Saporin for use herein may be purified from leaves, chemically synthesized, or synthesized by expression of DNA encoding a saporin polypeptide.

As used herein, a "targeted agent" is a nucleic acid molecule that is internally delivered to a cell by a receptor-binding internalized ligand, and that upon internalization in some manner alters or affects cellular metabolism, growth, activity, viability or other property or characteristic of the cell.

As used herein, a "therapeutic nucleic acid" describes any nucleic acid molecule used in the context of the invention that modifies gene transcription or translation. It includes, but is not limited to, the following types of nucleic acids: nucleic acids encoding a protein, antisense RNA, DNA intended to form triplex molecules, protein binding nucleic acids, and small nucleotide molecules. A therapeutic nucleic acid may be used to effect genetic therapy by serving as a replacement for a defective gene, by encoding a therapeutic product, such as TNF, or by encoding a cytotoxic molecule, especially an enzyme, such as saporin. The therapeutic nucleic acid may encode all or a portion of a gene, and may function by recombining with DNA already present in a cell, thereby replacing a defective portion of a gene. It may also encode a portion of a protein and exert its effect by virtue of co-suppression of a gene product.

PREPARATION OF RECEPTOR-BINDING INTERNALIZED LIGAND, NUCLEIC ACID BINDING DOMAIN AND CYTOCIDE-ENCODING AGENT COMPLEXES

As noted above, the present invention provides cytocide-encoding agents complexed with a conjugate of a receptor-binding internalized ligand and a nucleic acid binding domain. Upon binding to an appropriate receptor, the complex is internalized by the cell and trafficked through the cell via the endosomal compartment, where at least a portion of the complex may be cleaved.

A. Receptor-binding Internalized Ligands

As noted above, receptor-binding internalized ligands are used to deliver a cytocide-encoding agent to a cell expressing an appropriate receptor on its cell surface. Numerous molecules that bind specific receptors have been identified and are suitable for use in the present invention. Such molecules include growth factors, cytokines, and antibodies. Many growth factors and families of growth factors share structural and functional features and may be used in the present invention. One such family of growth factors specifically binds to heparin. The ability of heparin-binding growth factors to interact with heparin appears in general to be a reflection of a physiologically relevant interaction occurring in vivo between these factors and heparin sulfate proteoglycan molecules, which are found on the surface of cells and in extracellular matrix. Heparin-binding growth factors include fibroblast growth factors FGF-1 through FGF-9, vascular endothelial growth factor (VEGF), and heparin binding-epidermal growth factor (HBEGF). Antibodies that are specific to cell surface molecules expressed by a selected cell type are readily generated as monoclonals or polyclonal antisera. Many such antibodies are available (e.g., from American Type Culture Collection, Rockville, Md.). Other growth factors, such as PDGF (platelet-derived growth factor), EGF (epidermal growth factor), TGF-α (tumor growth factor), TGF-β, IGF-I (insulin-like growth factor), and IGF-II also bind to specific identified receptors on cell surfaces and may be used in the present invention. Cytokines, including interleukins, CSFs (colony stimulating factors), and interferons, have specific receptors, which are mostly found on hematopoeitic cells, and may be used as described herein. These ligands are discussed in more detail below.

Fragments of these ligands may be used within the present invention, so long as the fragment retains the ability to bind to the appropriate cell surface molecule. Likewise, ligands with substitutions or other alterations, but which retain binding ability, may also be used.

1. Fibroblast Growth Factors

One family of growth factors that has a broad spectrum of activities is the fibroblast growth factor (FGF) family. These proteins share the ability to bind to heparin, induce intracellular receptor-mediated tyrosine phosphorylation and the expression of the c-fos mRNA transcipt, and stimulate DNA synthesis and cell proliferation. This family of proteins includes FGFs designated FGF-1 (acidic FGF (aFGF)), FGF-2 (basic FGF (bFGF)), FGF-3 (int-2) (see, e.g., Moore et al., *EMBO J.* 5:919–924, 1986), FGF4 (hst-1/K-FGF) (see, e.g., Sakamoto et al., *Proc. Natl. Acad. Sci. USA* 86:1836–1840, 1986; U.S. Pat. No. 5,126,323), FGF-5 (see, e.g., U.S. Pat. No. 5,155,217), FGF-6 (hst-2) (see, e.g. published European Application EP 0 488 196 A2; Uda et al., *Oncogene* 7:303–309, 1992), FGF-7 (keratinocyte growth factor) (KGF) (see, e.g., Finch et al., *Science* 245:752–755, 1985; Rubin et al., *Proc. Natl. Acad Sci. USA* 86:802–806, 1989; and International Application WO 90/08771), FGF-8 (see, e.g., Tanaka et al., *Proc Natl. Acad. Sci. USA* 89:8528–8532, 1992); and FGF-9 (see, Miyamoto et al., *Mol. Cell. Biol.* 13:4251–4259, 1993).

DNA encoding FGF peptides and/or the amino acid sequences of FGFs are known to those of skill in the art. DNA encoding an FGF may be prepared synthetically based on a known amino acid or DNA sequence, isolated using methods known to those of skill in the art, or obtained from commercial or other sources. DNA encoding virtually all of the FGF family of peptides is known. For example, DNA encoding human FGF-1 (Jaye et al., *Science* 233:541–545, 1986; U.S. Pat. No. 5,223,483), bovine FGF-2 (Abraham et al., *Science* 233:545–548, 1986; Esch et al., *Proc. Natl. Acad. Sci. USA* 82:6507–6511, 1985; and U.S. Pat. No. 4,956,455), human FGF-2 (Abraham et al., *EMBO J.* 5:2523–2528, 1986; U.S. Pat. No. 4,994,559; U.S. Pat. No. 5,155,214; EP 470,183B; and Abraham et al., *Quant. Biol.* 51:657–668, 1986) and rat FGF-2 (see Shimasaki et al., *Biochem. Biophys. Res. Comm.*, 1988, and Kurokawa et al., *Nucleic Acids Res.* 16:5201, 1988), FGF-3, FGF-6, FGF-7 and FGF-9 are known (see also U.S. Pat. No. 5,155,214; U.S. Pat. No. 4,956,455; U.S. Pat. No. 5,026,839; U.S. Pat. No. 4,994,559, EP 0,488,196 A2, DNASTAR, EMBL or GenBank databases, and references discussed herein). Differences in amino acid sequences can occur among FGFs of different species as well as among FGFs from individual organisms or species. DNA encoding an FGF may differ from the above sequences by substitution of degenerate codons. Once the complete amino acid sequence of a peptide, such as an FGF peptide, and the DNA fragment encoding such peptide are available to those of skill in this art, it is routine to substitute degenerate codons and produce any of the possible DNA fragments that encode such peptide. It is also generally possible to synthesize DNA encoding such peptide based on the amino acid sequence. FGFs may be isolated from natural sources or made synthetically, such as by recombinant means or chemical synthesis.

Thus, as used herein, "FGF" refers to polypeptides having amino acid sequences of native FGF proteins, as well as modified sequences, having amino acid substitutions, deletions, insertions or additions in the native protein but retaining the ability to bind to FGF receptors and to be internalized.

FGF also encompasses muteins that possess the ability to bind to FGF-receptor expressing cells. Such muteins include, but are not limited to, those produced by replacing one or more of the cysteines with serine as described herein or that have any other amino acids deleted or replaced as long as the resulting protein has the ability to bind to FGF-receptor bearing cells and internalize the linked targeted agent. Typically, such muteins will have conservative amino acid changes, such as those set forth below. DNA encoding such muteins will, unless modified by replacement of degenerate codons, hybridize under conditions of at least low stringency to native DNA sequence encoding the starting FGF.

Acidic and basic FGF are about 55% identical at the amino acid level and are highly conserved among species. The other members of the FGF family have a high degree of amino acid sequence similarities and common physical and biological properties with FGF-1 and FGF-2, including the ability to bind to one or more FGF receptors. Basic FGF, int-2, hst-1/K-FGF, FGF-5, hst-2/FGF-6 and FGF-8 may have oncogenic potential; bFGF is expressed in melanomas, int-2 is expressed in mammary tumor virus and hst-1/K-FGF is expressed in angiogenic tumors. Acidic FGF, bFGF, KGF and FGF-9 are expressed in normal cells and tissues.

FGFs exhibit a mitogenic effect on a wide variety of mesenchymal, endocrine and neural cells and are also important in differentiation and development. Of particular interest is their stimulatory effect on collateral vascularization and angiogenesis. In some instances, FGF-induced mitogenic stimulation may be detrimental. For example, cell proliferation and angiogenesis are an integral aspect of tumor growth. Members of the FGF family, including bFGF, are thought to play a pathophysiological role, for example, in tumor development, rheumatoid arthritis, proliferative diabetic retinopathies and other complications of diabetes.

To reduce or eliminate mitogenesis, muteins of FGF are constructed as described below. Such muteins retain the ability to bind to high and low affinity receptors.

The effects of FGFs are mediated by high affinity receptor tyrosine kinases present on the cell surface of FGF-responsive cells (see, e.g., PCT WO 91/00916, WO 90/05522, PCT WO 92/12948; Imamura et al., *Biochem. Biophys. Res. Comm.* 155:583–590, 1988; Huang et al., *J. Biol. Chem.* 261:9568–9571, 1986; Partanen et al., *EMBO J.* 10:1347, 1991; and Moscatelli, *J. Cell. Physiol.* 131:123, 1987). Lower affinity receptors also appear to play a role in mediating FGF activities. The high affinity receptor proteins are single chain polypeptides with molecular weights ranging from 110 to 150 kD, depending on cell type that constitute a family of structurally related FGF receptors. Four FGF receptor genes have been identified, and three of these genes generate multiple mRNA transcripts via alternative splicing of the primary transcript. FGF-9 binds specifically to FGFR3, which is expressed in epithelial cells and cartilage rib bone. Epithelial cells exclusively express FGFR3IIIb, while mesenchymal cells express FGFR3IIIb as well as FGFR3IIIc.

2. Vascular Endothelial Growth Factors

Vascular endothelial growth factors (VEGFs) were identified by their ability to directly stimulate endothelial cell growth, but do not appear to have mitogenic effects on other types of cells. VEGFs also cause a rapid and reversible increase in blood vessel permeability. The members of this family have been referred to variously as vascular endothelial growth factor (VEGF), vascular permeability factor (VPF) and vasculotropin (see, e.g. Plouet et al., *EMBO J.* 8:3801–3806, 1989). Herein, they are collectively referred to as VEGF.

VEGF was originally isolated from a guinea pig hepto-carcinoma cell line, line 10 (see, e.g., U.S. Pat. No. 4,456,550), and has subsequently been identified in humans and in normal cells. It is expressed during normal development and in certain normal adult organs. Purified VEGF is a basic, heparin-binding, homodimeric glycoprotein that is heat-stable, acid-stable and may be inactivated by reducing agents.

DNA sequences encoding VEGF and methods to isolate these sequences may be found primarily in U.S. Pat. No. 5,240,848, U.S. Pat. No. 5,332,671, U.S. Pat. No. 5,219,739, U.S. Pat. No. 5,194,596, and Houch et al., *Mol. Endocrin.* 5:180, 1991. As used herein, "DNA encoding a VEGF peptide or polypeptide" refers to any of the DNA fragments set forth herein as coding such peptides, to DNA fragments known to those of skill in the art, and any DNA fragment that encodes a VEGF that binds to a VEGF receptor and is internalized thereby. VEGF DNA may be isolated from a human cell library, for example, using as a probe any of the VEGF DNA sequences set forth in SEQ ID NOs. 1–4 or in references cited herein. It is understood that once the complete amino acid sequence of a VEGF peptide, and the DNA sequence encoding such peptide is known degenerate codons may be substituted. It is also generally possible to synthesize DNA encoding such peptide based on the amino acid sequence.

VEGF family members arise from a single gene organized as eight exons and spanning approximately 14 kb in the human genome. Four molecular species of VEGF result from alternative splicing of mRNA and contain 121, 165, 189 and 206 amino acids. The four species have similar biological activities, but differ markedly in their secretion patterns. The predominant isoform secreted by a variety of normal and transformed cells is $VEGF_{165}$. Transcripts encoding $VEGF_{121}$ and $VEGF_{189}$ are detectable in most cells and tissues that express the VEGF gene. In contrast, $VEGF_{206}$ is less abundant and has been identified only in a human fetal liver cDNA library. $VEGF_{121}$ is a weakly acidic polypeptide that lacks the heparin binding domain and, consequently, does not bind to heparin. $VEGF_{189}$ and $VEGF_{206}$ are more basic than $VEGF_{165}$ and bind to heparin with greater affinity. Although not every identified VEGF isoform binds heparin, all isoforms are considered to be heparin-binding growth factors within the context of this invention.

The secreted isoforms, $VEGF_{121}$ and $VEGF_{165}$ are preferred VEGF proteins. The longer isoforms, $VEGF_{189}$ and $VEGF_{206}$, are almost completely bound to the extracellular matrix and need to be released by an agent, such as suramin, heparin or heparinase, or plasmin. Other preferred VEGF proteins contain various combinations of VEGF exons, such that the protein still binds VEGF receptor and is internalized. It is not necessary that a VEGF protein used in the context of this invention either retain any of its in vivo biological activities, such as stimulating endothelial cell growth, or bind heparin other than bind a VEGF receptor on a cell and be internalized. However, it may be desirable in certain contexts for VEGF to manifest certain of its biological activities. For example, if VEGF is used as a carrier for DNA encoding a molecule useful in wound healing, it would be desirable that VEGF exhibit vessel permeability activity and promotion of fibroblast migration and angiogenesis. It will be apparent from the teachings provided within the subject application which of the activities of VEGF are desirable to maintain.

VEGF promotes an array of responses in endothelium, including blood vessel hyperpermeability, endothelial cell growth, angiogenesis, and enhanced glucose transport. VEGF stimulates the growth of endothelial cells from a variety of sources (including brain capillaries, fetal and adult aortas, and umbilical veins) at low concentrations, but is reported to have no effect on the growth of vascular smooth muscle cells, adrenal cortex cells, keratinocytes, lens epithelial cells, or BHK-21 fibroblasts. VEGF also is a potent polypeptide regulator of blood vessel function; it causes a rapid but transient increase in microvascular permeability without causing endothelial cell damage or mast cell degranulation, and its action is not blocked by antihistamines. VEGF has also been reported to induce monocyte migration and activation and has been implicated as a tumor angiogenesis factor in some human gliomas. Also, VEGF is a chemoattractant for monocytes and VEGF has been shown to enhance the activity of the inflammatory mediator tumor necrosis factor (TNF).

Quiescent and proliferating endothelial cells bind VEGF with high-affinity, and endothelial cell responses to VEGF appear to be mediated by high affinity cell surface receptors (see, e.g., PCT Application WO 92/14748, U.S. application Ser. No. 08/657,236, de Vries et al., *Science* 255:989–91, 1992; Terman et al., *Biochem. Biophys. Res. Commun.* 187:1579–1586, 1992; Kendall et al., *Proc. Natl. Acad. Sci. USA* 90:10705–10709, 1993; and Peters et al., *Proc. Natl. Acad. Sci. USA* 90:8915–8919, 1993). Two tyrosine kinases have been identified as VEGF receptors. The first, known as fms-like tyrosine kinase or FLT is a receptor tyrosine kinase that is specific for VEGF. In adult and embryonic tissues, expression of FLT mRNA is localized to the endothelium and to populations of cells that give rise to endothelium. The second receptor, KDR (human kinase insert domain-containing receptor), and its mouse homologue FLK-1, are closely related to FLT. The KDR/FLK-1 receptor is expressed in endothelium during the fetal growth stage, during earlier stages of embryonic development, and in adult tissues. In addition, messenger RNA encoding FLT and KDR have been identified in rumor blood vessels and specifically by endothelial cells of blood vessels supplying glioblastomas. Similarly, FLT and KDR mRNAs are upregulated in tumor blood vessels in invasive human colon adenocarcinoma, but not in the blood vessels of adjacent normal tissues.

3. Heparin-binding Epidermal Growth Factors

Several new mitogens in the epidermal growth factor protein family have recently been identified that display the ability to bind the glycosaminoglycan heparin. Among these is the mitogen known as heparin-binding EGF-like growth factor HBEGF), which elutes from heparin-Sepharose™ columns at about 1.0–1.2 M NaCl and which was first identified as a secreted product of cultured human monocytes, macrophages, and the macrophage-like U-937 cell line (Higashiyama et al., *Science* 251:936–939, 1991; Besner et al., *Cell Regul.* 1:811–19, 1990). HBEGF has been shown to interact with the same high affinity receptors as EGF on bovine aortic smooth muscle cells and human A431 epidermoid carcinoma cells (Higashiyama, *Science* 251:936–939, 1991).

HBEGFs exhibit a mitogenic effect on a wide variety of cells including BALB/c 3T3 fibroblast cells and smooth muscle cells, but unlike VEGFs, are not mitogenic for endothelial cells (Higashiyama et al., *Science* 251:936–939, 1991). However, HBEGF has a stimulatory effect on collateral vascularization and angiogenesis. Members of the HBEGF family are thought to play a pathophysiological role, for example, in a variety of tumors, such as bladder carcinomas, breast tumors and non-small cell lung tumors. Thus, these cell types are likely candidates for delivery of cytocide-encoded agents.

HBEGF isolated from U-937 cells is heterogeneous in structure and contains at least 86 amino acids and two sites of O-linked glycosyl groups (Higashiyama et al., *J. Biol. Chem.* 267:6205–6212, 1992). The carboxyl-terminal half of the secreted HBEGF shares approximately 35% sequence identity with human EGF, including six cysteines spaced in the pattern characteristic of members of the EGF protein family. In contrast, the amino-terminal portion of the mature factor is characterized by stretches of hydrophilic residues and has no structural equivalent in EGF. Site-directed mutagenesis of HBEGF and studies with peptide fragments have indicated that the heparin-binding sequences of HBEGF reside primarily in a 21 amino acid stretch upstream of and slightly overlapping the EGF-like domain.

The effects of HBEGFs are mediated by EGF receptor tyrosine kinases expressed on cell surfaces of HBEGF-responsive cells (see, e.g., U.S. Pat. Nos. 5,183,884 and 5,218,090; and Ullrich et al., *Nature* 309:4113–425, 1984). The EGF receptor proteins, which are single chain polypeptides with molecular weights 170 kD, constitute a family of structurally related EGF receptors. Cells known to express the EGF receptors include smooth muscle cells, fibroblasts, keratinocytes, and numerous human cancer cell lines, such as the: A431 (epidermoid); KB3-1 (epidermoid); COLO 205 (colon); CRL 1739 (gastric); HEP G2 (hepatoma); LNCAP (prostate); MCF-7 (breast); MDA-MB-468 (breast); NCI 417D (lung); MG63 (osteosarcoma); U-251 (glioblastoma); D-54MB (glioma); and SW-13 (adrenal).

For the purposes of this invention, HBEGF need only bind a specific HBEGF receptor and be internalized. Any member of the HBEGF family, whether or not it binds heparin, is useful within the context of this invention as long as it meets the requirements set forth above. Members of the HBEGF family are those that have sufficient nucleotide identity to hybridize under normal stringency conditions (typically greater than 75% nucleotide identity). Subfragments or subportions of a full-length HBEGF may also be desirable. One skilled in the art may find from the teachings provided within that certain biological activities are more or less desirable, depending upon the application.

DNA encoding an HBEGF peptide or polypeptide refers to any DNA fragment encoding an HBEGF, as defined above. Exemplary DNA fragments include: any such DNA fragments known to those of skill in the art; any DNA fragment that encodes an HBEGF or fragment that binds to an HBEGF receptor and is internalized thereby; and any DNA fragment that encodes any of the HBEGF polypeptides set forth in SEQ ID NOs. 5–8. Such DNA sequences encoding HBEGF fragments are available from publicly accessible databases, such as: EMBL, GenBank (Accession Nos. M93012 (monkey) and M60278 (human)); the plasmid pMTN-HBEGF (ATCC #40900) and pAX-HBEGF (ATCC #40899) (described in PCT Application WO/92/06705); and Abraham et al., *Biochem. Biophys. Res. Comm.* 190:125–133, 1993). Unless modified by replacement of degenerate codons, DNA encoding HBEGF polypeptides will hybridize under conditions of at least low stringency to DNA encoding a native human HBEGF (e.g. SEQ ID NO. 9). In addition, DNA sequences with substitution of degenerate codons are also contemplated for use herein. It is when it is routine to substitute degenerate codons and produce any of the possible DNA fragments that encode such HBEGF polypeptides. It is also generally possible to synthesize DNA encoding such peptides based on the amino acid sequence.

4. Releasing Factors

In addition, various releasing factors may be used as ligands within the context of this invention. For example, growth hormone releasing factor (GRF or GHRH) (GenBank Accession No. X00094) binds pituitary cells that produce growth hormone. Corticotropin-releasing factor (CRF) binds via a CRF-receptor and causes release of ACTH. Thyroidtropin releasing hormone (GenBank Accession Nos. M63580, M58042, M160723, M63393; Yamada et al., *Mol. Endo.* 4:551, 1990) binds to TSH receptor to release TSH.

These ligands may be produced by recombinant or other means. For example, a nucleic acid molecule encoding one of these releasing factors may be synthesized by amplification using primers based on known DNA sequence. Appropriate restriction sites incorporated into the primers will facilitate cloning.

5. Other Receptor-binding Internalized Ligands

Other receptor-binding ligands may be used in the present invention. Any protein, polypeptide, analogue, or fragment that binds to a cell-surface receptor and is internalized may be used. In general, in addition to the specific heparin-binding growth factors discussed above, other growth factors and cytokines are especially well suited for use. These ligands may be produced by recombinant or other means in preparation for conjugation to the nucleic acid binding domain. The DNA sequences and methods to obtain the sequences of these receptor-binding internalized ligands are well known. For example, these ligands include CSF-1 (GenBank Accession Nos. M11038, M37435; Kawasaki et al., *Science* 230:291–296, 1985; Wong et al., *Science* 235:1504–1508, 1987); GM-CSF (GenBank Accession No. X0302 1; Miyatake et al., *EMBO J.* 4:2561–2568, 1985); IFN-α (interferon) (GenBank Accession No. A02076; Patent No. WO 8502862-A, Jul. 4, 1985); IFN-γ (GenBank Accession No. A02137; Patent No. WO 8502624-A, Jun. 20, 1985); hepatocyte growth factor (GenBank Accession No. X16323, S80567, X57574; Nakamura, et al., *Nature* 342:440–443, 1989; Nakamura et al., *Prog. Growth Factor Res.* 3:67–85, 1991; Miyazawa et al., *Eur. J. Biochem.* 197:15–22, 1991); IGF-Ia (Insulin-like growth factor Ia) (GenBank Accession No. X56773, S61841; Sandberg-Nordqvist et al., *Brain Res. Mol. Brain Res.* 12:275–277, 1992; Sandberg, Sandberg-Nordqvist et al., *Cancer Res.* 53:2475–2478, 1993); IGF-Ib (GenBank Accession No. X56774 S61860; Sandberg-Nordqvist et al., *Brain Res. Mol. Brain Res.* 12:275–277, 1992; Sandberg-Nordqvist, A. C., *Cancer Res.* 53:2475–2478, 1993); IGF-I (GenBank Accession No. X03563, N129644; Dull et al., *Nature* 310:771–781, 1984; Rall et al., *Meth. Enzymol.* 146:239–248, 1987); IGF-II (GenBank Accession No. J03242; Shen et al., *Proc. Natl. Acad. Sci. USA* 85:1947–1951, 1988); IL-1-α (interleukin 1 alpha) (GenBank Accession No. X02531, M15329; March et al., *Nature* 315:641–647, 1985; Nishida et al., *Biochem. Biophys. Res. Commun.* 143:345–352, 1987); IL-1-β (interleukin 1 beta) (GenBank Accession No. X02532, M15330, M15840; March et al., *Nature* 315:641–647, 1985; Nishida et al., *Biochem. Biophys. Res. Commun.* 143:345–352, 1987; Bensi et al., *Gene* 52:95–101, 1987); IL-1 (GenBank Accession No. K02770, M54933, M38756; Auron et al., *Proc. Natl. Acad. Sci. USA* 81:7907–7911, 1984; Webb et al., *Adv. Gene Technol.* 22:339–340, 1985); IL-2 (GenBank Accession No. A14844, A21785, X00695, X00200, X00201, X00202; Lupker et al., Patent No. EP 0307285-A, Mar. 15, 1989; Perez et al., Patent No. EP 0416673-A, Mar. 13, 1991; Holbrook et al., *Nucleic Acids Res.* 12:5005–5013, 1984; Degrave et al., *EMBO J.* 2:2349–2353, 1983; Taniguchi et al., *Nature* 302:305–310, 1983); IL-3 (GenBank Accession No. M14743, M20137; Yang et al., *Cell* 47:3–10, 1986; Otsuka et al., *J. Immunol.* 140:2288–2295, 1988); IL-4 (GenBank Accession No. M13982; Yokota et al., *Proc. Natl. Acad. Sci. USA* 83:5894–5898, 1986); IL-5 (GenBank Accession No. X04688, J03478; Azuma et al., *Nucleic Acids Res.* 14:9149–9158, 1986; Tanabe et al., *J. Biol. Chem.* 262:16580–16584, 1987); IL-6 (GenBank Accession No. Y00081, X04602, M54894, M38669, M14584; Yasukawa et al., *EMBO J.* 6:2939–2945, 1987; Hirano et al., *Nature* 324:73–76, 1986; Wong et al., *Behring Inst. Mitt.* 83:40–47, 1988; May et al., *Proc. Natl. Acad. Sci. USA* 83:8957–8961, 1986); IL-7 (GenBank Accession No. J04156; Goodwin et al., *Proc. Natl. Acad. Sci. USA* 86:302–306, 1989); IL-8 (GenBank Accession No. Z11686; Kusner et al., *Kidney Int.* 39:1240–1248, 1991); IL-10 (GenBank Accession No. X78437, M57627; Vieira et al., *Proc. Natl. Acad. Sci. USA* 88:1172–1176, 1991); IL-11 (GenBank Accession No. M57765 M37006; Paul et al., *Proc. Natl. Acad. Sci. USA* 87:7512–7516, 1990); IL-13 (GenBank Accession No. X69079, U10307; Minty et al., *Nature* 362:248–250, 1993; Smirnov, *Shemyakin and Ovchinnikov Institute of Bioorganic Chemistry*, Jun. 2, 1994); TNF-α (Tumor necrosis factor) (GenBank Accession No. A21522; Patent No. GB 2246569-A1, Feb. 5, 1992); TNF-β (GenBank Accession No. D12614; Matsuyama et al., *FEBS LETTERS* 302:141–144, 1992). DNA sequences of other suitable receptor-binding internalized ligands may be obtained from GenBank or EMBL DNA databases, reverse-synthesized from protein sequence obtained from PIR database or isolated by standard methods (Sambrook et al., supra) from cDNA or genomic libraries.

5. Modifications of Receptor-binding Internalized Ligands

These ligands may be customized for a particular application. Means for modifying proteins is provided below. Briefly, additions, substitutions and deletions of amino acids may be produced by any commonly employed recombinant DNA method.

An amino acid residue of a receptor-binding internalized ligand is non-essential if the polypeptide that has been modified by deletion of the residue possesses substantially the same ability to bind to its receptor and internalize a linked agent as the unmodified polypeptide.

As noted above, any polypeptide or peptide analogue, including peptidomimetics, that is reactive with an FGF receptor, a VEGF receptor, an HBEGF receptor, other growth factor receptor (e.g., PDGF receptor), cytokine receptor or other cell surface molecule including members of the families and fragments thereof, or constrained analogs of such peptides that bind to the receptor and internalize a linked targeted agent may be used in the context of this invention. Members of the FGF peptide family, including FGF-1 to FGF-9, are preferred. Modified peptides, especially those lacking proliferative function, and chimeric peptides, which retain the specific binding and internalizing activities are also contemplated for use herein.

A modification that is effected substantially near the N-terminus of a polypeptide is generally effected within the first about ten residues of the protein. Such modifications include the addition or deletion of residues, such as the addition of a cysteine to facilitate conjugation and form conjugates that contain a defined molar ratio, preferably a ratio of 1:1 of the polypeptides.

DNA encoding one of the receptor-binding internalized ligands discussed above may be mutagenized using standard methodologies to delete or replace any cysteine residues that are responsible for aggregate formation. If necessary, the identity of cysteine residues that contribute to aggregate formation may be determined empirically, by deleting and/ or replacing a cysteine residue and ascertaining whether the resulting protein aggregates in solutions containing physiologically acceptable buffers and salts. In addition, fragments of these receptor-binding internalized ligands may be constructed and used. The binding region of many of these ligands have been delineated. The receptor binding region of FGF2 has been identified by mutation analysis and FGF peptide agonists/antagonists to reside between residues 33–77 and between 102–129 of the 155 amino acid form (Baird et al., *PNAS* 85:2324; Erickson et al., *Biochem.* 88:3441). Exons 1–4 of VEGF are required for receptor binding; the C-terminal portion of HBEGF has been predicted to be involved in receptor binding. In addition to the C-terminal portion, loop A and loop C are required for binding. Mutation of either residue 42 (Arg) or residue 48 (Leu) abolish receptor binding. These two residues and the loop structure are conserved between EGF family members. Fragments may also be shown to bind and internalize by any one of the tests described herein.

Modification of the polypeptide may be effected by any means known to those of skill in this art. The preferred methods herein rely on modification of DNA encoding the polypeptide and expression of the modified DNA.

Merely by way of example, DNA encoding the FGF polypeptide may be isolated, synthesized or obtained from commercial sources (the amino acid sequences of FGF-1–FGF-9 are set forth in SEQ ID NOs. 10–18; DNA sequences may be based on these amino acid sequences or may be obtained from public DNA databases and references (see, e.g., GenBank, see also U.S. Pat. No. 4,956,455, U.S. Pat. No. 5,126,323, U.S. Pat. No. 5,155,217, U.S. Pat. No. 4,868,113, PCT Application WO 90/08771, EP Application 0 488 196 A2, and Miyamoto et al., *Mol. Cell. Biol.* 13:4251–4259, 1993). Expression of a recombinant FGF-2 protein in yeast and *E. coli* is described in Barr et al., *J. Biol. Chem.* 263:16471–16478, 1989, in PCT Application Serial No. PCT/US93/05702 and U.S. application Ser. No. 07/901, 718. Expression of recombinant FGF proteins may be performed as described herein or using methods known to those of skill in the art.

Similarly, DNA encoding any of the other receptor-binding internalized ligands, including VEGF, HBEGF, IL-1, IL-2, and other cytokines, GRH, CRF, TSH, and growth factors may also be isolated, synthesized, or obtained from commercial sources. As noted above, DNA sequences are available in public databases, such as GenBank. Based on these sequences, oligonucleotide primers may be designed and used to amplify the gene from cDNA or mRNA by polymerase chain reaction technique as one means of obtaining DNA.

Mutations may be made by any method known to those of skill in the art, including site-specific or site-directed mutagenesis of DNA encoding the protein and the use of DNA amplification methods using primers to introduce and amplify alterations in the DNA template, such as PCR splicing by overlap extension (SOE). Site-directed mutagenesis is typically effected using a phage vector that has single- and double-stranded forms, such as M13 phage vectors, which are well-known and commercially available. Other suitable vectors that contain a single-stranded phage origin of replication may be used (see, e.g., Veira et al., *Meth. Enzymol.* 15:3, 1987). In general, site-directed mutagenesis is performed by preparing a single-stranded vector that encodes the protein of interest (i.e., a member of the FGF family or a cytotoxic molecule, such as a saporin). An oligonucleotide primer that contains the desired mutation within a region of homology to the DNA in the single-stranded vector is annealed to the vector followed by addition of a DNA polymerase, such as *E. coli* DNA polymerase I (Klenow fragment), which uses the double stranded region as a primer to produce a heteroduplex in which one strand encodes the altered sequence and the other the original sequence. The heteroduplex is introduced into appropriate bacterial cells and clones that include the desired mutation are selected. The resulting altered DNA molecules may be expressed recombinantly in appropriate host cells to produce the modified protein.

Suitable conservative substitutions of amino acids are well-known and may be made generally without altering the biological activity of the resulting molecule. For example, such substitutions are generally made by interchanging within the groups of polar residues, charged residues, hydrophobic residues, small residues, and the like. If necessary, such substitutions may be determined empirically merely by testing the resulting modified protein for the ability to bind to and internalize upon binding to the appropriate receptors. Those that retain this ability are suitable for use in the conjugates and methods herein. In addition, muteins of the FGFs are known to those of skill in the art (see, e.g., U.S. Pat. No. 5,175,147; PCT Application No. WO 89/00198, U.S. Ser. No. 07/070,797; PCT Application No. WO 91/15229; and U.S. Ser. No. 07/505,124).

Binding to a ligand receptor followed by internalization are the only activities required for a ligand to be suitable for use herein. Many of the ligands are growth factors and cause mitogenesis. For example, all of the FGF proteins induce mitogenic activity in a wide variety of normal diploid mesoderm-derived and neural crest-derived cells and this activity is mediated by binding to an FGF cell surface receptor followed by internalization. A test of such "FGF mitogenic activity", which reflects the ability to bind to FGF receptors and to be internalized, is the ability to stimulate proliferation of cultured bovine aortic endothelial cells (see, e.g., Gospodarowicz et al., *J. Biol. Chem.* 257:12266–12278, 1982; Gospodarowicz et al., *Proc. Natl. Acad. Sci. USA* 73:4120–4124, 1976).

If the FGF or other growth factor ligand has been modified so as to lack mitogenic activity or other biological activities, binding and internalization may still be readily assayed by any one of the following tests or other equivalent tests. Generally, these tests involve labeling the ligand, incubating it with target cells, and visualizing or measuring intracellular label. For example, briefly, FGF may be fluorescently labeled with FITC or radiolabeled with $^{125}$I. Fluorescein-conjugated FGF is incubated with cells and examined microscopically by fluorescence microscopy or confocal microscopy for internalization. When FGF is labeled with $^{125}$I, the labeled FGF is incubated with cells at 4° C. Cells are temperature shifted to 37° C. and washed with 2 M NaCl at low pH to remove any cell-bound FGF. Label is then counted and thereby measuring internalization of FGF. Alternatively, the ligand can be conjugated with an nucleic acid binding domain by any of the methods described herein and complexed with a plasmid encoding saporin. As discussed below, the complex may be used to transfect cells and cytotoxicity measured.

B. Nucleic Acid Binding Domains

As previously noted, nucleic acid binding domains (NABD) interact with the target nucleic acid either in a sequence-specific manner or a sequence-nonspecific manner. When the interaction is non-specific, the nucleic acid binding domain binds nucleic acid regardless of the sequence. For example, poly-L-lysine is a basic polypeptide that binds to oppositely charged DNA. Other highly basic proteins or polycationic compounds, such as histones, protamines, and spermine and spermidine, also bind to nucleic acids in a nonspecific manner. In addition, $MnCl_2$ and cobalt hexamine also bind DNA and may serve to condense nucleic acid.

Many proteins have been identified that bind specific sequences of DNA. These proteins are responsible for genome replication, transcription and repair of damaged DNA. The transcription factors regulate gene expression and are a diverse group of proteins. These factors are especially well suited for purposes of the subject invention because of their sequence-specific recognition. Host transcription factors have been grouped into seven well-established classes based upon the structural motif used for recognition. The major families include helix-turn-helix (HTH) proteins, homeodomains, zinc finger proteins, steroid receptors, leucine zipper proteins, the helix-loop-helix (HLH) proteins, and β-sheets. Other classes or subclasses may eventually be delineated as more factors are discovered and defined. Proteins from those classes or proteins that do not fit within one of these classes but bind nucleic acid in a sequence-specific manner, such as SV40 T antigen and p53 may also be used.

These families of transcrption factors are generally well-known (see GenBank; Pabo and Sauer, *Ann. Rev. Biochem.* 61:1053–1095, 1992; and references below). Many of these factors are cloned and the precise DNA-binding region delineated in certain instances. When the sequence of the DNA-binding domain is known, a gene encoding it may be synthesized if the region is short. Alternatively, the genes may be cloned from the host genomic libraries or from cDNA libraries using oligonucleotides as probes or from genomic DNA or cDNA by polymerase chain reaction methods. Such methods may be found in Sambrook et al., supra.

Helix-turn-helix proteins include the well studied λ Cro protein, λcI, and *E. coli* CAP proteins (see Steitz et al., *Proc. Natl. Acad. Sci. USA* 79:3097–3100, 1982; Ohlendorf et al., *J. Mol. Biol.* 169:757–769, 1983). In addition, the lac repressor (Kaptein et al., *J. Mol. Biol.* 182:179–182, 1985) and Trp repressor (Scheritz et al., *Nature* 317:782–786, 1985) belong to this family. Members of the homeodomain family include the Drosophila protein Antennapaedia (Qian et al., *Cell.* 59:573–580, 1989) and yeast MATα2 (Wolberger et al., Cell. 67:517–528, 1991). Zinc finger proteins include TFIIIA (Miller et al., *EMBO J.* 4:1609–1614, 1985), Sp-1, zif268, and many others (see generally Krizek et al., *J. Am. Chem. Soc.* 113:4518–4523, 1991). Steroid receptor proteins include receptors for steroid hormones, retinoids, vitamin D, thyroid hormones, as well as other compounds. Specific examples include retinoic acid, knirps, progesterone, androgen, glucocosteroid and estrogen receptor proteins. The leucine zipper family was defined by a heptad repeat of leucines over a region of 30 to 40 residues. Specific members of this family include C/EBP, c-fos, c-jun, GCN4, sis-A, and CREB (see generally O'Shea et al., *Science* 254:539–544, 1991). The helix-loop-helix (HLH) family of proteins appears to have some similarities to the leucine zipper family. Well-known members of this family include myoD (Weintraub et al., *Science* 251:761–766, 1991); c-myc; and AP-2 (Williams and Tijan, *Science* 251:1067–1071, 1991). The β-sheet family uses an antiparallel β-sheet for DNA binding, rather than the more common α-helix. The family contains the MetJ (Phillips, *Curr. Opin. Struc. Biol.* 1:89–98, 1991), Arc (Breg et al., *Nature* 346:586–589, 1990) and Mnt repressors. In addition, other motifs are used for DNA binding, such as the cysteine-rich motif in yeast GAL4 repressor, and the GATA factor. Viruses also contain gene products that bind specific sequences. One of the most-studied such viral genes is the rev gene from HIV. The rev gene product binds a sequence called RRE (rev responsive element) found in the env gene. Other proteins or peptides that bind DNA may be discovered on the basis of sequence similarity to the known classes or functionally by selection.

Several techniques may be used to select other nucleic acid binding domains (see U.S. Pat. No. 5,270,170; PCT Application WO 93/14108; and U.S. Pat. No. 5,223,409). One of these techniques is phage display. (See, for example, U.S. Pat. No. 5,223,409.) In this method, DNA sequences are inserted into the gene III or gene VIII gene of a filamentous phage, such as M13. Several vectors with multicloning sites have been developed for insertion (McLafferty et al., *Gene* 128:29–36, 1993; Scott and Smith, *Science* 249:386–390, 1990; Smith and Scott, *Methods Enzymol.* 217:228–257, 1993). The inserted DNA sequences may be randomly generated or variants of a known DNA-binding domain. Generally, the inserts encode from 6 to 20 amino acids. The peptide encoded by the inserted sequence is displayed on the surface of the bacteriophage. Bacteriophage-expressing a desired nucleic acid-binding domain are selected for by binding to the cytocide-encoding agent. This target molecule may be single stranded or double stranded DNA or RNA. When the cytocide-encoding agent to be delivered is single-stranded, such as RNA, the appropriate target is single-stranded. When the molecule to be delivered is double-stranded, the target molecule is preferably double-stranded. Preferably, the entire coding region of the cytocide-encoding agent is used as the target. In addition, elements necessary for transcription that are included for in vivo or in vitro delivery may be present in the target DNA molecule. Bacteriophage that bind the target are recovered and propagated. Subsequent rounds of selection may be performed. The final selected bacteriophage are propagated and the DNA sequence of the insert is determined. Once the predicted amino acid sequence of the binding peptide is known, sufficient peptide for use herein as an nucleic acid binding domain may be made either by recombinant means or synthetically. Recombinant means is used when the receptor-binding internalized ligand/nucleic acid binding domain is produced as a fusion protein. In addition, the peptide may be generated as a tandem array of two or more peptides, in order to maximize affinity or binding of multiple DNA molecules to a single polypeptide.

As an example of the phage display selection technique, a DNA-binding domain/peptide that recognizes the coding region of saporin is isolated. Briefly, DNA fragments encoding saporin may be isolated from a plasmid containing these sequences. The plasmid FPFS1 contains the entire coding region of saporin. Digestion of the plasmid with NcoI and EcoRI restriction enzymes liberates the saporin specific sequence as a single fragment of approximately 780 bp. This fragment may be purified by any one of a number of methods, such as agarose gel electrophoresis and subsequent elution from the gel. The saporin fragment is fixed to a solid support, such as in the wells of a 96-well plate. If the double-stranded fragment does not bind well to the plate, a coating such as a positively charged molecule, may be used to promote DNA adherence. The phage library is added to the wells and an incubation period allows for binding of the phage to the DNA. Unbound phage are removed by a wash, typically containing 10 mM Tris, 1 mM EDTA, and without salt or with-a low salt concentration. Bound phage are eluted starting at a 0.1 M NaCl containing buffer. The NaCl concentration is increased in a step-wise fashion until all the phage are eluted. Typically, phage binding with higher affinity will only be released by higher salt concentrations.

Eluted phage are propagated in the bacteria host. Further rounds of selection may be performed to select for a few phage binding with high affinity. The DNA sequence of the insert in the binding phage is then determined. In addition, peptides having a higher affinity may be isolated by making variants of the insert sequence and subjecting these variants to further rounds of selection.

C. Cytocide-encoding Agents

A cytocide-encoding agent is a nucleic acid molecule (DNA or RNA) that, upon internalization by a cell, and subsequent transcription (if DNA) and[/or] translation into a cytocidal agent, is cytotoxic to a cell, for example by inhibiting cell growth by interfering with protein synthesis.

Cytocides include saporin, the ricins, abrin, gelonin, and other ribosome inactivating proteins, Pseudomonas exotoxin, diphtheria toxin, angiogenin, tritin, dianthins 32 and 30, momordin, pokeweed antiviral protein, mirabilis antiviral protein, bryodin, angiogenin, and shiga exotoxin, as well as other cytocides that are known to those of skill in the art. Alternatively, cytocide gene products may be noncytotoxic but activate a compound, which is endogenously produced or exogenously applied, from a nontoxic form to a toxic product that inhibits protein synthesis.

Also of interest are DNA molecules that encode an enzyme that results in cell death or renders a cell susceptible to cell death upon the addition of another product. For example, saporin is an enzyme that cleaves rRNA and inhibits protein synthesis. Other enzymes that inhibit protein synthesis are especially well suited for use in the present invention. In addition, enzymes may be used where the enzyme activates a compound with little or no cytotoxicity into a toxic product that inhibits protein synthesis.

Alternatively, the product may be a ribozyme, antisense, or other nucleic acid molecule that causes cell death.

1. Ribosome Inactivating Proteins

Ribosome-inactivating proteins (RIPs), which include ricin, abrin, and saporin, are plant proteins that catalytically inactivate eukaryotic ribosomes. Ribosome-inactivating proteins inactivate ribosomes by interfering with the protein elongation step of protein synthesis. For example, the ribosome-inactivating protein saporin (hereinafter also referred to as SAP) has been shown to inactivate 60S ribosomes by cleavage of the N-glycosidic bond of the adenine at position 4324 in the rat 28S ribosomal RNA (rRNA). The particular region in which $A_{4324}$ is located in the rRNA is highly conserved among prokaryotes and eukaryotes; $A_{4324}$ in 28S rRNA corresponds to $A_{2660}$ in *E. coli* 23S rRNA. Several of the ribosome inactivating proteins also appear to interfere with protein synthesis in prokaryotes, such as *E. coli*.

Of ribosome-inactivating proteins, saporin is preferred as a cytocide, but other suitable ribosome inactivating proteins (RIPs) and toxins may be used. Other suitable RIPs include, but are not limited to, ricin, ricin A chain, maize ribosome inactivating protein, gelonin, diphtheria toxin, diphtheria toxin A chain, trichosanthin, tritin, pokeweed antiviral protein (PAP), mirabilis antiviral protein (NMAP), Dianthins 32 and 30, abrin, monordin, bryodin, shiga (see, e.g., WO 93/24620) and others (see, e.g., Barbieri et al., *Cancer Surveys* 1:489–520, 1982, and European patent application No. 0466 222, incorporated herein by reference, which provide lists of numerous ribosome inactivating proteins and their sources; see also U.S. Pat. No. 5,248,608 to Walsh et al.). Some ribosome inactivating proteins, such as abrin and ricin, contain two constituent chains: a cell-binding chain that mediates binding to cell surface receptors and internalization of the molecule and a chain responsible for toxicity. Single chain ribosome inactivating proteins (type I RIPS), such as the saporins, do not have a cell-binding chain. As a result, unless internalized, they are substantially less toxic to whole cells than the ribosome inactivating proteins that have two chains.

Several structurally related ribosome inactivating proteins have been isolated from seeds and leaves of the plant *Saponaria officinalis* (soapwort) (GB Patent 2,194,241 B; GP Patent 2,216,891; EP Patent 89306016). Saporin proteins for use in this invention have amino acid sequences found in the natural plant host *Saponaria officinalis* or modified sequences, having amino acid substitutions, deletions, insertions or additions, but that still express substantial ribosome inactivating activity. Purified preparations of saporin are frequently observed to include several molecular isoforms of the protein. It is understood that differences in amino acid sequences can occur in saporin from different species as well as between saporin molecules from individual organisms of the same species. Among these, SO-6 is the most active and abundant, representing 7% of total seed proteins. Saporin is very stable, has a high isoelectric point, does not contain carbohydrates, and is resistant to denaturing agents, such as sodium dodecyl sulfate (SDS), and a variety of proteases. The amino acid sequences of several saporin-6 isoforms from seeds are known, and there appear to be families of saporin ribosome inactivating proteins differing in few amino acid residues. Any of these saporin proteins or modified proteins that are cytotoxic may be used in the present invention.

Some of the DNA molecules provided herein encode saporin that has substantially the same amino acid sequence and ribosome inactivating activity as that of saporin-6 (SO-6), including any of four known isoforms, which have heterogeneity at amino acid positions 48 and 91 (see, e.g., Maras et al., *Biochem. Internat.* 21:631–638, 1990, and Barra et al., *Biotechnol. Appl. Biochem.* 13:48–53, 1991; GB Patent 2,216,891 B and EP Patent 89306106; and SEQ ID NOs. 19–23). Other suitable saporin polypeptides include other members of the multi-gene family coding for isoforms of saporin-type ribosome inactivating proteins including SO-1 and SO-3 (Fordham-Skelton et al., *Mol. Gen. Genet.* 221:134–138, 1990), SO-2 (see, e.g., U.S. application Ser. No. 07/885,242; GB 2,216,891; see also Fordham-Skelton et al., *Mol. Gen. Genet.* 229:460–466, 1991), SO-4 (see, e.g., GB 2,194,241 B; see also Lappi et al., *Biochem. Biophys. Res. Commun.* 129:934–942, 1985) and SO-5 (see, e.g., GB 2,194,241 B; see also Montecucchi et al., *Int. J. Peptide Protein Res.* 33:263–267, 1989).

The saporin polypeptides for use in this invention include any of the isoforms of saporin that may be isolated from *Saponaria officinalis* or related species or modified forms that retain cytotoxic activity. In particular, such modified saporin may be produced by modifying the DNA encoding the protein (see, e.g., International PCT Application Serial No. PCT/US93/05702, and U.S. application Ser. No. 07/901, 718; see also U.S. patent application Ser. No. 07/885,242, and Italian Patent No. 1,231,914) by altering one or more amino acids or deleting or inserting one or more amino acids. Any such protein, or portion thereof, that exhibits cytotoxicity in standard in vitro or in vivo assays within at least about an order of magnitude of the saporin conjugates described herein is contemplated for use herein.

Preferably, the saporin DNA sequence contains mammalian-preferred codons (SEQ. ID NO. 79). Preferred codon usage as exemplified in *Current Protocols in Molecular Biology*, infra, and Zhang et al. (*Gene* 105:61, 1991) for mammals, yeast, Drosophila, *E. coli*, and primates is established for saporin sequence.

The cytocide-encoding agent, such as saporin DNA sequence, is introduced into a plasmid in operative linkage to an appropriate promoter for expression of polypeptides in the organism. The presently preferred saporin proteins are SO-6 and SO-4. The DNA can optionally include sequences, such as origins of replication that allow for the extrachromosomal maintenance of the saporin-containing plasmid, or can be designed to integrate into the genome of the host (as an alternative means to ensure stable maintenance in the host).

In addition to saporin discussed above, other cytocides that inhibit protein synthesis are useful in the present invention. The gene sequences for these cytocides may be isolated by standard methods, such as PCR, probe hybridization of genomic or cDNA libraries, antibody screenings of expression libraries, or clones may be obtained from commercial or other sources. The DNA sequences of many of these cytocides are well known, including ricin A chain (GenBank Accession No. X02388); maize ribosome inactivating protein (GenBank Accession No. L26305); gelonin (GenBank Accession No. L12243; PCT Application WO 92/03155; U.S. Pat. No. 5,376,546; diphtheria toxin (GenBank Accession No. K01722); trichosanthin (GenBank Accession No. M34858); tritin (GenBank Accession No. D13795); pokeweed antiviral protein (GenBank Accession No.

X78628); mirabilis antiviral protein (GenBank Accession No. D90347); dianthin 30 (GenBank Accession No. X59260); abrin (GenBank Accession No. X55667); shiga (GenBank Accession No. M19437) and Pseudomonas exotoxin (GenBank Accession Nos. K01397, M23348). When DNA sequences or amino acid sequences are known, DNA molecules encoding these proteins may be synthesized, and preferably contain mammalian-preferred codons.

D. Prodrug-encoding Agent

A nucleic acid molecule encoding a prodrug may alternatively be used within the context of the present invention. Prodrugs are inactive in the host cell until either a substrate is provided or an activating molecule is provided. Most typically, a prodrug activates a compound with little or no cytotoxicity into a toxic compound. Two of the more often used prodrug molecules, both of which may be used in the present invention, are HSV thymidine kinase and *E. coli* cytosine deaminase.

Briefly, a wide variety of gene products which either directly or indirectly activate a compound with little or no cytotoxicity into a toxic product may be utilized within the context of the present invention. Representative examples of such gene products include HSVTK (herpes simplex virus thymidine kinase) and VZVTK (varicella zoster virus thymidine kinase), which selectively phosphorylate certain purine arabinosides and substituted pyrimidine compounds. Phosphoryation converts these compounds to metabolites that are cytotoxic or cytostatic. For example, exposure of the drugs ganciclovir, acyclovir, or any of their analogues (e.g., FIAU, FIAC, DHPG) to cells expressing HSVTK allows conversion of the drug into its corresponding active nucleotide triphosphate form.

Other gene products that may be utilized within the context of the present invention include *E. coli* guanine phosphoribosyl transferase, which converts thioxanthine into toxic thioxanthine monophosphate (Besnard et al., *Mol. Cell. Biol.* 7:4139–4141, 1987); alkaline phosphatase, which converts inactive phosphorylated compounds such as mitomycin phosphate and doxorubicin-phosphate to toxic dephosphorylated compounds; fungal (e.g., *Fusarium oxysporum*) or bacterial cytosine deaminase, which converts 5-fluorocytosine to the toxic compound 5-fluorouracil (Mullen, *PNAS* 89:33, 1992); carboxypeptidase G2, which cleaves glutamic acid from para-N-bis(2-chloroethyl) aminobenzoyl glutamic acid, thereby creating a toxic benzoic acid mustard; and Penicillin-V amidase, which converts phenoxyacetabide derivatives of doxorubicin and melphalan to toxic compounds (see generally, Vrudhula et al., *J. of Med. Chem.* 36(7):919–923, 1993; Kern et al., *Canc. Immun. Immunother.* 31(4):202–206, 1990). Moreover, a wide variety of Herpesviridae thymidine kinases, including both primate and non-primate herpesviruses, are suitable. Such herpesviruses include Herpes Simplex Virus Type I (McKnight et al., *Nuc. Acids Res* 8:5949–5964, 1980), Herpes Simplex Virus Type 2 (Swain and Galloway, *J. Virol.* 46:1045–1050, 1983), Varicella Zoster Virus (Davison and Scott, *J. Gen. Virol.* 67:1759–1816, 1986), marmoset herpesvirus (Otsuka and Kit, *Virology* 135:316–330, 1984), feline herpesvirus type I (Nunberg et al., *J. Virol.* 63:3240–3249, 1989), pseudorabies virus (Kit and Kit, U.S. Pat. No. 4,514,497, 1985), equine herpesvirus type 1 (Robertson and Whalley, *Nuc. Acids Res.* 16:11303–11317, 1988), bovine herpesvirus type I (Mittal and Field, *J. Virol* 70:2901–2918, 1989), turkey herpesvirus (Martin et al., *J. Virol.* 63:2847–2852, 1989), Marek's disease virus (Scott et al., *J. Gen. Virol.* 70:3055–3065, 1989), herpesvirus saimiri (Honess et al., *J. Gen. Virol.* 70:3003–3013, 1989) and Epstein-Barr virus (Baer et al., *Nature* (London) 310:207–311, 1984). Such herpesviruses may be readily obtained from commercial sources such as the American Type Culture Collection ("ATCC", Rockville, Md.).

Furthermore, as indicated above, a wide variety of inactive precursors may be converted into active inhibitors. For example, thymidine kinase can phosphorylate nucleosides (e.g., dT) and nucleoside analogues such as ganciclovir (9-{[2-hydroxy-1-(hydroxymethyl)ethoxyl methyl]guanosine), famciclovir, buciclovir, penciclovir, valciclovir, acyclovir (9-[2-hydroxy ethoxy)methyl] guanosine), trifluorothymidine, 1-[2-deoxy, 2-fluoro, beta-D-arabino furanosyl]-5-iodouracil, ara-A (adenosine arabinoside, vivarabine), 1-beta-D-arabinofuranoxyl thymine, 5-ethyl-2'-deoxyuridine, 5-iodo-5'-amino-2,5'-dideoxyuridine, idoxuridine (5-iodo-2'-deoxyuridine), AZT (3' azido-3' thymidine), ddC (dideoxycytidine), AIU (5-iodo-5' amino 2',5'-dideoxyuridine) and AraC (cytidine arabinoside).

Other gene products may render a cell susceptible to toxic agents. Such products include tumor necrosis factor, viral proteins, and channel proteins that transport drugs.

A cytocide-encoding agent may be constructed as a prodrug, which when expressed in the proper cell type is processed or modified to an active form. For example, the saporin gene is constructed with an N- or C-terminal extension containing a protease-sensitive site. The extension renders the protein inactive and subsequent cleavage in a cell expressing the appropriate protease restores enzymatic activity.

E. Other Nucleic Acid Molecules

The conjugates provided herein may also be used to deliver a ribozyme, antisense, and the like to targeted cells. These nucleic acids may be present in the complex of ligand and nucleic acid binding domain or encoded by a nucleic acid in the complex. Alternatively, the nucleic acid may be directly linked to the ligand. Such products include antisense RNA, antisense DNA, ribozymes, triplex-forming oligonucleotides, and oligonucleotides that bind proteins. The nucleic acids can also include RNA trafficking signals, such as viral packaging sequences (see, e.g., Sullenger et al. (1994) *Science* 262:1566–1569). The nucleic acids also include DNA molecules that encode proteins that replace defective genes, such as the gene associated with cystic fibrosis (see, e.g., PCT Application WO 93/03709, U.S. application Ser. No. 07/745,900; and Riordan et al. (1989) *Science* 245:1066–1073).

Nucleic acids and oligonucleotides for use as described herein can be synthesized by any method known to those of skill in this art (see, e.g., WO 93/01286, U.S. application Ser. No. 07/723,454; U.S. Pat. No. 5,218,088; U.S. Pat. No. 5,175,269; U.S. Pat. No. 5,109,124). Identification of oligonucleotides and ribozymes for use as antisense agents and DNA encoding genes for targeted delivery for genetic therapy involve methods well known in the art. For example, the desirable properties, lengths and other characteristics of such oligonucleotides are well known. Antisense oligonucleotides are typically designed to resist degradation by endogenous nucleolytic enzymes by using such linkages as: phosphorothioate, methylphosphonate, sulfone, sulfate, ketyl, phosphorodithioate, phosphoramidate, phosphate esters, and other such linkages (see, e.g., Agrwal et al., *Tetrehedron Lett.* 28:3539–3542 (1987); Miller et al., *J. Am. Chem. Soc.* 93:6657–6665 (1971); Stec et al., *Tetrehedron Lett.* 26:2191–2194 (1985); Moody et al., *Nucl. Acids Res.* 12:4769–4782 (1989); Uznanski et al., *Nucl. Acids Res.* (1989); Letsinger et al., *Tetrahedron* 40:137–143 (1984);

Eckstein, *Annu. Rev. Biochem.* 54:367–402 (1985); Eckstein, *Trends Biol. Sci.* 14:97–100 (1989); Stein In: *Oligodeoxynucleotides. Antisense Inhibitors of Gene Expression*, Cohen, Ed, Macmillan Press, London, pp. 97–117 (1989); Jager et al., *Biochemistry* 27:7237–7246 (1988)).

Antisense nucleotides are oligonucleotides that bind in a sequence-specific manner to nucleic acids, such as mRNA or DNA. When bound to mRNA that has complementary sequences, antisense prevents translation of the mRNA (see, e.g., U.S. Pat. No. 5,168,053 to Altman et al.; U.S. Pat. No. 5,190,931 to Inouye, U.S. Pat. No. 5,135,917 to Burch; U.S. Pat. No. 5,087,617 to Smith and Clusel et al. (1993) *Nucl. Acids Res.* 21:3405–3411, which describes dumbbell antisense oligonucleotides). Triplex molecules refer to single DNA strands that bind duplex DNA forming a colinear triplex molecule, thereby preventing transcription (see, e.g., U.S. Pat. No. 5,176,996 to Hogan et al., which describes methods for making synthetic oligonucleotides that bind to target sites on duplex DNA).

Particularly useful antisense nucleotides and triplex molecules are molecules that are complementary or bind to the sense strand of DNA or mRNA that encodes a protein involved in cell proliferation, such as an oncogene or growth factor, (e.g., bFGF, int-2, hst-1/K-FGF, FGF-5, hst-2/FGF-6, FGF-8). Other useful antisense oligonucleotides include those that are specific for IL-8 (see, e.g., U.S. Pat. No. 5,241,049; and PCT Applications WO 89/004836; WO 90/06321; WO 89/10962; WO 90/00563; and WO 91/08483). These nucleic acids or nucleic acids that encode antisense can be linked to bFGF for the treatment of psoriasis. Anti-sense oligonucleotides or nucleic acids encoding antisense specific for nonmuscle myosin heavy chain and/or c-myb (see, e.g., Simons et al. (1992) *Circ. Res.* 70:835–843; PCT Application WO 93/01286, U.S. application Ser. No. 07/723,454: LeClerc et al. (1991) *J. Am. Coll. Cardiol.* 17 (2 Suppl. A): 105A, Ebbecke et al. (1992) *Basic Res. Cardiol.* 87:585–591) can be targeted by an FGF, for example to inhibit smooth muscle cell proliferation, such as occurs following angioplasty.

A ribozyme is an RNA molecule that specifically cleaves RNA substrates, such as mRNA, resulting in inhibition or interference with cell growth or expression. There are at least five known classes of ribozymes involved in the cleavage and/or ligation of RNA chains. Ribozymes can be targeted to any RNA transcript and can catalytically cleave such transcript (see, e.g., U.S. Pat. No. 5,272,262; U.S. Pat. No. 5,144,019; and U.S. Pat. Nos. 5,168,053, 5,180,818, 5,116,742 and 5,093,246 to Cech et al.). Any such ribosome or nucleic acid encoding the ribozyme may be delivered to a cell bearing a receptor for a receptor-internalized binding ligand.

The ribozymes antisense, and the like may be delivered to the targeted cells by DNA encoding the ribozyme linked to a eukaryotic promoter, such as a eukaryotic viral promoter, such that upon introduction into the nucleus, the ribozyme will be directly transcribed. In such instances, the construct will also include a nuclear translocation sequence, generally as part of the ligand or as part of a linker between the ligand and nucleic acid binding domain.

DNA that encodes a therapeutic product contemplated for use includes DNA encoding correct copies of defective genes, such as the defective gene (CFTR) associated with cystic fibrosis (see, e.g., International Application WO 93/03709, U.S. application Ser. No. 07/745,900; and Riordan et al. (1989) *Science* 245:1066–1073), and anticancer agents, such as tumor necrosis factors. Many genetic defects are caused by a mutation in a single gene. Introduction of the wild-type gene will serve to alleviate the deficiency. Such genes include HPRT, adenosine deaminase, Factor IX, Factor VIII, Factor XIII, β-hemoglobin, and the like. The conjugate preferably includes a nuclear translocation sequence (NTS). If the conjugate is designed such that the ligand and nucleic acid binding domain are cleaved in the cytoplasm, then the NTS should be included in a portion of the conjugate or linker that remains bound to the DNA. The nuclear translocation sequence (NTS) may be a heterologous sequence or a may be derived from the selected growth factor.

F. Construct Containing Cytocidal-encoding Agent

In the case of cytotocide molecules such as the ribosome inactivating proteins, very few molecules may need to be expressed to effect cell killing. Indeed, only a single molecule of diphtheria toxoid introduced into a cell is sufficient to kill the cell. With other cytocides or prodrugs, it may be that propagation or stable maintenance of the construct is necessary to attain a sufficient amount or concentration of the gene product for effective gene therapy. Examples of replicating and stable eukaryotic plasmids may be found in the scientific literature.

In general, constructs will also contain elements necessary for transcription and translation. If the cytocide-encoding agent is DNA, then it must contain a promoter. The choice of the promoter will depend upon the cell type to be transformed and the degree or type of control desired. Promoters can be constitutive or active in any cell type, tissue specific, cell specific, event specific, temporal-specific or inducible. Cell-type specific promoters and event type specific promoters are preferred. Examples of constitutive or nonspecific promoters include the SV40 early promoter (U.S. Pat. No. 5,118,627), the SV40 late promoter (U.S. Pat. No. 5,118,627), CMV early gene promoter (U.S. Pat. No. 5,168,062), and adenovirus promoter. In addition to viral promoters, cellular promoters are also amenable within the context of this invention. In particular, cellular promoters for the so-called housekeeping genes are useful. Viral promoters are preferred, because generally they are stronger promoters than cellular promoters.

Tissue specific promoters are particularly useful when a certain tissue type is to be targeted for transformation. By using one of this class of promoters, an extra margin of specificity can be attained. For example, when the indication to be treated is ophthalmological (e.g., secondary lens clouding), either the alpha-crystallin promoter or gamma-crystallin promoter is preferred. When a tumor is the target of gene delivery, cellular promoters for specific tumor markers or promoters more active in tumor cells should be chosen. Thus, to treat prostate tumor, the prostate-specific antigen promoter is especially useful. Similarly, the tyrosinase promoter or tyrosinase-related protein promoter is a preferred promoter for melanoma treatment. For treatment of diseases that are angiogenic or exacerbated by angiogenesis, the VEGF receptor promoter is preferred. The VEGF receptor is expressed in developing capillaries. For treatment of breast cancer, the promoters from heat shock protein 27 and erbB-2 are preferred; for treatment of colon or lung cancer, the promoter from carcinoembryonic antigen is preferred; for treatment of restenosis or other diseases involving smooth muscle cells, the promoter from α-actin or myosin heavy chain is preferred. For B lymphocytes, the immunoglobulin variable region gene promoter; for T lymphocytes, the TCR receptor variable region promoter; for helper T lymphocytes, the CD4 promoter; for liver, the albumin or α-fetoprotein promoter; for lungs, surfactant protein A promoter; are a few additional examples of tissue specific promoters. Many other examples of tissue specific promoters are readily available to one skilled in the art. Some of these promoters are temporally regulated, such as c-myc and cyclin D.

Endothelial-specific promoters are especially useful in targeting proliferative diseases involving endothelial cells, such as angiogenesis in tumors. For treating diseases dependent or exacerbated by angiogenesis or primary angiogenic diseases, the following promoters are especially useful: VEGF-receptor promoter (Morishita et al., *J. Biol. Chem.* 270:27948, 1995; GenBank Accession No. X89776); TEK or tie 2 promoter, a receptor tyrosine kinase expressed predominately in endothelium of actively growing blood vessels (Huang et al., *Oncogene* 11:2097, 1995; GenBank Accession No. L06139); tie (WO 96/09381; Korhonen et al., *Blood* 86:1828, 1995; GenBank Accession No. X60954; GenBankAccession No. S89716); urokinase receptor, which is expressed at high levels in endothelial cells during angiogenesis (Hollas et al., *Cancer Res.* 51:3690, 1991; Gum et al., *Anti-Cancer Res.* 15:1167, 1995; Soravia et al., *Blood* 86:624, 1995; GenBank Accession No. S78532); E- and P-selection, which has increased expression in endothelium of tumors, such as breast (Fox et al., *J. Pathol.* 177:369, 1995; Biancone et al., *J. Exp. Med.* 183:581, 1996; GenBank Accession No. M64485; GenBank Accession No. L01874); VCAM-1 (Iademarco et al., *J. Biol. Chem.* 267:16323, 1992; GenBank Accession No. M92431); endoglin, which is upregulated in the vasculature of tumors (Bellon et al., *Eur. J. Immunol.* 23:2340, 1993; Gougos and Letarte, *J. Biol. Chem.* 265:8361, 1990; GenBank Accession No. HSENDOG); endosialin, expressed preferentially in tumor capillaries (Rettig et al., *PNAS* 89:10832, 1992); alpha V-beta3 integrin (Villa-Garcia et al., *Blood* 3:668, 1994; Donahue et al., *BBA* 1219:228, 1994); endothelin-1, a growth factor for endothelial cells (GenBank Accession No. M25377; GenBank Accession No. J04819; GenBank Accession No. J05489); ICAM-3, expressed in tumor endothelium (Patey et al., *Am. J. Pathol.* 148:465, 1996; Fox et al., *J. Path.* 177:369, 1995; GenBank Accession No. S50015); E9 antigen, upregulated in tumor endothelium (Wang et al., *Int. J. Cancer* 54:363, 1993); von Willebrand factor (Jahroudi and Lynch, *Mol. Cell. Biol.* 14:999, 1994; GenBank Accession No. HUMVWFI; GenBank Accession No. HUMVWFA); CD44 (Hofmann et al., Cancer Res. 53:1516, 1993; Maltzman et al., *Mol. Cell. Biol.* 16:2283, 1996; GenBank Accession No. HUMCD44B); CD40 (Pammer et al., *Am. J. Pathol.* 148:1387, 1996; GenBank Accession No. HACD40L; GenBank Accession No. HSCD405FR); vascular-endothelial cadherin, highly expressed in endothelial cells of hemangiomas (Martin-Padura et al., *J. Pathol.* 175:51, 1995); notch 4 (Uyttendaele et al., *Development* 122:2251, 1996) and high molecular weight melanoma-associated antigen.

Inducible promoters may also be used. These promoters include MMTV LTR (PCT WO 91/13160), inducible by dexamethasone, metallothionein, inducible by heavy metals, and promoters with cAMP response elements, inducible by cAMP. By using an inducible promoter, the nucleic acid may be delivered to a cell and will remain quiescent until the addition of the inducer. This allows further control on the timing of production of the gene.

Event-type specific promoters are active or up-regulated only upon the occurrence of an event, such as tumorigenecity or viral infection. The HIV LTR is a well known example of an event-specific promoter. The promoter is inactive unless the tat gene product is present, which occurs upon viral infection. Some event-type promoters are also tissue-specific.

Additionally, promoters that are coordinately regulated with a particular cellular gene may be used. For example, promoters of genes that are coordinately expressed when a particular FGF receptor gene is expressed may be used. Then, the nucleic acid will be transcribed when the FGF receptor, such as FGFR1, is expressed, and not when FGFR2 is expressed. This type of promoter is especially useful when one knows the pattern of FGF receptor expression in a particular tissue, so that specific cells within that tissue may be killed upon transcription of a cytotoxic agent gene without affecting the surrounding tissues.

If the domain binds in a sequence specific manner, the construct must contain the sequence that binds to the nucleic acid binding domain. As described below, the target nucleotide sequence may be contained within the coding region of the cytocide, in which case, no additional sequence need be incorporated. Additionally, it may be desirable to have multiple copies of target sequence. If the target sequence is coding sequence, the additional copies must be located in non-coding regions of the cytocide-encoding agent. The target sequences of the nucleic acid binding domains are typically generally known. If unknown, the target sequence may be readily determined. Techniques are generally available for establishing the target sequence (e.g., see PCT Application WO 92/05285 and U.S. Ser. No. 586,769).

In addition to the promoter, repressor sequences, negative regulators, or tissue-specific silencers may be inserted to reduce non-specific expression of the cytocide or prodrug. Multiple repressor elements may be inserted in the promoter region. Repression of transcription is independent on the orientation of repressor elements or distance from the promoter.

Negative regulatory elements have been characterized in the promoter regions of a number of different genes. The repressor element functions as a repressor of transcription in the absence of factors, such as steroids, as does the NSE in the promoter region of the ovalbumin gene (Haecker et al., *Mol Endocrinology* 9:1113–1126, 1995). These negative regulatory elements bind specific protein complexes from oviduct, none of which are sensitive to steroids. Three different elements are located in the promoter of the ovalbumin gene. Oligonucleotides corresponding to portions of these elements repress viral transcription of the TK reporter. One of the silencer elements shares sequence identity with silencers in other genes (TCTCTCCNA).

Repressor elements have also been identified in the promoter region of collagen II gene. Gel retardation studies showed that nuclear factors from HeLa cells bind specifically to DNA fragments containing the silencer region, whereas chrondocyte nuclear extracts did not show any binding activity (Savanger et al., *J. Biol. Chem.* 265(12): 6669–6674, 1990). Repressor elements have also been shown to regulate transcription in the carbamyl phosphate synthetase gene (Goping et al., *Nucleic Acid Research* 23(10):1717–1721, 1995). This gene is expressed in only two different cell types, hepatocytes and epithelial cells of the intestinal mucosa. Negative regulatory regions have also been identified in the promoter region of the choline acetyltransferase gene, the albumin promoter (Hu et al., *J. Cell Growth Differ.* 3(9):577–588, 1992), phosphoglycerate kinase (PGK-2) gene promoter (Misuno et al., *Gene* 119(2): 293–297, 1992), and in the 6-phosphofructo-2-kinase/fructose-2, 6-bisphosphatase gene, in which the negative regulatory element inhibits transcription in non-hepatic cell lines (Lemaigre et al., *Mol. Cell Biol.* 11(2):1099–1106). Furthermore, the negative regulatory element Tse-1 has been identified in a number of liver specific genes, including tyrosine aminotransferase (TAT). TAT gene expression is liver specific and inducible by both glucocorticoids and the cAMP signaling pathway. The cAMP response element (CRE) has been shown to be the target for repression by Tse-1 and hepatocyte-specific elements (Boshart et al., *Cell* 61(5):905–916, 1990).

Other elements may be incorporated into the construct. In preferred embodiments, the construct includes a transcription terminator sequence, including a polyadenlization sequence, splice donor and acceptor sites, and an enhancer. Other elements useful for expression and maintenance of the construct in mammalian cells or other eukaryotic cells may also be incorporated (e.g., origin of replication). Because the constructs are conveniently produced in bacterial cells, elements that are necessary or enhance propagation in bacteria are incorporated. Such elements include an origin of replication, selectable marker and the like (see discussion below).

An additional level of control for initiating expression of the nucleic acid only in appropriate cells or enhancing uptake of complex is the delivery of two constructs, one of which encodes the cytocide and the other construct encodes a second gene that controls expression of the promoter driving the cytocide or prodrug or enhances uptake of the complexes into tumor masses or other target cells. By way of example, on one construct, the cytocide encoding agent is controlled by a promoter, such as a heat shock promoter. The second construct is a gene, such as a gene that elicits SOS pathway under control of a tumor-specific promoter. The two constructs are co-delivered or sequentially delivered. When delivered into tumor cells, the SOS gene is expressed and results in causing expression of the cytocide-encoding agent. In this case, the two constructs could be merged into one construct.

In the other type of multiple delivery system, the first construct is a cytocide gene under control of a promoter, such as those described above. The second construct, comprises a different promoter controlling expression of a gene, such as IL-2, that induces leakiness in a tumor mass to allow better penetration. When the second construct is introduced first, the tumor mass will be more readily accessible for the first construct to be delivered.

Typically, the constructs are plasmid vectors. A preferred construct is a modified pNASS vector (Clontech, Palo Alto, Calif.). In the modified vector, amp. R gene is replaced by kan. R gene, a poly A signal sequence is added upstream of the mammalian promoter. A T7 promoter is added downstream of the mammalian promoter and upstream of the cytocide or prodrug gene to facilitate verification of cytotoxic activity. Other suitable mammalian expression vectors are well known (see, e.g., Ausubel et al., 1995; Sambrook et al., supra; Invitrogen catalogue, San Diego, Calif.; Novagen, Madison, Wis.; Pharmacia catalogue, Uppsala, Sweden; and others).

G. Other Elements

1. Nuclear Translocation Signal

As used herein, a "nuclear translocation or targeting sequence" (NTS) is a sequence of amino acids in a protein that are required for translocation of the protein into a cell nucleus. Examples of NTSs are set forth in Table 2 below. Comparison with known NTSs, and if necessary testing of candidate sequences, should permit those of skill in the art to readily identify other amino acid sequences that function as NTSs. The NTS may be derived from another polypeptide, or it may be derived from another region in the same polypeptide. The NTS is typically synthesized as a DNA sequence encoding the NTS and inserted appropriately into either the ligand or NABD gene sequence.

TABLE 2

| Source | Sequence* | SEQ. ID NO. |
|---|---|---|
| SV40 large T | Pro$^{126}$LysLysArgLysValGlu | 24 |
| Polyoma large T | Pro$^{279}$ProLysLysAlaArgGluVal | 25 |
| Human c-Myc | Pro$^{320}$AlaAlaLysArgValLysLeuAsp | 26 |
| Adenovirus E1A | Lys$^{281}$ArgProArgPro | 27 |
| Yeast mat α$_2$ | Lys$^3$IleProIleLys | 28 |
| c-Erb-A | A. Gly$^{22}$LysArgLysArgLysSer | 29 |
|  | B. Ser$^{127}$LysArgValAlaLysArgLysLeu | 30 |
|  | C. Ser$^{181}$HisTrpLysGlnLysArgLysPhe | 31 |
| c-Myb | Pro$^{521}$LeuLeuLysLysIleLysGln | 32 |
| p53 | Pro$^{316}$GlnProLysLysLysPro | 33 |
| Nucleolin | Pro$^{277}$GlyLysArgLysLysGluMet ThrLysGlnLysGluValPro | 34 |
| HIV Tat | Gly$^{48}$ArgLysLysArgArgGlnArg ArgArgAlaPro | 35 |
| FGF-1 | AsnTyrLysLysProLysLeu | 36 |
| FGF-2 | HisPheLysAspProLysArg | 37 |
| FGF-3 | AlaProArgArgArgLysLeu | 38 |
| FGF-4 | IleLysArgLeuArgArg | 39 |
| FGF-5 | GlyArgArg | — |
| FGF-6 | IleLysArgGlnArgArg | 40 |
| FGF-7 | IleArgValArgArg | 41 |

*Superscript indicates position in protein

In order to deliver the nucleic acid to the nucleus, the conjugate should include an NTS. If the conjugate is designed such that the receptor-binding internalized ligand and linked nucleic acid binding domain is cleaved or dissociated in the cytoplasm, then the NTS should be included in a portion of the complex that remains bound to the nucleic acid, so that, upon internalization, the conjugate will be trafficked to the nucleus. Thus, the NTS is preferably included in the nucleic acid binding domain, but may additionally be included in the ligand. An NTS is preferred if the cytocide-encoding agent is DNA. If the cytocide-encoding agent is mRNA, an NTS may be omitted. The nuclear translocation sequence (NTS) may be a heterologous sequence or a may be derived from the selected ligand. All presently identified members of the FGF family of peptides contain an NTS (see, e.g., International Application WO 91/15229 and Table 2). A typical consensus NTS sequence contains an amino-terminal proline or glycine followed by at least three basic residues in a array of seven to nine amino acids (see, e.g., Dang et al., *J. Biol. Chem.* 264:18019–18023, 1989; Dang et al., *Mol. Cell. Biol.* 8:4049–4058, 1988, and Table 2).

2. Cytoplasm-translocation Signal

Cytoplasm-translocation signal sequence is a sequence of amino acids in a protein that cause retention of proteins in the lumen of the endoplasmic reticulum and/or translocate proteins to the cytosol. A signal sequence in mammalian cells is KDEL (Lys-Asp-Glu-Leu) (SEQ ID NO. 42) (Munro and Pelham, *Cell* 48:899–907, 1987). Some modifications of this sequence have been made without loss of activity. For example, the sequences RDEL (Arg-Asp-Glu-Leu) (SEQ ID NO. 43) and KEEL (Lys-Glu-Glu-Leu) (SEQ ID NO. 44) confer efficient or partial retention, respectively, in plants (Denecke et al., *Embo. J.* 11:2345–2355, 1992).

A cytoplasm-translocation signal sequence may be included in either the receptor-internalized binding ligand or the nucleic acid binding domain part or both. If cleavable linkers are used to link the ligand with the nucleic acid binding domain, the cytoplasm-translocation signal is preferably included in the nucleic acid binding domain, which will stay bound to the cytocide-encoding agent.

Additionally, a cytoplasmic-translocation signal sequence may be included in the receptor-internalized binding ligand, as long as it does not interfere with receptor binding. Similarly, the signal sequence placed in the nucleic acid binding domain should not interfere with binding to the cytocide-encoding agent.

3. Endosome-disruptive Peptides

In addition, or alternatively, membrane-disruptive peptides may be incorporated into the complexes. For example, adenoviruses are known to enhance disruption of endosomes. Virus-free viral proteins, such as influenza virus hemagglutinin HA-2, also disrupt endosomes and are useful in the present invention. Other proteins may be tested in the assays described herein to find specific endosome disrupting agents that enhance gene delivery. In general, these proteins and peptides are amphipathic (see Wagner et al., *Adv. Drug. Del. Rev.* 14:113–135, 1994).

Endosome-disruptive peptides, sometimes called fusogenic peptides, may be incorporated into the complex of receptor-internalized binding ligand, nucleic acid binding domain, and cytocide-encoding agent. Two such peptides derived from influenza virus are: GLFEAIEGFIENGWEGMIDGGGC (SEQ. ID NO. 45) and GLFEAIEGFIENGWEGMIDGWYGC (SEQ. ID NO. 46). Other peptides useful for disrupting endosomes may be identified by general characteristics: 25–30 residues in length, contain an alternating pattern of hydrophobic domains and acidic domains, and at low pH (e.g., pH 5) from amphipathic α-helices. A candidate endosome-disrupting peptide is tested by incorporating it into the complex and determining whether it increases the total number of cells expressing the target gene. The peptides are added to a complex having excess negative charge. For example, a DNA construct is complexed with an FGF-poly-L-lysine chemical conjugate so that only a portion of the negative charge of the DNA is neutralized. Poly-L-lysine is added to further bind the DNA and a fusogenic peptide is then added. Optional ratios of DNA, poly-L-lysine and fusogenic peptide are determined using assays, such as gene expression and cell viability.

The fusogenic peptides may alternatively be incorporated into the complex as a fusion protein with either the ligand or the nucleic acid binding domain or both. The endosome-disruptive peptide may be present as single or multiple copies at the N- or C-terminus of the ligand. A single fusion protein of the endosome-disruptive peptide, nucleic acid binding domain, and receptor-internalized binding ligand may be constructed and expressed. For insertion into a construct, DNA encoding the endosome-disruptive peptide may be synthesized by PCR using overlapping oligonucleotides and incorporating a restriction site at the 5' and 3' end to facilitate cloning. The sequence may be verified by sequence analysis.

4. Linkers

As used herein, a "linker" is a chemical or peptide that links a receptor-binding internalized ligand or fragment thereof and nucleic acid binding domain. In certain instances, a linker is used to conjugate the ligand directly to the nucleic acid. The linkers provided herein confer specificity, enhance intracellular availability, serum stability and/or solubility on the conjugate and may serve to promote condensation of nucleic acids for delivery to a cell.

The linkers provided herein confer specificity and serum stability on a conjugate, for example, by providing a substrate for certain proteases, particularly proteases that are present in only certain subcellular compartments or that are present at higher levels in tumor cells than normal cells. Specificity for proteases that are present in intracellular compartments and absent in blood is particularly preferred. The linkers may also include sorting signals such as cytoplasmic retention signals that direct the conjugate to particular intracellular loci or compartments. Additionally, the linkers may reduce steric hindrance between the ligand and other protein or linked nucleic acid by distancing the components of the conjugate. Linkers may also condense the nucleic acid. For this purpose, the linker comprises highly basic amino acids (e.g., Lys, Arg) and may even be poly-L-lysine.

In order to provide serum stability, increase solubility and/or intracellular concentration or condense nucleic acid, one or more linkers (are) inserted between the receptor-binding internalized ligand and the nucleic acid binding domain or nucleic acid. These linkers include peptide linkers, such as a substrate for an intracellular protease, and chemical linkers, such as acid labile linkers, ribozyme substrate linkers and others. Peptides linkers may be inserted using heterobifunctional reagents, described below, or, are linked to a ligand and nucleic acid binding domain by recombinant means. Chemical linkers are inserted by covalently coupling the linker to the ligand (e.g., FGF, other growth factor protein, or cytokine) and the nucleic acid binding domain, at the N- or C-terminus or an internal residue. Heterobifunctional agents, described below, may be used to effect such covalent coupling.

a. Protease Substrates

Peptides encoding protease-specific substrates may be introduced between the ligand and the nucleic acid binding domain. The peptides may be inserted using heterobifunctional reagents, for example, or inserted by recombinant means and expression of the resulting chimera.

Any protease specific substrate (see, e.g., O'Hare et al., *FEBS* 273:200–204, 1990; Forsberg et al., *J. Protein Chem.* 10:517–526, 1991; Westby et al., *Bioconjugate Chem.* 3:375–381, 1992) may be used as a linker as long as the substrate is cleaved in an intracellular compartment. Preferred substrates include those that are specific for proteases that are expressed at higher levels in tumor cells, that are preferentially expressed in the endosome, or that are absent in blood. The following substrates are suitable for use in the present invention: cathepsin B substrate, cathepsin D substrate, trypsin substrate, thrombin substrate, and recombinant subtilisin substrate.

b. Linkers that are Flexible and Increase Solubility of Conjugates

Flexible linkers, which reduce steric hindrance and increase in vitro solubility of the conjugates are contemplated for use, either alone or with other linkers, such as the protease specific substrate linkers. Typically, these linkers are simple polymers of small amino acids (i.e., small side groups) with uncharged polar side groups. These amino acids (Gly, Ser, Thr, Cys, Tyr, Asn, Gln) are more soluble in water. Of these amino acids, Gly and Ser are preferred. Such linkers include, but are not limited to, $(Gly_4Ser)_n$, $(Ser_4Gly)_n$ and $(AlaAlaProAla)_n$ in which n is 1 to 6, preferably 1–4, such as:

a. $Gly_4Ser$ SEQ ID NO: 47 CCATGGGCGG CGGCGGCTCT GCCATGG b. $(Gly_4Ser)_2$ SEQ ID NO: 48 CCATGGGCGG CGGCGGCTCT GGCGGCGGCG GCTCTGCCAT GG c. $(Ser_4Gly)_4$ SEQ ID NO: 49 CCATGGCCTC GTCGTCGTCG GGCTCGTCGT CGTCGGGCTC GTCGTCGTCG GGCTCGTCGT CGTCGGGCGC CATGG d. $(Ser_4Gly)_2$ SEQ ID NO: 50 CCATGGCCTC GTCGTCGTCG GGCTCGTCGT CGTCGGGCGC CATGG e. $(AlaAlaProAla)_n$, where n is 1 to 4, preferably 2 (see SEQ ID NO: 51)

C. Heterobifunctional Cross-linking Reagents

Numerous heterobifunctional cross-linking reagents may be used to form covalent bonds between amino groups and thiol groups and to introduce thiol groups into proteins, (see, e.g., the PIERCE CATALOG, ImmunoTechnology Catalog & Handbook, 1992–1993, which describes the preparation of and use of such reagents and provides a commercial source for such reagents; see also, e.g., Cumber et al., *Bioconjugate Chem.* 3:397–401, 1992; Thorpe et al., *Cancer Res.* 47:5924–5931, 1987; Gordon et al., *Proc. Natl. Acad Sci.* 84:308–312, 1987; Walden et al., *J. Mol. Cell Immunol.* 2:191–197, 1986; Carlsson et al., *Biochem. J.* 173:723–737, 1978; Mahan et al., *Anal. Biochem.* 162:163–170, 1987; Wawryznaczak et al., *Br. J. Cancer* 66:361–366, 1992; Fattom et al., *Infection & Immun.* 60:584–589, 1992). These reagents may be used to form covalent bonds between the receptor-binding internalized ligands with protease substrate peptide linkers and nucleic acid binding domain. These reagents include, but are not limited to: N-succinimidyl-3-(2-pyridyldithio)propionate (SPDP; disulfide linker); sulfo-succinimidyl 6-[3-(2-pyridyldithio)propionamido] hexanoate (sulfo-LC-SPDP); succinimidyloxycarbonyl-α-methyl benzyl thiosulfate (SMBT, hindered disulfate linker); succinimidyl 6-[3-(2-pyridyldithio) propionamido] hexanoate (LC-SPDP); sulfosuccinimidyl 4-(N-maleimidomethyl)cyclohexane-1-carboxylate (sulfo-SMCC); succinimidyl 3-(2-pyridyldithio)butyrate (SPDB; hindered disulfide bond linker); sulfosuccinimidyl 2-(7-azido-4-methylcoumarin-3-acetamide) ethyl-1,3'-dithiopropionate (SAED); sulfosuccinimidyl 7-azido-4-methylcoumarin-3-acetate (SAMCA); sulfosuccinimidyl 6-[alpha-methyl-alpha-(2-pyridyldithio)toluamido] hexanoate (sulfo-LC-SMPT); 1,4-di-[3'-(2'-pyridyldithio) propionamido]butane (DPDPB); 4-succinimidyloxycarbonyl- -methyl- -(2-pyridylthio) toluene (SMPT, hindered disulfate linker); sulfosuccinimidyl6[-methyl- -(2-pyridyldithio)toluamido] hexanoate (sulfo-LC-SMPT); m-maleimidobenzoyl-N-hydroxysuccinimide ester (MBS); m-maleimidobenzoyl-N-hydroxysulfosuccinimide ester (sulfo-MBS); N-succinimidyl(4-iodoacetyl)aminobenzoate (SIAB; thioether linker); sulfosuccinimidyl(4-iodoacetyl)amino benzoate (sulfo-SIAB); succinimidyl4(p-maleimidophenyl)butyrate (SMPB); sulfosuccinimidyl4-(p-maleimidophenyl)butyrate (sulfo-SMPB); azidobenzoyl hydrazide (ABH).

These linkers should be particularly useful when used in combination with peptide linkers, such as those that increase flexibility.

d. Acid Cleavable, Photocleavable, and Heat Sensitive Linkers

Acid cleavable linkers include, but are not limited to, bismaleimideothoxy propane, adipic acid dihydrazide linkers (see, e.g., Fattom et al., *Infection & Immun.* 60:584–589, 1992) and acid labile transferrin conjugates that contain a sufficient portion of transferrin to permit entry into the intracellular transferrin cycling pathway (see, e.g., Welhöner et al., *J. Biol. Chem.* 266:4309–4314, 1991). Conjugates linked via acid cleavable linkers should be preferentially cleaved in acidic intracellular compartments, such as the endosome.

Photocleavable linkers are cleaved upon exposure to light (see, e.g., Goldmacher et al., *Bioconj. Chem.* 3:104–107, 1992), thereby releasing the targeted agent upon exposure to light. (Hazum et al., *Proc. Eur. Pept. Symp.*, 16*th*, Brunfeldt, K (Ed), pp. 105–110, 1981; nitrobenzyl group as a photocleavable protective group for cysteine; Yen et al., *Makromol. Chem* 190:69–82, 1989; water soluble photocleavable copolymers, including hydroxypropylmethacrylamide copolymer, glycine copolymer, fluorescein copolymer and methylrhodamine copolymer; and Senter et al., *Photochem. Photobiol.* 42:231–237, 1985; nitrobenzyloxycarbonyl chloride cross linking reagents that produce photocleavable linkages). Such linkers are particularly useful in treating dermatological or ophthalmic conditions. In addition, other tissues, such as blood vessels that can be exposed to light using fiber optics during angioplasty in the prevention or treatment of restenosis may benefit from the use of photocleavable linkers. After administration of the conjugate, the eye or skin or other body part is exposed to light, resulting in release of the targeted moiety from the conjugate. Heat sensitive linkers would also have similar applicability.

H. Expression Vectors and Host Cells for Expression of Receptor-binding Internalized Ligands and Nucleic Acid Binding Domains Host organisms include those organisms in which recombinant production of heterologous proteins have been carried out, such as bacteria (for example, *E. coli*), yeast (for example, *Saccharomyces cerevisiae* and *Pichia pastoris*), mammalian cells, and insect cells. Presently preferred host organisms are *E. coli* bacterial strains.

The DNA construct encoding the desired protein is introduced into a plasmid for expression in an appropriate host. In preferred embodiments, the host is a bacterial host. The sequence encoding the ligand or nucleic acid binding domain is preferably codon-optimized for expression in the particular host. Thus, for example, if human FGF-2 is expressed in bacteria, the codons would be optimized for bacterial usage. For small coding regions the gene can be synthesized as a single oligonucleotide. For larger proteins, splicing of multiple oligonucleotides, mutagenesis, or other techniques known to those in the art may be used. For example, the sequence of a bacterial-codon preferred FGF-SAP fusion is shown in SEQ. ID NO. 80. The sequences of nucleotides in the plasmids that are regulatory regions, such as promoters and operators, are operationally associated with one another for transcription. The sequence of nucleotides encoding the growth factor or growth factor-chimera may also include DNA encoding a secretion signal, whereby the resulting peptide is a precursor protein. The resulting processed protein may be recovered from the periplasmic space or the fermentation medium.

In preferred embodiments, the DNA plasmids also include a transcription terminator sequence. As used herein, a "transcription terminator region" has either (a) a subsegment that encodes a polyadenylation signal and polyadenylation site in the transcript, and/or (b) a subsegment that provides a transcription termination signal that terminates transcription by the polymerase that recognizes the selected promoter. The entire transcription terminator may be obtained from a protein-encoding gene, which may be the same or different from the inserted gene or the source of the promoter. Transcription terminators are optional components of the expression systems herein, but are employed in preferred embodiments.

The plasmids used herein include a promoter in operable association with the DNA encoding the protein or polypeptide of interest and are designed for expression of proteins in a bacterial host. It has been found that tightly regulatable promoters are preferred for expression of saporin. Suitable promoters for expression of proteins and polypeptides herein are widely available and are well known in the art. Inducible promoters or constitutive promoters that are linked to regulatory regions are preferred. Such promoters include, but are not limited to, the T7 phage promoter and other T7-like phage promoters, such as the T3, T5 and SP6 promoters, the trp, lpp, and lac promoters, such as the lacUV5, from *E. coli*; the P10 or polyhedron gene promoter of baculovirus/insect cell expression systems (see, e.g., U.S. Pat. Nos. 5,243,041, 5,242,687, 5,266,317, 4,745,051, and 5,169,784) and inducible promoters from other eukaryotic expression systems. For expression of the proteins such promoters are inserted in a plasmid in operative linkage with a control region such as the lac operon.

Preferred promoter regions are those that are inducible and functional in *E. coli*. Examples of suitable inducible promoters and promoter regions include, but are not limited to: the *E coli* lac operator responsive to isopropyl β-D-thiogalactopyranoside (IPTG; see, et al. Nakamura et al., *Cell* 18:1109–1117, 1979); the metallothionein promoter metal-regulatory-elements responsive to heavy-metal (e.g., zinc) induction (see, e.g., U.S. Pat. No. 4,870,009 to Evans et al.); the phage T7lac promoter responsive to IPTG (see, e.g., U.S. Pat. No. 4,952,496; and Studier et al., *Meth. Enzymol.* 185:60–89, 1990) and the TAC promoter.

The plasmids also preferably include a selectable marker gene or genes that are functional in the host. A selectable marker gene includes any gene that confers a phenotype on bacteria that allows transformed bacterial cells to be identified and selectively grown from among a vast majority of untransformed cells. Suitable selectable marker genes for bacterial hosts, for example, include the ampicillin resistance gene (Amp$^r$), tetracycline resistance gene (Tc$^r$) and the kanamycin resistance gene (Kan$^r$). The kanamycin resistance gene is presently preferred.

The plasmids may also include DNA encoding a signal for secretion of the operably linked protein. Secretion signals suitable for use are widely available and are well known in the art. Prokaryotic and eukaryotic secretion signals functional in *E. coli* may be employed. The presently preferred secretion signals include, but are not limited to, those encoded by the following *E. coli* genes: ompA, ompT, ompF, ompC, beta-lactamase, and alkaline phosphatase, and the like (von Heijne, *J. Mol. Biol.* 184:99–105, 1985). In addition, the bacterial pelB gene secretion signal (Lei et al., *J. Bacteriol.* 169:4379, 1987), the phoA secretion signal, and the cek2 functional in insect cell may be employed. The most preferred secretion signal is the *E. coli* ompA secretion signal. Other prokaryotic and eukaryotic secretion signals known to those of skill in the art may also be employed (see, e.g., von Heijne, *J. Mol. Biol.* 184:99–105, 1985). Using the methods described herein, one of skill in the art can substitute secretion signals that are functional in either yeast, insect or mammalian cells to secrete proteins from those cells.

Particularly preferred plasmids for transformation of *E. coli* cells include the pET expression vectors (see U.S. Pat. No. 4,952,496; available from Novagen, Madison, Wis.; see also literature published by Novagen describing the system). Such plasmids include pET 11a, which contains the T7lac promoter, T7 terminator, the inducible *E. coli* lac operator, and the lac repressor gene; pET 12a–c, which contains the T7 promoter, T7 terminator, and the *E. coli* ompT secretion signal; and pET 15b (Novagen, Madison, Wis.), which contains a His-Tag™ leader sequence for use in purification with a His column and a thrombin cleavage site that permits cleavage following purification over the column, the T7-lac promoter region and the T7 terminator.

Other preferred plasmids include the pKK plasmids, particularly pKK 223-3, which contains the tac promoter, (available from Pharmacia; see also Brosius et al., *Proc. Natl. Acad Sci.* 81:6929, 1984; Ausubel et al., *Current Protocols in Molecular Biology*; U.S. Pat. Nos. 5,122,463, 5,173,403, 5,187,153, 5,204,254, 5,212,058, 5,212,286, 5,215,907, 5,220,013, 5,223,483, and 5,229,279). Plasmid pKK has been modified by replacement of the ampicillin resistance marker gene, by digestion with EcoRI, with a kanamycin resistance cassette with EcoRI sticky ends (purchased from Pharmacia; obtained from pUC4K, see, e.g., Vieira et al. (*Gene* 19:259–268, 1982; and U.S. Pat. No. 4,719,179). Baculovirus vectors, such as pBlueBac (also called pJVETL and derivatives thereof), particularly pBlueBac III, (see, e.g., U.S. Pat. Nos. 5,278,050, 5,244,805, 5,243,041, 5,242,687, 5,266,317, 4,745,051, and 5,169,784; available from Invitrogen, San Diego) may also be used for expression of the polypeptides in insect cells. The pBlueBac III vector is a dual promoter vector and provides for the selection of recombinants by blue/white screening as this plasmid contains the β-galactosidase gene (lacZ) under the control of the insect recognizable ETL promoter and is inducible with IPTG. A DNA construct may be made in baculovirus vector pBluebac III and then co-transfected with wild type virus into insect cells *Spodoptera frugiperda* (sf9 cells; see, e.g., Luckow et al., *Bio/technology* 6:47–55, 1988, and U.S. Pat. No. 4,745,051).

Other plasmids include the pIN-IIIompA plasmids (see U.S. Pat. No. 4,575,013; see also Duffaud et al., *Meth. Enz.* 153:492–507, 1987), such as pIN-IIIompA2. The pIN-IIIompA plasmids include an insertion site for heterologous DNA linked in transcriptional reading frame with four functional fragments derived from the lipoprotein gene of *E. coli*. The plasmids also include a DNA fragment coding for the signal peptide of the ompA protein of *E. coli*, positioned such that the desired polypeptide is expressed with the ompA signal peptide at its amino terminus, thereby allowing efficient secretion across the cytoplasmic membrane. The plasmids further include DNA encoding a specific segment of the *E. coli* lac promoter-operator, which is positioned in the proper orientation for transcriptional expression of the desired polypeptide, as well as a separate functional *E. coli* lack gene encoding the associated repressor molecule that, in the absence of lac operon inducer, interacts with the lac promoter-operator to prevent transcription therefrom. Expression of the desired polypeptide is under the control of the lipoprotein (lpp) promoter and the lac promoter-operator, although transcription from either promoter is normally blocked by the repressor molecule. The repressor is selectively inactivated by means of an inducer molecule thereby inducing transcriptional expression of the desired polypeptide from both promoters.

Preferably, the DNA fragment is replicated in bacterial cells, preferably in *E. coli*. The preferred DNA fragment also includes a bacterial origin of replication, to ensure the maintenance of the DNA fragment from generation to generation of the bacteria. In this way, large quantities of the DNA fragment can be produced by replication in bacteria. Preferred bacterial origins of replication include, but are not limited to, the f1-ori and col E1 origins of replication. Preferred hosts contain chromosomal copies of DNA encoding T7 RNA polymerase operably linked to an inducible promoter, such as the lacUV promoter (see U.S. Pat. No. 4,952,496). Such hosts include, but are not limited to, lysogens *E. coli* strains HMS174(DE3)pLysS, BL21(DE3) pLysS, HMS174(DE3) and BL21(DE3). Strain BL21(DE3) is preferred. The pLys strains provide low levels of T7 lysozyme, a natural inhibitor of T7 RNA polymerase.

The DNA fragments provided may also contain a gene coding for a repressor protein. The repressor protein is capable of repressing the transcription of a promoter that contains sequences of nucleotides to which the repressor protein binds. The promoter can be derepressed by altering the physiological conditions of the cell. For example, the alteration can be accomplished by adding to the growth medium a molecule that inhibits the ability to interact with the operator or with regulatory proteins or other regions of the DNA or by altering the temperature of the growth media. Preferred repressor proteins include, but are not limited to the *E. coli* lacI repressor responsive to IPTG induction, the temperature sensitive λ cI857 repressor, and the like. The *E. coli* lacI repressor is preferred.

DNA encoding full-length FGF-2 or FGF-2 mutein is linked to DNA encoding an nucleic acid binding domain, such as protamine, and introduced into the pET vectors, including pET-11a and pET-12a expression vectors (Novagen, Madison, Wis.), for intracellular and periplasmic expression, respectively, of FGF-protamine fusion proteins.

I. Preparation of Complexes Containing Receptor-binding Internalized Ligands/Nucleic Acid Binding Domain Conjugates and Cytocide-encoding Agents Within the context of this invention, specificity of delivery in a cell-specific manner is achieved through the ligand. The choice of the receptor-binding internalized ligand to use will depend upon the receptor expressed by the target cells. The receptor type of the target cell population may be determined by conventional techniques such as antibody staining, PCR of cDNA using receptor-specific primers, and biochemical or functional receptor binding assays. It is preferable that the receptor be cell type-specific or have increased expression or activity (i.e., higher rate of internalization) within the target cell population. Typically, a nucleic acid binding domain is coupled to a receptor-binding internalized ligand, either by chemical conjugation or as a fusion protein. As described below, the ligand may alternatively be coupled directly to the nucleic acid and then complexed with a nucleic acid binding protein, such as poly-lysine, which serves to condense the nucleic acid. Linkers as described above may optionally be used.

The complexes are tested in vitro and in vivo for the desired effect. Thus, if the nucleic acid encodes a cytocide, cell cytotoxicity or inhibition of protein synthesis or other function is measured. Cell death is conveniently assayed by counting the number of living cells in the presence and absence of delivery. Other assays, such as MTS, $^3$H-leu uptake, $^3$H-thymidine incorporation, flow cytometry, or staining cells with viable dyes are also suitable.

1. Chemical Conjugation a. Preparation of Receptor-binding Internalized Ligands

Receptor-binding internalized ligands are prepared as discussed above by any suitable method, including recombinant DNA technology, isolation from a suitable source, purchase from a commercial source, or chemical synthesis. The selected linker or linkers is (are) linked to the receptor-binding internalized ligands by chemical reaction, generally relying on an available thiol or amine group on the receptor-binding internalized ligands. Heterobifunctional linkers are particularly suited for chemical conjugation. Alternatively, if the linker is a peptide linker, then the linker may be incorporated into the ligand as a fusion protein.

Any protein that binds and internalizes through a receptor interaction may be used herein. In particular, any member of the FGF family of peptides or portion thereof that binds to an FGF receptor and internalizes a linked agent may be used herein. Although any of the growth factors may be conjugated in this manner, FGF, VEGF, and HBEGF conjugation are discussed merely by way of example and not by way of limitation.

If necessary or desired, the heterogeneity of preparations of ligand (e.g., FGF) containing chemical conjugates and fusion proteins can be reduced by modifying the ligand by deleting or replacing a site(s) that causes the heterogeneity. Such sites in FGF are typically cysteine residues that upon folding of the protein remain available for interaction with other cysteines or for interaction with more than one cytotoxic molecule per molecule of FGF peptide. Thus, such cysteine residues do not include any cysteine residue that is required for proper folding of the FGF peptide or for binding to an FGF receptor and internalization. For chemical conjugation, one cysteine residue that in physiological conditions is available for interaction is not replaced but is used as the site for linking the cytotoxic moiety. The resulting modified FGF is thus conjugated with a single species of nucleic acid binding domain (or nucleic acid).

The polypeptide reactive with an FGF receptor may be modified by removing one or more reactive cysteines that are not required for receptor binding, but that are available for reaction with appropriately derivatized cytotoxic agent, so that the resulting FGF protein has only one cysteine residue available for conjugation with the cytotoxic agent. If necessary, the contribution of each cysteine to the ability to bind to FGF receptors may be determined empirically. Each cysteine residue may be systematically replaced with a conservative amino acid change or deleted. The resulting mutein is tested for the requisite biological activity of the ability to bind to FGF receptors and internalize. If the mutein retains at least 50% of wild-type activity, then the cysteine residue is not required. Additional cysteines are systematically deleted and replaced and the resulting muteins are tested for activity. In this manner the minimum number and identity of the cysteines needed for receptor binding and internalization may be determined. Retention of proliferative activity is indicative, though not definitive, of the retention of such activities. Proliferative activity may be measured by any suitable proliferation assay, such as the assay, exemplified below, that measures the increase in cell number of bovine aortic endothelial cells.

It is noted, however, that modified or mutant FGFs may exhibit reduced or no proliferative activity, but may be suitable for use herein, if they retain the ability to target cytocide-encoding agent to cells bearing FGF receptors and result in internalization. Certain residues of FGF-2 have been associated with proliferative activity. Modification of these residues arg 116, lys 119, tyr 120, trp 123 to ile 116, glu 119, ala 120, ala 123 may be made individually (see SEQ ID NOs. 81–84) to remove this function. In addition, a double modification of Arg 118 to Lys and lys 119 to glu also gives markedly reduced proliferative ability. The resulting-protein is tested for proliferative activity by a standard assay.

Any of FGF-1–FGF-9 may be used. The complete amino acid sequence of each of FGF-1–FGF-9 is known (see, e.g., SEQ ID NO. 10 FGF-1) and SEQ ID NOs. 12–18 (FGF-3–FGF-9, respectively)). Comparison among the amino acid sequences of FGF-1–FGF-9 reveals that one Cys is conserved among FGF family of peptides (see Table 3). These cysteine residues may be required for secondary structure and are not preferred residues to be altered. Each of the remaining cysteine residues may be systematically deleted and/or replaced by a serine residue or other residue that would not be expected to alter the structure of the protein and tested for biological activity as described above.

The cysteine residues in the FGF family that may be essential for retention of biological activity and that are not preferred residues for deletion or replacement are as follows: FGF-2, $cys^{101}$; FGF-3, $cys^{113}$; FGF4, $cys^{155}$; FGF-5, $cys^{160}$;

FGF-6, cys$^{147}$; FGF-7, cys$^{137}$; FGF-8, cys$^{127}$; and FGF-9, cys$^{134}$. For example, FGF-1 has cysteines at positions 31, 98 and 132; FGF-2 has cysteines at positions 34, 78, 96 and 101; FGF-3 has cysteines at positions 50 and 115; FGF-4 has cysteines at positions 88 and 155; FGF-5 has cysteines at positions 19, 93, 160 and 202; FGF-6 has cysteines at positions 80 and 147; FGF-7 has cysteines at positions 18, 23, 32, 46, 71, 133 and 137; FGF-8 has cysteines at positions 10, 19, 109 and 127; and FGF-9 has cysteines at positions 68 and 134.

Since FGF-3, FGF-4 and FGF-6 have only two cysteines, for purposes of chemical conjugation, preferably neither cysteine is deleted or replaced, unless another residue, preferably one near either terminus, is replaced with a cysteine. With respect to the other FGF family members, at least one cysteine must remain available for conjugation with the cytotoxic conjugate and probably two cysteines, but at least the cysteine residues set forth in Table 3. A second cysteine may be required to form a disulfide bond. Thus, any FGF peptide that has more than three cysteines is be modified for chemical conjugation by deleting or replacing the other cysteine residues. FGF peptides that have three cysteine residues are modified by elimination of one cysteine, conjugated to a cytotoxic moiety and tested for the ability to bind to FGF receptors and internalize the cytotoxic moiety.

In accord with the methods herein, several muteins of basic FGF for chemical conjugation have been produced (preparation of muteins for recombinant expression of the conjugate is described below). DNA, obtained from pFC80 (see PCT Application Serial No. PCT/US93/05702; U.S. application Ser. No. 07/901,718; see also SEQ ID NO. 52) encoding basic FGF has been mutagenized. Mutagenesis of cysteine 78 of basic FGF (FGF-2) to serine ([C78S]FGF) or cysteine 96 to serine ([C96S]FGF) produced two mutants that retain virtually complete proliferative activity of native basic FGF as judged by the ability to stimulate endothelial cell proliferation in culture. The activities of the two mutants and the native protein do not significantly differ as assessed by efficacy or maximal response. Sequence analysis of the modified DNA verified that each of the mutants has one codon for cysteine converted to that for serine. The construction and biological activity of FGF-1 with cysteine substitutions of one, two or all three cysteines has been disclosed (U.S. Pat. No. 5,223,483). The mitogenic activity of the mutants was similar to or increased over the native protein. Thus, any of the cysteines may be mutated and FGF-1 will still bind and be internalized.

The resulting mutein FGF or unmodified FGF is reacted with a nucleic acid binding domain and optionally a linker. The bFGF muteins may react with a single species of derivatized nucleic acid binding domain (mono-derivatized nucleic acid binding domain), thereby resulting in monogenous preparations of FGF-nucleic acid binding domain conjugates and homogeneous compositions of FGF-nucleic acid binding domain chemical conjugates. The resulting chemical conjugates do not aggregate and retain the requisite biological activities.

VEGF or HBEGF may be isolated from a suitable source or may be produced using recombinant DNA methodology, discussed below. To effect chemical conjugation herein, the growth factor protein is conjugated generally via a reactive amine group or thiol group to the nucleic acid binding domain directly or through a linker to the nucleic acid binding domain. The growth factor protein is conjugated either via its N-terminus, C-terminus, or elsewhere in the polypeptide. In preferred embodiments, the growth factor protein is conjugated via a reactive cysteine residue to the linker or to the nucleic acid binding domain. The growth factor can also be modified by addition of a cysteine residue, either by replacing a residue or by inserting the cysteine, at or near the amino or carboxyl terminus, within about 20, preferably 10 residues from either end, and preferably at or near the amino terminus.

In certain embodiments, the heterogeneity of preparations may be reduced by mutagenizing the growth factor protein to replace reactive cysteines, leaving, preferably, only one available cysteine for reaction as described above for FGFs. As described above, only binding and internalization is required. Proliferative activity may be removed by mutagenesis and is a preferred embodiment for some applications.

In the case of VEGF, VEGF$_{121}$ contains 9 cysteines and each of VEGF$_{165}$, VEGF$_{189}$ and VEGF$_{206}$ contain 7 additional residues in the region not present in VEGF$_{121}$. Any of the 7 are likely to be non-essential for targeting and internalization of linked cytotoxic agents. Recently, the role of Cys-25, Cys-56, Cys-67, Cys-101, and Cys-145 in dimerization and biological activity was assessed (Claffery et al., Biochem. Biophys. Acta 1246:1–9, 1995). Dimerization requires Cys-25, Cys-56, and Cys-67. Substitution of any one of these cysteine residues resulted in secretion of a monomeric VEGF, which was inactive in both vascular permeability and endothelial cell mitotic assays. In contrast, substitution of Cys 145 had no effect on dimerization, although biological activities were somewhat reduced. Substitution of Cys-101 did not result in the production of a secreted or cytoplasmic protein. Thus, substitution of Cys-145 is preferred.

The VEGF monomers are preferably linked via non-essential cysteine residues to the linkers or to the targeted agent. VEGF that has been modified by introduction of a Cys residue at or near one terminus, preferably the N-terminus is preferred for use in chemical conjugation. For use herein, preferably the VEGF is dimerized prior to linkage to the linker and/or targeted agent. Methods for coupling proteins to the linkers, such as the heterobifunctional agents, or to nucleic acids, or to proteins are known to those of skill in the art and are also described herein.

Each of the HBEGF polypeptides described herein have six cysteine residues. Each of the six cysteines may independently be replaced and the resulting mutein tested for the ability to bind to HBEGF receptors and to be internalized. Alternatively, the resulting mutein-encoding DNA is used as part of a construct containing DNA encoding the nucleic acid binding domain linked to the HBEGF-encoding DNA. The construct is expressed in a suitable host cell and the resulting protein tested for the ability to bind to HBEGF receptors and internalize. It is known that the first 21 amino acids contain receptor binding property. As long as this ability is retained the mutein is suitable for use herein.

Methods for chemical conjugation of proteins are known to those of skill in the art. The preferred methods for chemical conjugation depend on the selected components, but preferably rely on disulfide bond formation. For example, if the targeted agent is SPDP-derivatized saporin, then it is advantageous to dimerize the VEGF moiety prior coupling or conjugating to the derivatized saporin. If VEGF is modified to include a cysteine residue at or near the N-, preferably, or C-terminus, then dimerization should follow coupling to the nucleic acid binding domain. To effect chemical conjugation herein, the HBEGF polypeptide is linked via one or more selected linkers or directly to the nucleic acid binding domain.

b. Preparation of Nucleic Acid Binding Domains for Chemical Conjugation

A nucleic acid binding domain is prepared for chemical conjugation. For chemical conjugation, a nucleic acid binding domain may be derivatized with SPDP or another suitable chemical. If the binding domain does not have a Cys residue available for reaction, one can be either inserted or substituted for another amino acid. If desired, mono-derivatized species may be isolated, essentially as described.

For chemical conjugation, the nucleic acid binding domain may be derivatized or modified such that it includes a cysteine residue for conjugation to the receptor-binding internalized ligand. Typically, derivatization proceeds by reaction with SPDP, which results in a heterogeneous population. For example, a nucleic acid binding domain that is derivatized by SPDP to a level of 0.9 moles pyridine-disulfide per mole of nucleic acid binding domain includes a population of non-derivatized, mono-derivatized and di-derivatized proteins. Nucleic acid binding domain proteins, which are overly derivatized with SPDP, may lose ability to bind nucleic acid because of reaction with sensitive lysines (Lambert et al., *Cancer Treat. Res.* 37:175–209, 1988).

The use of purified mono-derivatized nucleic acid binding domain has distinct advantages over the non-purified material. The amount of receptor-binding internalized ligand that can react with nucleic acid binding domain is limited to one molecule with the mono-derivatized material. The quantity of non-derivatized nucleic acid binding domain in the preparation of the non-purified material can be difficult to judge and this may lead to errors in being able to estimate the correct proportion of derivatized nucleic acid binding domain to add to the reaction mixture. However, because of the removal of a negative charge by the reaction of SPDP with lysine, the various species, exhibit charge differences. This charge difference may be exploited in the purification of mono-derivatized nucleic acid binding domain by Mono-S cation exchange chromatography. There may still be sources of heterogeneity with the mono-derivatized nucleic acid binding domain used here but is acceptable as long as binding to the cytocide-encoding agent is not impacted. For example, because more than one amino group on the nucleic acid binding domain may react with the succinimidyl moiety, it is possible that more than one amino group on the surface of the protein is reactive.

As an alternative to derivatizing to introduce a sulfhydryl, the nucleic acid binding domain can be modified by the introduction of a cysteine residue by well known recombinant methods. Preferred loci for introduction of a cysteine residue include the N-terminus region, preferably within about one to twenty residues from the N-terminus of the nucleic acid binding domain.

Using either methodology (reacting mono-derivatized nucleic acid binding domain or introducing a Cys residue into nucleic acid binding domain), the resulting preparations of chemical conjugates are monogenous and should be free of aggregates.

2. Fusion Protein of Receptor-binding Internalized Ligands and Nucleic Acid Binding Domain As a preferred alternative, the conjugate is a fusion protein of receptor-binding internalized ligand, optional linker, and nucleic acid binding domain. A fusion protein is a more homogeneous preparation. As well, aggregate formation can be reduced in preparations containing the fusion proteins by modifying the receptor-binding internalized ligand, such as by removal of nonessential cysteines, and/or the nucleic acid binding domain to prevent interactions between conjugates via free cysteines. Optionally, one or more coding regions for an endosome-disruptive peptide or cytoplasmic retention signal may be constructed as part of the fusion protein.

DNA encoding the polypeptides may be isolated, synthesized or obtained from commercial sources or prepared as described herein. Expression of recombinant polypeptides may be performed as described herein or by other well known methods; and DNA encoding these polypeptides may be used as the starting materials for the methods herein.

As described above, DNA encoding FGF, VEGF, HBEGF hepatocyte growth factor, IL-1, IL-2, IL-3, IL4, IL-5, IL-6, IL-8, IL-10, IL-11, IL-13, TNF, GM-CSF, IFN and IGF polypeptides and others and/or the amino acid sequences of these factors are described above. DNA may be prepared synthetically based on the amino acid or DNA sequence or may be isolated using methods known to those of skill in the art, such as PCR, probe hybridization of libraries, and the like or obtained from commercial or other sources. For example, suitable methods are described in the Examples for amplifying FGF encoding cDNA from plasmids containing FGF encoding cDNA.

As described herein, such DNA may then be mutagenized using standard methodologies to delete or replace any cysteine residues that are responsible for aggregate formation. If necessary, the identity of cysteine residues that contribute to aggregate formation may be determined empirically, by deleting and/or replacing a cysteine residue and ascertaining whether the resulting growth factor with the deleted cysteine forms aggregates in solutions containing physiologically acceptable buffers and salts. Loci for insertion of cysteine residues may also be determined empirically. Generally, regions at or near (within 20, preferably 10 amino acids) the C- or, preferably, the N-terminus are preferred.

The DNA construct encoding the fusion protein can be inserted into a plasmid and expressed in a selected host, as described above, to produce a recombinant receptor-binding internalized ligand-nucleic acid binding domain conjugate. Multiple copies of the chimera can be inserted into a single plasmid in operative linkage with one promoter. When expressed, the resulting protein will then be a multimer. Typically, two to six copies of the chimera are inserted, preferably in a head to tail fashion, into one plasmid.

a. Preparation of Muteins of a Fusion Protein

Removal of cysteines not required for binding and internalization is preferred for both chemical conjugation and recombinant methods. Thus, ligands that have more than two cysteines are modified by replacing the remaining cysteines with serines or other residues. The resulting muteins may be tested for the requisite biological activity as described above. As exemplified herein, conjugates containing bFGF muteins in which $Cys^{78}$ and $Cys^{96}$ have been replaced with serine residues have been prepared.

In other preferred embodiments, muteins of growth factor ligands that lack proliferative ability, or cell migration inducement and the like.

b. DNA Constructs and Expression of the DNA Constructs

To produce fusion protein, DNA encoding the receptor-binding internalized ligand is modified so that as long as internalization is not required, the ligand does not include any cysteines available for reaction. In preferred embodiments, DNA encoding an FGF polypeptide is linked to DNA encoding a nucleic acid binding domain. The DNA encoding the FGF polypeptide or other receptor-binding internalized ligand is modified in order to remove the translation stop codon and other transcriptional or translational stop signals that may be present and to remove or replace DNA encoding the available cysteines. The DNA is then ligated to the DNA encoding the nucleic acid binding domain polypeptide directly or via a linker region between the first codon of the nucleic acid binding domain and the last codon of the FGF. The size of the linker region is not limited as long as the resulting conjugate binds and is internalized by a target cell. Presently, spacer regions of from about one to about seventy-five to ninety codons are preferred. The order of the receptor-binding internalized ligand and nucleic acid binding domain in the fusion protein may be reversed. If the nucleic acid binding domain is N-terminal, then it is modified to remove the stop codon and any stop signals.

As discussed above, any ligand including the heparin-binding proteins, FGF, VEGF, HBEGF, cytokine, growth factor and the like may be modified and expressed in accord with the methods herein. The DNA encoding the resulting receptor-binding internalized ligand-nucleic acid binding domain can be inserted into a plasmid and expressed in a selected host, as described above, to produce a monogenous preparation. Fusion proteins of FGF-2 and protamine are especially suitable for use in the present invention.

Multiple copies of the modified receptor-binding internalized ligand/nucleic acid binding domain chimera can be inserted into a single plasmid in operative linkage with one promoter. When expressed, the resulting protein will be a multimer. Typically two to six copies of the chimera are inserted, preferably in a head to tail fashion, into one plasmid.

Merely by way of example, DNA encoding human bFGF-SAP having SEQ ID NO. 52 has been mutagenized as described in the Examples using splicing by overlap extension (SOE). Another preferred coding region is set forth in SEQ ID NO. 53. In both instances, the DNA is modified by replacing the cysteines at positions 78 and 96 with serine. The codons encoding cysteine residues at positions 78 and 96 of FGF were converted to serine codons by SOE. Each application of the SOE method uses two amplified oligonucleotide products, which have complementary ends as primers and which include an altered codon at the locus at which the mutation is desired, to produce a hybrid product. A second amplification reaction that uses two primers that anneal at the non-overlapping ends amplify the hybrid to produce DNA that has the desired alteration.

3. Binding of the Receptor-binding Internalized Ligand/Nucleic Acid Binding Domain Conjugate to Cytocide-encoding or Prodrug-encoding Agents The receptor-binding internalized ligand/nucleic acid binding domain is incubated with the cytocide-encoding or prodrug-encoded agent, preferably a circular DNA molecule, to be delivered under conditions that allow binding of the nucleic acid binding domain to the agent. Conditions will vary somewhat depending on the nature of the nucleic acid binding domain, but will typically occur in 0.1 M NaCl and 20 mM HEPES or other similar buffer. Alternatively, salt conditions can be varied to increase the packing or condensation of DNA. The extent of binding is preferably tested for each preparation. After complexing, additional nucleic acid binding domain, such as poly-L-lysine, may be added to further condense the nucleic acid.

In addition to binding of the nucleic acid binding domain to nucleic acid, the complex needs to be condensed for efficient uptake by a cell. A toroidal shape allows efficient uptake, whereas rod shapes are not efficiently taken up. Thus, conditions for binding that favor the formation of toroids are preferred. If a nucleic acid binding domain itself does not cause toroid formation, an addition composition that causes toroid formation should be added. Such compositions include poly-L-lysine, spermine, spermidine, cobalt hexamine, $MnCl_2$, protainines and the like.

For preparing complexes, the nucleic acid is diluted and added to the conjugate with gentle agitation, so as not to cause frothing. The length of DNA is irrelevant to toroid formation.

Merely by way of example, test constructs have been made and tested. One construct is a chemical conjugate of bFGF and poly-L-lysine. The bFGF molecule is a variant in which the Cys residue at position 96 has been changed to a serine; thus, only the Cys at position 78 is available for conjugation. This bFGF is called FGF2-3. The poly-L-lysine was derivatized with SPDP and coupled to FGF2-3. This FGF2-3/poly-L-lysine conjugate was used to deliver a plasmid able to express the β-galactosidase gene.

The ability of a construct to bind nucleic acid molecules may be conveniently assessed by agarose gel electrophoresis. Briefly, a plasmid, such as pSVβ, is digested with restriction enzymes to yield a variety of fragment sizes. For ease of detection, the fragments may be labeled with 32P either by filling in of the ends with DNA polymerase I or by phosphorylation of the 5'-end with polynucleotide kinase following dephosphorylation by alkaline phosphatase. The plasmid fragments are then incubated with the receptor-binding internalized ligand/nucleic acid binding domain in this case, FGF2-3/poly-L-lysine in a buffered saline solution, such as 20 mM HEPES, pH 7.3, 0.1M NaCl. The reaction mixture is electrophoresed on an agarose gel alongside similarly digested, but nonreacted fragments. If a radioactive label was incorporated, the gel may be dried and autoradiographed. If no radioactive label is present, the gel may be stained with ethidium bromide and the DNA visualized through appropriate red filters after excitation with UV. Binding has occurred if the mobility of the fragments is retarded compared to the control. In the example case, the mobility of the fragments was retarded after binding with the FGF2-3/poly-L-lysine conjugate. If there is insufficient binding, poly-L-lysine may be additionally added until binding is observed.

The amount of compaction and shape of compaction may be measured in several different ways. Visualization by electron microscopy, measurement of circular dichroism, and laser light scatterings can all distinguish toroids from rods.

Further testing of the conjugate is performed to show that it binds to the cell surface receptor and is internalized into the cell. It is not necessary that the receptor-binding internalized ligand part of the conjugate retain complete biological activity. For example, FGF is mitogenic on certain cell types. As discussed above, this activity may not always be desirable. If this activity is present, a proliferation assay is performed. Likewise, for each desirable activity, an appropriate assay may be performed. However, for application of the subject invention, the only criteria that need be met are receptor binding and internalization.

Receptor binding and internalization may be measured by the following three assays. (1) A competitive inhibition assay of the complex to cells expressing the appropriate receptor demonstrates receptor binding. (2) Receptor binding and internalization may be assayed by measuring expression of a reporter gene, such as β-gal (e.g., enzymatic activity), in cells that have been transformed with a complex of a plasmid encoding a reporter gene and a conjugate of a receptor-binding internalized ligand and nucleic acid binding domain. This assay is particularly useful for optimizing conditions to give maximal transformation. Thus, the optimum ratio of receptor-binding internalized ligand/nucleic acid binding domain to nucleic acid and the amount of DNA per cell may readily be determined by assaying and comparing the enzymatic activity of β-gal. As such, these first two assays are useful for preliminary analysis and failure to show receptor binding or β-gal activity does not per se eliminate a candidate receptor-binding internalized ligand/nucleic acid binding domain conjugate or fusion protein from further analysis. (3) The preferred assay is a cytotoxicity assay performed on cells transformed with a cytocide-encoding agent bound by receptor-binding internalized ligand/nucleic acid binding domain. While, in general, any cytocidal molecule may be used, ribosome inactivating proteins are preferred and saporin, or another type I ribosome inactivating protein, is particularly preferred. A statistically significant reduction in cell number demonstrates the ability of the receptor-binding internalized ligand/nucleic acid binding domain conjugate or fusion to deliver nucleic acids into a cell. Any cell expressing the appropriate receptor may be used. For FGF as a ligand, cell lines including COS and rabbit smooth muscle cells may be used.

4. Conjugation of Ligand to Nucleic Acid and Toroid Formation

As an alternative, the receptor-internalized binding ligand may be conjugated to the nucleic acid, either directly or through a linker. Methods for conjugating nucleic acids, at the 5' ends, 3' ends and elsewhere, to the amino and carboxyl termini and other sites in proteins are known to those of skill in the art (for a review see, e.g., Goodchild, (1993) In: *Perspectives in Bioconjugate Chemistry*, Mears, Ed., American Chemical Society, Washington, D.C. pp. 77–99). For example, proteins have been linked to nucleic acids using ultraviolet irradiation (Sperling et al. (1978) *Nucleic Acids Res.* 5:2755–2773; Fiser et al. (1975) *FEBS Lett.* 52:281–283), bifunctional chemicals (Baumert et al. (1978) *Eur. J. Biochem.* 89:353–359; and Oste et al. (1979) *Mol. Gen. Genet.* 168:81–86) and photochemical cross-linking (Vanin et al. (1981) *FEBS Lett.* 124:89–92; Rinke et al. (1980) *J. Mol. Biol.* 137:301–314; Millon et al. (1980) *Eur. J. Biochem.* 110:485–454).

In particular, the reagents (N-acetyl-N'-(p-glyoxylylbenzolyl)cystamine and 2-iminothiolane have been used to couple DNA to proteins, such as α-macroglobulin (α2M) via mixed disulfide formation (see Cheng et al., *Nucleic Acids Res.* 11:659–669, 1983). N-acetyl-N'-(p-glyoxylylbenzolyl)cystamine reacts specifically with nonpaired guaninine residues and, upon reduction, generates a free sulfhydryl group. 2-iminothiolane reacts with proteins to generate sulfhydryl groups that are then conjugated to the derivatized DNA by an intermolecular disulfide interchange reaction. Any linkage may be used provided that the targeted nucleic acid is active upon internalization of the conjugate. Thus, it is expected that cleavage of the linkage may be necessary, although it is contemplated that for some reagents, such as DNA encoding ribozymes linked to promoters or DNA encoding therapeutic agents for delivery to the nucleus, such cleavage may not be necessary.

Thiol linkages, which are preferred, can be readily formed using heterobiofunctional reagents. Such linkages are reversible in a cell to release the nucleic acid from the ligand. Amines have also been attached to the terminal 5' phosphate of unprotected oligonucleotides or nucleic acids in aqueous solutions by reacting the nucleic acid with a water-soluble carbodiimide, such as 1-ethyl-3'[3-dimethylaminopropyl] carbodiimide (EDC) or N-ethyl-N'(3-dimethylaminopropylcarbodiimidehydrochloride (EDCI), in imidazole buffer at pH 6 to produce the 5'phosphorimidazolide. Contacting the 5'phosphorimidazolide with amine-containing molecules, such as an FGF, and ethylenediamine, results in stable phosphoramidates (see, e.g., Chu et al., *Nucleic Acids Res.* 11:6513–6529, 1983; and WO 88/05077). In particular, a solution of DNA is saturated with EDC, at pH 6 and incubated with agitation at 4° C. overnight. The resulting solution is then buffered to pH 8.5 by adding, for example about 3 volutes of 100 mM citrate buffer, and adding about 5 µg–about 20 µg of an FGF, and agitating the resulting mixture at 4° C. for about 48 hours. The unreacted protein may be removed from the mixture by column chromatography using, for example, Sephadex G75 (Pharmacia) using 0.1 M ammonium carbonate solution, pH 7.0 as an eluting buffer. The isolated conjugate may be lyophilized and stored until used.

U.S. Pat. No. 5,237,016 provides methods for preparing nucleotides that are bromacetylated at their 5' termini and reacting the resulting oligonucleotides with thiol groups. Oligonucleotides derivatized at their 5'-termini bromoacetyl groups can be prepared by reacting 5'-aminohexyl-phosphoramidate oligonucleotides with bromoacetic acid-N-hydroxysuccinimide ester as described in U.S. Pat. No. 5,237,016. This patent also describes methods for preparing thiol-derivatized nucleotides, which can then be reacted with thiol groups on the selected growth factor. Briefly, thiol-derivatized nucleotides are prepared using a 5'-phosphorylated nucleotide in two steps: (1) reaction of the phosphate group with imidazole in the presence of a diimide and displacement of the imidazole leaving group with cystamine in one reaction step; and (2) reduction of the disulfide bond of the cystamine linker with dithiothreitol (see, also, Orgel et al. ((1986) *Nucl. Acids Res.* 14:651, which describes a similar procedure). The 5'-phosphorylated starting oligonucleotides can be prepared by methods known to those of skill in the art (see, e.g., Maniatis et al. (1982) *Molecular Cloning: A Laboratory Manual*, Cold Spring Harbor Laboratory, New York, p. 122).

The nucleic acid, such as a methylphosphonate oligonucleotide (MP-oligomer), may be derivatized by reaction with SPDP or SMPB. The resulting MP-oligomer may be purified by HPLC and then coupled to an FGF, such as an FGF or FGF mutein, modified by replacement of one or more cysteine residues, as described above. The MP-oligomer (about 0.1 µM) is dissolved in about 40–50 µl of 1:1 acetonitrile/water to which phosphate buffer (pH 7.5, final concentration 0.1 M) and a 1 mg MP-oligomer in about 1 ml phosphate buffered saline is added. The reaction is allowed to proceed for about 5–10 hours at room temperature and is then quenched with about 15 µL 0.1 iodoacetamide. FGF-oligonucleotide conjugates can be purified on heparin sepharose Hi Trap columns (1 ml, Pharmacia) and eluted with a linear or step gradient. The conjugate should elute in 0.6 M NaCl.

The ligand may be conjugated to the nucleic acid construct encoding the cytocide or cytotoxic agent or may be conjugated to a mixture of oligonucleotides complementary to one strand of the construct. The oligonucleotides are then added to single stranded construct produced by melting a double-stranded construct or grown and isolated as single-stranded. As a general guideline, the oligonucleotides should hybridize at a higher temperature than the construct alone, if a double-stranded construct is used as the starting material. The gaps are filled in by DNA polymerase I to generate a construct with one strand conjugated to ligand and one strand unconjugated. Oligonucleotides conjugated to ligand and complementary to the other strand may be used in addition to generate a mixture of constructs with different strands linked to ligand. Any remaining single stranded plasmid may be digested with a single strand specific endonuclease. The ligand-conjugated constructs are then mixed with a nucleic acid binding domain, such as protamine or polylysine, to effect condensation of the construct for delivery. Optimal ratios of ligand to DNA may be determined experimentally by receptor-mediated transfection of a construct containing a reporter gene.

As discussed above, for efficient uptake by a cell, the nucleic acid is in a toroidal shape. If the linker portion of the conjugate does not cause the proper condensation, then a molecule, such as poly-L-lysine, spermine or the like, is added. Testing for toroids and receptor binding and internalization is described above.

J. Formulation and Administration of Pharmaceutical Compositions

The conjugates and complexes provided herein are useful in the treatment and prevention of various diseases, syndromes, and hyperproliferative disorders. As used herein, "treatment" means any manner in which the symptoms of a condition, disorder or disease are ameliorated or otherwise beneficially altered. Treatment also encompasses any pharmaceutical use of the compositions herein. As used herein, "amelioration" of the symptoms of a particular disorder refers to any lessening, whether permanent or temporary, lasting or transient, that can be attributed to or associated with administration of the composition. For example, these conjugates and complexes may be used to treat complications of the eye following laser surgery, glaucoma surgery, and removal of pterygii. Following these treatments, reoccurrence of the problem often ensues due to proliferation of cells in the cornea or eye. The conjugates and complexes inhibit the proliferation of these cells. The conjugates and complexes may be used in general to treat pathophysiological conditions, especially FGF-, VEGF-, or HBEGF-mediated pathophysiological conditions by specifically targeting to cells having corresponding receptors.

As used herein, "FGF-mediated pathophysiological condition" refers to a deleterious condition characterized by or caused by proliferation of cells that are sensitive to FGF mitogenic stimulation. Basic FGF-mediated pathophysiological conditions include, but are not limited to, melanoma, other tumors, rheumatoid arthritis, restenosis, Dupuytren's Contracture and certain complications of diabetes, such as proliferative retinopathy.

As used herein, "HBEGF-mediated pathophysiological condition" refers to a deleterious condition characterized by or caused by proliferation of cells that are sensitive to HBEGF mitogenic stimulation. HBEGF-mediated pathophysiological conditions include conditions involving pathophysiological proliferation of smooth muscle cells, such as restenosis, certain tumors, such as solid tumors including breast and bladder tumors, tumors involving pathophysiological expression of EGF receptors, dermatological disorders, such as psoriasis, and ophthalmic disorders involving epithelial cells, such as recurrence of pterygii and secondary lens clouding.

Similarly, tumors and hyperproliferating cells expressing cytokine receptors or growth factor receptors may be eliminated. Such diseases include restenosis, Dupuytren's Contracture, diabetic retinopathies, rheumatoid arthritis, Kaposi's sarcoma, lymphomas, leukemias, tumors such as renal cell carcinoma, colon carcinoma, breast cancer, bladder cancer, pituitary abnormalities, and disorders with underlying vascular proliferation, such as diseases in the back of the eye (e.g., proliferative vitreoritinopathy, inacular degeneration and diabetic retinopathy). For treatment of the back of the eye especially, use of the VEGF-receptor promoter to control expression of the cytocide or cytotoxic agent is preferred. The conjugates may be used to prevent corneal haze or clouding that results from exposure of the cornea to laser radiation during eye surgery, particularly LRK. The haze or clouding appears to result from fibroblastic keratocyte proliferation in the subepithelial zone following photoablation of the cornea.

The conjugates may be used to treat a "hyperproliferative skin disorder." As used herein, it is a disorder that is manifested by a proliferation of endothelial cells of the skin coupled with an underlying vascular proliferation, resulting in a localized patch of scaly or horny or thickened skin or a tumor of endothelial origin. Such disorders include actinic and atopic dermatitis, toxic eczema, allergic eczema, psoriasis, skin cancers and other tumors, such as Kaposi's sarcoma, angiosarcoma, hemangiomas, and other highly vascularized tumors, and vascular proliferative responses, such as varicose veins.

As well, the conjugates may be used to treat or prevent restenosis, a process and the resulting condition that occurs following angioplasty in which the arteries become reclogged. After treatment of arteries by balloon catheter or other such device, denudation of the interior wall of the vessel occurs, including removal of the endothelial cells that constitute the lining of the blood vessels. As a result of this removal and the concomitant vascular injury, smooth muscle cells (SMCs), which form the blood vessel structure, proliferate and fill the interior of the blood vessel. This process and the resulting condition is restenosis.

Pharmaceutical carriers or vehicles suitable for administration of the conjugates and complexes provided herein include any such carriers known to those skilled in the art to be suitable for the particular mode of administration. In addition, the conjugates and complexes may be formulated as the sole pharmaceutically active ingredient in the composition or may be combined with other active ingredients.

The conjugates and complexes can be administered by any appropriate route, for example, orally, parenterally, including intravenously, intradermally, subcutaneously, or topically, in liquid, semi-liquid or solid form and are formulated in a manner suitable for each route of administration. Preferred modes of administration depend upon the indication treated. Dermatological and ophthalmologic indications will typically be treated locally; whereas, tumors and restenosis, will typically be treated by systemic, intradermal, or intramuscular modes of administration.

The conjugates and complexes herein may be formulated into pharmaceutical compositions suitable for topical, local, intravenous and systemic application. For the ophthalmic uses herein, local administration, either by topical administration or by injection is preferred. Time release formulations are also desirable. Effective concentrations of one or more of the conjugates and complexes are mixed with a suitable pharmaceutical carrier or vehicle. As used herein an "effective amount" of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Repeated administration may be required to achieve the desired amelioration of symptoms.

As used herein, "an ophthalmically effective amount" is that amount which, in the composition administered and by the technique administered, provides an amount of therapeutic agent to the involved eye. tissues sufficient to prevent or reduce corneal haze following excimer laser surgery, prevent closure of a trabeculectomy, prevent or substantially slow the recurrence of pterygii, and other conditions.

The concentrations or amounts of the conjugates and complexes that are effective requires delivery of an amount, upon administration, that ameliorates the symptoms or treats the disease. Typically, the compositions are formulated for single dosage administration. Therapeutically effective concentrations and amounts may be determined empirically by testing the conjugates and complexes in known in vitro and in vivo systems, such as those described here; dosages for humans or other animals may then be extrapolated therefrom.

The conjugate is included in the pharmaceutically acceptable carrier in an amount sufficient to exert a therapeutically useful effect in the absence of undesirable side effects on the patient treated. The conjugates may be delivered as pharmaceutically acceptable salts, esters or other derivatives of the conjugates include any salts, esters or derivatives that may be readily prepared by those of skill in this art using known methods for such derivatization and that produce compounds that may be administered to animals or humans without substantial toxic effects. It is understood that number and degree of side effects depends upon the condition for which the conjugates and complexes are administered. For example, certain toxic and undesirable side effects are tolerated when treating life-threatening illnesses, such as tumors, that would not be tolerated when treating disorders of lesser consequence. The concentration of conjugate in the composition will depend on absorption, inactivation and excretion rates thereof, the dosage schedule, and amount administered as well as other factors known to those of skill in the art.

Preferably, the conjugate and complex are substantially pure. As used herein, "substantially pure" means sufficiently homogeneous to appear free of readily detectable impurities as determined by standard methods of analysis, such as thin layer chromatography (TLC), gel electrophoresis, high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

Typically a therapeutically effective dosage should produce a serum concentration of active ingredient of from about 0.1 ng/ml to about 50–100 µg/ml. The pharmaceutical compositions typically should provide a dosage of from about 0.01 mg to about 100–2000 mg of conjugate, depending upon the conjugate selected, per kilogram of body weight per day. For example, for treatment of restenosis a daily dosage of about between 0.05 and 0.5 mg/kg (based on FGF-SAP chemical conjugate or an amount of conjugate provided herein equivalent on a molar basis thereto) should be sufficient. Local application for ophthalmic disorders and dermatological disorders should provide about 1 ng up to 100 µg, preferably about 1 ng to about 10 µg, per single dosage administration. It is understood that the amount to administer will be a function of the conjugate selected, the indication treated, and possibly the side effects that will be tolerated.

Therapeutically effective concentrations and amounts may be determined for each application herein empirically by testing the conjugates and complexes in known in vitro and in vivo systems (e.g., murine, rat, rabbit, or baboon models), such as those described herein; dosages for humans or other animals may then be extrapolated therefrom. Demonstration that the conjugates and complexes prevent or inhibit proliferation of serum stimulated corneal keratocytes or fibroblasts explanted from eyes, as shown herein, and demonstration of any inhibition of proliferation of such tissues in rabbits should establish human efficacy. The rabbit eye model is a recognized model for studying the effects of topically and locally applied drugs (see, e.g., U.S. Pat. Nos. 5,288,735, 5,263,992, 5,262,178, 5,256,408, 5,252,319, 5,238,925, 5,165,952; see also Mirate et al., Curr. Eye Res. 1:491–493, 1981).

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The conjugates and complexes may be formulated for local or topical application, such as for topical application to the skin and mucous membranes, such as in the eye, in the form of gels, creams, and lotions and for application to the eye or for intracisternal or intraspinal application. Such solutions, particularly those intended for ophthalmic use, may be formulated as 0.01%–10% isotonic solutions, pH about 5–7, with appropriate salts. The ophthalmic compositions may also include additional components, such as hyaluronic acid. The conjugates and complexes may be formulated as aerosols for topical application (see, e.g., U.S. Pat. Nos. 4,044,126, 4,414,209, and 4,364,923).

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of toxicity such as sodium chloride or dextrose. Parental preparations can be enclosed in ampules, disposable syringes or multiple dose vials made of glass, plastic or other suitable material.

If administered intravenously, suitable carriers include physiological saline or phosphate buffered saline (PBS), and solutions containing thickening and solubilizing agents, such as glucose, polyethylene glycol, and polypropylene glycol and mixtures thereof. Liposomal suspensions may also be suitable as pharmaceutically acceptable carriers. These may be prepared according to methods known to those skilled in the art.

Upon mixing or addition of the conjugate(s) with the vehicle, the resulting mixture may be a solution, suspension, emulsion or the like. The form of the resulting mixture depends upon a number of factors, including the intended mode of administration and the solubility of the conjugate in the selected carrier or vehicle. The effective concentration is sufficient for ameliorating the symptoms of the disease, disorder or condition treated and may be empirically determined based upon in vitro and/or in vivo data, such as the data from the mouse xenograft model for tumors or rabbit ophthalmic model. If necessary, pharmaceutically acceptable salts or other derivatives of the conjugates and complexes may be prepared.

The active materials can also be mixed with other active materials, that do not impair the desired action, or with materials that supplement the desired action, including viscoelastic materials, such as hyaluronic acid, which is sold under the trademark HEALON (solution of a high molecular weight (MW of about 3 millions) fraction of sodium hyaluronate; manufactured by Pharmacia, Inc. see, e.g., U.S. Pat. Nos. 5,292,362, 5,282,851, 5,273,056, 5,229,127, 4,517,295 and 4,328,803), VISCOAT (fluorine-containing (meth) acrylates, such as, 1H,1H,2H,2H-heptadecafluorodecylmethacrylate; see, e.g., U.S. Pat. Nos. 5,278,126, 5,273,751 and 5,214,080; commercially available from Alcon Surgical, Inc.), ORCOLON (see, e.g., U.S. Pat. Nos. 5,273,056; commercially available from Optical Radiation Corporation), methylcellulose, methyl hyaluronate, polyacrylamide and polymethacrylamide (see, e.g., U.S. Pat. No. 5,273,751). The viscoelastic materials are present generally in amounts ranging from about 0.5 to 5.0%, preferably 1 to 3% by weight of the conjugate material and serve to coat and protect the treated tissues. The compositions may also include a dye, such as methylene blue or other inert dye, so that the composition can be seen when injected into the eye or contacted with the surgical site during surgery.

The conjugates and complexes may be formulated for local or topical application, such as for topical application to the skin and mucous membranes, such as in the eye, in the form of gels, creams, and lotions and for application to the eye. Such solutions, particularly those intended for ophthalmic use, may be formulated as 0.01%–10% isotonic solutions, pH about 5–7, with appropriate salts. Suitable ophthalmic solutions are known (see, e.g., U.S. Pat. No. 5,116,868, which describes typical compositions of ophthalmic irrigation solutions and solutions for topical application). Such solutions, which have a pH adjusted to about 7.4, contain, for example, 90–100 mM sodium chloride, 4–6 mM dibasic potassium phosphate, 4–6 mM dibasic sodium phosphate, 8–12 mM sodium citrate, 0.5–1.5 mM magnesium chloride, 1.5–2.5 mM calcium chloride, 15–25 mM sodium acetate, 10–20 mM D.L.-sodium β-hydroxybutyrate and 5–5.5 mM glucose.

The conjugates and complexes may be prepared with carriers that protect them against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others. For example, the composition may be applied during surgery using a sponge, such as a commercially available surgical sponges (see, e.g., U.S. Pat. Nos. 3,956,044 and 4,045,238; available from Weck, Alcon, and Mentor), that has been soaked in the composition and that releases the composition upon contact with the eye. These are particularly useful for application to the eye for ophthalmic indications following or during surgery in which only a single administration is possible. The compositions may also be applied in pellets (such as Elvax pellets(ethylene-vinyl acetate copolymer resin); about 1–5 μg of conjugate per 1 mg resin) that can be implanted in the eye during surgery.

Ophthalmologically effective concentrations or amounts of one or more of the conjugates and complexes are mixed with a suitable pharmaceutical carrier or vehicle. The concentrations or amounts of the conjugates and complexes that are effective requires delivery of an amount, upon administration, that prevents or substantially reduces corneal clouding, trabeculectomy closure, or pterygii recurrence.

The conjugates and complexes herein are formulated into ophthalmologically acceptable compositions and are applied to the affected area of the eye during or immediately after surgery. In particular, following excimer laser surgery, the composition is applied to the cornea; following trabeculectomy the composition is applied to the fistula; and following removal of pterygii the composition is applied to the cornea. The compositions may also be used to treat pterygii. The conjugates and complexes are applied during and immediately following surgery and may, if possible be applied post-operatively, until healing is complete. The compositions are applied as drops for topical and subconjunctival application or are injected into the eye for intraocular application. The compositions may also be absorbed to a biocompatible support, such as a cellulosic sponge or other polymer delivery device, and contacted with the affected area.

The ophthalmologic indications herein are typically be treated locally either by the application of drops to the affected tissue(s), contacting with a biocompatible sponge that has absorbed a solution of the conjugates and complexes or by injection of a composition. For the indications herein, the composition will be applied during or immediately after surgery in order to prevent closure of the trabeculectomy, prevent a proliferation of keratocytes following excimer laser surgery, or to prevent a recurrence of pterygii. The composition may also be injected into the affected tissue following surgery and applied in drops following surgery until healing is completed. For example, to administer the formulations to the eye, it can be slowly injected into the bulbar conjunctiva of the eye.

Conjugates and complexes with photocleavable linkers are among those preferred for use in the methods herein. Upon administration of such composition to the affected area of the eye, the eye is exposed to light of a wavelength, typically visible or UV that cleaves the linker, thereby releasing the cytotoxic agent.

If oral administration is desired, the conjugate should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules or troches. Pharmaceutically compatible binding agents and adjuvant materials can be included as part of the composition.

The tablets, pills, capsules, troches and the like can contain any of the following ingredients, or compounds of a similar nature: a binder, such as microcrystalline cellulose, gum tragacanth and gelatin; an excipient such as starch and lactose, a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, and fruit flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The conjugates and complexes can also be administered as a component of an elixir, suspension, syrup, wafer, chewing gum or the like. A syrup may contain, in addition to the active compounds, sucrose as a sweetening agent and certain preservatives, dyes and colorings and flavors.

The active materials can also be mixed with other active materials that do not impair the desired action, or with materials that supplement the desired action, such as cisplatin for treatment of tumors.

Finally, the compounds may be packaged as articles of manufacture containing packaging material, one or more conjugates and complexes or compositions as provided herein within the packaging material, and a label that indicates the indication for which the conjugate is provided.

The following examples are included for illustrative purposes only and are not intended to limit the scope of the invention.

EXAMPLES

Example 1

ISOLATION OF DNA ENCODING SAPORIN

A. Materials and Methods

1. Bacterial Strains

*E. coli* strain JA221 (lpp⁻ hdsM+trpE5 leuB6 lacY recA1 F'[lacI$^q$ lac+pro$^+$]) is publicly available from the American Type Culture Collection (ATCC), Rockville, Md. 20852, under the accession number ATCC 33875. (JA221 is also available from the Northern Regional Research Center (NRRL), Agricultural Research Service, U.S. Departrment of Agriculture, Peoria, Ill. 61604, under the accession number NRRL B-1521 1; see also U.S. Pat. No. 4,757,013 to Inouye; and Nakamura et al., *Cell* 18:1109–1117, 1979). Strain INV1α is commercially available from Invitrogen, San Diego, Calif.

2. DNA Manipulations

The restriction and modification enzymes employed herein are commercially available in the U.S. Native saporin and rabbit polyclonal antiserum to saporin were obtained as previously described in Lappi et al., *Biochem. Biophys. Res. Comm.* 129:934–942. Ricin A chain is commercially available from Sigma, Milwaukee, Wis. Antiserum was linked to Affi-gel 10 (Bio-Rad, Emeryville, Calif.) according to the manufacturer's instructions. Sequencing was performed using the Sequenase kit of United States Biochemical Corporation (version 2.0) according to the manufacturer's instructions. Minipreparation and maxipreparation of plasmids, preparation of competent cells, transformation, M13 manipulation, bacterial media, Western blotting, and ELISA assays were according to Sambrook et al., (*Molecular Cloning: A Laboratory Manual*, Cold Spring Harbor Laboratory Press, Cold Spring Harbor, N.Y., 1989). The purification of DNA fragments was done using the Geneclean II kit (Bio 101) according to the manufacturer's instructions. SDS gel electrophoresis was performed on a Phastsystem (Pharmacia).

Western blotting was accomplished by transfer of the electrophoresed protein to nitrocellulose using the Phast-Transfer system, as described by the manufacturer. The antiserum to SAP was used at a dilution of 1:1000. Horseradish peroxidase labeled anti-IgG was used as the second antibody (see Davis et al., *Basic Methods In Molecular Biology*, New York, Elsevier Science Publishing Co., pp 1–338, 1986).

B. Isolation of DNA Encoding Saporin

1. Isolation of Genomic DNA and Preparation of Polymerase Chain Reaction (PCR) Primers

*Saponaria officinalis* leaf genomic DNA was prepared as described in Bianchi et al., *Plant Mol. Biol.* 11:203–214, 1988. Primers for genomic DNA amplifications were synthesized in a 380B automatic DNA synthesizer. The primer corresponding to the "sense" strand of saporin 5'-CTGCAGAATTCGCATGGATCCTGCTTCAAT-3' (SEQ ID NO. 54) includes an EcoR I restriction site adapter immediately upstream of the DNA codon for amino acid-15 of the native saporin N-terminal leader sequence. The primer 5'-CTGCAGAATTCGCCTCGTTTGACTACTTTG-3' (SEQ ID NO. 55) corresponds to the "antisense" strand of saporin and complements the coding sequence of saporin starting from the last 5 nucleotides of the DNA encoding the carboxyl end of the mature peptide. Use of this primer introduced a translation stop codon and an EcoRI restriction site after the sequence encoding mature saporin.

2. Amplification of DNA Encoding Saporin

Unfractionated *Saponaria officinalis* leaf genomic DNA (1 μl) was mixed in a final volume of 100 μl containing 10 mM Tris-HCl (pH 8.3), 50 mM KCl, 0.01% gelatin, 2 mM $MgCl_2$, 0.2 mM dNTPs, 0.8 μg of each primer. Next, 2.5 U Taq DNA polymerase (Perkin Elmer Cetus) were added and the mixture was overlaid with 30 μl of mineral oil (Sigma). Incubations were done in a DNA Thermal Cycler (Ericomp). One cycle included a denaturation step (94° C. for 1 min), an annealing step (60° C. for 2 min), and an elongation step (72° C. for 3 min). After 30 cycles, a 10 μl aliquot of each reaction was run on a 1.5% agarose gel to verify the structure of the amplified product.

The amplified DNA was digested with EcoRI and subcloned into EcoRI-restricted M13mp18 (New England Biolabs, Beverly, Mass.; see also Yanisch-Perron et al. (1985), "Improved M13 phage cloning vectors and host strains: Nucleotide sequences of the M13mp18 and pUC19 vectors", *Gene* 33:103). Single-stranded DNA from recombinant phages was sequenced using oligonucleotides based on internal points in the coding sequence of saporin (see Bennati et al., *Eur. J. Biochem.* 183:465–470, 1989). Nine of the M13mp18 derivatives were sequenced and compared. Of the nine sequenced clones, five had unique sequences, set forth as SEQ ID NOs. 19–23, respectively. The clones were designated M13mp18-G4, -G1, -G2, -G7, and -G9. Each of these clones contains all of the saporin coding sequence and 45 nucleotides of DNA encoding the native saporin N-terminal leader peptide.

Saporin DNA sequence was also cloned in the pET11a vector. Briefly, the DNA encoding SAP-6 was amplified by polymerase chain reaction (PCR) from the parental plasmid pZ1B1. The plasmid pZ1B1 contains the DNA sequence for human FGF-2 linked to SAP-6 by a two-amino-acid linker (Ala-Met). PZ1B1 also includes the T7 promoter, lac operator, ribosomal binding site, and T7 terminator present in the pET-11a vector. For SAP-6 DNA amplification, the 5' primer (5' CATATGTGTGTCACATCAATCACATTAGAT 3') (SEQ ID NO. 105), corresponding to the sense strand of SAP-6, incorporated a NdeI restriction enzyme site used for cloning. It also contained a Cys codon at position −1 relative to the start site of the mature protein sequence. No leader sequence was included. The 3' primer (5' CAGGTTTG-GATCCTTTACGTT 3') (SEQ ID NO. 106) corresponding to the antisense strand of SAP-6 had a BamHI site used for cloning. The amplified DNA was gel-purified and digested with NdeI and BamHI. The digested SAP-6 DNA fragment was subcloned into the NdeI/BamHI-digested pZ1B1. This digestion removed FGF-2 and the 5' portion of SAP-6 (up to nucleotide position 650) from the parental rFGF2-SAP vector (PZ1B1) and replaced this portion with a SAP-6 molecule containing a Cys at position −1 relative to the start site of the native mature SAP-6 protein. The resultant plasmid was designated as pZ50B. pZ50B was transformed into E. coli strain NovaBlue for restriction and sequencing analysis. The appropriate clone was then transformed into E. coli strain BL21(DE3) for expression and large-scale production.

C. Mammalian Codon Optimization of Saporin cDNA.

Mammalian expression plasmids encoding β-galactosidase (β-gal), pSV-β and pNASS-β, were obtained from Clontech (Palo Alto, Calif.). Plasmid pSVβ expresses β-gal from the SV40 early promoter. Plasmid pNASSb is a promoterless mammalian reporter vector containing the β-gal gene.

The amino acid sequence for the plant protein saporin (SAP) was reverse translated using mammalian codons. The resulting mammalian optimized cDNA was divided into 4 fragments (designated 5'-3' A-D) for synthesis by PCR using overlapping oligos. To facilitate subcloning of each fragment and piecing together of the entire cDNA, restriction enzyme sites were added to the ends of each fragment, and added or removed within each fragment without changing the corresponding amino acid sequence. In addition, the 5' end of the cDNA was modified to include a Kozak sequence for optimal expression in mammalian cells. Fragments A, B, and D were each synthesized by annealing 4 oligos (2 sense, 2 antisense) with 20 base overlaps and using PCR to fill-in and amplify the fragments. The PCR products were then purified using GeneClean (Bio101), digested with restriction enzymes recognizing the sites in the primers, and subcloned into pBluescript (SK+) (Stratagene). The sequence of the inserts was verified using Sequenase Version 2.0 (united States Biochemical/Amersham). Fragment C was synthesized in two steps: The 5' and 3' halves of the fragment were independently synthesized by PCR using 2 overlapping oligos. The products of these using 2 reactions were then purified and combined and the full-length fragment C was generated by PCR using the outermost oligos as primers. Full-length fragment C was subcloned into pBluescript for sequencing. Fragments A and B were ligated together in pBluescript at an overlapping KspI site. Fragments C and D were ligated together in pBluescript at an overlapping PvuII site. Fragments A–B and C–D were then joined in pBluescript at an overlapping AvaI site to give the full-length mammalian optimized SAP cDNA. β-gal sequences were excised from the plasmids pNASS-β and pSV-β (Clontech) by digestion with NotI and replaced with the synthetic SAP gene, which has NotI ends. Orientation of the insert was confirmed by restriction enzyme digestion. Large scale plasmid preparations were performed using Qiagen Maxi 500 columns.

The oligos used to synthesize each SAP fragment are (5'-3'):

A1(sense):CGTATCAGGCGGCCGCCGCCATGGTGACCTCCATCACCCTGGACCTGGTGAACCCCACCGCCGGCC (SEQ ID NO.: 89)

A2(antisense):TTGGGGTCCTTCACGTTGTTGCGGATCTTGTCCACGAAGGAGGAGTACTGGCCGGCGGTGGGGTTCACC (SEQ ID NO.: 90)

A3(sense):AACAACGTGAAGGACCCCAACCTGAAGTACGGCGGCACCGACATCGCCGTGATCGGCCCCCCCTC (SEQ ID NO.: 91)

A4(antisense):GTGCCGCGGGAGGACTGGAAGTTGATGCGCAGGAACTTCTCCTTGGAGGGGGGGCCGATCACGGC (SEQ ID NO.: 92)

B1(sense):CTCCCGCGGCACCGTGTCCCTGGGCCTGAAGCGCGACAACCTGTACGTGGTGGCCTACCTGGCCATGGACAACAC (SEQ ID NO.: 93)

B2(antisense):GCGGTCAGCTCGGCGGAGGTGATCTCGGACTTGAAGTAGTAGGCGCGGTTCACGTTGGTGTTGTCCATGGCCAGGTA (SEQ ID NO.: 94)

B3(sense):GCCGAGCTGACCGCCCTGTTCCCTGAGGCCACCACCGCCAACCAGAAGGCCCTGGAGTACACCGAGGACTACCAGTCC (SEQ ID NO.: 95)

B4(antisense):AGCCCGAGCTCCTTGCGGGACTTGTCGCCCTGGGTGATCTGGGCGTTCTTCTCGATGGACTGGTAGTCCTCGGTGT (SEQ ID NO.: 96)

C1(sense):TATAGAATTCCTCGGGCTGGGCATCGACCTGCTGCTGACCTTCATGGAGGCCGTGAACAAGAAGGCCCGCGTGG (SEQ ID NO.: 97)

C2(antisense):CGGCGGTCATCTGGATGGCGATCAGCAGGAAGCGGGCCTCGTTCTTCACCACGCGGGCCTTCTTGTTC (SEQ ID NO.: 98)

C3(sense):CGCCATCCAGATGACCGCCGAGGTGGCCCGCTTCCGCTACATCCAGAACCTGGTGACCAAGAACTTCCCC (SEQ ID NO.: 99)

C4(antisense):GGCGGATCCCAGCTGACCTCGAACTGGATCACCTTGTTGTCGGAGTCGAACTTGTTGGGGAAGTTCTTGGTCACCA (SEQ ID NO.: 100)

D1(sense):CCGGGATCCGTCAGCTGGCGCAAGATCTCCACCGCCATCTACGGCGACGCCAAGAACGGCG (SEQ ID NO.: 101)

D2(antisense):GCACCTTGCCGAAGCCGAAGTCGTAGTCCTTGTTGAACACGCCGTTCTTGGCGTCGCCGTAGAT (SEQ ID NO.: 102)

D3(sense):TTCGGCTTCGGCAAGGTGCGCCAGGTGAAGGACCTGCAGATGGGCCTGCTGATGTACC (SEQ ID NO.: 103)

D4(antisense):TGAACGTGGCGGCCGCCTACTTGGGCTTGCCCAGGTACATCAGCAGGCCCAT (SEQ ID NO.: 104)

D. pOMPAG4 Plasmid Construction

M13 mp18-G4 was digested with EcoR I, and the resulting fragment was ligated into the EcoR I site of the vector pIN-IIIompA2 (see, e.g., see, U.S. Pat. No. 4,575,013 to Inouye; and Duffaud et al., *Meth. Enz.* 153:492–507, 1987) using the methods described herein. The ligation was accomplished such that the DNA encoding saporin, including the N-terminal extension, was fused to the leader peptide segment of the bacterial ompA gene. The resulting plasmid pOMPAG4 contains the lpp promoter (Nakamura et al., *Cell* 18:1109–1117, 1987), the *E. coli* lac promoter operator sequence (lac O) and the *E. coli* ompA gene secretion signal in operative association with each other and with the saporin and native N-terminal leader-encoding DNA listed in SEQ ID NO. 19. The plasmid also includes the *E. coli* lac repressor gene (lac I).

The M13 mp18-G1, -G2, -G7, and -G9 clones, containing SEQ ID NOs. 20–23, respectively, are digested with EcoR I and ligated into EcoR I digested pIN-IIIompA2 as described for M13 mp18-G4 above in this example. The resulting plasmids, labeled pOMPAG1, pOMPAG2, pOMPAG7, pOMPA9, are screened, expressed, purified, and characterized as described for the plasmid pOMPAG4.

INV1α competent cells were transformed with pOMPAG4 and cultures containing the desired plasmid structure were grown further in order to obtain a large preparation of isolated pOMPAG4 plasmid using methods described herein.

E. Saporin Expression in *E. coli*

The pOMPAG4 transformed *E. coli* cells were grown under conditions in which the expression of the saporin-containing protein is repressed by the lac repressor until the end of the log phase of growth, at which time IPTG was added to induce expression of the saporin-encoding DNA.

To generate a large-batch culture of pOMPAG4 transformed *E. coil* cells, an overnight culture (approximately 16 hours growth) of JA221 *E. coil* cells transformed with the plasmid pOMPAG4 in LB broth (see, e.g., Sambrook et al., *Molecular Cloning: A Laboratory Manual*, Cold Spring Harbor Laboratory Press, Cold Spring Harbor, N.Y., 1989) containing 125 mg/ml ampicillin was diluted 1:100 into a flask containing 750 ml LB broth with 125 mg/ml ampicillin. Cells were grown at logarithmic phase with shaking at 37° C. until the optical density at 550 nm reached 0.9 measured in a spectrophotometer.

In the second step, saporin expression was induced by the addition of IPTG (Sigma) to a final concentration of 0.2 mM. Induced cultures were grown for 2 additional hours and then harvested by centrifugation (25 min., 6500×g). The cell pellet was resuspended in ice cold 1.0 M TRIS, pH 9.0, 2 mM EDTA (10 ml were added to each gram of pellet). The resuspended material was kept on ice for 20–60 minutes and then centrifuged (20 min., 6500×g) to separate the periplasmic fraction of *E. coli*, which corresponds to the supernatant, from the intracellular fraction corresponding to the pellet.

The *E. coil* cells containing C-SAP construct in pET11a were grown in a high-cell density fed-batch fermentation with the temperature and pH controlled at 30° C. and 6.9, respectively. A glycerol stock (1 ml) was grown in 50 ml Luria broth until the $A_{600}$ reached 0.6 Inoculum (10 ml) was injected into a 7-1-Applikon (Foster City, Calif.) fermentor containing 21 complex batch medium consisting of 5 g/l of glucose, 1.25 g/l each of yeast extract and tryptone (Difco Laboratories), 7 g/l of $K_2HPO_4$, 8 g/l of $KH_2PO_4$, 1.66 g/l of $(NH_4)_2SO_4$, 1 g/l of $MgSO_4.7H_2O$, 2 ml/l of a trace metal solution (74 g/l of trisodium citrate, 27 g/l of $FeCl_3.6H_2O$, 2.0 g/l of $CoCl_2.6H_2O$, 2.0 g/l of $Na_2MoO_4.2H_2O$, 1.9 g/l of $CuSO_4.5H_2O$, 1.6 g/l of $MnCl_2.4H_2O$, 1.4 g/l of $ZnCl_2.4H_2O$, 1.0 g/l of $CaCl_2.2H_2O$, 0.5 g/l of $H_3BO_3$). 2 ml/l of a vitamin solution (6 g/l of thiamin.HCl, 3.05 g/l of niacin, 2.7 g/l of pantothenic acid, 0.7 g/l of pyridoxine.HCl, 0.21 g/l of riboflavin, 0.03 g/l of biotin, 0.02 g/l of folic acid), and 100 mg/l of carbenicillin. The culture was grown for 12 h before initiating the continuous addition of a 40× solution of complex batch media lacking the phosphates and containing only 25 ml/l, each, of trace metal and vitamin solutions. The feed addition continued until the $A_{600}$ of the culture reached 85, at which time (approximately 9 h) the culture was induced with 0.1 mM isopropyl β-D-thiogalactopyranoside. During 4 h of post-induction incubation, the culture was fed with a solution containing 100 g/l of glucose, 100 g/l of yeast extract, and 200 g/l of tryptone. Finally, the cells were harvested by centrifugation (8000×g, 10 min) and frozen at −80° C. until further processed.

The cell pellet (≈400 g wet mass) containing C-SAP was resuspended in 3 vol Buffer B (10 mM sodium phosphate pH 7.0, 5 mM EDTA, 5 mM EGTA, and 1 mM dithiothreitol). The suspension was passed through a microfluidizer three times at 124 Mpa on ice. The resultant lysate was diluted with NanoPure $H_2O$ until conductivity fell below 2.7 mS/cm. All subsequent procedures were performed at room temperature.

The diluted lysate was loaded onto an expanded bed of Streamline SP cation-exchange resin (300 ml) equilibrated with buffer C (20 mM sodium phosphate pH 7.0, 1 mM EDTA) at 100 ml/min upwards flow. The resin was washed with buffer C until it appeared clear. The plunger was then lowered at 2 cm/min while washing continued at 70 ml/min. Upwards flow was stopped when the plunger was approximately 8 cm away from the bed and the plunger was allowed to move to within 0.5 cm of the packed bed. The resin was further washed at 70 ml/min downwards flow until $A_{280}$ reached baseline. Buffer C plus 0.25 M NaCl was then used to elute proteins containing C-SAP at the same flow rate.

The eluate was buffer exchanged into buffer D (50 mM sodium borate pH 8.5, 1 mM EDTA) using the Sartocon Mini crossflow filtration system with a 10000 NMolecular Massco module (Sartorius). The sample was then applied to a column of Source 15S (30 ml) equilibrated with buffer D. A 10-column-volume linear gradient of 0–0.3 M NaCl in buffer D was used to elute C-SAP at 30 ml/min.

F. Assay for Cytotoxic Activity

The ribosome inactivating protein activity of recombinant saporin was compared to the ribosome inactivating protein activity of native SAP in an in vitro assay measuring cell-free protein synthesis in a nuclease-treated rabbit reticulocyte lysate (Promega). Samples of immunoaffinity-purified saporin were diluted in PBS and 5 µl of sample was added on ice to 35 µl of rabbit reticulocyte lysate and 10 µl of a reaction mixture containing 0.5 µl of Brome Mosaic Virus RNA, 1 mM amino acid mixture minus leucine, 5 µCi of tritiated leucine and 3 µl of water. Assay tubes were incubated 1 hour in a 30° C. water bath. The reaction was stopped by transferring the tubes to ice and adding 5 µl of the assay mixture, in triplicate, to 75 µl of 1 N sodium hydroxide, 2.5% hydrogen peroxide in the wells of a Milliliter HA 96-well filtration plate (Millipore). When the red color had bleached from the samples, 300 µl of ice cold 25% trichloroacetic acid (TCA) were added to each well and the plate left on ice for another 30 min. Vacuum filtration was performed with a Millipore vacuum holder. The wells were washed three times with 300 µl of ice cold 8% TCA. After drying, the filter paper circles were punched out of the 96-well plate and counted by liquid scintillation techniques.

The $IC_{50}$ for the recombinant and native saporin were approximately 20 pM. Therefore, recombinant saporin-containing protein has full protein synthesis inhibition activity when compared to native saporin.

Example 2

PREPARATION OF FGF MUTEINS

A. Materials and Methods

1. Reagents

Restriction and modification enzymes were purchased from BRL (Gaithersburg, Md.), Stratagene (La Jolla, Calif.) and New England Biolabs (Beverly, Mass.).

Plasmid pFC80, containing the basic FGF coding sequence, was a gift of Drs. Paolo Sarmientos and Antonella Isacchi of Farmitalia Carlo Erba (Milan, Italy). Plasmid pFC80, has been described in the PCT Application Serial No. WO 90/02800 and PCT Application Serial No. PCT/US93/05702, which are herein incorporated in their entirety by reference. The sequence of DNA encoding bFGF in pFC80 is that set forth in PCT Application Serial No. PCT/US93/05702 and in SEQ ID NO. 52.

Plasmid isolation, production of competent cells, transformation and M13 manipulations were carried out according to published procedures (Sambrook et al., *Molecular Cloning, a Laboratory Manual*, Cold Spring Harbor Laboratory Press, Cold Spring Harbor, N.Y., 1989). Purification of DNA fragments was achieved using the Geneclean II kit, purchased from Bio 101 (LaJolla, Calif.). Sequencing of the different constructions was performed using the Sequenase kit (version 2.0) of USB (Cleveland, Ohio).

2. Sodium Dodecyl Sulphate (SDS) Gel Electrophoresis and Western Blotting

SDS gel electrophoresis was performed on a PhastSystem utilizing 20% gels (Pharmacia). Western blotting was accomplished by transfer of electrophoresed protein to nitrocellulose using the PhastTransfer system (Pharmacia), as described by the manufacturer. The antisera to SAP and basic FGF were used at a dilution of 1:1000. Horseradish peroxidase labeled anti-IgG was used as the second antibody as described (Davis, L., Dibner et al. (1986) Basic Methods in Molecular Biology, p. 1, Elsevier Science Publishing Co., New York).

B. Preparation of the Mutagenized FGF by Site-directed Mutagenesis

Cysteine to serine substitutions were made by oligonucleotide-directed mutagenesis using the Amersham (Arlington Heights, Ill.) in vitro-mutagenesis system 2.1. Oligonucleotides encoding the new amino acid were synthesized using a 380B automatic DNA synthesizer (Applied Biosystems, Foster City, Calif.).

1. Mutagenesis

The oligonucleotide used for in vitro mutagenesis of cysteine 78 was AGGAGTGTCTGCTAACC (SEQ ID NO. 56), which spans nucleotides 225–241 of SEQ ID NO. 52). The oligonucleotide for mutagenesis of cysteine 96 was TTCTAAATCGGTTACCGATGACTG (SEQ ID NO. 57), which spans nucleotides 279–302 of SEQ ID NO. 52). The mutated replicative form DNA was transformed into *E. coli* strain JM109 and single plaques were picked and sequenced for verification of the mutation. The FGF mutated gene was then cut out of M13, ligated into the expression vector pFC80, which had the non-mutated form of the gene removed, and transformed into *E. coli* strain JM109. Single colonies were picked and the plasmids sequenced to verify the mutation was present. Plasmids with correct mutation were then transformed into the *E. coli* strain FICE 2 and single colonies from these transformations were used to obtain the mutant basic FGFs. Approximately 20 mg protein per liter of fermentation broth was obtained.

2. Purification of Mutazenized FGF

Cells were grown overnight in 20 ml of LB broth containing 100 μg/ml ampicillin. The next morning the cells were pelleted and transferred to 500 ml of M9 medium with 100 μg/ml ampicillin and grown for 7 hours. The cells were pelleted and resuspended in lysis solution (10 mM TRIS, pH 7.4, 150 mM NaCl, lysozyme, 10 μg/mL, aprotinin, 10 μg/mL, leupeptin, 10 μg/mL, pepstatin A, 10 μg/mL and 1 mM PMSF; 45–60 ml per 16 g of pellet) and incubated while stirring for 1 hour at room temperature. The solution was frozen and thawed three times and sonicated for 2.5 minutes. The suspension was centrifuged; the supernatant saved and the pellet resuspended in another volume of lysis solution without lysozyme, centrifuged again and the supernatants pooled. Extract volumes (40 ml) were diluted to 50 ml with 10 mM TRIS, pH 7.4 (buffer A). Pools were loaded onto a 5 ml Hi-Trap heparin-Sepharose column (Pharmacia, Uppsala, Sweden) equilibrated in 150 mM sodium chloride in buffer A. The column was washed with 0.6 M sodium chloride and 1 M sodium chloride in buffer A and then eluted with 2 M sodium chloride in buffer A. Peak fractions of the 2 M elution, as determined by optical density at 280 nm, were pooled and purity determined by gel electrophoresis. Yields were 10.5 mg of purified protein for the $CYS^{78}$ mutant and 10.9 mg for the $Cys^{96}$ mutant.

The biological activity of [C78S]FGF and [C96S]FGF was measured on adrenal capillary endothelial cells in culture. Cells were plated at 3,000 per well in a 24 well plate in 1 ml of 10% calf serum-HDMEM. Cells were allowed to attach, and samples were added in triplicate at the indicated concentration and incubated for 48 h at 37° C. An equal quantity of samples was added and further incubated for 48 h. Medium was aspirated; cells were treated with trypsin (1 ml volume) to remove cells to 9 ml of Hematall diluent and counted in a Coulter Counter. The results show that the two mutants that retain virtually complete proliferative activity of native basic FGF as judged by the ability to stimulate endothelial cell proliferation in culture.

Example 3

PREPARATION OF MONO-DERIVATIZED NUCLEIC ACID BINDING DOMAIN (MYOD)

MyoD at a concentration of 4.1 mg/ml is dialyzed against 0.1 M sodium phosphate, 0.1 M sodium chloride, pH 7.5. A 1.1 molar excess (563 μg in 156 μl of anhydrous ethanol) of SPDP (Pharmacia, Uppsala, Sweden) is added and the reaction mixture immediately agitated and put on a rocker platform for 30 minutes. The solution is then dialyzed against the same buffer. An aliquot of the dialyzed solution is examined for extent of derivatization according to the Pharmacia instruction sheet. The extent of derivatization is typically 0.79 to 0.86 moles of SPDP per mole of nucleic acid binding domain.

Derivatized myoD (32.3 mg) is dialyzed in 0.1 M sodium borate, pH 9.0 and applied to a Mono S 16/10 column equilibrated with 25 mM sodium chloride in dialysis buffer. A gradient of 25 mM to 125 mM sodium chloride in dialysis buffer elutes free and derivatized nucleic acid binding domain. The flow rate is 4.0 ml/min, 4 ml fractions are collected. Aliquots of fractions were assayed for protein concentration (BCA Protein Assay, Pierce Chemical, Chicago, Ill.) and for pyridylthione released by reducing agent. Individual fractions (25 to 37) are analyzed for protein concentration and pyridyl-disulfide concentration. The data indicate a separation according to the level of derivatization by SPDP. The initial eluting peak is composed of myoD that is approximately di-derivatized; the second peak is mono-derivatized and the third peak shows no derivatization. The di-derivatized material accounts for approximately 20% of the three peaks; the second accounts for approximately 48% and the third peak contains approximately 32%. Material from the second peak is pooled and gives an average ratio of pyridyl-disulfide to myoD of 0.95. Fraction 33, which showed a divergent ratio of pyridine-2-thione to +protein, was excluded from the pool. Fractions that showed a ratio of SPDP to myoD greater than 0.85 but less than 1.05 are pooled, dialyzed against 0.1 M sodium chloride, 0.1 M sodium phosphate, pH 7.5 and used for derivatization with basic FGF.

Example 4

PREPARATION OF MODIFIED NUCLEIC ACID BINDING DOMAIN (MYOD)

As an alternative to derivatization, myoD is modified by addition of a cysteine residue at or near the N-terminusencoding portion of the DNA. The resulting myoD can then react with an available cysteine on an FGF or react with a linker or a linker attached to an FGF to produce conjugates that are linked via the added Cys.

Modified myoD is prepared by modifying DNA encoding the myoD (GenBank Accession No. X56677). DNA encoding Cys is inserted at position −1 or at a codon within 10 or fewer residues of the N-terminus. The resulting DNA is inserted into pET11a and pET15b and expressed in BL21 cells (NOVAGEN, Madison, Wis.).

A. Preparation of myoD with an Added Cysteine Residue at the N-terminus

Primer #1 corresponding to the sense strand of myoD, nucleotides 121–144, incorporates a NdeI site and adds a Cys codon 5' to the start site for the mature protein

5'-CATATGTGTGAGCTACTGTCGCCACCGCTC-3' (SEQ ID NO. 58)

Primer #2 is an antisense primer complementing the coding sequence of nucleic acid binding domain spanning nucleotides 1054–1077 and contains a BamHI site.

5'-GGATCCGAGCACCTGGTATATCGGTGGGGG-3' (SEQ ID NO. 59)

MyoD DNA is amplified by PCR as follows using the above primers. A clone containing a full-length DNA (or cDNA) for myoD (1 μl) is mixed in a final volume of 100 μl containing 10 mM Tris-HCl (pH 8.3), 50 mM KCl, 0.01% gelatin, 2 mM $MgCl_2$, 0.2 mM dNTPs, 0.8 μg of each primer. Next, 2.5 U TaqI DNA polymerase (Boehringer Mannheim) is added and the mixture is overlaid with 30 μl of mineral oil (Sigma). Incubations are done in a DNA Thermal Cycler. Cycles include a denaturation step (94° C. for 1 min), an annealing step (60° C. for 2 min), and an elongation step (72° C. for 3 min). After 35 cycles, a 10 μl aliquot of each reaction is run on a 1.5% agarose gel to verify the correct structure of the amplified product.

The amplified DNA is gel purified and digested with NdeI and BamHI and subcloned into NdeI and BamHI-digested plasmid containing FGF/myoD. This digestion and subcloning step removes the FGF-encoding DNA and 5' portion of SAP up to the BamHI site at nucleotides 555–560 (SEQ ID NO. 52) and replaces this portion with DNA encoding a myoD molecule that contains a cysteine residue at position −1 relative to the start site of the native mature SAP protein.

B. Preparation of Nucleic Acid Binding Domain with a Cysteine Residue at Position 4 or 10 of the Native Protein These constructs are designed to introduce a cysteine residue at position 4 or 10 of the native protein by replacing the Ser residue at position 4 or the Val residue at position 10 with cysteine.

MyoD is amplified by polymerase chain reaction (PCR) from the parental plasmid encoding the FGF-nucleic acid binding domain fusion protein using primers that incorporate a TGT or TGC codon at position 4 or 10.

The PCR conditions are performed as described above, using the following cycles: denaturation step 94° C. for 1 minute, annealing for 2 minutes at 60° C., and extension for 2 minutes at 72° C. for 35 cycles. The amplified DNA is gel purified, digested with NdeI and BamHI, and subcloned into NdeI and BamHI digested pET11a This digestion removes the FGF and 5' portion of nucleic acid binding domain (up to the newly added BamHI) from the parental FGF-myoD vector and replaces this portion with a myoD molecule containing a Cys at position 4 or 10 relative to the start site of the native protein.

The resulting plasmid is digested with NdeI/BamHI and inserted into pET15b (NOVAGEN, Madison, Wis.), which has a His-Tag™ leader sequence (SEQ ID NO. 60), that has also been digested NdeI/BamHI.

DNA encoding unmodified myoD can be similarly inserted into a pET5b or pET11A and expressed as described below for the modified SAP-encoding DNA.

C. Expression of the Modified Nucleic acid Binding Domain-encoding DNA

BL2 1 (DE3) cells are transformed with the resulting plasmids and cultured as described in Example 2, except that all incubations were conducted at 30° C. instead of 37° C. Briefly, a single colony is grown in LB $AMP_{100}$ to and $OD_{600}$ of 1.0–1.5 and then induced with IPTG (final concentration 0.1 mM) for 2 h. The bacteria are spun down.

D. Purification of Modified Nucleic Acid Binding Domain

Lysis buffer (20 mM $NAPO_4$, pH 7.0, 5 mM EDTA, 5 mM EGTA, 1 mM DTT, 0.5 μg/ml leupeptin, 1 μg/ml aprotinin, 0.7 μg/ml pepstatin) was added to the myoD cell paste produced from pZ50B1 in BL21 cells, as described above) in a ratio of 1.5 ml buffer/g cells. This mixture is evenly suspended via a Polytron homogenizer and passed through a microfluidizer twice.

The resulting lysate is centrifuged at 50,000 rpm for 45 min. The supernatant is diluted with SP Buffer A (20 mM $NAPO_4$, 1 mM EDTA, pH 7.0) so that the conductivity is below 2.5 mS/cm. The diluted lysate supernatant is then loaded onto a SP-Sepharose column, and a linear gradient of 0 to 30% SP Buffer B (1 M NaCl, 20 mM $NAPO_4$, 1 mM EDTA, pH 7.0) in SP Buffer A with a total of 6 column volumes is applied. Fractions containing myoD are combined and the resulting nucleic acid binding domain had a purity of greater than 90%. A buffer exchange step is used to get the SP eluate into a buffer containing 50 mM $NaBO_3$, 1 mM EDTA, pH 8.5 (S Buffer A). This sample is then applied to a Resource S column (Pharmacia, Sweden) pre-equilibrated with S Buffer A. Pure nucleic acid binding domain is eluted off the column by 10 column volumes of a linear gradient of 0 to 300 mM NaCl in SP Buffer A.

In this preparation, ultracentrifugation is used clarify the lysate; other methods, such as filtration and using floculents also can be used. In addition, Streamline S (PHARMACIA, Sweden) may also be used for large scale preparations.

Example 5

PREPARATION OF CONJUGATES CONTAINING FGF MUTEINS

. Coupling of FGF Muteins to Nucleic Acid Binding Domain

1. Chemical Synthesis of [C78S]FGF-nucleic Acid Binding Domain (CCFN2) and [C96S]FGF-nucleic Acid Binding Domain (CCFN3)

[C78S]FGF or [C96S]FGF (1 mg; 56 nmol) that had been dialyzed against phosphate-buffered saline is added to 2.5 mg mono-derivatized nucleic acid binding domain (a 1.5 molar excess over the basic FGF mutants) and left on a rocker platform overnight. The next morning the ultraviolet-visible wavelength spectrum is taken to determine the extent of reaction by the release of pyridyithione, which adsorbs at 343 nm with a known extinction coefficient. The ratio of pyridylthione to basic FGF mutant for [C78S]FGF is 1.05 and for [C96S]FGF is 0.92. The reaction mixtures are treated identically for purification in the following manner: reaction mixture is passed over a HiTrap heparin-Sepharose column (1 ml) equilibrated with 0.15 M sodium chloride in buffer A at a flow rate of 0.5 ml/min. The column is washed with 0.6 M NaCl and 1.0 M NaCl in buffer A and the product eluted with 2.0 M NaCl in buffer A. Fractions (0.5 ml) are analyzed by gel electrophoresis and absorbance at 280 nm. Peak tubes are pooled and dialyzed versus 10 mM sodium phosphate, pH 7.5 and applied to a Mono-S 515 column equilibrated with the same buffer. A 10 ml gradient between 0 and 1.0 M sodium chloride in equilibration buffer is used to elute the product. Purity is determined by gel electrophoresis and peak fractions were pooled.

Under these conditions, virtually 100% of the mutant FGFs reacts with mono-derivatized myoD. Because the free surface cysteine of each mutant acts as a free sulfhydryl, it is unnecessary to reduce cysteines after purification from the bacteria. The resulting product is purified by heparin-Sepharose (data not shown), thus establishing that heparin binding activity of the conjugate is retained.

2. Expression of the Recombinant FGFC78/96S-nucleic Acid Binding Domain Fusion Proteins (FPFN4)

A two-stage method is used to produce recombinant FGF[C78/96S]-myoD protein (hereinafter FPFN4). Two hundred and fifty ml of LB medium containing ampicillin (100 μg/ml) are inoculated with a fresh glycerol stock of bacteria containing the plasmid. Cells are grown at 30° C. in an incubator shaker to an $OD_{600}$ of 0.7 and stored overnight at 4° C. The following day, cells are pelleted and resuspended in fresh LB medium (no ampicillin). The cells are divided into 5 1-liter batches and grown at 30° C. in an incubator shaker to an $OD_{600}$ of 1.5. IPTG is added to a final concentration of 0.1 mM and growth is continued for about 2 to 2.5 hours at which time cells were harvested by centrifugation.

Example 6

RECOMBINANT PRODUCTION OF FGF-NUCLEIC ACID BINDING DOMAIN FUSION PROTEIN

A. General Descriptions

1. Bacterial Strains and Plasmids

E. coli strains BL21(DE3), BL21(DE3)pLysS, HMS174 (DE3) and HMS 174(DE3)pLysS were purchased from NOVAGEN, Madison, Wis. Plasmid pFC80, described below, has been described in the WIPO International Patent Application No. WO 90/02800, except that the bFGF coding sequence in the plasmid designated pFC80 herein has the sequence set forth as SEQ ID NO. 52, nucleotides 1–465. The plasmids described herein may be prepared using pFC80 as a starting material or, alternatively, by starting with a fragment containing the cII ribosome binding site (SEQ ID NO. 61) linked to the FGF-encoding DNA (SEQ ID NO. 52).

E. coli strain JA221 (lpp⁻ hdsM+ trpE5 leuB6 lacY recA1 F'[lacI$^q$ lac⁺ pro⁺]) is publicly available from the American Type Culture Collection (ATCC), Rockville, Md. 20852, under the accession number ATCC 33875. (JA221 is also available from the Northern Regional Research Center (NRRL), Agricultural Research Service, U.S. Department of Agriculture, Peoria, Ill. 61604, under the accession number NRRL B-1521 1; see also U.S. Pat. No. 4,757,013 to Inouye; and Nakamura et al., Cell 18:1109–1117, 1979). Strain INV1α is commercially available from Invitrogen, San Diego, Calif.

B. Construction of Plasmids Encoding FGF/Nucleic Acid Binding Domain Fusion Proteins 1. Construction of FGFM 13 that Contains DNA Encoding the cI Ribosome Binding Site Linked to FGF A Nco I restriction site is introduced into the nucleic acid binding domain-encoding DNA by site-directed mutagenesis using the Amersham in vitro-mutagenesis system 2.1. The oligonucleotide employed to create the Nco I restriction site is synthesized using a 380B automatic DNA synthesizer (Applied Biosystems). This oligonucleotide containing the Nco I site replaces the original nucleic acid binding domain-containing coding sequence.

In order to produce a bFGF coding sequence in which the stop codon was removed, the FGF-encoding DNA is subcloned into a M13 phage and subjected to site-directed mutagenesis. Plasmid pFC80 is a derivative of pDS20 (see, e.g., Duester et al., Cell 30:855–864, 1982; see also U.S. Pat. Nos. 4,914,027, 5,037,744, 5,100,784, and 5,187,261; see also PCT International Application No. WO 90/02800; and European Patent Application No. EP 267703 A1), which is almost the same as plasmid pKG1800 (see Bernardi et al., DNA Sequence 1:147–150, 1990; see also McKenney et al. (1981) pp. 383–415 in Gene Amplification and Analysis 2: Analysis of Nucleic Acids by Enzymatic Methods, Chirikjian et al. (eds.), North Holland Publishing Company, Amsterdam) except that it contains an extra 440 bp at the distal end of galK between nucleotides 2440 and 2880 in pDS20. Plasmid pKG1800 includes the 2880 bp EcoR I-Pvu II of pBR322 that contains the contains the ampicillin resistance gene and an origin of replication.

Plasmid pFC80 is prepared from pDS20 by replacing the entire galK gene with the FGF-encoding DNA of SEQ ID NO. 52, inserting the trp promoter (SEQ ID NO. 62) and the bacteriophage lambda cII ribosome binding site (SEQ. ID No. 61; see, e.g., Schwarz et al., Nature 272:410, 1978) upstream of and operatively linked to the FGF-encoding DNA. The Trp promoter can be obtained from plasmid pDR720 (Pharmacia PL Biochemicals) or synthesized according to SEQ ID NO. 62. Plasmid pFC80, contains the 2880 bp EcoR I-BamH I fragment of plasmid pSD20, a synthetic Sal I-Nde I fragment that encodes the Trp promoter region:

EcoR I
AATTCCCCTGTTGACAATTAATCATCGAACTAG
TTAACTAGTACGCAGCTTGGCTGCAG and the cII ribosome binding site (SEQ ID NO.61)):
GTCGACCAAGCTTGGGCATACATTCAATCAA
TTGTTATCTAAGGAAATACTTA<u>CATATG</u>

The FGF-encoding DNA is removed from pFC80 by treating it as follows. The pFC80 plasmid was digested by Hga I and SalI, which produces a fragment containing the CII ribosome binding site linked to the FGF-encoding DNA. The resulting fragment is blunt ended with Klenow's reagent and inserted into M13mp18 that has been opened by Sma I and treated with alkaline phosphatase for blunt-end ligation. In order to remove the stop codon, an insert in the ORI minus direction is mutagenized using the Amersham kit, as described above, using the following oligonucleotide (SEQ ID NO. 63): GCTAAGAGCGCCATGGAGA, which contains one nucleotide between the FGF carboxy terminal serine codon and a Nco I restriction site; it replaces the following wild type FGF encoding DNA having SEQ ID NO. 64:

GCT AAG AGC TGA CCA TGG AGA
Ala Lys Ser STOP Pro Trp Arg

The resulting mutant derivative of M13mp18, lacking a native stop codon after the carboxy terminal serine codon of bFGF, was designated FGFM13. The mutagenized region of FGFM13 contained the correct sequence (SEQ ID NO. 65).

2. Preparation of a Plasmid that Encodes the FGF/MyoD Fusion Protein

Plasmid FGFM13 is cut with Nco I and Sac I to yield a fragment containing the CII ribosome binding site linked to the bFGF coding sequence with the stop codon replaced.

An M13mp18 derivative containing the myoD coding sequence is also cut with restriction endonucleases Nco I and Sac I, and the bFGF coding fragment from FGFM13 was inserted by ligation to DNA encoding the fusion protein bFGF-myoD into the M13mp18 derivative to produce mpFGF-myoD, which contains the CII ribosome binding site linked to the FGF-nucleic acid binding domain fusion gene.

Plasmid mpFGF-myoD is digested with Xba I and EcoR I and the resulting fragment containing the bFGF-myoD coding sequence is isolated and ligated into plasmid pET-11a (available from NOVAGEN, Madison, Wis.; for a description of the plasmids see U.S. Pat. No. 4,952,496; see also Studier et al., *Meth. Enz.* 185:60–89, 1990; Studier et al., *J. Mol. Biol.* 189:113–130, 1986; Rosenberg et al., *Gene* 56:125–135, 1987) that has also been treated with EcoR I and Xba I.

*E. coli* strain BL21(DE3)pLysS (NOVAGEN, Madison Wis.) may be transformed with the plasmid containing the fusion gene.

Plasmid FGF/myoD may be digested with EcoR I, the ends repaired by adding nucleoside triphosphates and Klenow DNA polymerase, and then digested with Nde I to release the FGF-encoding DNA without the CII ribosome binding site. This fragment is ligated into pET 11a, which is BamH I digested, treated to repair the ends, and digested with Nde I. The resulting plasmid includes the T7 transcription terminator and the pET-11a ribosome binding site.

Plasmid FGF/myoD may be digested with EcoR I and Nde I to release the FGF-encoding DNA without the CII ribosome binding site and ends are repaired as described above. This fragment may be ligated into pET 12a, which had been BamH I digested and treated to repair the ends. The resulting plasmid includes DNA encoding the OMP T secretion signal operatively linked to DNA encoding the fusion protein.

3. Preparation of a Plasmid that Encodes FGF2-protamine Fusion Protein

Protamines are small basic DNA binding proteins, approximately 6.8 kD in molecular weight with a isoelectric point of 12.175. Twenty-four of the fifty one amino acids are strongly basic. Human protamine has been shown to condense genomic DNA for packaging into the sperm head. The positive charges of the protamine react with the negative charges of the phosphate backbone of the DNA.

A FGF-protamine fusion protein that has the ability to bind to the FGF receptor and bind DNA with high affinity is constructed for expression in *E. coli*. The sequence for the human protamine gene is obtained from GenBank (accession no. Y00443). Four overlapping oligonucleotides (60 mers) are generated and used to amplify the protamine gene. The amplified product is purified and ligated into the bacterial expression vector pET11a (Novagen). To facilitate subcloning, a NcoI and BamHI site are incorporated into the primers. The fragment is synthesized by annealing the 4 oligos (2 sense and 2 antisense) with 20 base overlaps and using PCR to fill-in and amplify the fragments. The PCR products are digested with NcoI and BamHI, and subcloned into pBluescript SK+. The insert sequence is verified. The sequenced product is then cloned downstream and in-frame with FGF2, which has been previously cloned into the pET11a expression plasmid. The oligos used to generate fragment A are (5'-3'):

PT1:
TACATGCCATGGCCAGGTACAGATGCTGTCG CAGCCAGAGCCGGAGCAGATATTACCGCC (SEQ ID NO.: 85)

PT2:
GCAGCTCCGCCTCCTTCGTCTGCGACTTCT TTGTCTCTGGCGGTAATATCTGCTCCGGCT (SEQ ID NO.: 86)

PT3:
GACGAAGGAGGCGGAGCTGCCAGACACGGA GGAGAGCCATGAGGTGCTGCCGCCCCAGGT (SEQ ID NO.: 87)

PT4:
ATATATCCTAGGTTAGTGTCTTCTACATCTC GGTCTGTACCTGGGGCGGCAGCACCTCA (SEQ ID NO.: 88)

Competent bacterial cells, BL21 (DE3), are transformed with the pET11-FGF2-protamine construct. The cells are initially plated on LB agar plates containing 100 μg/ml ampicillin. A glycerol stock made from an individual colony added to 1 ml fresh LB broth and then to 250 ml of LB broth. The cells are grown to an $OD_{600}$ of 0.7 and induced with IPTG. The culture is harvested 4 hours after induction. The suspension is centrifuged; the supernatant is saved and the pellet is resuspended in lysis buffer, centrifuged again and the supernatants pooled. A sample of the pellet and the supernatant are analyzed by Western analysis using antibodies to FGF2 to determine the percentage of fusion protein within each fraction. Soluble protein is purified. Briefly, the cells are pelleted and resuspended in buffer A (10 mM sodium phosphate, pH 6.0, containing 10 mM EDTA, 10 mM EGTA and 50 mM NaCl) and passed through a microfluidizer (Microfluidics Corp., Newton, Mass.) to break open the bacteria and shear DNA. The resultant mixture is diluted and loaded onto an expanded bed Streamline SP cation-exchange resin. The column is washed with step gradients of increasing concentrations of NaCl. The eluted material is analyzed by Western analysis for fractions containing the fusion protein. These fractions are pooled, diluted, and loaded onto a Heparin-Sepharose affinity column. After washing, the bound proteins are eluted in a batch-wise manner in buffer containing 1 M NaCl and then in buffer containing 2 M NaCl. Peak fractions of the 2M elution, as determined by optical density at 280 nm, are pooled and the purity determined by gel electrophoresis and Western analysis. The final pool of material will be loaded onto a column of Sephacryl S-100 equilibrated with 20 mM HEPES pH 7.4, 150 mM NaCl.

Fusion protein located in the pellet is isolated, solubilized and refolded. Briefly, each culture pellet is thawed completely and resuspended in buffer A (10 mM Tris, 1 mM EDTA, pH 8.0+0.1 mg/ml lyzozyme). The mixture is sonicated on ice, centrifuged at 16,000×g, and the supernatant discarded. Inclusion bodies are solubilized with solubilization buffer: (6 M guanidine-HCl, 100 mM Tris, 150 mM NaCl, 50 mM EDTA, 50 mM EGTA, pH 9.5,), vortexed, incubated for 30 minutes at room temperature, and centrifuged at 35,000×g for 15 minutes. The supernatant is saved and diluted 1:10 in dilution buffer (100 mM Tris, 10 mM EDTA, 1% monothioglycerol, 0.25 M L-arginine, pH 9.5). The material is stirred, covered, at 4° C. for 2 hours and then centrifuged at 35,000×g for 20 minutes. The supernatant is dialyzed in against 5 liters PBS, pH 8.8, for 24 hours at 4° C. with 3 changes of fresh PBS. The material is concentrated approximately 10-fold using size-exclusion spin columns. The soluble refolded material is then analyzed by gel electrophoresis.

Expression of the FGF-protamine fusion protein can be achieved in mammalian cells by excising the insert with restriction enzymes NdeI and BamHI and ligating into a mammalian expression vector.

C. Expression of the Recombinant bFGF-nucleic Acid Binding Domain Fusion Proteins A two-stage method is used to produce recombinant bFGF-myoD protein (hereinafter bFGF-nucleic acid binding domain fusion protein).

Three liters of LB broth containing ampicillin (50 μg/ml) are inoculated with plasmid-containing bacterial cells (strain BL21(DE3)pLysS) from an overnight culture (1:100 dilution). Cells are grown at 37° C. in an incubator shaker to an OD$_{600}$ of 0.7. IPTG (Sigma Chemical, St. Louis, Mo.) is added to a final concentration of 0.2 mM and growth was continued for 1.5 hours at which time cells were centrifuged.

Experiments have shown that growth at 30° C. instead of 37° C. improves yields. Thus, cells are grown at 30° C. to an OD600 of 1.5 prior to induction. Following induction, growth is continued for about 2 to 2.5 hours at which time the cells are harvested by centrifugation.

The pellet is resuspended in lysis solution (45–60 ml per 16 g of pellet; 20 mM TRIS, pH 7.4, 5 mM EDTA, 10% sucrose, 150 mM NaCl, lysozyme, 100 μg/ml, aprotinin, 10 μg/ml, leupeptin, 10 μg/ml, pepstatin A, 10 μg/ml and 1 mM PMSF) and incubated with stirring for 1 hour at room temperature. The solution is sonicated for 2.5 minutes. The suspension is centrifuged at 12,000×g for 1 hour; the resulting first-supernatant saved and the pellet is resuspended in another volume of lysis solution without lysozyme. The resuspended material is centrifuged again to produce a second-supernatant, and the two supernatants are pooled and dialyzed against borate buffered saline, pH 8.3.

D. Affinity Purification of bFGF-nucleic Acid Binding Domain Fusion Protein

Thirty ml of the dialyzed solution containing the bFGF-nucleic acid binding domain fusion protein is applied to HiTrap heparin-Sepharose column (Pharmacia, Uppsala, Sweden) equilibrated with 0.15 M NaCl in 10 mM TRIS, pH 7.4 (buffer A). The column is washed first with equilibration buffer; second with 0.6 M NaCl in buffer A; third with 1.0 M NaCl in buffer A; and finally eluted with 2 M NaCl in buffer A into 1.0 ml fractions. Samples were assayed by the ELISA method.

bFGF-nucleic acid binding domain fusion protein binds the heparin-Sepharose column at similar affinity as native and recombinantly-produced bFGF, indicating that the heparin affinity is retained in the bFGF-SAP fusion protein.

E. Characterization of the bFGF-nucleic Acid Binding Domain Fusion Protein by Western Blot SDS gel electrophoresis is performed on a Phastsystem utilizing 20% acrylamide gels (Pharmacia). Western blotting is accomplished by transfer of the electrophoresed protein to nitrocellulose using the PhastTransfer system (Pharmacia), as described by the manufacturer. Antisera to bFGF is used at a dilution of 1:1000. Horseradish peroxidase labeled anti-IgG is used as the second antibody (Davis et al., *Basic Methods in Molecular Biology*, New York, Elsevier Science Publishing Co., pp 1–338, 1986).

Anti-FGF antisera should bind to a protein with an approximate molecular weight of 53,000, which corresponds to the sum of the independent molecular weights of nucleic acid binding domain (35,000) and bFGF (18,000).

Example 7

PREPARATION OF FGF-NUCLEIC ACID BINDING DOMAIN CONJUGATES THAT CONTAIN LINKERS ENCODING PROTEASE SUBSTRATES

A. Synthesis of Oligos Encoding Protease Substrates

Complementary single-stranded oligos in which the sense strand encodes a protease substrate, have been synthesized either using a cyclone machine (Millipore, Mass.) according the instructions provided by the manufacturer, or were made by Midland Certified Reagent Co. (Midland, Tex.) or by National Biosciences, Inc. (MN). The following oligos have been synthesized.

1. Cathepsin B substrate linker 5'-CCATGGCCCTGGC CCTGGCCCTGGCCCTGGCCATGG SEQ ID NO: 66

2. Cathepsin D substrate linker 5'-CCATGGGCCGATC GGGCTTCCTGGGCTTCGGCTTCCTGGGCTT CGCCAT GG-3' SEQ ID NO: 67

3. Trypsin substrate linker 5'-CCATGGGCCGATC GGGCGGTGGGTGCGCTGGTAATAGAGTCA GAAGATCAGTCGGAAGCAGCCTGTCTTG CGGTGGTCTC GACCTGCAGG CCATGG-3' SEQ ID NO: 68

4. Gly$_4$Ser 5'-CCATGGGCGGCGGCGGCTCTGCCA TGG-3' SEQ ID NO: 47

5. (Gly$_4$Ser)$_2$ 5'-CCATGGGCGGCGGCGGCGGTCTGG CGGCGGCGGCTC TGCCATGG-3' SEQ ID NC: 48

6. (Ser$_4$Gly)$_4$ 5'-CCATGGCCTCGTCGTCGTCGGGCT CGTCGTCGTCGGGCTCGTCGTCGTCGGGCTGC GTCGTGTCGGGC GCCATGG-3' SEQ ID NO: 49

7. (Ser$_4$Gly)$_2$ 5-CCATGGCCTCGTCGTCGTCGGGC TCGGTGTCGTCGGGCGCCATGG-3' SEQ ID NO: 50

8. Thrombin substrate linker CTG GTG CCG CGC GGC AGC SEQ ID NO. 69 Leu Val Pro Arg Gly Ser 9. Enterokinase substrate linker GAC GAC GAC GAC CCA SEQ ID NO. 70 Asp Asp Asp Asp Lys 10. Factor Xa substrate ATC GAM GGT CGT SEQ ID NO. 71 Ile Glu Gly Arg B. Preparation of DNA Constructs Encoding FGF-Linker-nucleic Acid Binding Domain The complementary oligos are annealed by heating at 95° C. for 15 min., cooled to room temperature, and then incubated at 4° C. for a minute to about an hour. Following incubation, the oligos are digested with NcoI and ligated overnight at a 3:1 (insert:vector) ratio at 15° C. to NcoI-digested plasmid which has been treated with alkaline phosphatase (Boehringer Mannheim).

Bacteria (Novablue (NOVAGEN, Madison, Wis.)) are transformed with the ligation mixture (1 μl) and plated on LB-amp or LB-Kan, depending upon the plasmid). Colonies are selected, clones isolated and sequenced to determine orientation of the insert. Clones with correct orientation are used to transform strain expression strain BL21(DE3) (NOVAGEN, Madison, Wis.). Glycerol stocks are generated from single transformed colonies. The transformed strains are cultured as described in Example 2 and fusion proteins with linkers were expressed.

The DNA and amino acid sequences of exemplary fusion proteins, containing cathepsin B substrate (FPFS9), cathepsin D substrate (FPFS5), Gly$_4$Ser (FPFS7), (Gly$_4$Ser)$_2$ (FPFS8), trypsin substrate (FPFS6), (Ser$_4$Gly)$_4$ (FPFS12) and (Ser$_4$Gly)$_2$ (FPFS11) linkers, respectively, are set forth in SEQ ID NOs. 72–78.

Example 8

FGF-POLY-L-LYSINE (FGF2–K) COMPLEXED WITH A PLASMID ENCODING P-GALACTOSIDASE

A. Derivatization of poly-L-lysine

Polylysine polymer with average lengths of 13, 39, 89, 152, and 265 (K$_{13}$, K$_{39}$, K$_{84}$, K$_{152}$, K$_{265}$) are purchased from a commercial vendor (Sigma, St. Louis, Mo.) and dissolved in 0.1 M NaPO4, 0.1 M NaCl, 1 mM EDTA, pH 7.5 (buffer A) at 3–5 mg/ml. Approximately 30 mg of poly-L-lysine solution is mixed with 0.187 ml of 3 mg/ml N-succinimidyl-3(pyridyldithio)proprionate (SPDP) in anhydrous ethanol resulting in a molar ratio of SPDP/poly-L-lysine of 1.5 and incubated at room temperature for 30 minutes. The reaction mixture is then dialyzed against 4 liters of buffer A for 4 hours at room temperature.

B. Conjugation of Derivatized Polylysine to FGF2-3

A solution containing 28.5 mg of poly-L-lysine-SPDP is added to 12.9 mg of FGF2-3 ([C96S]-FGF2) in buffer A and incubated overnight at 4° C. The molar ratio of poly-L-lysine-SPDP/FGF2-3 is approximately 1.5. Following incubation, the conjugation reaction mixture is applied to a 6 ml Resource S (Pharmacia, Uppsala, Sweden) column. A gradient of 0.15 M to 2.1 M NaCl in 20 mM NaPO4, 1 mM EDTA, pH 8.0 (Buffer B) over 24 column volumes is used for elution. The FGF2-3/poly-L-lysine conjugate, called FGF2-K, is eluted off the column at approximately 1.8–2 M NaCl concentration. Unreacted FGF2-3 is eluted off by 0.5–0.6 M NaCl.

The fractions containing FGF2-K are concentrated and loaded onto a gel-filtration column (Sephacryl S100) for buffer exchange into 20 mM HEPES, 0.1 M NaCl, pH 7.3. The molecular weight of FGF-K152 as determined by size exclusion HPLC is approximately 42 kD. To determine if the conjugation procedure interferes with the ability of FGF2-3 to bind heparin, the chemical conjugate FGF2-K is loaded onto a heparin column and eluted off the column at 1.8–2.0 M NaCl. In comparison, unconjugated FGF2-3 is eluted off heparin at 1.4–1.6 M NaCl. This suggests that poly-L-lysine contributes to FGF2-3 ability to bind heparin. The ability of poly-L-lysine 152 to bind heparin is not determined; poly-L-lysine 84 elutes at approximately 1.6 M NaCl. Histone HI-polylysine was purchased and cytochrome C was conjugated to polylysine as described herein.

A sample of FGF2-K is electrophoresed on SDS-PAGE under non-reducing and reducing conditions. The protein migrates at the same molecular weight as FGF. Under non-reducing conditions the conjugate does not enter the gel because of its high charge density (FIG. 1, lanes 1, 2, non-reducing; lanes 3, 4, reducing).

Figure 2:
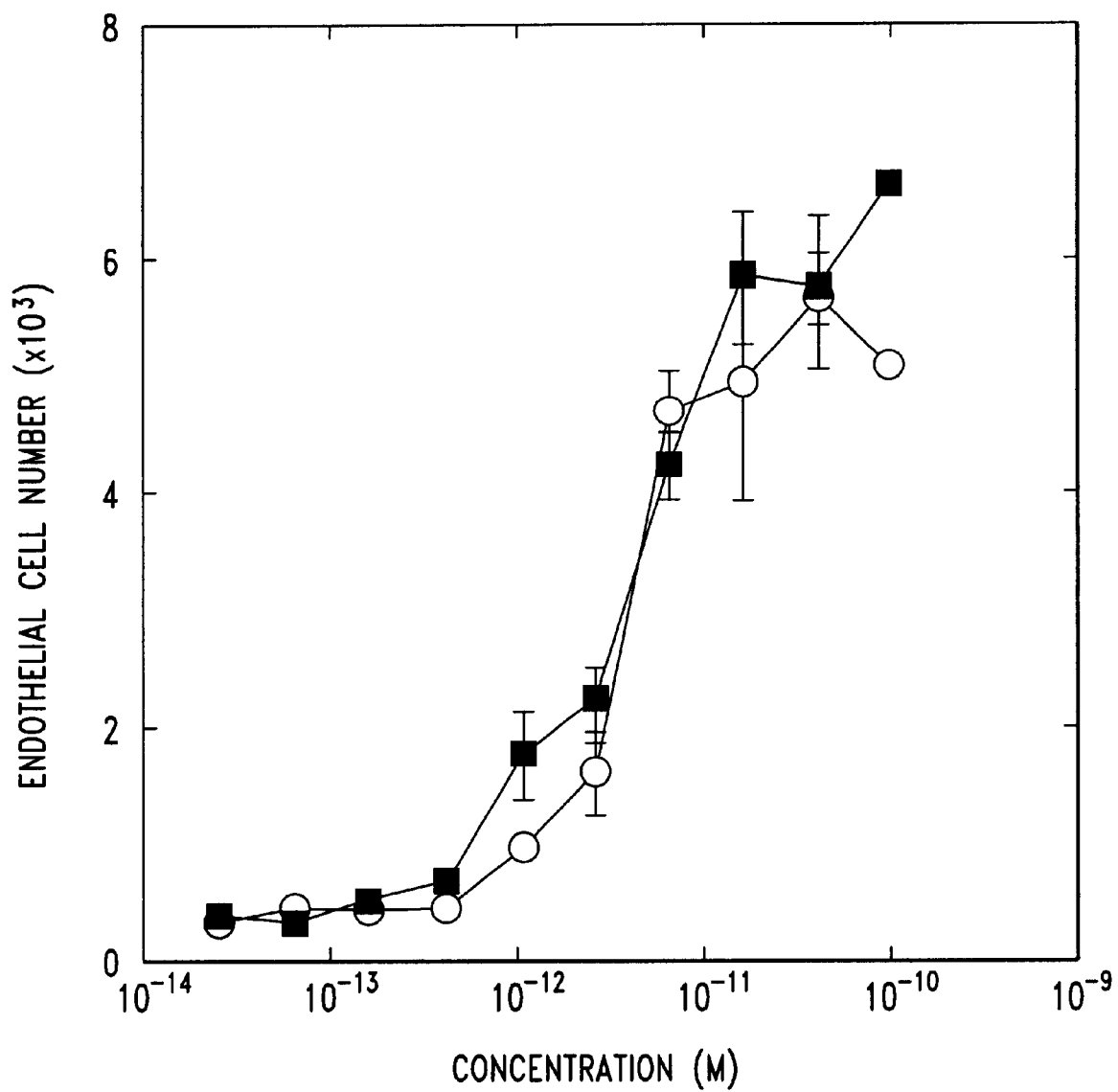
FIG. 2 is a graph depicting the proliferation of bovine aortic endothelial cells in response to FGF2 (closed box) and FGF2–K152 (open circle) conjugate.

A standard proliferation assay using aortic bovine endothelial cells is performed to determine if the conjugation procedure reduced the ability of FGF2-3 ability to stimulate mitogenesis. The results reveal that FGF2-K is equivalent to FGF2-3 in stimulating proliferation (FIG. 2).

C. FGF2-3-poly-L-lysine-nucleic Acid Complex Formation

Figure 3A:
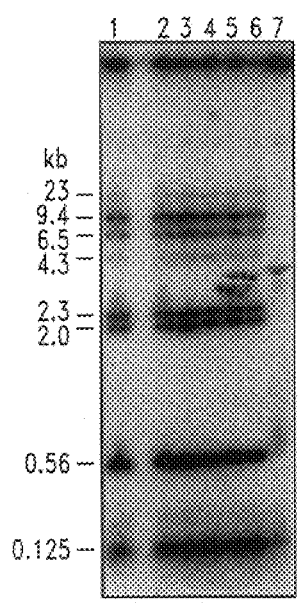
FIG. 3 is a photograph of a gel showing the effects of various lengths of poly-L-lysine on the ability to interact with DNA. Thirty-five ng of labeled DNA were added to increasing concentrations of either FGF2 or FGF2–K: lanes 1, 0 ng; lanes 2, 0.1 ng; lanes 3, 1 ng; lanes 4, 10 ng; lanes 5, 20 ng; lanes 6, 35 ng; lanes 7, 100 ng. Panel A: FGF2; panel B, FGF2–K152; panel C, FGF2–K13; panel D, FGF2–K84; panel E, EGF2–K267; panel F, FGF2–K39. The lengths of the digested DNA are indicated.
Figure 3B:
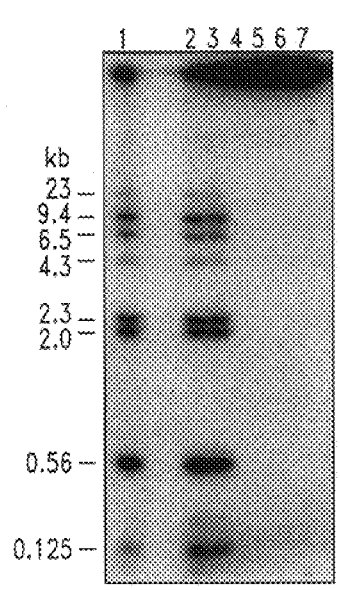
Figure 3C:
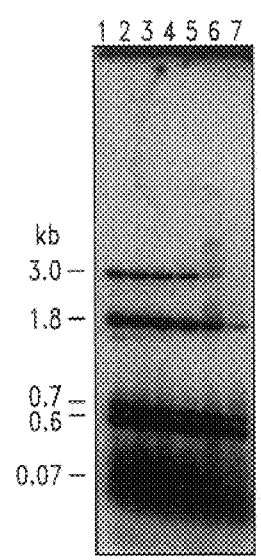
Figure 3D:
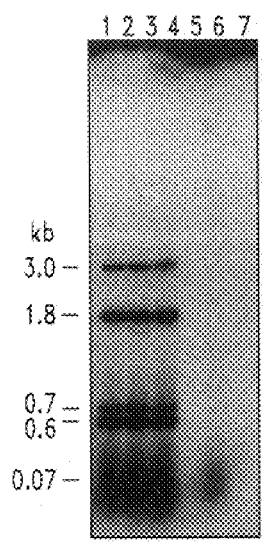
Figure 3E:
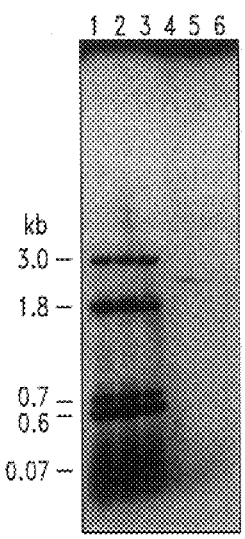
Figure 3F:
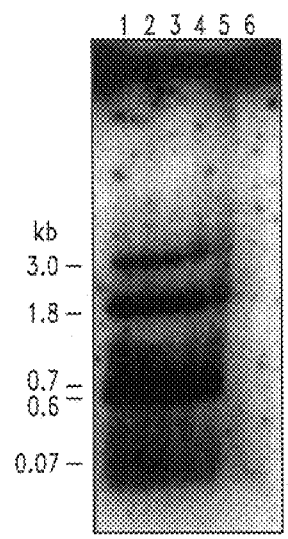

Optimal conditions for complex formation are established. Varying quantities (0.2 to 200 μg) of β-galactosidase encoding plasmid nucleic acid pSVβ or pNASS-β (lacking a promoter) are slowly mixed with 100 μg of FGF2-K in 20 mM HEPES pH 7.3, 0.15 M NaCl. The reaction is incubated for 1 hour at room temperature. Nucleic acid binding to the FGF-lysine conjugate is confirmed by gel mobility shift assay using $^{32}$P-labeled SV40-β-gal nucleic acid cut with HincII restriction endonuclease. In brief, SV40β-gal nucleic acid is digested with HincII restriction endonucleases; ends are labeled by $T_4$ PNK following dephosphorylation with calf intestinal alkaline phosphatase. To each sample of 35 ng of $^{32}$P-labeled nucleic acid increasing amounts of FGF-polylysine conjugate is added to the mixture. The protein/nucleic acid mixture is electrophoresed in an agarose gel with 1×TAE buffer. Binding of the conjugate to the radio-labeled DNA is shown by a shift in the complex to the top of the well. (FIG. 3.) As seen in FIG. 3D, as little as 10 ng of $K_{84}$ causes a complete shift of restriction fragments indicating binding. With $K_{13}$, 100 ng of poly-L-lysine was required (FIG. 3C). With $K_{265}$, 10 ng was required (FIG. 3E).

Figure 4:
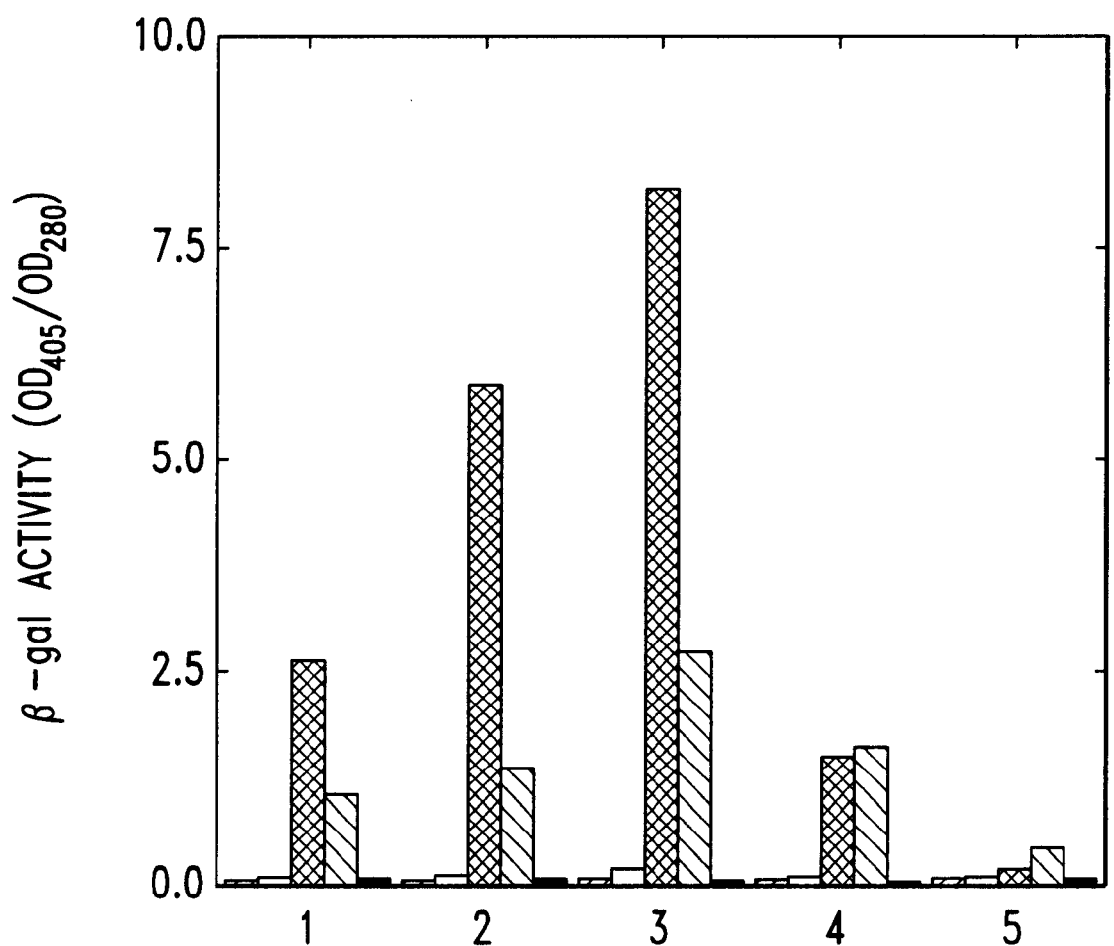
FIG. 4 is a chart depicting the activity of β-gal following transfection of FGF2/poly-L-lysine/DNAβ-gal into COS cells. Lane 1, 10:1 (w/w) ratio of FGF2/poly-L-lysine conjugate to DNA; lane 2, 5:1 ratio; lane 3, 2:1 ratio; lane 4, 1:1 ratio; lane 5, 0.5:1 ratio. The five bars, from left to right, are FGF2, FGF2–K13, FGF2–K39, FGF2–K84, and FGF2–K152.

The optimal length of poly-L-lysine and weight ratios is determined by conjugation of FGF2-3 to poly-lysine of different lengths. DNA encoding β-galactosidase was complexed with the conjugates at 10:1, 5:1, 2:1, 1:1, and 0.5:1 (FIG. 4, lanes 1–5, respectively) (w/w) ratios. The ability of these FGF2-K complexes to bind DNA was determined by measuring the ability of FGF to promote the uptake of plasmid DNA into cells. FGF2-K conjugates were evaluated at various protein to DNA ratios for their ability to deliver pSVβ-gal DNA into cells (FIG. 4).

Briefly, the complexes were incubated for 1 hr at room temperature and then added to COS cells for 48 hrs. Cell extracts were prepared and assayed for β-gal enzyme activity. Briefly, cells are washed with 1 ml of PBS ($Ca^{+2}$ and $Mg^{+2}$ free) and lysed. The lysate was vortexed and cell debris removed by centrifugation. The lysate was. assayed for β-gal activity as recommended by the manufacturer (Promega, Madison, Wis.). The β-gal activity was normalized to total protein. As seen in FIG. 4, lane 3, a 2:1 (w/w) ratio of FGF2-K:DNA gave maximal enzyme activity.

In addition, toroid formation, which correlates with increased gene expression, was assessed by electron microscopy. A representative toroid at a protein to DNA ratio of 2:1 is shown in FIG. 5, upper panel. Toroidal structures are absent, or only partially formed, at low ratios (e.g., 0.5:1) (FIG. 5, lower panel).

Figure 6A:
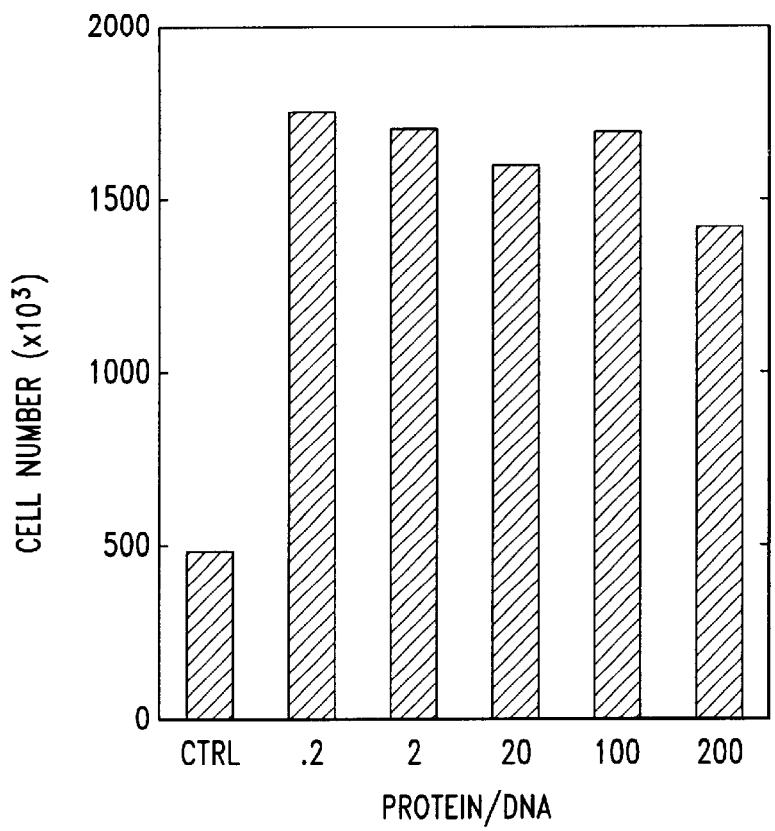
FIG. 6 is a graph depicting proliferation of bovine aortic-endothelial cells. In the upper panel, cells were treated with FGF2–K152–DNA; in the lower panel, cells were treated with a mixture of FGF2, K152, and DNA.
Figure 6B:
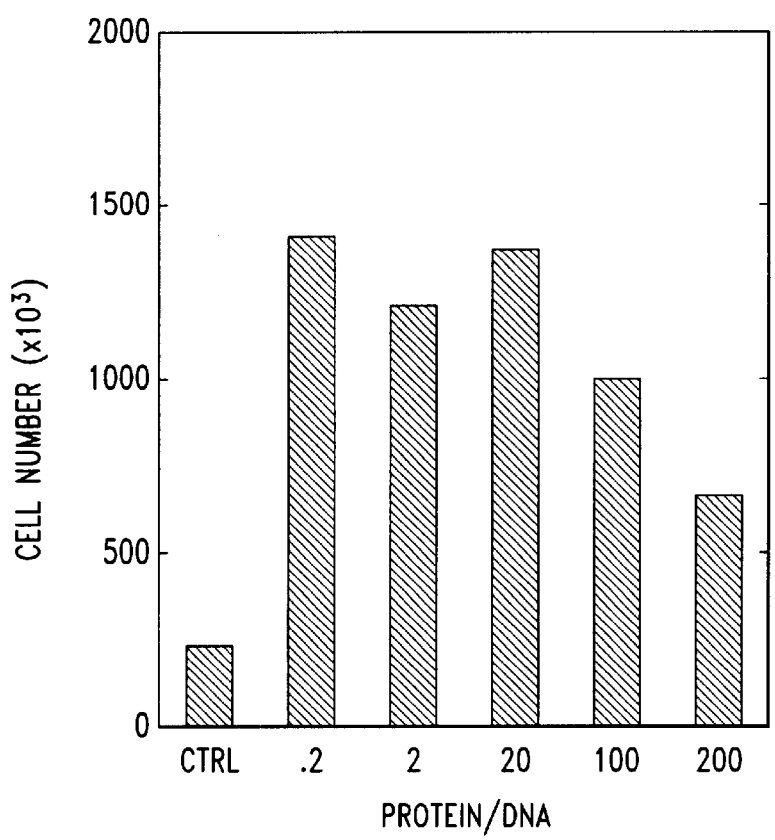

A proliferation assay is performed to determine if the condensed nucleic acid had an effect on the ability of FGF2-K to bind to cognate receptor and stimulate mitogenesis. The proliferation assay shows that only the highest dose of nucleic acid (200 μg) has a slightly inhibitory effect on proliferation as compared to FGF2-3 plus poly-L-lysin+DNA (FIG. 6).

A FGF2-K84-DNA at a protein:DNA ratio of 2:1 is introduced into COS cells and an endothelial cell line, ABAE, both of which express FGF receptors. The cells are subsequently assayed for β-galactosidase enzyme activity. COS and ABAE cells are grown on coverslips and incubated with the different ratios of FGF2-K:DNA for 48 hours. The cells are then fixed and stained with X-gal. Maximal β-galactosidase enzyme activity is seen when 50 μg of pSVβ per 100 μg of FGF2-3-polylysine conjugate is used.

Figure 7A:
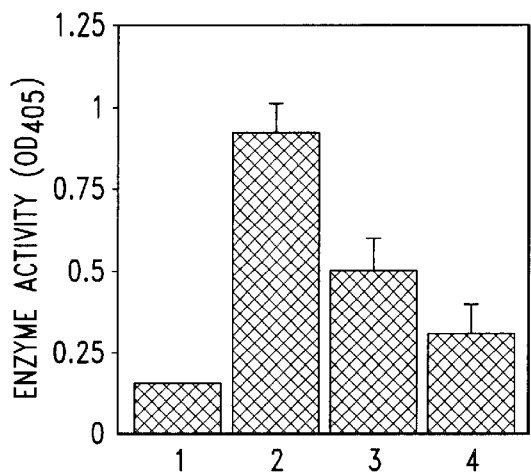
FIG. 7A is a graph displaying β-gal activity after transfection of FGF2/poly-L-lysine/pSVβ-gal into COS cells (lane 2), B16 cells (lane 3), NIH 3T3 cells (lane 4), and DNA alone (lane 1).

FGF2-K84-pSVβ-gal at a protein to DNA ratio of 2:1 was added to various cell lines and incubated for 48 hr. Cell extracts were prepared, assayed for β-gal activity and total protein. As shown in FIG. 7A, COS, B16, NIH3T3, and BHK cell lines were all able to take up complex and express β-gal.

Figure 7B:
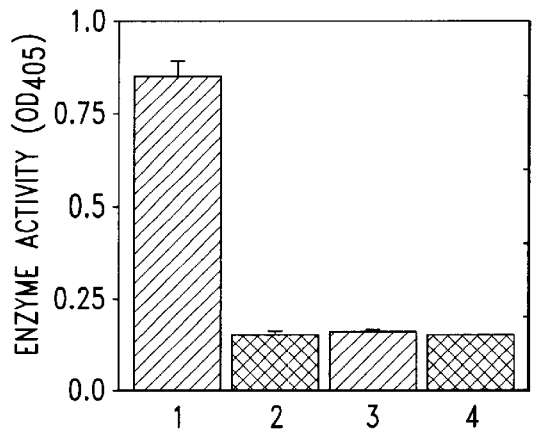
FIG. 7B is a graph depicting β-gal expression in COS cells, pSVβ-gal (lanes 1, 3) or pNASSβ-gal (lanes 2, 4) were incubated with (lanes 1, 2) or without (lanes 3, 4) FGF2–K84 and the complexes incubated on COS cells for 48 hrs.
Figure 7C:
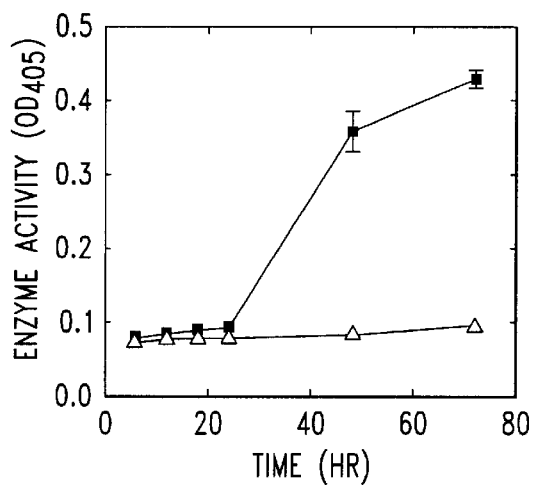
FIG. 7C is a graph showing activity of β-gal activity at various times following transfection with either plasmid alone or with complexes of FGF21K84/pSV β-gal. -Δ-, DNA alone; -■-, FGF2–K4–DNA.
Figure 7D:
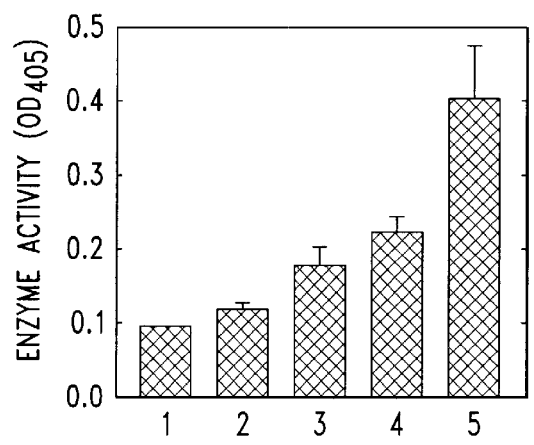
FIG. 7D is a graph showing β-gal activity after transfection of various concentrations of FGF2/K84/pSVβ-gal. Lane 1, 0 µg; lane 2, 0, 1 µg; lane 3, 1 µg; lane 4, 5 µg; lane 5, 10 µg.

The expression of β-gal requires FGF2 for targeting into cells. pSVβ or pNASSβ plasmid DNA was incubated with (FIG. 7B, lanes 1, 2) or without (lanes 3, 4) FGF2-K84 for 1 hr at room temperature. Complexes were added to COS cells for 48 hr. Cell extracts were assayed for β-gal activity and normalized to total protein. Only background β-gal activity was seen unless the plasmid was complexed with FGF2/K84. Expression of β-gal is seen to be both time and dose-dependent (FIGS. 7C and 7D).

Sensitivity of the receptor mediated gene delivery system is determined using the optimized FGF2-K/DNA ratio for complex formation. Increasing amounts of the FGF2-K/DNA complex is added to cells. 100 μg of FGF2-K was mixed with 50 ug of pSVβ for 1 hour at room temperature. The COS and endothelial cells are incubated with increasing amounts of condensed material (0 ng, 1 ng, 10 ng, 100 ng, 1000 ng and 10,000 ng). The cells are incubated for 48 hours and then were assayed for β-galactosidase activity. In addition, cells grown on cover slips are treated with 1000 ng of FGF2-K-DNA for 48 hours, then fixed and stained using X-gal. The β-gal enzyme assay reveals that with increasing amounts of material there is an increase in enzyme activity. (FIG. 7D) Cells incubated with X-gal show blue staining throughout the cytoplasm in approximately 3% of the cells on the coverslip.

Figure 8A:
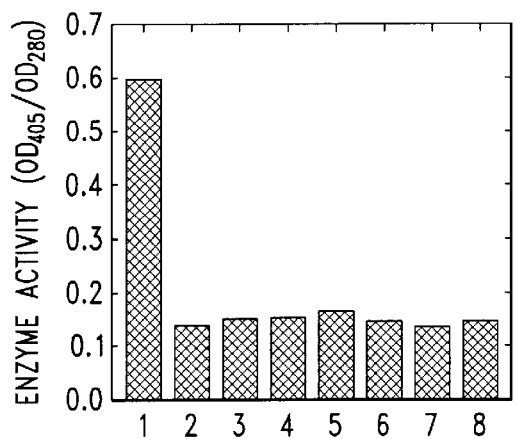
FIG. 8A is a graph showing β-gal activity in COS cells following transfection of FGF2–K84–pSVβ-gal (lane 1), FGF2+K84+pSVβ-gal (lane 2), FGF2+pSVβ-gal (lane 3), K84+pSVβ-gal (lane 4); pSVβ-gal (lane 5), FGF2–K84 (lane 6), FGF2 (lane 7) and K84 (lane 8).
Figure 8B:
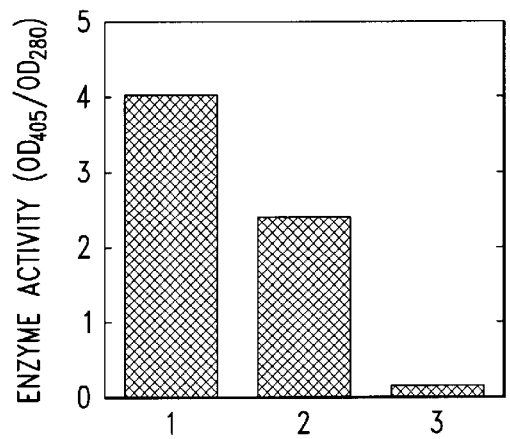
FIG. 8B is a graph showing competition for cell bindings. Lane 1, FGF2–K84–pSVβ-gal complex transfected into COS cells; lane 2, FGF2–K84–pSVβ-gal plus 100 µg FGF2; lane 3, no complex.
Figure 8C:
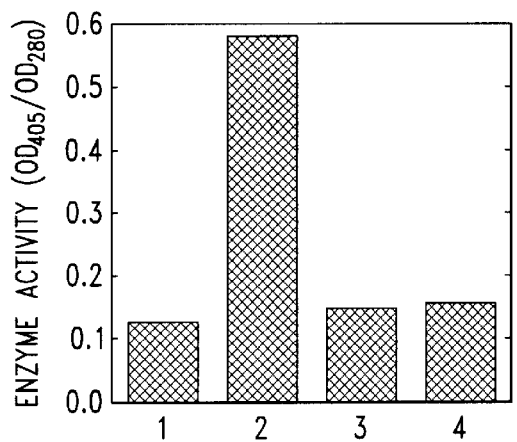
FIG. 8C is a graph showing the attenuation of β-gal activity upon the addition of heparin during transfection. Lane 1, FGF2–K84–pSVβ-gal+10 µg heparin; lane 2, FGF2–K84–pSVβ-gal; lane 3, heparin alone; lane 4, pSVβ-gal alone.
Figure 8D:
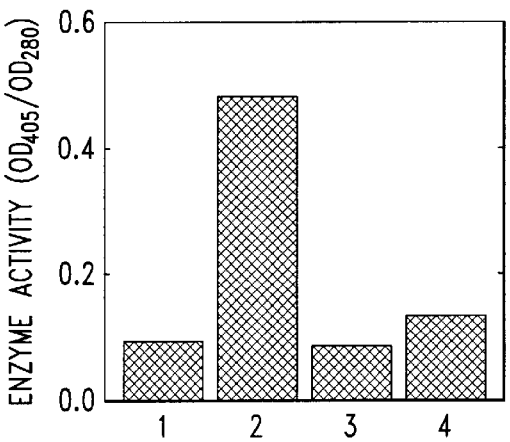
FIG. 8D is a graph showing ligand targeting of DNA, pSVβ-gal DNA alone (lane 1), FGF2–K84 (lane 2), histone H1–K84 (lane 3) and cytochrome C-K84 (lane 4) were condensed with pSVβ-gal DNA and added to BHK cells. β-gal activity was measured 48 hr later.

Targeting of the complexes is specific for the FGF receptor. First, as seen in FIG. 8A, FGF2–K84–pSVβ-gal resulted in enzyme activity (lane 1), while only background levels of activity were seen with FGF2+K84+DNA (lane 2), FGF2+ DNA (lane 3), K84+DNA (lane 4), DNA (lane 5), FGF2–K84 (lane 6), FGF2 alone (lane 7) and K84 alone (lane 8). The expression of β-gal is specifically inhibited if free FGF2 is added during transfection (FIG. 8B). Moreover, the addition of heparin attenuates the expression of β-gal (FIG. 8C). Moreover, histone HI and cytochrome C were ineffective in delivering pSVβ-gal (FIG. 8C).

Taken together, these findings support the hypothesis that the targeted DNA is introduced into receptor-bearing cells via the high affinity FGF receptor. Because histone can bind heparin sulfate yet fails to elicit a signal, the introduction of DNA appears independent of the low affinity FGF receptor or non-specific endocytosis.

D. Effect of Endosome-disruptive Peptides

Figure 9A:
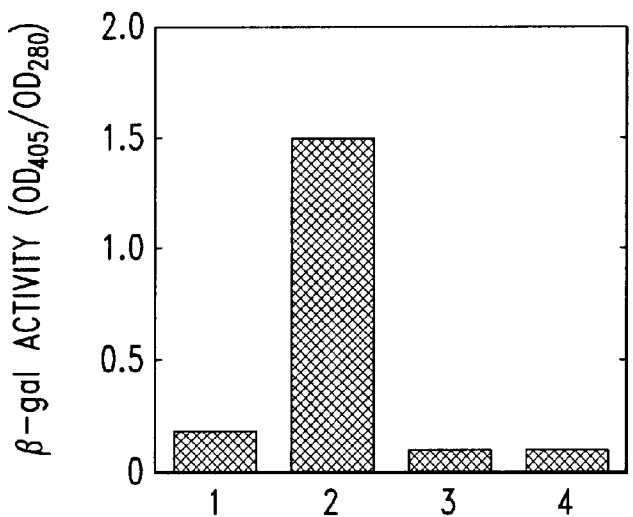
FIG. 9A is a graph showing the effect of chloroquine on β-gal expression, pSVβ-gal and FGF2–K84 were mixed in the absence (lane 1) or presence (lane 2) of 100 µM chloroquine and incubated for 1 hr at room temperature prior to addition of the complexes to COS cells. Lane 3, chloroquine alone; lane 4, DNA alone.

Targeting is mediated by passage of the complex through endosomes. Chloroquine, which was added to complexes before transfection, resulted in an 8-fold increase in β-gal activity (FIG. 9A).

Based on this, the effect of endosome disruptive peptides was evaluated. The peptide INF7, GLF EAIEGFIEN GWEGMIDGWYGC, derived from influenza virus, was synthesized. A complex between FGF2–K84 (5 μg) and pSVβ-gal plasmid DNA (5 μg) was formed. At this ratio, approximately half of the negative charge of the negative charge of the DNA was neutralized by the conjugate. K84, poly-L-lysine, was further added to saturate binding to the remaining DNA. The INF7 peptide was added 30 minutes later. The complex is added to COS cells and β-gal activity is assayed 48 or 72 hr later.

Figure 13A:
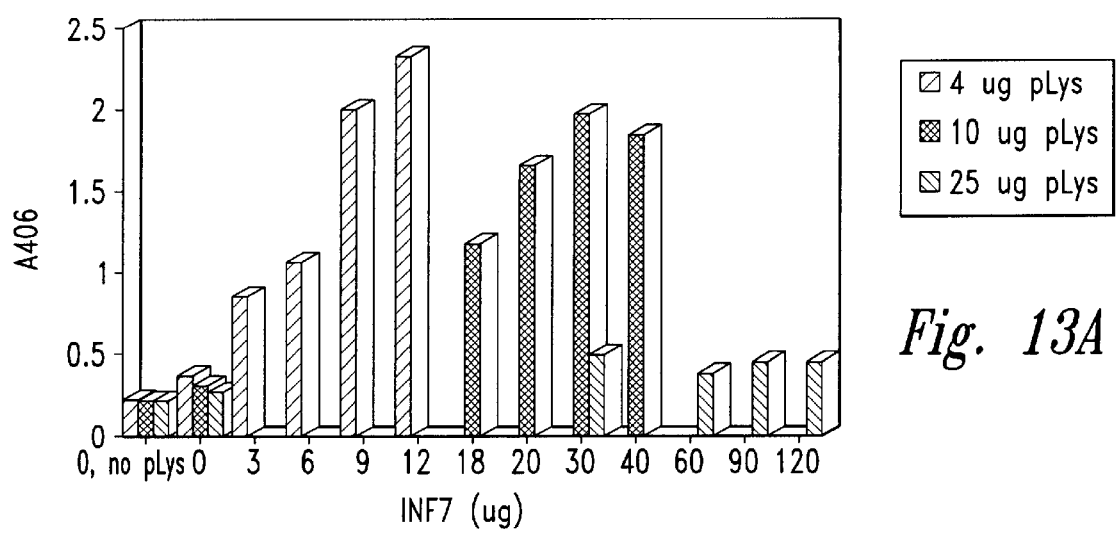
FIG. 13A is a graph showing β-gal activity with an endosome disruptive peptide in the complex.
Figure 13B:
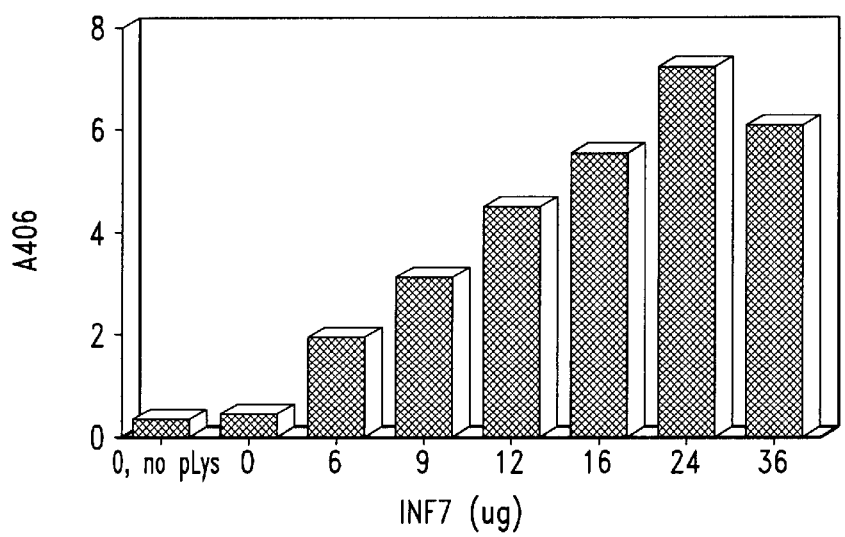
FIG. 13B is a graph showing β-gal activity with an endosome disruptive peptide in the complex.
Figure 13C:
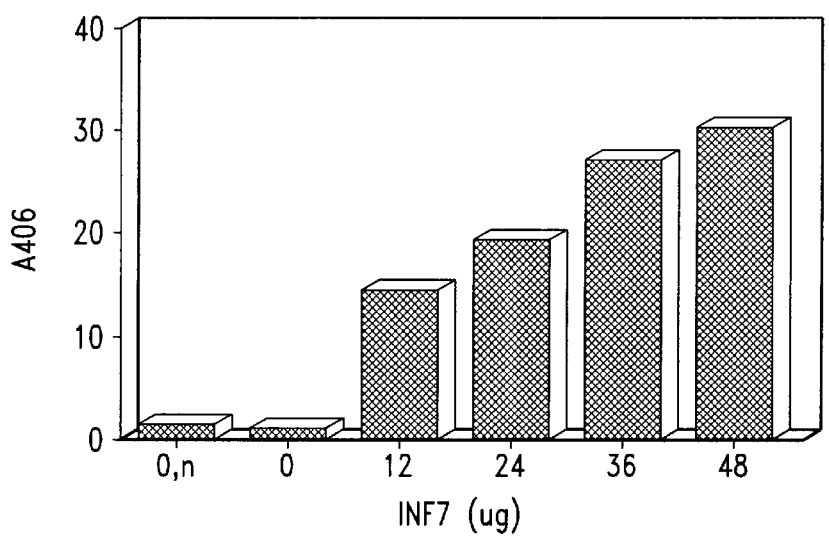
FIG. 13C is a graph showing β-gal activity with an endosome disruptive peptide in the complex.
Figure 14:
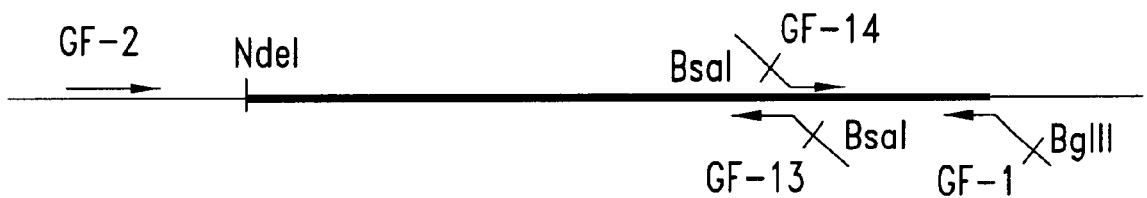
FIG. 14 is a schematic showing the features of inverse-PCR strategy to create FGF-2 mutants.
Figure 24:
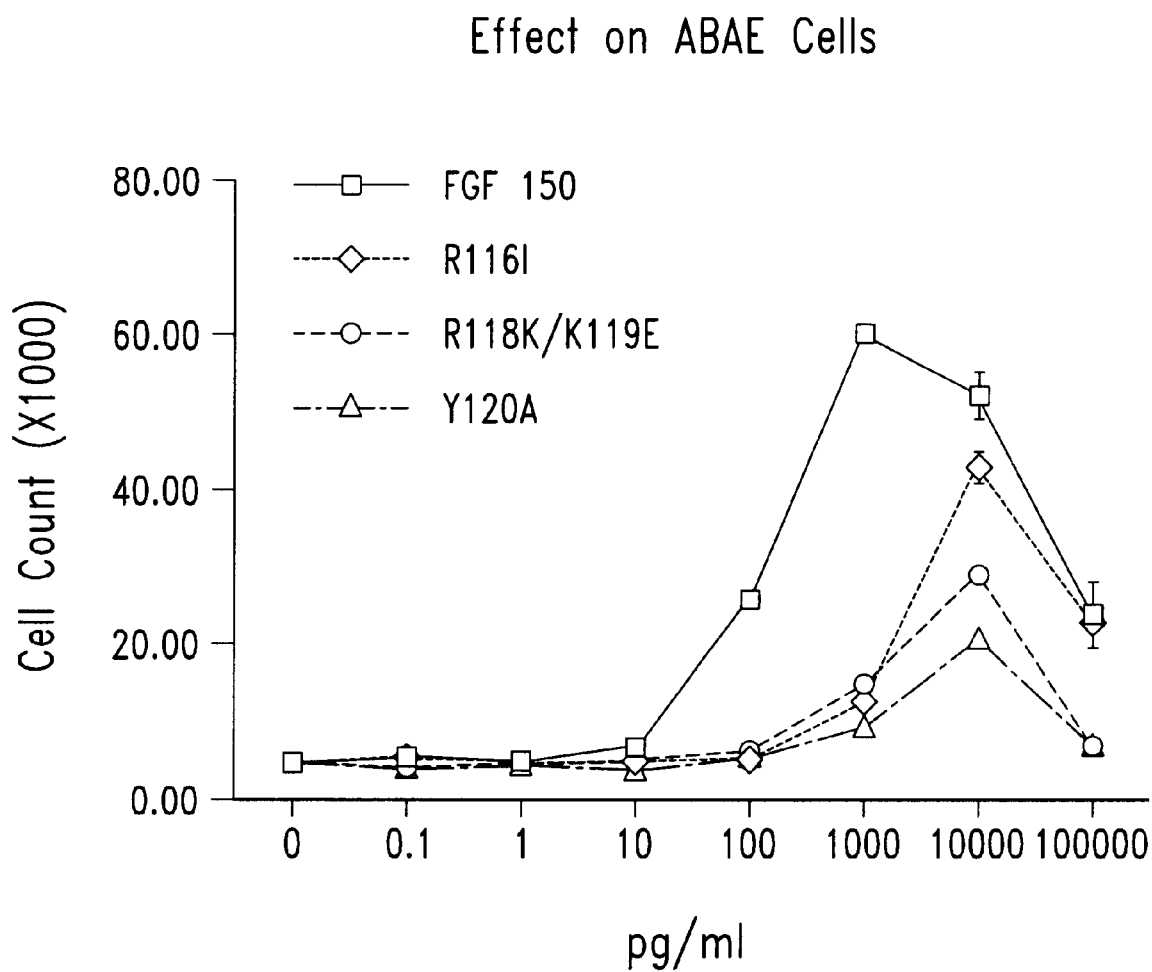
FIG. 24 is a graph showing the proliferative ability of wild type FGF (FGF150) and FGF mutants.

The amount of free polylysine necessary to neutralize the DNA and allow INF7 to complex was determined. Polylysine was added at 4, 10, or 25 μg to the FGF2–K84/pSVβ-gal complex. To each of these complexes four different concentrations of INF7 were added. Maximal β-gal expression was seen with 4 μg of K84 and 12 μg of INF7 (FIG. 13A). When higher amounts of poly-lysine were used, more cell death resulted. The optimal amount of INF7 was determined using 4 μg of polylysine. As seen in FIG. 13B, 24 μg of INF7 gave maximal β-gal activity. At 72 hr, 48 μg of INF7 gave maximal β-gal activity (approximately 20–32 fold enhancement) (FIG. 13C).

Figure 9B:
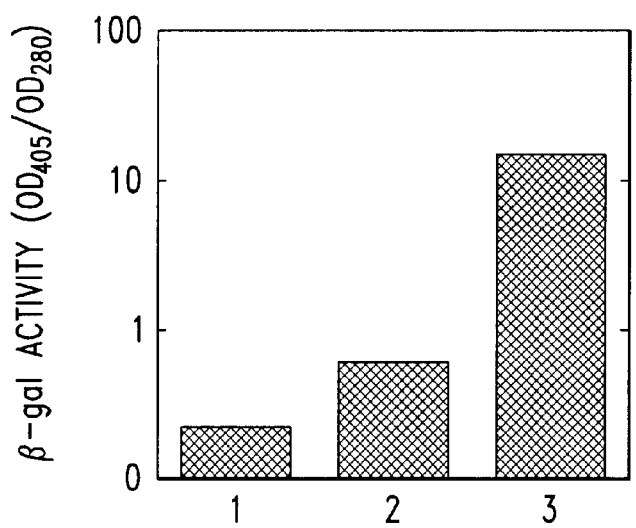
FIG. 9B is a graph showing the effect of endosome disruptive peptide on β-gal expression. Lane 1, control; lane 2, FGF2–K84–pSVβ-gal; lane 3, FGF2–K84–pSVβ-gal+EDP.

When an endosome disruptive peptide was included in the complex, expression of β-gal was increased 26-fold (FIG. 9B). Concomitant with this increased level of expression was an increase in the number of cells expressing β-gal. As seen in FIG. 9C, when endosome disruptive peptide (EDP) was present (right panel), 1%–5% of cells express β-gal in comparison to 0.1%–0.3% without EDP added (left panel).

Example 9

CYTOTOXIC ACTIVITY OF FGF/POLY-L-LYSINE BOUND TO SAP DNA PLASMID

The cytotoxicity assay measures viable cells after transfection with a cytocide-encoding agent. When FGF-2 is the receptor-binding internalized ligand, COS7 cells, which express FGFR, may be used as targets, and T47D, which does not express a receptor for FGF-2 at detectable levels, may be used as negative control cells.

Cells are plated at 38,000 cells/well and 48,000 cells/well in a 12-well tissue culture plate in RPMI 1640 supplemented with 5% FBS. The complex FGF2–K/pZ200M (a plasmid which expresses saporin) is incubated with COS7 or T47D cells for 48 hrs. Controls include FGF2–K alone, pZ200M alone, and FGF-2 plus poly-L-lysine plus pZ200M. Following incubation, cells are rinsed in PBS lacking $Mg^{++}$ and $Ca^{++}$. Trypsin at 0.1% is added for 10 min and cells are harvested and washed. Cell number from each well is determined by a Coulter particle counter (or equivalent method). A statistically significant decrease in cell number for cells incubated with FGF2–K/pZ200M compared to FGF2–K or pZ200M alone indicates sufficient cytotoxicity.

Figure 10:
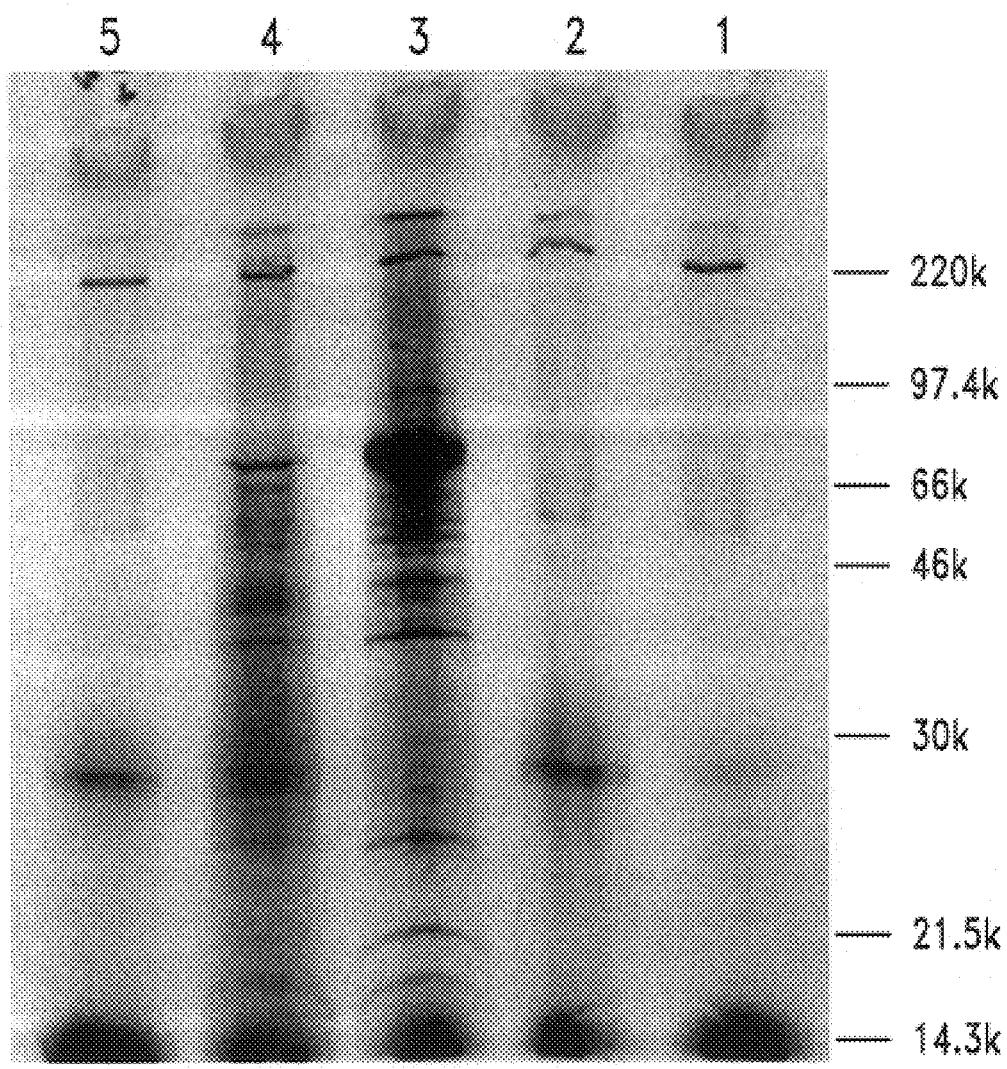
FIG. 10 is a photograph of a fluorograph analyzing cell-free translation products. Lane 1, no RNA; lane 2, saporin RNA; lane 3, luciferase RNA; lane 4, saporin RNA and luciferase RNA; lane 5, saporin RNA followed 30 min later with luciferase RNA.

FGF2-polylysine-DNASAP complexes show selective cytotoxicity. To optimize the expression of the plant RIP, saporin, in mammalian cells, a synthetic saporin gene using preferred mammalian codons and introduced a "Kozak" sequence for translation initiation. The synthetic gene was then cloned into SV40 promoter and promoterless expression vectors. Because the expression of SAP from SAP-encoding DNA would only be feasible if the mammalian ribosome can synthesize the protein (SAP) prior to its inactivation by the SAP synthesized, the enzymatic activity of saporin encoded by the synthetic gene was tested. SAP was cloned into a T7/SP6 promoter plasmid and sense RNA was generated using T7 RNA polymerase. The RNA was then added to a mammalian in vitro translation assay. The results from this cell-free in vitro translation assay clearly show that the saporin expressed in a mammalian system can inhibit the expression of protein mutagenesis (FIG. 10). When added above to the lysate, SAP mRNA is translated into a protein that has the anticipated molecular weight of the saporin protein (lane 2). Similarly, when luciferase mRNA is added to the lysate, a molecule consistent with the luciferase protein is detected (lane 3). In contrast, if SAP mRNA is added to the lysate along with or 30 minutes prior to luciferase mRNA, saporin activity is detected (lanes 4 and 5).

Figure 11:
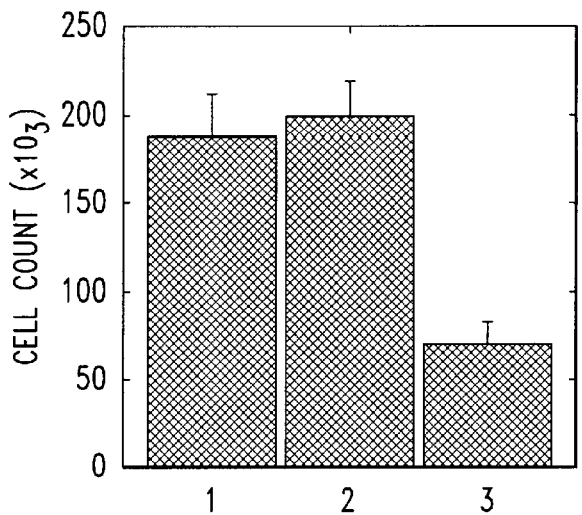
FIG. 11 is a graph depicting direct cytotoxicity of cells transfected by a CaPO$_4$ with an expression vector encoding saporin. Lane 1, mock transfection; lane 2, transfection with pSVβ-gal; lane 3, transfection with saporin-containing vector.

Transfection of cells with SAP DNA demonstrates cytotoxicity. When a mammalian expression vector encoding saporin is transiently expressed in NIH 3T3 cells using $CaPO_4$, there is a >65% decrease in cell survival (lane 3) compared to cells mock transfected (lane 1) or transfected with DNA encoding β-gal (lane 2) (FIG. 11).

Figure 12A:
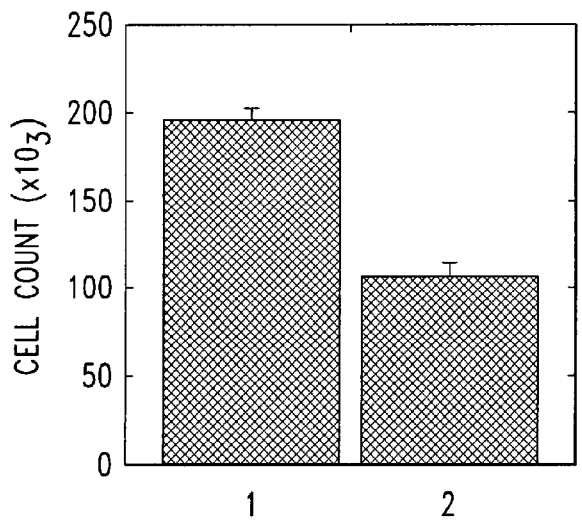
FIG. 12 is a pair of graphs showing cytotoxicity of cells transfected with FGF2–K84–pSVSAP. Left panel, BHK21 cells; right panel, NIH 3T3 cells. Lane 1, FGF2–K84–pSVβ-gal; lane 2, FGF2–K84–pSVSAP.
Figure 12B:
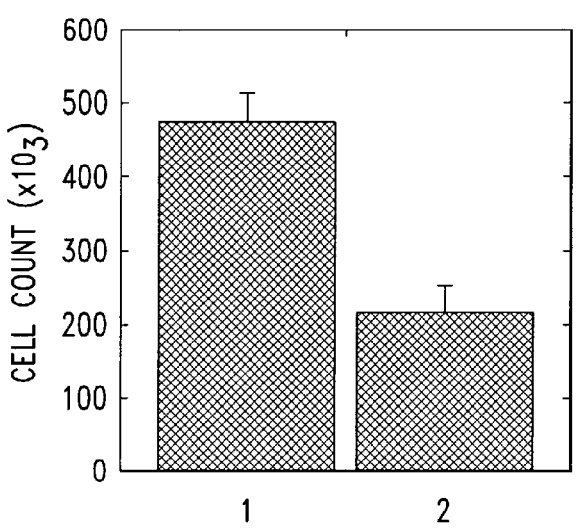

To determine whether the FGF2–K can transfer plasmid DNA encoding SAP into FGF receptor bearing cells, FGF2–K was condensed with the pSV40-SAP plasmid DNA at a ratio of 2:1 (w:w). BHK 21 and NIH 3T3 cells were used as the target cells. The cells (24,000 cells/well) were incubated with either FGF2–K–DNASAP or an FGF2–K–DNAβ-gal complex. After 72 hours of incubation, cell number was determined. As shown in FIG. 12, there is a significant decrease in cell number when cells are incubated with the FGF2–K–DNASAP complex compared to cells incubated with the FGF2–K–DNAβ-gal complex.

Example 10

USE OF TISSUE-SPECIFIC PROMOTERS IN MAMMALIAN EXPRESSION VECTORS (pNASS-β AND pNASS-SAP)

Two promoterless expression plasmids are used for insertion of tissue-specific promoters. These plasmids, pNASS-β (for β-galactosidase expression) and pNASS-SAP (for saporin expression), have unique EcoR I and Xho I sites for insertion of promoters. The plasmids containing a promoter are isolated from amplified cultures according to standard procedures and then purified for experimental use by double banding through CsTFA according to the manufacturer's protocol (Pharmacia Biotech).

Smooth Muscle α-Actin

The sequence of the human smooth muscle α-actin promoter is known (Reddy et al., *J. Biol. Chem.* 265:1683–1687, 1990; GenBank accession number J05193). A luciferase expression plasmid containing α-actin promoter sequence from −894 bp to +12 bp (relative to the start of transcription) is obtained from Dr. C. Chandra Kumar (Schering-Plough Research Institute, Kenilworth, N.J.). This plasmid is used as a template for a PCR reaction designed to amplify the −670 bp to +12 bp fragment of the promoter. The primers incorporate an EcoR I site at the 5' end and a Xho I site at the 3' end. The sense primer used in this reaction was:

```
                                   (SEQ ID NO. 107)
5'-TATATAGAATTCGTAGACAAAGCTAATGCACCAAAA-3'
       EcoRI
```

The antisense primer used was:

```
                                   (SEQ ID NO. 108)
5'-TATATACTCGAGCACTGGGTGGTGTTCAGGGAAGCT-3'
       XhoI
```

A reaction mix is prepared in an 0.65 ml eppendorf tube and contains: 25 μl H$_2$O, 5 μl 10×PCR buffer with Mg$^{++}$ (Boehringer Mannheim), 10 μl 2 mM dNTP mix, 5 μl 20 μM stock of each primer. A wax bead is added, and the tube heated at 68° C. for 5 min. After cooling to room temperature, the remaining components are added: 34.5 μl H$_2$O, 5 μl 10×PCR buffer, 0.5 μl Taq DNA polymerase (Boehringer Mannheim), and 10 μl (200 ng) template DNA. The PCR reaction is carried out in an Ericomp TwinBlock EasyCycler using the following cycles: one cycle of a denaturation step (95° C. for 5 min), 20 cycles of a denaturation step, an annealing step, and an elongation step (95° C. for 1 min; 60° C. for 2 min; 72° C. for 2 min), and one cycle of an elongation step (72° C. for 7 min). An aliquot of the reaction is run on an agarose gel and the amplified product is purified using the Geneclean II Kit (Bio101). The purified DNA is then digested with EcoR I and Xho I and is subjected to another round of electrophoresis and Geneclean purification. The digested promoter fragment was ligated into EcoR I/Xho I digested pNASS-SAP and pNASS-β followed by transformation into competent DH5α cells and plating on LB plates containing ampicillin. Ampicillin-resistant colonies are screened for promoter insertion by PCR. Individual colonies are inoculated into 25 μl of a reaction mix consisting of 540 μl H$_2$O, 6.25 μl 10 mM dNTP mix, 62.5 μl 10×PCR buffer, 6.25 μl of each of the primers specified above, and 3.2 μl Taq DNA polymerase. Amplification conditions are: one cycle of a denaturation step (99° C. for 5 min), 20 cycles of a denaturation step, an annealing step, and an elongation step (99° C. for 1 min; 65° C. for 2 min; 72° C. for 2 min) and one cycle of an elongation step (72° C. for 7 min). Clones containing promoter insertions are identified by agarose gel electrophoresis of the PCR products and are used to inoculate cultures for DNA preparation. DNA is isolated from 50 ml cultures using Qiagen's Maxi columns and protocols. The sequence of the promoter inserts is confirmed by dideoxy sequencing with Sequenase version 2.0 (US Biochemicals).

The sequence of the PCR-generated α-actin promoter is:

```
EcoRI
GAATTCGTAGACAAAGCTAATGCACCAAAAAAATGAATGTAGTTATAGTAATGCTAACATCCAAATTCCT    (SEQ ID NO. 109)

CTTTGTAAGACATAGGCCTGTCAACCTTGTCTCCATACTTCAATTCCTATTTCCACTCACCTCCCTCAAG

AACTTGATTTATAAACAGTGTGCCTACCATAAAATCATCACTCCCTCTATGTATTTATAGACGACTGAAG

GAATATCTTTCTTCTTTGCATGCTACCGTGGTAGAAGGGTTTTAAAAGTCCGTGCTAGGCAGAGGCAGCC

CTTTCTGCCCCTTTCTGTTCTCAGTTTATTAGGAAATGGCCTGAAATTCCAGCATGATAGCAAGCTGGCA

TCCTCTGTGGAATGTGCAAACCATGCCTGCATCTGCCCATTACCCTAGCTCAGTGTCTCTGGGCATTTCT

GCAGTTGTTCTGAAGGCTTGGCGTGTTTATCTCCCACAGGCGGCTGAACCGCCTCCCGTTTCATGAGCAG

ACCAGTGGAATGCAGTGGAAGAGACCCAGGCCTCCGGCCACCCAGATTAGAGAGTTTTGTGCTGAGGTCC

CTATATGGTTGTGTTAGACTGAACGACAGGCTCAAGTCTGTCTTTGCTCCTTGTTTGGGAAGSAAGTGGG

AGGAGAGCAGGCCAAGGGGCTATATAACCCTTCAGCTTTCAGCTTCCCTGAACACCACCCAGTGCTCGAG
                                                                XhoI
```

Tyrosinase Promoter

The sequence of the human tyrosinase promoter is known (Ponnazhagan et al., *J. Investigative Dermatolog*, 102: 744–748, 1994; GenBank accession number U03039). A chloramphenicol acetyltransferase expression plasmid (pHTY-CAT) containing tyrosinase promoter sequence from an XmnI site at −2020 bp to a Pst I site at +13 bp is obtained from Dr. Byoung S. Kwon (Indiana University, Indianapolis, Ind.). The tyrosinase promoter is excised fom pHTY-CAT by digestion with Pst I, which cuts just upstream of the promoter as well as at position +13. This Pst I fragment is then cloned into the Pst I site of pBluescriptII SK+ (Stratagene). Following transformation into DH5α, DNA isolated from individual clones is screened for inserts by digestion with Sal I. There are two Sal I sites in the desired end product, one located near the 5' end of the promoter fragment isolated from pHTY-CAT and the second located within the multi-cloning site of pBluescript. In the desired orientation, the Bluescript site is positioned downstream of the promoter such that the entire promoter can be excised by digestion with Sal I. The ends generated by Sal I are compatible with those generated by digestion with XhoI. Therefore, the Sal I promoter fragment is cloned into Xho I-digested pNASS-SAP and pNASS-β. Following transformation into DH5α, clones with the promoter in the desired orientation are identified by restriction analysis.

αA4-Crystallin Promoter

The sequence of the human αA-crystallin promoter is known (Jaworski et al., *J. Mol. Evolution*, 33: 495–505, 1991; GenBank accession number S79457). The region corresponding to −400 bp to +50 bp is synthesized by PCR using overlapping oligos. For cloning purposes, an EcoR I site is introduced at the 5' end and an Xho I site at the 3' end of the promoter. The promoter is synthesized as two fents (A and B) that overlap at a Pvu II site. The two fragments are then ligated together at the Pvu II site to give the intact promoter. Fragment A covers the 5' half of the promoter and is synthesized using the following primers:

A reaction mix for amplification is prepared by combining 15 μl H$_2$O, 5 μl 10×PCR buffer with Mg$^{++}$, 10 μl 2 mM dNTP mix, 5 μl of 20 μM stock of each external primer (A1 and A4 or B1 and B4), and 5 μl of 0.2 μM stock of each internal primer (A2 and A3 or B2 and B3). A wax bead is added and the samples heated at 68° C. for 5 min and then cooled to room temperature. After cooling, the following is added to each reaction: 44.5 μl H$_2$O, 5 μl 10×PCR buffer, 0.5 μl Taq polymerase. The first PCR cycle is a denaturation step (95° C. for 5 min), followed by 25 cycles of a denaturation step, an annealing step, and an elongation step (95° C. for 1 min; 70° C. for 2 min; 72° C. for 2 min). An additional elongation step is performed for one cycle (72° C. for 7 min). The reactions are run on an agarose gel and the amplified product is purified using Geneclean II (Bio101). The purified DNAs are then digested with EcoR I and BamH I (fragment A) or Bam HI and Xho I (fragment B) and cloned into the corresponding sites of pBluescript II SK+ (Stratagene). The resulting ligations are transformed into competent DH5α cells and clones containing insert are identified by restriction digestion of DNA preparations. Each clone is further characterized by DNA sequence analysis to confirm identity. The crystallin promoter fragments are excised from the Bluescript intermediates using EcoRI and Pvu II for fragment A and Pvu II and Xho I for fragment B. These fragments are then ligated into the EcoRI and XhoI sites of pNASS-β or pNASS-SAP to give the intact crys-

```
Sense A1:
      EcoRI
5'-TATAGAATTCCTGTGTCTAACGGGGTGTGTGCTCTCCCTCCTCTGGCGACCATGAGGAAACCCCCG    (SEQ ID NO. 110)
GCAGGACAAGGTG-3'

Sense A2:
5'-CCTGCCCAGTGACTGGCAGATGAGAAGCTCCATTGTCGCCCCAGGGAGTATGGGGCACAGGCGCCTC   (SEQ ID NO. 111)
CTTGGGTTG-3'

Antisense A3:
5'-ATCTGCCAGTCACTGGGCAGGGGCTACGTGCCAGGGACCATGCTAGTTCTCTGCACACCTTGTCCTG   (SEQ ID NO. 112)
CCGGGGGTT-3'

Antisense A4:
       BamHI      PvuII
5'-TATAGGATCCTGGACTCAGCTGAGGCCCGCCTGGGCACCCTGGGGCTCCCGGGAGGCAGACAACCCA   (SEQ ID NO. 113)
AGGAGGCGCCTGTG-3'
```

Fragment B covers the 3' half of the promoter and is synthesized using the following primers:

tallin promoter driving expression of the β-gal or saporin genes. The sequence of the inserted crystallin promoter is:

```
Sense B1:
       BamHI     PvuII
5'-TATAGGATCCGGGCCTCAGCTGAGTCCAGGCCTCGGGGACAGTCCGTGCACG    (SEQ ID NO. 114)
CTCCTGGGGCTGGGGGCGGGC-3'

Sense B2:
5'-TTCATGAGCTCACGCCTTTCCAGAGAAATCCCTTAATGCCGCCATTCTGCTG    (SEQ ID NO. 115)
GTGGCATATATAGGGAGGGCTCGGCCTTG-3'

Antisense B3:
5'-GGAAAGGCGTGAGCTCATGAAGAAGGCTGCTCAGTCAGCAGAAACGTGGC      (SEQ ID NO. 116)
TGGGACAAGTGCCCGCCCCAGCCCCAGGAG-3'

Antisense B4:
         XhoI
5'-TATATACTCGAGCGGGACCTGGAGGCTGGCAGGAGTCAGCGGGGCCTCT      (SEQ ID NO. 117)
GGCAGCCAGTGTGGAGCCAAGGCCGAGCCCTCCCTATA-3'
```

```
EcoRI
GAATTCCTGTGTCTAACGGGGTGTGTGCTCTCCCTCCTCTGGCGACCATGAGGAAACCCCCGGCAGGAC  (SEQ ID NO. 118)

AAGGTGTGCAGAGAACTAGCATGGTCCCTGGCACGTAGCCCCTGCCCAGTGACTGGCAGATGAGAAGCTC

CATTGTCGCCCCAGGGAGTATGGGGCACAGGCGCCTCCTTGGGTTGTCTGCCTCCCGGGAGCCCCAGGGT

GCCCAGGCGGGCCTCAGCTGAGTCCAGGCCTCGGGGACAGTCCGTGCACGCTCCTGGGGCTGGGGCGGG

CACTTGTCCCAGCCACGTTTCTGCTGACTGAGCAGCCTTCTTCATGAGCTCACGCCTTTCCAGAGAAATC

CCTTAATGCCGCCATTCTGCTGGTGGCATATATAGGGAGGGCTCGGCCTTGGCTCCACACTGGCTGCCAG

AGGCCCCGCTGACTCCTGCCAGCCTCCAGGTCCCCGCTCGAG
                                   XhoI
``` c-myc promoter

The sequence of the human c-myc gene including the promoter region is known (Gazin et al., *EMBO J.*, 3: 383–387, 1984; Genbank accession number X00364). A plasmid containing the human c-myc gene in pBluescriptII KS+ is obtained from Dr. Mark Groudine (Fred Hutchinson Cancer Research Center, Seattle, Wash.). The promoter region extending from −2.1 kb to +49 bp is isolated by digestion with Hind III and Nae I and subcloned into the HindIII/Nae I sites of pBluescript II SK+. The c-myc promoter is then excised from this intermediate as an EcoRI to Nae I fragment (the EcoRI site is upstream of the promoter within the Bluescript multicloning site) and ligated into EcoRI and blunt-ended Xho I sites of pNASS-β and pNASS-SAP.

Example 11

CONSTRUCTION OF NON-MITOGENIC FGF2 MUTANTS

Five individual mutants of FGF2 are constructed to reduce or eliminate mitogenic capability. The five mutations are: (1) R116I (Heath et. al. *Biochemistry*, 1991); (2) R118K/K119E; (3) K119E (Springer et al., 1994); (4) Y120A (Springer et al., supra); (5) W123A (Springer et al., supra).

A "semi-inverse" PCR technique is used to change the coding sequence of FGF2 using four primers to create two fragments. Two of the primers, which prime on complementary strands incorporate the individual mutation, overlap only at the amino acid to be changed. In addition, these two primers include a non-complementary overhang containing a Bsa I restriction enzyme site. Bsa I recognizes the sequence 5'-GGTCTC-3' and cuts downstream of its recognition sequence, thus removing the recognition sequence. The primers are designed such that digestion with Bsa I leaves complementary overhangs that, when ligated together, restore the original 155 amino acid FGF2, except containing one amino-acid change.

The two fragments are completed using two other primers, GF-1 and GF-2. The GF-2 primer anneals upstream of the ATG/NdeI site in pFC80 and allows extension toward the mutation primer in FGF2 (primer GF-13 for R116I mutant). The GF-1 primer anneals at the 3' end of FGF2 and incorporates a BglII site. Thus, GF-1 reverse-primes toward the second mutation primer (GF-14 for R116I mutant). Each fragment is digested with Bsa I and with either Nde I (fragment generated by GF-2/GF-13 primers) or Bgl II (fragment generated by GF-1/GF-14 primers). The two fragments are ligated together into pET11a digested with Nde I and Bam HI.

To create K119E, primer GF-15 replaced GF-14 and GF-16 replaced GF-13. To create Y120A, primer GF-17 replaced GF-14 and GF-18 replaced GF-13. To create W123A, primer GF-19 replaced GF-14 and GF-20 replaced GF-13. The double mutant R118K/K119E was created during PCR using GF-15 and GF-16 primers.

Primer Sequences (All 5' to 3'):
- GF-1: ATTAATTATAGATCTCAGCTCTTAGCAG ACATTGG (SEQ ID NO. 119)
- GF-2: GCTTGGGCATACATTCAATCAATTGTTATC (SEQ ID NO. 120)

R116I Primers (codon change of CGG to ATA):
- GF-13: CGTAATATGGTCTCAATATGTAAGTATT GTAGTTATTAGA (SEQ ID NO. 121)
- GF-14: CGTAATATGGTCTCAATATCAAGGAAA TACACCAGTTGG (SEQ ID NO. 122)

K119E Primers (codon change of AAA to GAA):
- GF-15: CGGATATGGTCTCAGAATACACCAGTT GGTATGTG (SEQ ID NO. 123)
- GF-16: CGTAATATGGTCTCAATTCCCTTGACCG GTAAGTATTG (SEQ ID NO. 124)

Y120A Primers (codon change of TAC to GCA):
- GF-17: CGAATATGGTCTCAGCAACCAGTTGGTA TGTGGCA (SEQ ID NO. 125)
- GF-18: CGTAACATGGTCTCATTGCTTTCCTT GACCGGTAAGT (SEQ ID NO. 126)

W123A Primers (codon change of TGG to GCA):
- GF-19 GCTATTAGGTCTCAGCATATGTGGCATT GAAACGAAC (SEQ ID NO. 127)
- GF-20 CGAATTAGGTCTCAATGCACTGGTGT ATTTCCTTGACC (SEQ ID NO. 128)

PCR Conditions
1 Cycle of: 95° C./5'
5 Cycles of: 94° C./45", 42° C./30", 72° C./30"
5 Cycles of: 94° C./30", 45° C./1", 72° C./15"
10 Cycles of: 94° C./30", 55° C./2', 72° C./2'
15 Cycles of: 94° C./45", 60° C./1', 72° C./30"
1 Cycle of: 72° C./7'.

Three of the mutants and wild-type FGF2 are expressed and purified over a heparin column. Purified proteins are analyzed by Coomassie staining of an SDS-PAGE gel and by Western blot analysis (FIG. 24). Purified proteins are dialyzed to reduce the salt concentration and assayed for their ability to stimulate proliferation of ABAE cells. As shown in FIG. 25, mutants exhibit reduced ability to stimulate proliferation of endothelial cells compared to wild-type FGF2.

Example 12

TOXIGENE EXPRESSION IN ANGIOPLASTY MODEL OF RABBIT COMMON ILIAC ARTERIES

On day 0, balloon catheter denudation is performed on both common iliac arteries in 12 New Zealand White rabbits. The appropriate vessel is accessed via the femoral artery. All animals are systemically dosed on day 3, day 4 and day 5 and sacrificed on day 7 by euthanasia with an overdose of pentobarbital (60 mg/kg). The iliac arteries are excised and recombinant β-galactosidase expression evaluated both by histochemical staining (X-gal and immunoreactivity with anti-β-gal antibody) and by enzymatic activity of β-galactosidase in tissue extracts.

Rabbits are anesthetized by intramuscular administration of 35 mg/kg Ketamine and 5 mg/kg Xylazine. Both femoral areas are shaved free of hair. The surgical site is scrubbed with chlorhexidine soap and swabbed with Betadine solution and 70% EtOH. Under sterile conditions, a longitudinal incision about 2–3 cm is made in the right groin region to provide access to the femoral artery. Additionally, systemic heparin (150 IU/kg) is provided via an ear vein.

A Fogarty 4F balloon catheter is introduced into the iliac artery through the superficial femoral artery to 6 cm beyond the arteriotomy. The balloon is inflated with approximately 0.35 ml of saline to provide moderate resistance at 0.35 ATM for 10 sec, then withdrawn 4.0–4.2 cm, and deflated. Inflation and deflation is repeated twice at 1 min. intervals. Following denudation, the superficial femoral artery is ligated with 4-0 silk suture at the site of catheter entry. The skin surrounding the incision is apposed with wound clips (Autoclip 18 mm).

On days 3, 4, and day 5 after balloon denudation, FGF2–K SV40-β-gal (β-gal gene under control of SV40 promoter), FGF2–K actin-β-gal (β-gal gene under control of actin promoter), and FGF2–K pNASS-β-gal (vector lacking a promoter) are administered at a dose of 50 μg/kg in a 1 ml volume. On day 7, the animals are intravenously injected with 60 mg/kg pentobarbital. The right and left iliac arteries in each rabbit are removed, and the proximal ends of each segment are marked with a suture.

For experiments involving histological examination of vessels, perfusion fixation is carried out in situ. In this procedure, arteries are cleared of blood via perfusion with normal saline followed by fixation in situ by perfusion with 2% formaldehyde, 0.2% paraldehyde in PBS, pH 7.4. All perfusion-fixed arteries are excised and immersed in fixative for a further 2 hours. Arteries that are not fixed by perfision prior to removal are immediately frozen for later measurement of β-galactosidase activity in tissue extracts.

β-galactosidase activity is measured in the following assay. Briefly, tissue is dispersed by homogenization for 1 min in 1 ml of 0.1 M phosphate buffer pH7.4, 0.2% Triton X-100. Tissue is further extracted at room temperature for 30 minutes and non-solubilized material is collected by centrifugation (14000 rpm×30 min. at 4° C.). β-galactosidase activity in the supernatant is determined using a chemiluminescent β-galactosidase assay kit (Clontech, Palo Alto, Calif.).

Figure 15:
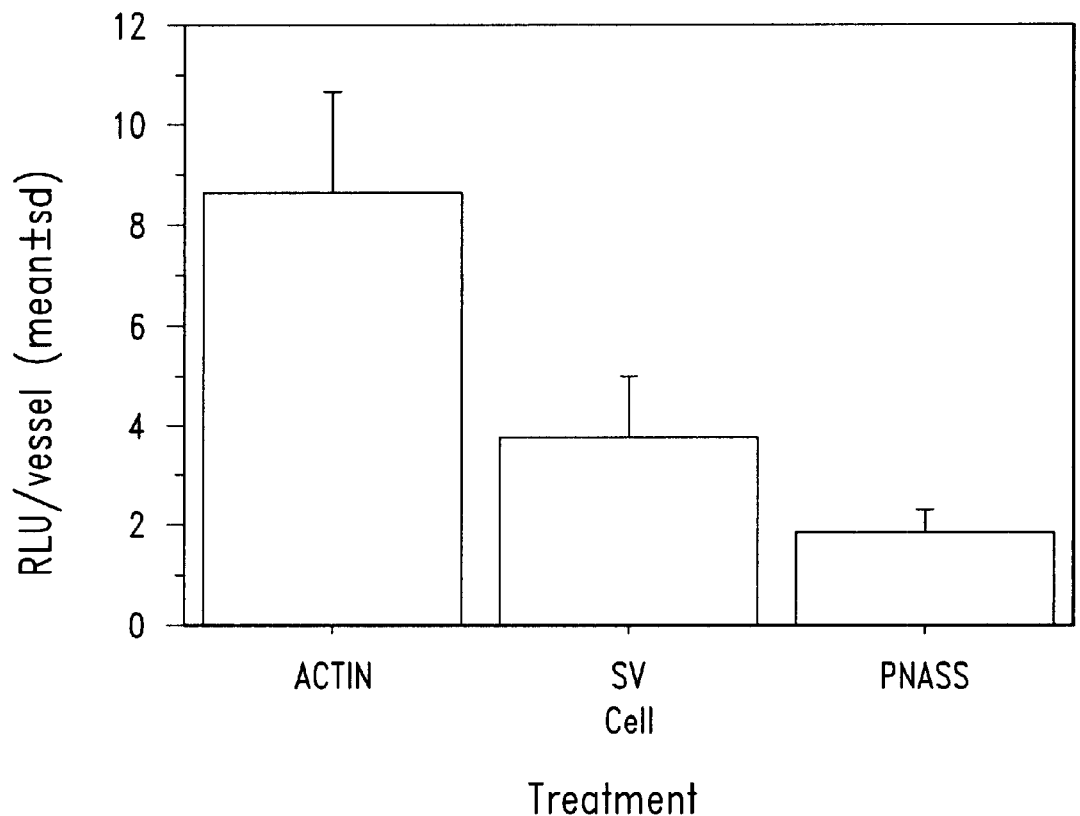
FIG. 15 is a graph illustrating the expression levels of β-gal activity in rabbit injured illiac artery.

FIG. 15 shows the amount of Relative Light Units (RLU) per vessel. Animals treated with FGF2–K84-Actin β-gal show the highest level of β-gal activity. Some β-gal activity is also detected in animals adminstered with the promoterless construct (PNASS). Two possible explanations are: (1) an active cryptic promoter within the plasmid causing read through transcription of the β-gal gene, and (2) endogenous β-gal gene expression. However, by statistical analysis, using both the Fisher and student t-test, there is statistically significant more expression when an actin promoter is used over no promoter.

Figure 16:
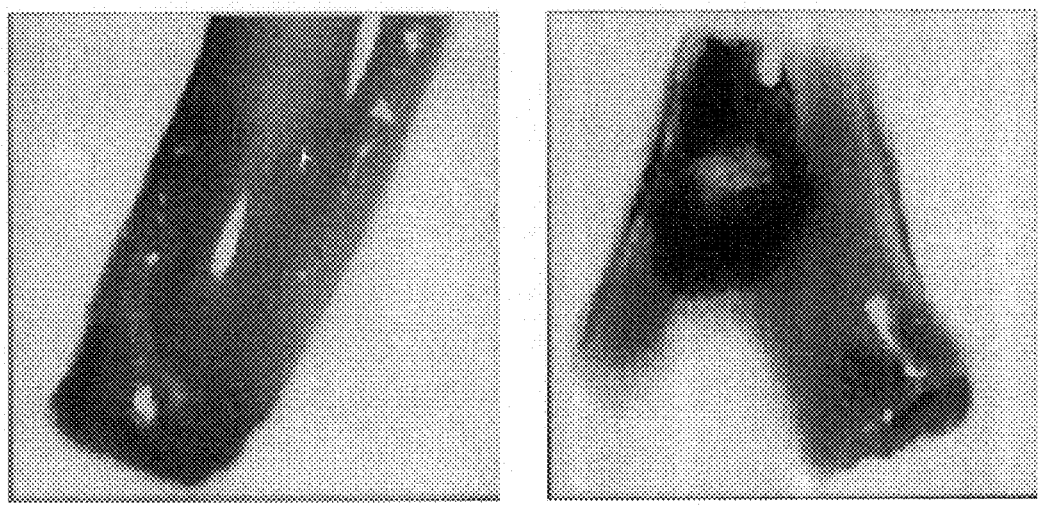
FIG. 16 is an X-gal stain of arterial segments after delivery of β-gal under control of α-actin promoter or no promoter.

Tissues are also harvested and prepared for histochemical analysis. Prior to sectioning, arterial segments are stained with X-gal. As shown in FIG. 16, animals treated with FGF2–K84-Actin β-gal showed positive staining compared to lack of staining in animals treated with the promoterless constructs. Arterial sections are taken from mammals treated with FGF2–K84-Actin β-gal and FGF2–K84-promoterless β-gal, stained with X-gal and counter stained with Fast Red. As shown in FIG. 17, X-gal staining is only apparent in the tissue from animals treated with the FGF2–K84-Actin β-gal complexes. To verify expression of β-gal, tissue sections are incubated with an antibody specific for the bacterial β-gal protein. As seen in FIG. 18, strong reactivity is detected in tissue sections from animals treated with FGF2–K84-Actin β-gal complexes. No immunoreactivity is seen in the vessels when FGF2–K84-pNASS β-gal is administered.

Figure 19:
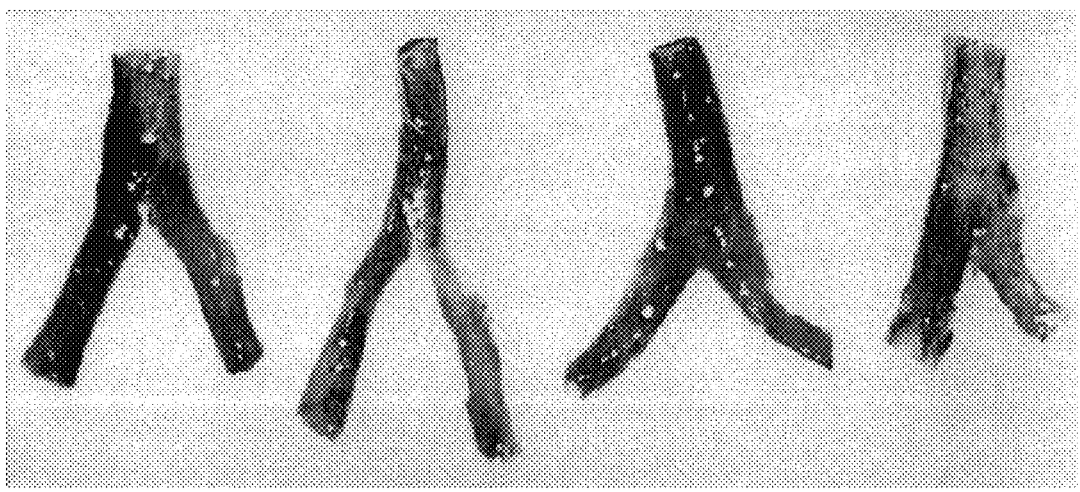
FIG. 19 is an X-gal stain of arterial segments after delivery of β-gal under control of α-actin promoter or no promoter.
Figure 20:
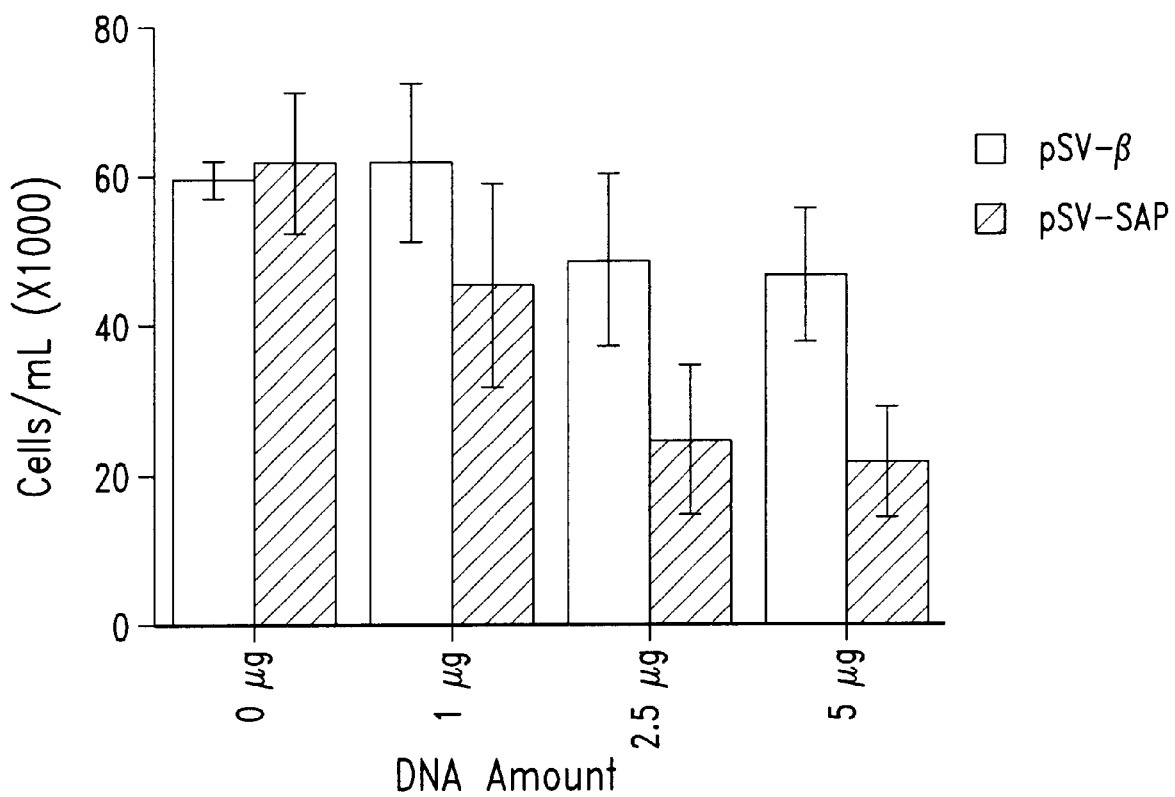
FIG. 20 is a graph illustrating cell death after delivery of DNA by transient transfection encoding either saporin or β-galactosidase under control of SV40 promoter.

A second experiment is performed in which only one iliac artery is denuded. Either FGF2–K84-Actin β-gal or a mixture of FGF2–K84, Actin β-gal, and poly lysine is administered as above. As shown in FIG. 19, significant β-gal expression from the complex as compared to the mixture is seen in the injured artery.

Example 13

TOXIGENE EXPRESSION AFTER ADMINISTRATION IN LUNG METASTESES

Groups of BDF1 female mice (ten animals per test group, total 30 animals) were injected in the tail vein with $5\times10^5$ $B_{16}F_{10}$ cells in 0.2 ml. On day 9, animals are weighed and randomized into treatment groups. On days 10, 11, and 12, animals are treated with 0.25 μg/kg of FGF2–K-SV40β-gal, or FGF2–K-pNassβ-gal. On day 14, animals are weighed and evaluated for toxicity.

β-galactosidase activity is measured either in lung cell extracts or by histochemistry stain as described above. The mean animal body weight is computed for days 9 and 14. The fraction of tumor volume in treated to control animals (T/C) is calculated for all test group with >65% survivors on day 14. A T/C value of 86% indicates toxicity.

Example 14

IN VITRO DELIVERY OF SAP DNA

Biological activity of SAP in pSV-SAP DNA is tested by transient 5 transfection in NIH3T3 cells. As a negative control, cells are also treated with FGF2–$K_{84}$-pNASS–SAP. As seen in FIG. 21, there are significantly fewer cells in the pSV-SAP transfected wells compared to the pSV-β wells. A duplicate plate of cells transfected with pSV-β was worked up for a β-gal assay which showed very high expression levels, thus confirming successful transfection.

Example 15

IN VIVO DELIVERY OF TOXIGENES COMPLEXED WITH SAP DNA REDUCTION IN TUMOR SIZE WITH INTRATUMORAL INJECTION OF FGF2–K–DNA SAP COMPLEXES

Groups of three BDF1 mice are injected subcutaneously in the left gland with $5\times10^5$ $B_{16}F_{10}$ cells suspended in PBS w/o $Ca^{++}$ and $Mg^{++}$ at a concentration of $25\times10^6$/ml. When tumor diameters reach 0.5–1.0 $mm^3$, animals are randomized and given intratumoral injections of test compounds. The animals are dosed with a single injection of FGF2–K-SV40β-gal, FGF2–K-pNASS–SAP, FGF2–K-pSV40SAP (FGF2–K 15 μg-DNA 7.5 μg/50 μl) or excipient.

Groups:

| | |
|---|---|
| 1. Excipient | 50 µl/tumor/mouse |
| 2. FGF2-K-SV40β-gal | 50 µl/tumor/mouse |
| 3. FGF2-K-NASSβ-gal | 50 µl/tumor/mouse |
| 4. FGF2-K-SV40SAP | 50 µl/tumor/mouse |

Within each group, animals receive treatment intra-tumor at time 0, and tumor is removed at 48 or 72 hours. Mice are checked daily; tumor size is measured in 2 directions by caliper once a day. The tumors are removed at 48 or 72 hours for histological examinations and divided into 2 segments. One segment is frozen and the other fixed in 10% NBF.

Figure 22:
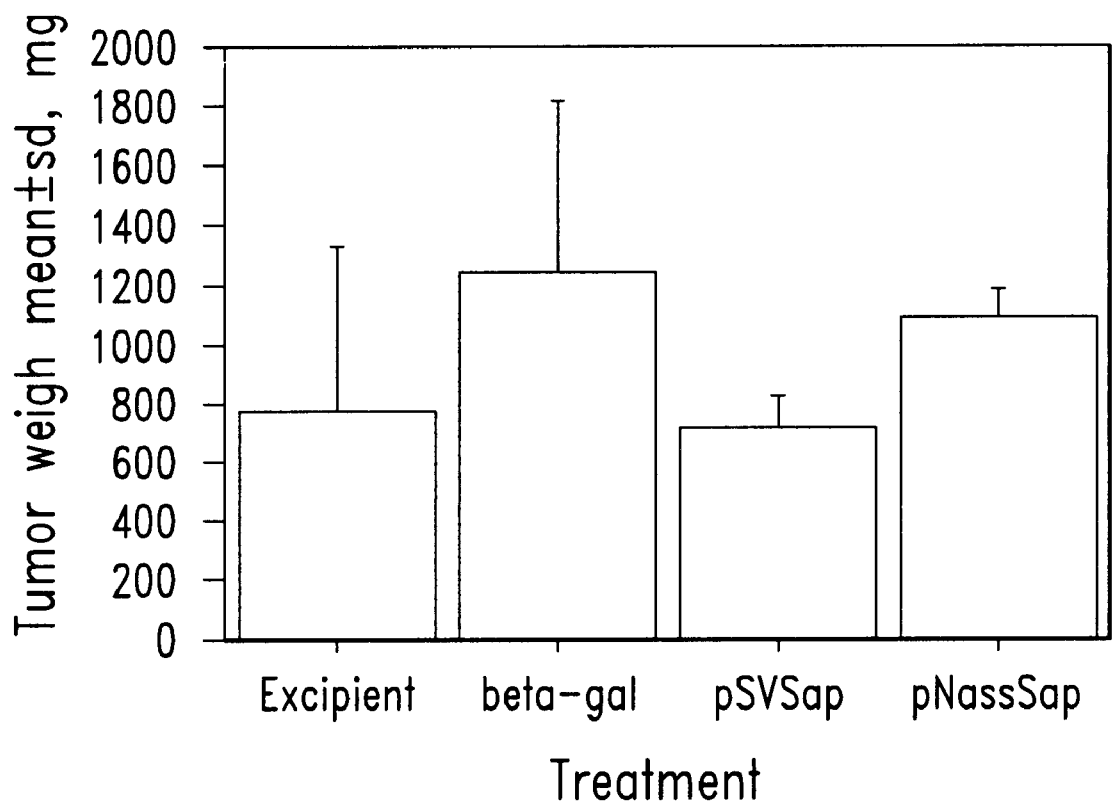
FIG. 22 shows tumor weight after two deliveries of a complex containing DNA encoding β-gal or saporin under control of SV40 promoter or saporin without a promoter or excipient.

At the start of treatment all animals have tumors of approximately equivalent size. However, as shown in FIG. 22, at both 48 hr and 72 hr, animals receiving FGF2-K-SV40SAP have smaller tumors, as measured by weight and volume, than those animals receiving FGF2-K-SV40β-gal. Tumor size is also decreased in the FGF2-K-SV40SAP treated group compared to the the FGF2-K-SV40 β-gal treated group when the animals are given 2 injections of the material (FIG. 23).

Example 16

CONDENSATION OF NUCLEIC ACID

Ligand-polycation condensation of nucleic acids is described. In this example FGF2-polylysine is used to condense DNA. Briefly, DNA is diluted in 0.1 M HEPES, 0.1 M NaCl. Depending on the final volume, either a 15 ml conical tube or a 1.5 ml eppendorf centrifuge tube is used. FGF2-polylysine conjugate is added to the tube. Diluted DNA is added dropwise into the tube containing the conjugate. During addition, the solution is mixed by gentle vortexing (no higher than a setting of 3). Once formed, 50 µl of the complex is added to cells in a 12 well tissue culture plate.

A typical condensation is prepared for addition to 4 wells. For this, 0.492 µg/ml of FGF2–K84 and 3 µg/ml of DNA is required. A total of 5 µg of FGF2–K is added per well at a protein to DNA ratio of 2:1.

From the foregoing it will be appreciated that, although specific embodiments of the invention have been described herein for purposes of illustration, various modifications may be made without deviating from the spirit and scope of the invention. Accordingly, the invention is riot limited except as by the appended claims.

What is claimed is:

1. A gene delivery composition having the formula:
   polypeptide that binds to a fibroblast growth factor (FGF) receptor-nucleic acid molecule, wherein:
   the nucleic acid molecule being chemically conjugated or fused to the polypeptide that binds to an FGF receptor;
   and wherein the gene delivery composition binds to an FGF receptor and is internalized specifically in cells bearing the FGF receptor.

2. The composition of claim 1 wherein the nucleic acid molecule is a agent.

3. The composition of claim 2 wherein the cytocide-encoding agent encodes a ribosome inactivating protein.

4. The composition of claim 3 wherein the ribosome inactivating protein is saporin.

5. The composition of claim 2 wherein the cytocide-encoding agent encodes its elongation factor 2.

6. The composition of claim 3 wherein the ribosome inactivating protein is gelonin.

7. The composition of claim 5 wherein the protein is diphtheria toxin.

8. The composition of claim 1 wherein the nucleic acid molecule is a prodrug-encoding agent.

9. The composition of claim 8, wherein the prodrug-encoding agent encodes HSV-thymidine kinase or cytosine deaminase.

10. The composition of claim 5 wherein the composition further comprises a polycation.

11. The composition of claim 10 wherein the polycation is selected from the group consisting of poly-L-lysine, protamine, histone and spermine.

12. The composition of claim 1 wherein the nucleic acid molecule encodes a ribozyme or an antisense molecule.

13. A method of delivering a nucleic acid molecule to a cell, comprising contacting a cell with the composition according to any one of claims 1–10 wherein the nucleic acid molecule is internalized in the cell.

14. The composition of either of claims 5, 2, 8, or 12 wherein the polypeptide that binds to an FGF receptor is selected from the group consisting of an FGF-1 polypeptide, an FGF-2 polypeptide, an FGF-3 polypeptide, an FGF-4 polypeptide, an FGF-5 polypeptide, an FGF-6 polypeptide, an FGF-7 polypeptide, an FGF-8 polypeptide and an FGF-9 polypeptide.

15. The composition of claim 14 wherein the polypeptide that binds to an FGF receptor is an FGF-2 polypeptide.

16. The composition of claim 15 wherein FGF-2 of SEQ ID NO:11 has a serine residue at position 96.

17. The composition of claim 1 wherein the nucleic acid molecule further comprises a tissue-specific promoter operably linked thereto.

18. The composition of claim 17 wherein the tissue-specific promoter is selected from the group consisting of alpha-crystalline promoter, tyrosinase promoter, α-fetoprotein promoter, prostate specific antigen promoter, CEA promoter, α-actin promoter, VEGF receptor promoter, erbB-2 promoter, C-myc promoter, cyclin D promoter, FGF receptor promoter gamma-crystalline promoter, tek promoter, tie promoter, urokinase receptor promoter, E-selectin promoter, P-selectin promoter, VCAM-1 promoter, endoglin promoter, endosialin promoter, $alpha_v$ integrin promoter, $\beta_3$ integrin promoter, endothelin-1 promoter, ICAM-3 promoter, E9 promoter, von Willebrand Factor promoter, CD-44 promoter, CD40 promoter, vascular endothelial cadherin promoter, notch 4 promoter and high molecular weight melanoma-associated antigen promoter.

19. The composition of claim 14 wherein the polypeptide that binds to an FGF receptor is an FGF-7 polypeptide.

20. The composition of either of claims 1, 2, 8, or 12 further comprising between one to six linkers that are selected from the group consisting of a cleavable linker, a linker that provides a sorting signal, and a linker that reduces steric hindrance, the addition of said one to six linkers resulting in the following formula:
   polypeptide that binds to an FGF receptor—L—ucleic acid molecule,
   wherein L is one to six linkers; and
   wherein the conjugate retains the ability to bind to an FGF receptor and internalize the nucleic acid molecule.

21. The composition of claim 20 wherein the linker is selected from the group consisting of a GlySer linker, a SerGly linker, or an AlaAlaProAla (SEQ ID NO: 51) linker.

22. The composition of claim 21 wherein the linker is encoded by a sequence selected from the group consisting of SEQ ID NO: 47, SEQ ID NO: 48, SEQ ID NO: 49, and SEQ ID NO: 50.

23. The composition of claim 20 wherein the linker is a disulfide bond.

24. The composition of claim 20 wherein the polypeptide that binds to an FGF receptor is selected from the group consisting of an FGF-1 polypeptide, an FGF-2 polypeptide, an FGF-3 polypeptide, an FGF-4 polypeptide, an FGF-5 polypeptide, an FGF-6 polypeptide, an FGF-7 polypeptide, an FGF-8 polypeptide and an FGF-9 polypeptide.

25. The composition of claim 20 wherein the polypeptide that binds to an FGF receptor is an FGF-2 polypeptide.

26. The composition of claim 25 wherein FGF-2 of SEQ ID NO:11 has a serine residue at position 96.

27. The composition of claim 20 wherein the polypeptide that binds to an FGF receptor is an FGF-7 polypeptide.

28. The composition of claim 27 wherein the protease is selected from the group consisting of cathepsin B, cathepsin D and trypsin.

29. The composition of claim 20 wherein the cleavable linker is cleavable by a protease.

* * * * *